(12) United States Patent
Tanoury et al.

(10) Patent No.: US 10,640,501 B2
(45) Date of Patent: May 5, 2020

(54) METHODS OF PREPARING INHIBITORS OF INFLUENZA VIRUSES REPLICATION

(71) Applicant: Vertex Pharmaceuticals Incorporated, Boston, MA (US)

(72) Inventors: Gerald J. Tanoury, Marlborough, MA (US); William Aloysius Nugent, Manomet, MA (US); Vadims Dvornikovs, Lancaster, MA (US); Peter Jamison Rose, Littleton, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 16/000,939

(22) Filed: Jun. 6, 2018

(65) Prior Publication Data

US 2018/0282330 A1 Oct. 4, 2018

Related U.S. Application Data

(60) Division of application No. 15/150,476, filed on May 10, 2016, now Pat. No. 10,023,569, which is a
(Continued)

(51) Int. Cl.
*C07D 471/04* (2006.01)
*A61K 31/506* (2006.01)
*B01J 31/04* (2006.01)

(52) U.S. Cl.
CPC .......... *C07D 471/04* (2013.01); *A61K 31/506* (2013.01); *B01J 31/04* (2013.01); *B01J 2231/44* (2013.01); *B01J 2531/824* (2013.01)

(58) Field of Classification Search
CPC ................ C07D 471/04; A61K 31/506; B01J 2531/824; B01J 2231/44; B01J 31/04
See application file for complete search history.

(56) References Cited

U.S. PATENT DOCUMENTS 4,349,552 A 9/1982 Takaya et al.
5,051,412 A 9/1991 Macor
(Continued)

FOREIGN PATENT DOCUMENTS

EP 1748829 7/2007
WO 1988/001997 3/1988
(Continued)

OTHER PUBLICATIONS

Kim, Hyun Sook et al., "Heterogeneous organocatalysis for the asymmetric desymmetrization of meso-cyclic anhydrides using silica gel-supported bis-cinchona alkaloids", Tetrahe, Elsevier Science Publishers, Amsterdam, NL, vol. 60, No. 52, Dec. 20, 2004, pp. 12051-12057.
(Continued)

*Primary Examiner* — Alexander R Pagano
*Assistant Examiner* — Ebenezer O Sackey
(74) *Attorney, Agent, or Firm* — Honigman LLP; Andrew N. Weber; Jonathan P. O'Brien

(57) ABSTRACT

A method of preparing Compound (1) or a pharmaceutically acceptable salt thereof:

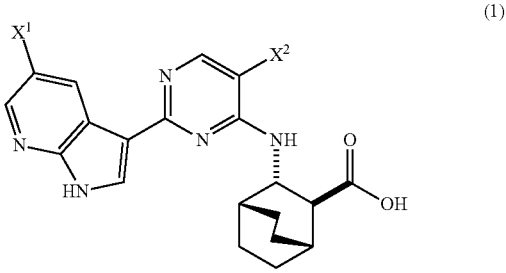

(1)

comprises: (a) reacting Compound (X):

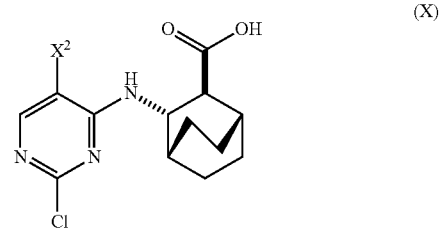

(X)

or a pharmaceutically acceptable salt thereof with Compound (Y):

(Y)

(Continued)

in the presence of a palladium catalyst and a carbonate or phosphate base to form compound (Z):

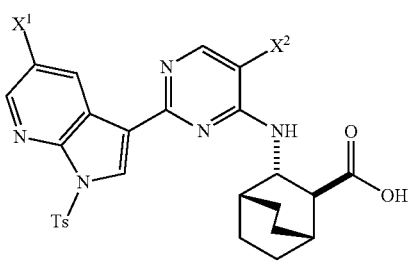

or a pharmaceutically acceptable salt thereof; and (b) deprotecting the Ts group of Compound (Z) to form Compound (1) or a pharmaceutically acceptable salt thereof.

10 Claims, 1 Drawing Sheet

Related U.S. Application Data continuation of application No. PCT/US2014/065121, filed on Nov. 12, 2014.

(60) Provisional application No. 61/903,893, filed on Nov. 13, 2013.

(56) References Cited

U.S. PATENT DOCUMENTS

| | | | |
|---|---|---|---|
| 5,304,121 A | 4/1994 | Sahatjian |
| 5,338,849 A | 8/1994 | Festal et al. |
| 5,395,840 A | 3/1995 | Miiller et al. |
| 5,886,026 A | 3/1999 | Hunter et al. |
| 6,099,562 A | 8/2000 | Ding et al. |
| 6,169,181 B1 | 1/2001 | Romines et al. |
| 6,265,403 B1 | 7/2001 | Fraley et al. |
| 6,313,126 B1 | 11/2001 | Mewshaw et al. |
| 6,699,883 B1 | 3/2004 | Doemling et al. |
| 6,825,190 B2 | 11/2004 | Moon et al. |
| 6,900,201 B2 | 5/2005 | Noe et al. |
| 7,041,687 B2 | 5/2006 | Binch et al. |
| 7,135,550 B2 | 11/2006 | Come et al. |
| 7,432,375 B2 | 10/2008 | Graczyk et al. |
| 7,491,730 B2 | 2/2009 | Forster et al. |
| 7,507,826 B2 | 3/2009 | Salituro et al. |
| 7,514,448 B2 | 4/2009 | Green et al. |
| 7,645,769 B2 | 1/2010 | Khan et al. |
| 7,659,283 B2 | 2/2010 | Collier et al. |
| 7,700,609 B2 | 4/2010 | Jimenez et al. |
| 7,767,816 B2 | 8/2010 | Farmer et al. |
| 7,795,259 B2 | 9/2010 | Binch et al. |
| 7,872,129 B2 | 1/2011 | Forster et al. |
| 8,017,619 B2 | 9/2011 | Jimenez et al. |
| 8,017,781 B2 | 9/2011 | Brenchley et al. |
| 8,101,770 B2 | 1/2012 | Charrier et al. |
| 8,163,917 B2 | 4/2012 | Farmer et al. |
| 8,173,635 B2 | 5/2012 | Jimenez et al. |
| 8,188,281 B2 | 5/2012 | Salituro et al. |
| 8,247,421 B2 | 8/2012 | Mortimore et al. |
| 8,288,400 B2 | 10/2012 | Jimenez et al. |
| 8,338,597 B2 | 12/2012 | Charrier et al. |
| 8,367,697 B2 | 2/2013 | Jimenez et al. |
| 8,372,835 B2 | 2/2013 | Binch et al. |
| 8,445,681 B2 | 5/2013 | Brenchley et al. |
| 8,450,489 B2 | 5/2013 | Farmer et al. |
| 8,461,149 B2 | 6/2013 | Pierard et al. |
| 8,501,446 B2 | 8/2013 | Salituro et al. |
| 8,507,687 B2 | 8/2013 | Keshavarz-Shokri et al. |
| 8,513,414 B2 | 8/2013 | Tanoury et al. |
| 8,518,953 B2 | 8/2013 | Pierce et al. |
| 8,530,489 B2 | 9/2013 | Mortimore et al. |
| 8,541,445 B2 | 9/2013 | Jimenez et al. |
| 8,563,530 B2 | 10/2013 | Chang et al. |
| 8,563,576 B2 | 10/2013 | Brenchley et al. |
| 8,569,337 B2 | 10/2013 | Jimenez et al. |
| 8,580,802 B2 | 11/2013 | Salituro et al. |
| 8,598,361 B2 | 12/2013 | Jimenez et al. |
| 8,722,889 B2 | 5/2014 | Salituro et al. |
| 8,796,453 B2 | 8/2014 | Tanoury et al. |
| 8,822,681 B2 | 9/2014 | Farmer et al. |
| 8,829,007 B2 | 9/2014 | Charifson et al. |
| 8,946,425 B2 | 2/2015 | Tanoury et al. |
| 8,987,454 B2 | 3/2015 | Salituro et al. |
| 9,051,319 B2 | 6/2015 | Charifson et al. |
| 9,090,614 B2 | 7/2015 | Tanoury et al. |
| 9,120,790 B2 | 9/2015 | Farmer et al. |
| 9,345,708 B2 | 5/2016 | Charifson et al. |
| 9,394,302 B2 | 7/2016 | Charifson et al. |
| 9,518,056 B2 | 12/2016 | Charifson et al. |
| 9,771,361 B2 | 9/2017 | Nti-Addae et al. |
| 9,808,459 B2 | 11/2017 | Charifson et al. |
| 10,005,737 B2 | 6/2018 | Charrier et al. |
| 10,023,569 B2 | 7/2018 | Tanoury et al. |
| 10,039,762 B2 | 8/2018 | Charifson et al. |
| 2002/0052386 A1 | 5/2002 | Armistead et al. |
| 2002/0065270 A1 | 5/2002 | Moriarty et al. |
| 2002/0147189 A1 | 10/2002 | Cai et al. |
| 2002/0183329 A1 | 12/2002 | Gross et al. |
| 2002/0183352 A1 | 12/2002 | Stack et al. |
| 2002/0183353 A1 | 12/2002 | Stack et al. |
| 2002/0183354 A1 | 12/2002 | Tran et al. |
| 2002/0193400 A1 | 12/2002 | Husbands et al. |
| 2003/0078268 A1 | 4/2003 | Zhao et al. |
| 2003/0100579 A1 | 5/2003 | Gross et al. |
| 2003/0153560 A1 | 8/2003 | Salituro et al. |
| 2003/0166668 A1 | 9/2003 | Van Zandt et al. |
| 2004/0009968 A1 | 1/2004 | Binch et al. |
| 2004/0009996 A1 | 1/2004 | Moon et al. |
| 2004/0043388 A1 | 3/2004 | Come et al. |
| 2004/0044203 A1 | 3/2004 | Wittman et al. |
| 2004/0236110 A1 | 11/2004 | Ladouceur et al. |
| 2005/0137201 A1 | 6/2005 | Aronov et al. |
| 2005/0148603 A1 | 7/2005 | Jimenez et al. |
| 2005/0208582 A1 | 9/2005 | Ohi et al. |
| 2005/0228005 A1 | 10/2005 | Moon et al. |
| 2005/0288290 A1 | 12/2005 | Borzilleri et al. |
| 2006/0003968 A1 | 1/2006 | Green et al. |
| 2006/0004014 A1 | 1/2006 | Hoffman et al. |
| 2006/0110331 A1 | 5/2006 | Dang et al. |
| 2006/0122185 A1 | 6/2006 | Green et al. |
| 2006/0122213 A1 | 6/2006 | Pierard et al. |
| 2006/0183761 A1 | 8/2006 | Ledeboer et al. |
| 2006/0183900 A1 | 8/2006 | Huang et al. |
| 2006/0183911 A1 | 8/2006 | Charrier et al. |
| 2006/0258662 A1 | 11/2006 | Binch et al. |
| 2007/0043063 A1 | 2/2007 | Salituro et al. |
| 2007/0049615 A1 | 3/2007 | Ibrahim et al. |
| 2007/0066641 A1 | 3/2007 | Ibrahim et al. |
| 2007/0072896 A1 | 3/2007 | Khan et al. |
| 2007/0135466 A1 | 6/2007 | Ledeboer et al. |
| 2007/0203142 A1 | 8/2007 | Farmer et al. |
| 2007/0207995 A1 | 9/2007 | Salituro et al. |
| 2007/0213327 A1 | 9/2007 | Collier et al. |
| 2008/0242663 A1 | 10/2008 | Ashton et al. |
| 2008/0300267 A1 | 12/2008 | Okram et al. |
| 2009/0048250 A1 | 2/2009 | Aronov et al. |
| 2009/0088445 A1 | 4/2009 | Ledeboer et al. |
| 2009/0118278 A1 | 5/2009 | Forester et al. |
| 2009/0176763 A1 | 7/2009 | Salituro et al. |
| 2009/0291937 A1 | 11/2009 | Jimenez et al. |
| 2010/0069629 A1 | 3/2010 | Shimma et al. |
| 2010/0099686 A1 | 4/2010 | Charrier et al. |
| 2010/0120792 A1 | 5/2010 | Ivashchenko et al. |
| 2010/0189773 A1 | 7/2010 | Mortimore et al. |
| 2010/0280026 A1 | 11/2010 | Jimenez et al. |
| 2010/0311743 A1 | 12/2010 | Farmer et al. |

(56) References Cited

U.S. PATENT DOCUMENTS

| | | |
|---|---|---|
| 2011/0081364 A1 | 4/2011 | Binch et al. |
| 2011/0224197 A1 | 9/2011 | Henkel et al. |
| 2011/0263575 A1 | 10/2011 | Pierard et al. |
| 2012/0010197 A1 | 1/2012 | Charrier et al. |
| 2012/0028966 A1 | 2/2012 | Charrier et al. |
| 2012/0093738 A1 | 4/2012 | Pilgaonkar et al. |
| 2012/0122879 A1 | 5/2012 | Charrier et al. |
| 2012/0136000 A1 | 5/2012 | Jimenez et al. |
| 2012/0149680 A1 | 6/2012 | Jimenez et al. |
| 2012/0165307 A1 | 6/2012 | Farmer et al. |
| 2012/0165368 A1 | 6/2012 | Brenchley et al. |
| 2012/0171245 A1 | 7/2012 | Charifson et al. |
| 2012/0178778 A1 | 7/2012 | Jimenez et al. |
| 2012/0183577 A1 | 7/2012 | Jimenez et al. |
| 2012/0184524 A1 | 7/2012 | Boyall et al. |
| 2012/0184534 A1 | 7/2012 | Brenchley et al. |
| 2012/0190699 A1 | 7/2012 | Charrier et al. |
| 2012/0258958 A1 | 10/2012 | Salituro et al. |
| 2012/0309963 A1 | 12/2012 | Mortimore et al. |
| 2013/0096302 A1 | 4/2013 | Binch et al. |
| 2013/0102782 A1 | 4/2013 | Tanoury et al. |
| 2013/0184259 A1 | 7/2013 | Charrier et al. |
| 2013/0237516 A1 | 9/2013 | Farmer et al. |
| 2013/0252939 A1 | 9/2013 | Jimenez et al. |
| 2013/0303764 A1 | 11/2013 | Tanoury et al. |
| 2013/0310418 A1 | 11/2013 | Brenchley et al. |
| 2013/0345197 A1 | 12/2013 | Salituro et al. |
| 2013/0345218 A1 | 12/2013 | Charifson et al. |
| 2014/0005192 A1 | 1/2014 | Charifson et al. |
| 2014/0005197 A1 | 1/2014 | Charifson et al. |
| 2014/0018352 A1 | 1/2014 | Pierard et al. |
| 2014/0045812 A1 | 2/2014 | Mortimore et al. |
| 2014/0094473 A1 | 4/2014 | Charifson et al. |
| 2014/0142119 A1 | 5/2014 | Charifson et al. |
| 2014/0148434 A1 | 5/2014 | Boyall et al. |
| 2014/0243273 A1 | 8/2014 | Kadiyala et al. |
| 2014/0249138 A1 | 9/2014 | Salituro et al. |
| 2014/0296201 A1 | 10/2014 | Charifson et al. |
| 2014/0309421 A1 | 10/2014 | Tanoury et al. |
| 2014/0336171 A1 | 11/2014 | Farmer et al. |
| 2015/0099875 A1 | 4/2015 | Charrier et al. |
| 2015/0099884 A1 | 4/2015 | Tanoury et al. |
| 2015/0152103 A1 | 6/2015 | Salituro et al. |
| 2015/0191468 A1 | 7/2015 | Charifson et al. |
| 2015/0284388 A1 | 10/2015 | Tanoury et al. |
| 2016/0008359 A1 | 1/2016 | Farmer et al. |
| 2016/0152614 A1 | 6/2016 | Charifson et al. |
| 2016/0168147 A1 | 6/2016 | Brummel et al. |
| 2016/0250213 A1 | 9/2016 | Simone et al. |
| 2016/0251353 A1 | 9/2016 | Nti-Addae et al. |
| 2016/0251354 A1 | 9/2016 | Tanoury et al. |
| 2017/0100400 A1 | 4/2017 | Charifson et al. |
| 2018/0065962 A1 | 3/2018 | Farmer et al. |
| 2019/0151314 A1 | 5/2019 | Charifson et al. |

FOREIGN PATENT DOCUMENTS

| | | |
|---|---|---|
| WO | 1995/033748 | 12/1995 |
| WO | 1999/021859 | 5/1999 |
| WO | 2000/040554 | 7/2000 |
| WO | 2000/040581 | 7/2000 |
| WO | 2000/043393 | 7/2000 |
| WO | 2000/064898 | 11/2000 |
| WO | 2001/001986 | 1/2001 |
| WO | 2001/014374 | 3/2001 |
| WO | 2001/087887 | 11/2001 |
| WO | 2002/014317 | 2/2002 |
| WO | 2002/020013 | 3/2002 |
| WO | 2002/024636 | 3/2002 |
| WO | 2002/051837 | 7/2002 |
| WO | 2002/072587 | 9/2002 |
| WO | 2002/085896 | 10/2002 |
| WO | 2002/085911 | 10/2002 |
| WO | 2002/088129 | 11/2002 |
| WO | 2002/088131 | 11/2002 |
| WO | 2002/088135 | 11/2002 |
| WO | 2002/088136 | 11/2002 |
| WO | 2002/088140 | 11/2002 |
| WO | 2002/088144 | 11/2002 |
| WO | 2002/088146 | 11/2002 |
| WO | 2002/089811 | 11/2002 |
| WO | 2002/092602 | 11/2002 |
| WO | 2003/000688 | 1/2003 |
| WO | 2003/091246 | 11/2003 |
| WO | 2003/101990 | 12/2003 |
| WO | 2004/013140 | 2/2004 |
| WO | 2004/014912 | 2/2004 |
| WO | 2004/016609 | 2/2004 |
| WO | 2004/016610 | 2/2004 |
| WO | 2004/043388 | 5/2004 |
| WO | 2004/076454 | 9/2004 |
| WO | 2004/078756 | 9/2004 |
| WO | 2004/082638 | 9/2004 |
| WO | 2004/089913 | 10/2004 |
| WO | 2004/106298 | 12/2004 |
| WO | 2005/000813 | 1/2005 |
| WO | 2005/012304 | 2/2005 |
| WO | 2005/028475 | 3/2005 |
| WO | 2005/033072 | 4/2005 |
| WO | 2005/044181 | 5/2005 |
| WO | 2005/062795 | 7/2005 |
| WO | 2005/085244 | 9/2005 |
| WO | 2005/095400 | 10/2005 |
| WO | 2005/105213 | 11/2005 |
| WO | 2006/009755 | 1/2006 |
| WO | 2006/015123 | 2/2006 |
| WO | 2006/030031 | 3/2006 |
| WO | 2006/038001 | 4/2006 |
| WO | 2006/041773 | 4/2006 |
| WO | 2006/050076 | 5/2006 |
| WO | 2006/052913 | 5/2006 |
| WO | 2006/063167 | 6/2006 |
| WO | 2006/069258 | 6/2006 |
| WO | 2006/124863 | 11/2006 |
| WO | 2006/127587 | 11/2006 |
| WO | 2007/002325 | 1/2007 |
| WO | 2007/002433 | 1/2007 |
| WO | 2007/017145 | 2/2007 |
| WO | 2007/084557 | 7/2007 |
| WO | 2007/095188 | 8/2007 |
| WO | 2007/107221 | 9/2007 |
| WO | 2007/117494 | 10/2007 |
| WO | 2007/122410 | 11/2007 |
| WO | 2007/127175 | 11/2007 |
| WO | 2007/129195 | 11/2007 |
| WO | 2007/146057 | 12/2007 |
| WO | 2008/003958 | 1/2008 |
| WO | 2008/005457 | 1/2008 |
| WO | 2008/023159 | 2/2008 |
| WO | 2008/076392 | 6/2008 |
| WO | 2008/079346 | 7/2008 |
| WO | 2008/112642 | 9/2008 |
| WO | 2008/112646 | 9/2008 |
| WO | 2008/112651 | 9/2008 |
| WO | 2008/113711 | 9/2008 |
| WO | 2008/123800 | 10/2008 |
| WO | 2009/023269 | 2/2009 |
| WO | 2009/040556 | 4/2009 |
| WO | 2009/046983 | 4/2009 |
| WO | 2009/059943 | 5/2009 |
| WO | 2009/106442 | 9/2009 |
| WO | 2009/125395 | 10/2009 |
| WO | 2009/145814 | 12/2009 |
| WO | 2010/008454 | 1/2010 |
| WO | 2010/008459 | 1/2010 |
| WO | 2010/011756 | 1/2010 |
| WO | 2010/148197 | 12/2010 |
| WO | 2011/000566 | 1/2011 |
| WO | 2011/008915 | 1/2011 |
| WO | 2011/130146 | 10/2011 |
| WO | 2011/137022 | 11/2011 |
| WO | 2012/083121 | 6/2012 |
| WO | 2012/083122 | 6/2012 |
| WO | 2013/006634 | 1/2013 |

(56) References Cited

FOREIGN PATENT DOCUMENTS

| | | |
|---|---|---|
| WO | 2013/019828 | 2/2013 |
| WO | 2013/070606 | 5/2013 |
| WO | 2013/184985 | 12/2013 |
| WO | 2014/201332 | 12/2014 |
| WO | 2015/027005 | 2/2015 |
| WO | 2015/073476 | 5/2015 |
| WO | 2015/073491 | 5/2015 |
| WO | 2016/054309 | 4/2016 |
| WO | 2016/054312 | 4/2016 |
| WO | 2016/183116 | 11/2016 |

OTHER PUBLICATIONS

Payack, Joseph F. et al., "A Concise Synthesis of a Novel Antiangiogenic Tyrosine Kinase Inhibitor", J. Org. Chem., 2005, vol. 70, No. 1, pp. 175-178.
Alvarez, Mercedes et al., "Synthesis of 3-Aryl- and 3-Heteroaryl-7-azaindoles", Synthesis, Thieme Stuttgart, New York, No. 4, 1999, pp. 615-620.
Amano, Mutsuki et al., "Formation of Actin Stress Fibers and Focal Adhesions Enhanced by Rho-Kinase", Science, vol. 275, Feb. 28, 1997, pp. 1308-1311.
Amano, Mutsuki et al., "Identification of a Putative Target for Rho as the Serine-Threonine Kinase Protein Kinase N", Science vol. 271, 199602-02, pp. 648-650.
Banfi, Luca et al., "Triisopropyl Borate", E-Eros Encyclopedia of Reagents for Organic Synthesis—2nd Edition, John Wiley & Sons, Ltd, GB, Jan. 1, 2006, pp. 10177-10179.
Bennett, J. Claide, M.D. et al., "Cecil Textbook of Medicine", W.B. Saunders Company, 20th Edition, vol. 1, 1996, pp. 1004-1010.
Berge, Stephen M. et al., "Pharmaceutical Salts" Journal of Pharmaceutical Sciences, vol. 66, No. 1, Jan. 1977, pp. 1-19.
Bettayeb, Karima et al., "Meriolins, a New Class of Cell Death-Inducing Kinase Inhibitors with Enhanced Selectivity for Cyclin-Dependent Kinases", Cancer Research, vol. 67, No. 17, Sep. 1, 2007, pp. 8325-8334.
Biswas, Siddhartha K. et al., "Mutational Analysis of the Conserved Motifs of Influenza A Virus Polymerase Basic Protein 1", Journal of Virology, The American Society for Microbiology, Mar. 1, 1994, pp. 1819-1826.
Boysen, Mike, "Boronsäuren", ROEMPP, Jan. 2011.
Burns, Timothy F. et al., "Silencing of the Novel p53 Target Gene Snk/Plk2 Leads to Mitotic Catastrophe in Paclitaxel (Taxol)-Exposed Cells", Molecular and cellular Biology, vol. 23, No. 16, Aug. 2003, pp. 5556-5571.
Caira, Mino R., "Crystalline Polymorphism of Organic Compounds", Topics in Current Chemistry, Springer, Berlin, DE, vol. 198, Jan. 1, 1998, pp. 163-208.
Catlett-Falcone, Robyn et al, "Constitutive Activation of Stat3 Signaling Confers Resistance to Apoptosis in Human U266 Myeloma Cells", Immunity, vol. 10, Jan. 1999, pp. 105-115.
Chelucci, Giorgio et al., "An easy route to optically active 1-substituted-1-pyridyl-methylamines by diastereoselective reduction of enantiopure N-tert-butanesulfinyl ketimines", Tetrahedron: Asymmetry, Elsevier, 2006, vol. 17, No. 22, pp. 3163-3169.
Chiba, Yoshihiko et al., "Augmented acetylcholine-induced translocation of RhoA in bronchial smooth muscle from antigen-induced airway hyperresponsive rats", British Journal of Pharmacology, vol. 133, 2001, pp. 886-890.
Chiba, Yoshihiko et al., "Augmented acetylcholine-induced, Rho-mediated Ca2+ sensitization of bronchial smooth muscle contraction in antigen-induced airway hyperresponsive rats", British Journal of Pharmacology, vol. 127, 1999, pp. 597-600.
Chiba, Yoshihiko et al., "Characteristics of muscarinic cholilnoceptors in airways of antigen-induced airway hyperresponsive rats", Comp. Biochem. Physiol. C Pharmacol. Toxicol. Endocrinol., vol. 111C, No. 3, 1995, pp. 351-357.
Chitaley, Kanchan et al., "Antagonism of Rho-kinase stimulates rat penile erection via a nitric oxide-independent pathway", Nature Medicine, Nature Publishing Group, vol. 7, No. 1, Jan. 2001, pp. 119-122.
Clapham, Kate M. et al., "Functionalized Heteroarylpyridazines and Pyridazin-3(2H)-one Derivatives via Palladium-Catalyzed Cross-Coupling Methodology", Journal of Organic Chemistry, vol. 73, No. 6, 2008, pp. 2176-2181.
Clark, Michael P. et al., "Discovery of a Novel, First-in-Class, Orally Bioavailable Azaindole Inhibitor (VX-787) of Influenza PB2", Journal of Medicinal Chemistry, vol. 57, No. 15, Jul. 14, 2014, pp. 6668-6678.
De Clercq, Erik, "Antiviral agents active against influenza A viruses", Nature Reviews Drug Discovery, vol. 5, Dec. 31, 2006, pp. 1015-10 .
Dymock, Brian W. et al., "Selective JAK inhibitors", Future Medicinal Chemistry, vol. 6, No. 12, 2014, pp. 1439-1471.
Eto, Masato et al., "Thrombin Suppresses Endothelial Nitric Oxide Synthase and Upregulates Endothelin-Converting Enzyme-1 Expression by Distinct Pathways", Circulation Research, vol. 89, 2001, pp. 583-590.
Eto, Yasuhiro et al., "Gene transfer of dominant negative Rho kinase suppresses neointimal formation after balloon injury in pigs", Am. J. Physiol. Heart Circ. Physiol., American Physiological Society, vol. 278, 2000, pp. H1744-H1750.
Fan, Yu et al., "Apoptosis induction with polo-like kinase-1 antisense phosph-orothioate oligodeoxynucleotide of colon cancer cell line SW480", World J. Gastroenterol., vol. 11, No. 29, 2005, pp. 4596-4599.
Fernandez, David et al., "Synthesis of Polyheterocyclic Nitrogen-Containing Marine Natural Products#", Monatshefte Fur Chemie, Chemical Monthly, AU, vol. 135, 2004, pp. 615-627.
Fournier, Alyson E. et al., "Rho Kinase Inhibition Enhances Axonal Regeneration in the Injured CNS", The Journal of Neuroscience, vol. 23, No. 4, Feb. 15, 2003, pp. 1416-1423.
Frank, David A, "STAT Signaling in the Pathogenesis and Treatment of Cancer", Molecular Medicine, vol. 5, Jul. 1999, pp. 432-456.
Fresneda, Pilar M. et al., "Synthesis of the indole alkaloids meridianins from the tunicate Aplidium meridianum", Tetrahedron, Pergamon, vol. 57, No. 12, 2001, pp. 2355-2363.
Fu, Xiahong et al., "The effects of the Rho-kinase inhibitor Y-27632 on arachidonic acid-, GTPgammaS-, and phorbol ester-induced induced Ca2+-sensitization of smooth muscle", FEBS Letters, vol. 440, 1998, pp. 183-187.
Fukata, Yuko et al., "Rho-Rho-kinase pathway in smooth muscle contraction and cytoskeletal reorganization of non-muscle cells", Trends Pharmacological Sciences, vol. 22, No. 1, Jan. 2001, pp. 32-39.
Galli, Stephan J., MD, "New Concepts About the Mast Cell", New England Journal of Medicine, vol. 328, No. 4, 1993, pp. 257-265.
Garcia-Bustos, Jose F. et al., "PIK1, an essential phosphatidylinositol 4-kinase associated with the yeast nucleus", The EMBO Journal, vol. 13, No. 10, 1994, pp. 2352-2361.
Genda, Takuya et al., "Cell Motility Mediated by Rho and Rho-Associated Protein Kinase Plays a Critical Role in Intrahepatic Metastasis of Human Hepatocellular Carcinoma", Hepatology, vol. 30, No. 4, Oct. 1999, pp. 1027-1036.
Gonzalez, Susana et al., "Characterization of Influenza Virus PB1 Protein Binding to Viral RNA: Two Separate Regions of the Protein Contribute to the Interaction Domain", Journal of Virology, The American Society for Microbiology, vol. 73, No. 1, Jan. 1, 1999, pp. 631-637.
Gordon, John R. et al, "Mast cells as a source of both preformed and immunologically inducible TNF-alpha/cachectin", Nature, vol. 346, Jul. 19, 1990, pp. 274-276.
Guan, Ran et al., "Small Interfering RNA-Mediated Polo-Like Kinase 1 Depletion Preferentially Reduces the Survival of p53-Defective, Oncogenic Transformed Cells and Inhibits Tumor Growth in Animals", Cancer Res., vol. 65, No. 7, Apr. 1, 2005, pp. 2698-2704.

(56) References Cited

OTHER PUBLICATIONS

Ha, Hyung-Ho et al., "Novel heterocycle-substituted pyrimidines as inhibitors of NF-κb transcription regulation related to TNF-alpha cytokine release", Bioorganic & Medicinal Chemistry Letters, Elsevier, vol. 18, 2008, pp. 653-656.
Hamanaka, Ryoji et al., "Polo-like Kinase Is a Cell Cycle-regulated Kinase Activated during Mitosis", Journal of Biological Chemistry, vol. 270, No. 36, Sep. 8, 1995, pp. 21086-21091.
Hanks, Steven K. et al., "Protein kinases 6. The eukaryotic protein kinase superfamily: kinase (catalytic) domain structure and classification", FASEB J., vol. 9, No. 8, 1995, pp. 576-596.
Harrington, Elizabeth A. et al., "VX-680, a potent and selective small-molecule inhibitor of the Aurora kinases, suppresses tumor growth in vivo", Nature Medicine, vol. 10, No. 3, Feb. 22, 2004, pp. 262-267.
Hatanaka, Masashi. et al., "Preparation and antioxidant activity of alpha-pyridoin and its derivatives", Bioorganic & Medicinal Chemistry, Elsevier, 2005, vol. 13, pp. 6763-6770.
Herbert, R. et al., "1H-Pyrrolo[2,3-b]pyridines. Part II. Fragmentation of Some 1H-Pyrrolo[2,3-b]pyridines induced by Electron Impact", J. Chem. Soc., Phys. Org., 1970, pp. 459-463.
Hernandez-Perera, Octavio et al., "Involvement of Rho GTPases in the Transcriptional Inhibition of Preproendothelin-1 Gene Expression by Simvastatin in Vascular Endothelial Cells", Circulation Research, vol. 87, 2000, pp. 616-622.
Hiles, Ian D. et al., "Phosphatidylinositol 3-Kinase: Structure and Expression of the 110 kd Catalytic Subunit", Cell, vol. 70, No. 3, Aug. 7, 1992, pp. 419-429.
Hirose, Masaya et al., "Molecular Dissection of the Rho-associated Protein Kinase (p160ROCK)-regulated Neurite Remodeling in Neuroblastoma N1E-115 Cells", Journal of Cell Biology, vol. 141, No. 7, Jun. 29, 1998, pp. 1625-1636.
Honjo, Meguni et al., "Effects of Protein Kinase Inhibitor, HA1077 on Intraocular Pressure and Outflow Facility in Rabbit Eyes", Arch. Ophthalmol, vol. 119, Aug. 2001, pp. 1171-1178.
Hoshijima, Masahiko et al., "The Low Molecular Weight GTPase Rho Regulates Myofibril Formation and Organization in Neonatal Rat Ventricular Myocytes", The Journal of Biological Chemistry, USA, vol. 273, No. 13, Mar. 27, 1998, pp. 7725-7730.
Huang, Shenlin, et al., "Synthesis of 2-amino-4-(7-azaindol-3-yl)pyrimidines as cyclin dependent kinase 1 (CDK1) inhibitors", Bioorganic & Medicinal Chemistry Letters, Elsevier, vol. 16, 2006, pp. 4818-4821.
Hudson, J.W. et al., "Late mitotic failure in mice lacking Sak, a polo-like kinase", Current Biology, vol. 11, No. 6, Mar. 20, 2001, pp. 441-446.
Iizuka, Kunihiko et al., "Evaluation of Y-27632, a Rho-kinase inhibitor, as a bronchodilator in guinea pigs", European Journal of Pharmacology, vol. 406, No. 2, 2000, pp. 273-279.
Ikeda, Fusao et al., "Reduction of Hepatic Ischemia/Reperfusion-Induced Injury by a Specific ROCK/Rho Kinase Inhibitor Y-27632", Journal of Surgical Research, Elsevier Science (USA), vol. 109, 2003, pp. 155-160.
International Search Report issued for PCT Application No. PCT/US2005/010846 dated Aug. 19, 2005.
International Search Report issued for PCT Application No. PCT/US2007/001225 dated Jul. 20, 2007.
International Search Report issued for PCT Application No. PCT/US2007/026190 dated May 20, 2008.
International Search Report issued for PCT Application No. PCT/US2008/009786 dated Jan. 19, 2009.
International Search Report issued for PCT Application No. PCT/US2009/001534 dated Apr. 2, 2010.
International Search Report issued for PCT Application No. PCT/US2010/038988 dated Aug. 20, 2010.
International Search Report issued for PCT Application No. PCT/US2012/045431 dated Feb. 5, 2013.
International Search Report issued for PCT Application No. PCT/US2012/049097 dated Sep. 25, 2012.
International Search Report issued for PCT Application No. PCT/US2012/063712 dated Jan. 8, 2013.
International Search Report issued for PCT Application No. PCT/US2014/051988 dated Nov. 3, 2014.
International Search Report issued for PCT Application No. PCT/US2014/065114 dated Jan. 29, 2015.
International Search Report issued for PCT Application No. PCT/US2014/065121 dated Apr. 8, 2015.
International Search Report issued for PCT Application No. PCT/US2014/065144 dated Mar. 2, 2015.
International Search Report issued for PCT Application No. PCT/US2015/053385 dated Dec. 17, 2015.
International Search Report issued for PCT Application No. PCT/US2015/053393 dated Dec. 15, 2015.
International Search Report issued for PCT Application No. PCT/US2016/031705 dated Jun. 22, 2016.
IPRP issued for PCT/US2005/010846 dated Oct. 4, 2006.
IPRP issued for PCT/US2007/001225 dated Jul. 22, 2008.
IPRP issued for PCT/US2010/038988 dated Dec. 20, 2011.
Ishibashi, Toshiyuki et al., "Inhibition of Rho/Rho-kinase signaling downregulates plasminogen activator inhibitor-1 synthesis in cultured human monocytes", Biochimica Et Biophysica Acta, Elsevier, vol. 1590, 2002, pp. 123-130.
Ishizaki, Toshimasa et al., "p160ROCK, a Rho-associated coiled-coil forming protein kinase, works downstream of Rho and induces focal adhesions", FEBS Letters, vol. 404, No. 2, 1997, pp. 118-124.
Ishizaki, Toshimasa et al., "The small GTP-binding protein Rho binds to and activates a 160 kDa Ser/Thr protein kinase homologous to myotonic dystrophy kinase", The EMBO Journal, vol. 15, No. 8, 1996, pp. 1885-1893.
Itoh, Kazuyuki et al., "An essential part for Rho-associated kinase in the transcellular invasion of tumor cells", Nature Medicine, vol. 5, No. 2, Feb. 1999, pp. 221-225.
Jaeschke, Georg et al., "Highly Enantioselective Ring Opening of Cyclic Meso-Anhydrides to Isopropyl Hemiesters with Ti-TADDOLates: An Alternative to Hydrolytic Enzymes?", The Journal of Organic Chemistry, American Chemical Society, US, vol. 63, No. 4, Jan. 1, 1998, pp. 1190-1197.
Jiang, Jun-Jie J. et al., "Advances in the Inhibitors of Janus Kinase", Medicinal chemistry, vol. 4, No. 8, 2014, pp. 540-548.
Jorden, Danica, "World Alzheimer Day: French Doctor Denounces Routine Alzheimer Medications", ZCommunications, Sep. 22, 2015, Whole document.
Kandabashi, Tadashi, MD et al., "Inhibition of Myosin Phosphatase by Upregulated Rho-Kinase Plays a Key Role for Coronary Artery Spasm in a Porcine Model with Interleukin-1beta", Circulation, vol. 101, No. 11, Mar. 21, 2000, pp. 1319-1323.
Karpov, Alexei S. et al., "Concise Synthesis of Meridianins by Carbonylative Alkynylation and a Four-Component Pyrimidine Synthesis", Angewandte Chemie., International Edition, Wiley VCH Verlag, Weinheim, DE, vol. 44, 2005, pp. 6951-6956.
Katsumata, Naoki et al., "Enhanced Myosin Light Chain Phosphorylations as a Central Mechanism for Coronary Artery Spasm in a Swine Model With Interleukin-1beta", Circulation, vol. 96, No. 12, 1997, pp. 4357-4363.
Kelly, Terence A. et al., "Novel Non-Nucleoside Inhibitors of Human Immunodeficiency Virus Type 1 Reverse Transcriptase. 6. 2-Indol-3-yl and 2-Azaindol-3-yl-dipyridodiazepinones1", Journal of Medicinal Chemistry, vol. 40, No. 15, 1997, pp. 2430-2433.
Khaselev, N. et al., "The Role of the C-C Double Bond in Alcohol Elimination from MH+ Ions of Unsaturated Bicyclic Esters upon Chemical Ionization", Journal of Mass Spectrometry, vol. 30, No. 11, Nov. 1, 1995, pp. 1533-1538.
Kimura, Kazushi et al., "Regulation of Myosin Phosphatase by Rho and Rho-Associated Kinase (Rho-Kinase)", Science, vol. 273, Jul. 12, 1996, pp. 245-248.
Kirken, R. A., "Targeting Jak3 for Immune Suppression and Allograft Acceptance", Transplantation Proceedings, Elsevier, vol. 33, No. 7-8, 2001, pp. 3268-3270.
Klages, Birgit et al., "Activation of G12/G13 Results in Shape Change and Rho/Rho-Kinase-mediated Myosin Light Chain Phosphorylation in Mouse Platelets", Journal of Cell Biology, vol. 144, No. 4, Feb. 9, 1999, pp. 745-754.
Knighton, Daniel R. et al., "Crystal Structure of the Catalytic Subunit of Cyclic Adenosine Monophosphate-Dependent Protein Kinase", Science, vol. 253, Jul. 26, 1991, pp. 407-414.

(56) References Cited

OTHER PUBLICATIONS

Kunz, Jeannette et al., "Target of Rapamycin in Yeast, TOR2, Is an Essential Phosphatidylinositol Kinase Homolog Required for G1 Progression", Cell, vol. 73, No. 3, May 7, 1993, pp. 585-596.

Kupittayanant, S. et al., "The effects of inhibiting Rho-associated kinase with Y-27632 on force and intracellular calcium in human myometrium", Pflugers Arch—Eur J Physiol, vol. 443, 2001, pp. 112-114.

Kuwahara, Koichiro et al., "The effects of the selective ROCK inhibitor, Y27632, on ET-1-induced hypertrophic response in nenatal rat cardiac myocytes—possible involvement of Rho/ROCK pathway in cardiac muscle cell hypertrophy'" Federation of European Biochemial Societies Letters, vol. 452, 1999, pp. 314-318.

Lane, Heidi A. et al., "Antibody Microinjection Reveals an Essential Role for Human Polo-like Kinase 1 (Plk1) in the Functional Maturation of Mitotic Centrosomes", Journal of Cell Biology, vol. 135, No. 6-2, Dec. 1996, pp. 1701-1713.

Laufs, Ulrich et al., "Post-transcriptional Regulation of Endothelial Nitric Oxide Synthase mRNA Stability by Rho GTPase*", The Journal of Biological Chemistry, USA, vol. 273, No. 37, Sep. 11, 1998, pp. 24266-24271.

Leung, Thomas et al., "A Novel Serine/Threonine Kinase Binding the Ras-related RhoA GTPase Which Translocates the Kinase to Peripheral Membranes", Journal of Biological Chemistry, vol. 270, No. 49, Dec. 8, 1995, pp. 29051-29054.

Leung, Thomas et al., "The p160 RhoA-Binding Kinase ROKalpha is a Member of a Kinase Family and is Involved in the Reorganization of the Cytoskeleton", Molecular and Cellular Biology, vol. 16, No. 10, Oct. 1996, pp. 5313-5327.

Li, Jun et. al "SAK, A New Polo-Like Kinase, Is Transcriptionally Repressed by p53 and Induces Apoptosis upon RNAi Silencing", Neoplasia, vol. 7, No. 4, Apr. 2005, pp. 312-323.

Li, Wenjie et al., "An Improved Protocol for the Preparation of 3-Pyridyl- and Some Arylboronic Acids", Journal of Organic Chemistry, vol. 67, No. 15, 2002, pp. 5394-5397.

Li, Zhongkui et al., "Function of Polo-like Kinase 3 in NF-κB-mediated Proapoptotic Response", Journal of Biological Chemistry, vol. 280, No. 17, Apr. 29, 2005, pp. 16843-16850.

Liu, Xiaoqi et al., "Polo-like kinase (Plk)1 depletion induces apoptosis in cancer cells", Proc. Nat'l. Acad. Sci., USA, vol. 100, No. 10, May 13, 2003, pp. 5789-5794.

Liu, Yanbing et al., "Bis-Suzuki reactions of 2,3-dihaloindoles. A convenient synthesis of 2,3-diarylindoles", Tetrahedron Letters, vol. 41, 2000, pp. 8717-8721.

Lowery, Drew M. et al., "Structure and function of Polo-like Kinases", Oncogene, Nature Publishing Group, vol. 24, 2005, pp. 248-259.

M.A. MalllKOBCKNN, "JleKapcTBeHHble cpeAcTBa", 2001, vol. 1, p. 14.

Ma, Sheng et al., "Role of Plk2 (Snk) in Mouse Development and Cell Proliferation", Molecular and Cellular Biology, vol. 23, No. 19, Oct. 2003, pp. 6936-6943.

Macmillan, Jennifer C. et al., "Comparative Expression of the Mitotic Regulators SAK and PLK in Colorectal Cancer", Annals of Surgical Oncology, vol. 8, No. 9, 2001, pp. 729-740.

Madaule, Pascal et al., "A novel partner for the GTP-bound forms of rho and rac", FEBS Letters, vol. 377, No. 2, 1995, pp. 243-248.

Madaule, Pascal et al., "Role of citron kinase as a target of the small GTPase Rho in cytokinesis", Nature, vol. 394, Jul. 30, 1998, pp. 491-494.

Malaviya, Ravi et al., "Genetic and Biochemical Evidence for a Critical Role of Janus Kinase (JAK)-3 in Mast Cell-Mediated Type I Hypersensitivity Reactions", Biochemical and Biophysical Research Communications, vol. 257, No. 3, 1999, pp. 807-813.

Malaviya, Ravi et al., "Targeting Janus Kinase 3 in Mast Cells Prevents Immediate Hypersensitivity Reactions and Anaphylaxis", Journal of Biological Chemistry, vol. 274, No. 38, Sep. 17, 1999, pp. 27028-27038.

Martinez, Ana et al. "Glycogen Synthase Kinase 3 Inhibitors in the Next Horizon for Alzheimer's Disease Treatment", International Journal of Alzheimer's Disease, vol. 2011, 2011 pp. 1-7.

Masumoto, Akihiro et al., "Possible Involvement of Rho-kinase in the Pathogenesis of Hypertension in Humans", Hypertension, vol. 38, No. 6, Dec. 2001, pp. 1307-1310.

Masumoto, Akihiro et al., "Suppression of Coronary Artery Spasm by the Rho-Kinase Inhibitor Fasudil in Patients With Vasospastic Angina", Circulation, vol. 105, 2002, pp. 1545-1547.

Matsui, Takeshi et al.,"Rho-associated kinase, a novel serine/threonine kinase, as a putative target for small GTP binding protein Rho", The EMBO Journal, vol. 15, No. 9, 1996, pp. 2208-2216.

Mills, Thomas M. et al., "Effect of Rho-kinase inhibition on vasoconstriction in the penil circulation", J. Appl. Physiol., vol. 91, 2001, pp. 1269-1273.

Miyagi, Yasushi, M.D., Ph.D. et al., "Upregulation of rho A and rho kinase messenger RNAs in the basilar artery of a rat model of subarachnoid hemorrhage", J. Neurosurg., vol. 93, No. 3, Sep. 2000, pp. 471-476.

Mizunuma, Kazuyuki et al., "Prevention of Ischemia-Reperfusion-Induced Hepatic Microcirculatory Disruption by Inhibiting Stellate Cell Contraction Using Rock Inhibitor1", Transplantation, USA, vol. 75, No. 5, Mar. 15, 2003, pp. 579-586.

Morishige, Kunio et al., "Asenovirus-Mediated Transfer of Dominant-Negative Rho-Kinase Induces a Regression of Coronary Arteriosclerosis in Pigs in Vivo", Arterioscler. Thromb. Vasc. Biol., vol. 21, Apr. 2001, pp. 548-554.

Morissette, Sherry L. et al., "High-throughput crystallization: polymorphs, salts, co-crystals and solvates of pharmaceutical solids", Advanced Drug Delivery Reviews, vol. 56, 2004, pp. 275-300.

Mukai, Yasushi et al., "Involvement of Rho-kinase in hypertensive vascular disease: a novel therapeutic target in hypertension", The FASEB Journal, vol. 15, No. 6, Apr. 2001, pp. 1062-1064.

Müller-Ladner, Ulf et al., "Activation of the IL-4 STAT Pathway in Rheumatoid Synovium", Journal of Immunology, vol. 164, No. 4, 2000, pp. 3894-3901.

Nakagawa, Osamu et al., "ROCK-I and ROCK-II, two isoforms of Rho-associated coiled-coil forming protein serine/threonine kinase in mice", FEBS Letters, vol. 392, No. 2, 1996, pp. 189-193.

Nakazawa, Misako et al., "PA subunit of RNA polymerase as a promising target for anti-influenza virus agents", Antiviral Research, Elsevier, vol. 78, No. 3, Jan. 17, 2008, pp. 194-201.

Narayanan, A. et al., "Developments in antivirals against influenza, smallpox and hemorrhagic fever viruses", Expert Opinion on Investigational Drugs, Ashley Publications Ltd., London, GB, vol. 20, No. 2, Feb. 1, 2011, pp. 239-254.

Nemecek, Conception et al., "Design of Potent IGF1-R Inhibitors Related to Bis-azaindoles", Chemical Biology & Drug Design, vol. 76, No. 2, Aug. 9, 2010, pp. 100-106.

Nielsen, Mette et al., "Constitutive activation of a slowly migrating isoform of Stat3 in mycosis fungoides: Tyrphostin AG490 inhibits Stat3 activation and growth of mycosis fungoides tumor cell lines", Proc. Nat. Acad. Sci., USA, vol. 94, No. 13, Jun. 1997, pp. 6764-6769.

Niggli, Verena, "Rho-kinase in human neutrophils: a role in signalling for myosin light chain phosphorylation and cell migration", FEBS Letters, vol. 445, No. 1, 1999, pp. 69-72.

Niiro, Naohisa et al., "Up-Regulation of rho a and rho-Kinase mRHAs in the Rat Myometrium during Pregnancy", Biochemiacl and Biophysical Research Communications, vol. 230, 1997, pp. 356-359.

Nilius, Bernd et al., "Role of Rho and Rho kinase in the activation of volume-regulated anion channels in bovine endothelial cells", Journal of Physiology, vol. 516, No. 1, 1999, pp. 67-74.

Nobes, Catherine D. et al., "Rho GTPases Control Polarity, Protrusion, and Adhesion during Cell Movement", Journal of Cell Biology, vol. 144, No. 6, Mar. 2, 1999, pp. 1235-1244.

Pungpo, Pornpan et al., "Three-dimensional quantitative structure-activity relationship study on HIV-1 reverse transcriptase inhibitors in the class of dipyridodiazepinone derivatives, using comparative molecular field analysis" Journal of Molecular Graphics and Modeling, Elsevier Science Inc., vol. 18, 2000, pp. 581-590.

(56) References Cited

OTHER PUBLICATIONS

Rao, P. Vasantha et al., "Modulation of Aqueous Humor Outflow Facility by the Rho Kinase-Specific Inhibitor Y-27632", Investigative Ophthalmology & Visual Science, vol. 42, No. 5, Apr. 2001, pp. 1029-1037.

Rees, Rowland W. et al., "Y-27632, a Rho-Kinase Inhibitor, Inhibits Proliferation and Adrenergic Contraction of Prostatic Smooth Muscle Cells", The Journal of Urology, USA, vol. 170, Dec. 2003, pp. 2517-2522.

Retzer, Michaela et al., "Mildly oxidised low density lipoprotein induces platelet shape change via Rho-kinase-dependent phosphorylation of myosin light chain and moesin", Federation of European Biochemial Societies Letters, vol. 466, 2000, pp. 70-74.

Rizki, Aylin et al., "Polo-like Kinase 1 Is Involved in Invasion through Extracellular Matrix", American Association of Research, vol. 67, No. 23, Dec. 1, 2007, pp. 11106-11110.

Sah, Valerie P. et al., "Rho Is Required for Galphaq and alpha1-Adrenergic Receptor Signaling in Cardiomyocytes", The Journal of Biological Chemistry, USA, vol. 27, No. 49, Dec. 6, 1996, pp. 31185-31190.

Sahai, Erik et al., "Transformation mediated by RhoA requires activity of ROCK kinases", Current Biology, vol. 9, No. 3, 1999, pp. 136-145.

Sanborn, M.D., William J. et al., "Tofacitinib, an Oral Janus Kinase Inhibitor, in Active Ulcerative Colitis", The New England Journal of Medicine, vol. 367, No. 7, Aug. 16, 2012, pp. 616-624.

Sato, Motohiko et al., "Involvement of Rho-Kinase-Mediated Phosphorylation of Myosin Light Chain in Enhancement of Cerebral Vasospasm", Circulation Research, vol. 87, No. 2, Aug. 4, 2000, pp. 195-200.

Satoh, Shin-Ichi et al., "Antiischemic Properties of Fasudil in Experimental Models of Vasospastic Angina", Jpn. J. Pharmacol., vol. 87, 2001, pp. 34-40.

Satoh, Shinji et al., "Augmented Agonist-induced Ca2+-Sensitization of Coronary Artery Contraction in Genetically Hypertensive Rats: Evidence for Altered Signal Transduction in the Coronary Smooth Muscle Cells", J. Clin. Invest., vol. 94, No. 4, Oct. 1994, pp. 1397-1403.

Sawada, Naoki et al., "Inhibition of Rho-Associated Kinase Results in Suppression of Neointimal Formation of Balloon-Injured Arteries", Circulation, vol. 101, May 2, 2000, pp. 2030-2023.

Schmidtke, M. et al., "A rapid assay for evaluation of antiviral activity against coxsackie virus 53, influenza virus A, and herpes simplex virus type 1", Elsevier, Journal of Virological Methods, vol. 95, 2001, pp. 133-143.

Schneider, Cederic et al., "In Situ Anionic Shielding for Regioselective Metalation: Directed peri and Iterative Metalation Routes to Polyfunctionalized 7-Azaindoles", Angew. Chem. Int. Ed., vol. 51, No. 11, Mar. 12, 2012, pp. 2722-2726.

Schwaller, Juerg et al., "Transformation of hematopoietic cell lines to growth-factor independence and induction of a fatal myelo- and lymphoproliferative disease in mice by retrovirally transduced TEL/JAK2 fusion genes", The EMBO Journal, vol. 17, No. 18, 1998, pp. 5321-5333.

Seasholtz, Tammy M. et al., "Rho and Rho Kinase Mediate Thrombin-Stimulated Vascular Smooth Muscle Cell DNA Synthesis and Migration", Circulation Research, vol. 84, No. 4, 1999, pp. 1186-1193.

Segain, Jean-Pierre et al., "Rho Kinase Blockade Prevents Inflammation Via Nuclear Factor kB Inhibition: Evidence in Crohn's Disease and Experimental Colitis", Gastroenterology, vol. 124, No. 5, May 2003, pp. 1180-1187.

Seidel, H. Martin et al., "Pharmaceutical intervention in the JAK/STAT signaling pathway", Oncogene, vol. 19, No. 21, 2000, pp. 2645-2656.

Sheu, Tiffany G. et al., "Dual Resistance to Adamantanes and Oseltamivir Among Seasonal Influenza A(H1N1) Viruses: 2008-2010", Journal of Infectious Diseases, vol. 203, No. 1, Jan. 1, 2011, pp. 13-17.

Shibata, Rei et al., Role of Rho-Associated Kinase in Neointima Formation After Vascular Injury, Circulation, vol. 130, Jan. 16, 2001, pp. 284-289.

Shimokawa, Hiroaki et al., "Anti-anginal Effect of Fasudil, a Rho-Kinase Inhibitor, in Patients With Stable Effort Angina: A Multicenter Study", Journal of Cardiovascular Pharmacology, vol. 40, No. 5, 2002, pp. 751-761.

Shimokawa, Hiroaki et al., "Cellular and Molecular Mechanisms of Coronary Artery Spasm: Lessons From Animal Models", Jpn. Cir. J., vol. 64, No. 1, 2000, pp. 1-12.

Shimokawa, Hiroaki et al., "Long-term inhibition of Rho-kinase induces a regression of arteriosclerotic coronary lesions in a percine model in vivo", Cardiovascular Research, Elsevier, vol. 51, 2001, pp. 169-177.

Shimokawa, Hiroaki et al., "Rho-kinase as a Novel Therapeutic Target in Treatment of Cardiovascilar Diseases", Journal of Cardiovascular Pharmacology, vol. 39, No. 3, 2002, pp. 319-327.

Smith, Mark R. et al., "Malignant Transformation of Mammalian Cells Initiated by Constitutive Expression of the Polo-like Kinase1", Biochemical and Biophysical Research Communications, vol. 234, No. 2, 1997, pp. 397-405.

Somlyo, Avril V. et al., Rho-Kinase Inhibitor Retards Migration and in Vivo Dissemination of Human Prostate Cancer Cells, Biochemical and Biophysical Research Communications, vol. 269, No. 3, 2000, pp. 652-659.

Stewart, Gavin W. et al., "Process Development and Large-Scale Synthesis of a c-Met Kinase Inhibitor", Organic Process Research & Development, vol. 14, No. 8, 2010, pp. 849-858.

Strebhardt, Klaus et al., "Targeting polo-like kinase 1 for cancer therapy", Nature Reviews, Cancer, Nature Publishing Group, London, GB, vol. 6, No. 4, Apr. 1, 2006, pp. 321-330.

Stump, Kristine L. et al., "A highly selective, orally active inhibitor of Janus kinase 2, CEP-33779, ablates disease in two mouse models of rheumatoid arthritis", Arthritis Research & Therapy, BioMed Central, London, GB, vol. 13, No. 2, Apr. 21, 2011, p. 1, abstract.

Subbarao, E. Kanta et al., "Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influenza A Virus Vaccine", Journal of Virology, The American Society for Microbiology, vol. 69, No. 10, Oct. 1, 1995, pp. 5969-5977.

Sudbeck, Elise A. et al., "Structure-based Design of Specific Inhibitors of Janus Kinase 3 as Apoptosis-inducing Antileukemic Agents", Clinical Cancer Research, vol. 5, No. 6, Jun. 1999, pp. 1569-1582.

Suzuki, Kotaro et al., "Role of common cytokine receptor gamma chain (gamma(c))- and Jak3-dependent signaling in the proliferation and survival of murine mast cells", Blood, 2000, 96(6), pp. 2172-2180.

Tachibana, E. et al., "Intra-arterial infusion of fasudil hydrochloride for treating vasospasm following subarachnoid haemorrhage", Acta Neurochir (Wien), 1999, 141(1), pp. 13-19.

Tahara, Masahiro et al., "RhoA/Rho-Kinase Cascade Is Involved in Oxytocin-Induced Rat Uterine Contraction", Endocrinology, vol. 143, No. 3, Mar. 2002, pp. 920-929.

Tobita, K. et al., "Plaque Assay and Primary Isolation of Influenza A Viruses in an Established Line of Canine Kidney Cells (MDCK) in the Presence of Trypsin", Med. Microbiol. Immunol., vol. 162, 1975, pp. 9-14.

Traxler, Peter M., "Protein tyrosine kinase inhibitors in cancer treatment", Expert Opinion on Therapeutic Patents, vol. 7, No. 6, 1997, pp. 571-588.

Trieu, Vuong N. et al., "A Specific Inhibitor of Janus Kinase-3 Increases Survival in a Transgenic Mouse Model of Amyotrophic Lateral Sclerosis", Biochemical and Biophysical Research Communications, vol. 267, No. 1, 2000, pp. 22-25.

Uehata, Masayoshi et al., "Calcium sensitization of smooth muscle mediated by a Rho-associated protein kinase in hypertension", Nature, vol. 389, Oct. 30, 1997, pp. 990-994.

Utsunomiya, T. et al., "Antianginal effects of hydroxyfasudil, a Rho-kinase inhibitor, in a canine model of effort angina", British Journal of Pharmacology, vol. 134, No. 8, 2001, pp. 1724-1730.

(56) References Cited

OTHER PUBLICATIONS

Van Baelen, Gitte et al., "Synthesis of 5-methyl-5H-pyrrolo[2,3-c]quinoline and 4-methyl-4H-pyrrolo[2,3-c] isoquinoline: two new unnatural D-ring stripped isomers of the cryptolepine series", Arkivoc, Jan. 1, 2009, pp. 174-182.
Venkatesh, Srini et al., "Role of the Development Scientist in Compound Lead Selection and Optimization", Journal of Pharmaceutical Sciences, vol. 89, No. 2, Feb. 2000, pp. 145-154.
Vertex Pharmaceuticals Incorporated, "VX-787 Showed Significant Antiviral Activity and Reduced the Severity and Duration of Influenza Symptoms in Phase 2 Challenge Study", Mar. 4, 2013.
Vippagunta, Shuda R. et al., "Crystalline Solids", Advanced Drug Delivery Reviews, vol. 48, 2001, pp. 3-26.
Wada, Makoto et al "siRNA targeting PLK-1 induces apoptosis of synoviocytes in rheumatoid arthritis", Biochemical and Biophysical Research Communications, vol. 357, No. 2, 2007, pp. 353-359.
Watanabe, Go et al., "Protein Kinase N (PKN) and PKN-Related Protein Rhophilin as Targets of Small GTPase Rho", Science, vol. 271, Feb. 2, 1996, pp. 645-648.
Weichert, Wilko et al., "Polo-like kinase isoform expression is a prognostic factor in ovarian carcinoma", British Journal of Cancer, vol. 90, No. 4, 2004, pp. 815-821.
Weichert, Wilko et al., "Polo-like kinase isoforms in breast cancer: expression patterns and prognostic implications", Virchows Archiv, vol. 446, No. 4, 2005, pp. 442-450.
West, Anthony R., "Solid state chemistry and its implications", John Wiley & Sons, 1984, pp. 358 & 365.
Written Opinion of the International Searching Authority issued for PCT Application No. PCT/US2005/010846 dated Aug. 19, 2005.
Written Opinion of the International Searching Authority issued for PCT Application No. PCT/US2007/001225 dated Jul. 20, 2007.
Written Opinion of the International Searching Authority issued for PCT Application No. PCT/US2007/025688 dated Apr. 6, 2008.
Written Opinion of the International Searching Authority issued for PCT Application No. PCT/US2007/026190 dated May 20, 2008.
Written Opinion of the International Searching Authority issued for PCT Application No. PCT/US2008/009786 dated Jan. 19, 2009.
Written Opinion of the International Searching Authority issued for PCT Application No. PCT/US2009/001534 dated Apr. 2, 2010.
Written Opinion of the International Searching Authority issued for PCT Application No. PCT/US2009/003716 dated Nov. 20, 2009.
Written Opinion of the International Searching Authority issued for PCT Application No. PCT/US2009/003723 dated Nov. 20, 2009.
Xu, Zhengren et al., "Palladium-Catalyzed Indole and Azaindole Synthesis by Direct Annulation of Electron-Poor o-Chloroanilines and o-Chloroaminopyridines with Aldehydes", Synthesis, vol. 2008, No. 24, Dec. 1, 2008, pp. 3981-3987.
Yanazume, Tetsuhiko et al., "Rho/ROCK Pathway Contributes to the Activation of Extracellular Signal-regulated Kinase/GTA-4 during Myocardial Cell Hypertrophy", The Journal of Biological Chemistry, USA, vol. 277, No. 10, Mar. 8, 2002, pp. 8618-8625.
Yoshii, Akihiro et al. "Relaxation of Contracted Rabbit Tracheal and Human Bronchial Smooth Muscle by Y-27632 through Inhibition of Ca2+ Sensitization", American Journal of Respiratory Cell and Molecular Biology, vol. 20, No. 6, 1999, pp. 1190-1200.
Yu, Chao-Lan et al., "Constitutive Activation of the Janus Kinase-STAT Pathway in T Lymphoma Overexpressing the Lck protein tyrosine kinase1", Journal of Immunology, vol. 159, No. 11, 1997, pp. 5206-5210.
Zhou, Yan et al., "Nonsteroidal Anti-Inflammatory Drugs Can Lower Amyloidogenic Aβ42 by Inhibiting Rho", Science, vol. 302, No. 14, Nov. 2003, pp. 1215-1218.

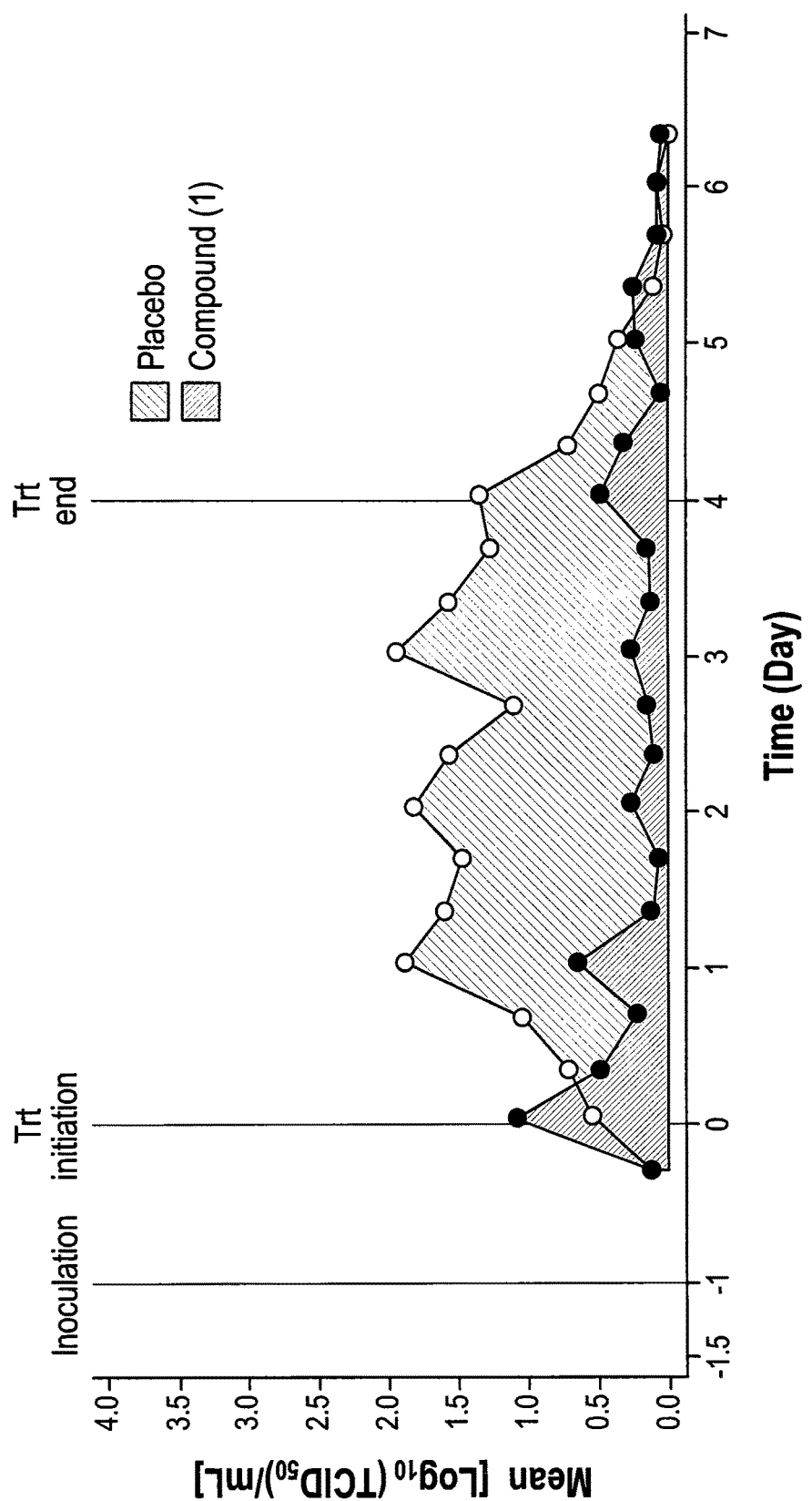

METHODS OF PREPARING INHIBITORS OF INFLUENZA VIRUSES REPLICATION

CROSS REFERENCE TO RELATED APPLICATION

This patent application is a divisional of U.S. application Ser. No. 15/150,476, filed on May 10, 2016, which is a continuation of PCT application no. PCT/US2014/065121, filed on Nov. 12, 2014, which claims priority to U.S. provisional application No. 61/903,893, filed on Nov. 13, 2013. Each of these documents is hereby incorporated by reference in its entirety.

FIELD OF THE INVENTION

The present invention relates to processes and intermediates for the preparation of compounds useful as inhibitors of Influenza virus replication.

BACKGROUND OF THE INVENTION

Influenza spreads around the world in seasonal epidemics, resulting in the deaths of hundreds of thousands annually—millions in pandemic years. For example, three influenza pandemics occurred in the 20th century and killed tens of millions of people, with each of these pandemics being caused by the appearance of a new strain of the virus in humans. Often, these new strains result from the spread of an existing influenza virus to humans from other animal species.

Influenza is primarily transmitted from person to person via large virus-laden droplets that are generated when infected persons cough or sneeze; these large droplets can then settle on the mucosal surfaces of the upper respiratory tracts of susceptible individuals who are near (e.g. within 6 feet) infected persons. Transmission might also occur through direct contact or indirect contact with respiratory secretions, such as touching surfaces contaminated with influenza virus and then touching the eyes, nose or mouth. Adults might be able to spread influenza to others from 1 day before getting symptoms to approximately 5 days after symptoms start. Young children and persons with weakened immune systems might be infectious for 10 or more days after onset of symptoms.

Influenza viruses are RNA viruses of the family Orthomyxoviridae, which comprises five genera: Influenza virus A, Influenza virus B, Influenza virus C, ISA virus and Thogoto virus.

The Influenza virus A genus has one species, influenza A virus. Wild aquatic birds are the natural hosts for a large variety of influenza A. Occasionally, viruses are transmitted to other species and may then cause devastating outbreaks in domestic poultry or give rise to human influenza pandemics. The type A viruses are the most virulent human pathogens among the three influenza types and cause the most severe disease. The influenza A virus can be subdivided into different serotypes based on the antibody response to these viruses. The serotypes that have been confirmed in humans, ordered by the number of known human pandemic deaths, are: H1N1 (which caused Spanish influenza in 1918), H2N2 (which caused Asian Influenza in 1957), H3N2 (which caused Hong Kong Flu in 1968), H5N1 (a pandemic threat in the 2007-2008 influenza season), H7N7 (which has unusual zoonotic potential), H1N2 (endemic in humans and pigs), H9N2, H7N2, H7N3 and H10N7.

The Influenza virus B genus has one species, influenza B virus. Influenza B almost exclusively infects humans and is less common than influenza A. The only other animal known to be susceptible to influenza B infection is the seal. This type of influenza mutates at a rate 2-3 times slower than type A and consequently is less genetically diverse, with only one influenza B serotype. As a result of this lack of antigenic diversity, a degree of immunity to influenza B is usually acquired at an early age. However, influenza B mutates enough that lasting immunity is not possible. This reduced rate of antigenic change, combined with its limited host range (inhibiting cross species antigenic shift), ensures that pandemics of influenza B do not occur.

The Influenza virus C genus has one species, influenza C virus, which infects humans and pigs and can cause severe illness and local epidemics. However, influenza C is less common than the other types and usually seems to cause mild disease in children.

Influenza A, B and C viruses are very similar in structure. The virus particle is 80-120 nanometers in diameter and usually roughly spherical, although filamentous forms can occur. Unusually for a virus, its genome is not a single piece of nucleic acid; instead, it contains seven or eight pieces of segmented negative-sense RNA. The Influenza A genome encodes 11 proteins: hemagglutinin (HA), neuraminidase (NA), nucleoprotein (NP), M1, M2, NS1, NS2(NEP), PA, PB1, PB1-F2 and PB2.

HA and NA are large glycoproteins on the outside of the viral particles. HA is a lectin that mediates binding of the virus to target cells and entry of the viral genome into the target cell, while NA is involved in the release of progeny virus from infected cells, by cleaving sugars that bind the mature viral particles. Thus, these proteins have been targets for antiviral drugs. Furthermore, they are antigens to which antibodies can be raised. Influenza A viruses are classified into subtypes based on antibody responses to HA and NA, forming the basis of the H and N distinctions (vide supra) in, for example, H5N1.

Influenza produces direct costs due to lost productivity and associated medical treatment, as well as indirect costs of preventative measures. In the United States, influenza is responsible for a total cost of over $10 billion per year, while it has been estimated that a future pandemic could cause hundreds of billions of dollars in direct and indirect costs. Preventative costs are also high. Governments worldwide have spent billions of U.S. dollars preparing and planning for a potential H5N1 avian influenza pandemic, with costs associated with purchasing drugs and vaccines as well as developing disaster drills and strategies for improved border controls.

Current treatment options for influenza include vaccination, and chemotherapy or chemoprophylaxis with anti-viral medications. Vaccination against influenza with an influenza vaccine is often recommended for high-risk groups, such as children and the elderly, or in people that have asthma, diabetes, or heart disease. However, it is possible to get vaccinated and still get influenza. The vaccine is reformulated each season for a few specific influenza strains but cannot possibly include all the strains actively infecting people in the world for that season. It may take six months for the manufacturers to formulate and produce the millions of doses required to deal with the seasonal epidemics; occasionally, a new or overlooked strain becomes prominent during that time and infects people although they have been vaccinated (as by the H3N2 Fujian flu in the 2003-2004 influenza season). It is also possible to get infected just before vaccination and get sick with the very strain that the vaccine is supposed to prevent, as the vaccine may take several weeks to become effective.

Further, the effectiveness of these influenza vaccines is variable. Due to the high mutation rate of the virus, a particular influenza vaccine usually confers protection for no more than a few years. A vaccine formulated for one year may be ineffective in the following year, since the influenza virus changes rapidly over time, and different strains become dominant.

Also, because of the absence of RNA proofreading enzymes, the RNA-dependent RNA polymerase of influenza vRNA makes a single nucleotide insertion error roughly every 10 thousand nucleotides, which is the approximate length of the influenza vRNA. Hence, nearly every newly-manufactured influenza virus is a mutant—antigenic drift. The separation of the genome into eight separate segments of vRNA allows mixing or reassortment of vRNAs if more than one viral line has infected a single cell. The resulting rapid change in viral genetics produces antigenic shifts and allows the virus to infect new host species and quickly overcome protective immunity.

Antiviral drugs can also be used to treat influenza, with neuraminidase inhibitors being particularly effective, but viruses can develop resistance to the standard antiviral drugs.

Thus, there is still a need for drugs for treating influenza infections, such as for drugs with expanded treatment window, and/or reduced sensitivity to viral titer. Further, there is a need for methods for preparing such drugs efficiently.

SUMMARY OF THE INVENTION

The present invention generally relates to methods of preparing Compound (1) or a pharmaceutically acceptable salt thereof and to methods of preparing certain intermediate compounds therefor:

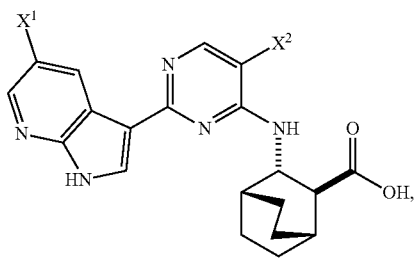

(1)

wherein $X^1$ and $X^2$ are each independently —F or —Cl.

In one embodiment, the invention is directed to a method of preparing Compound (1) or a pharmaceutically acceptable salt thereof. The method comprises (a) reacting Compound (X)

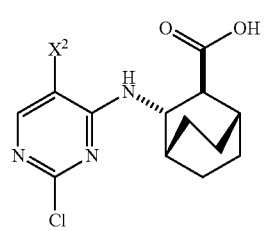

(X)

or a pharmaceutically acceptable salt thereof with Compound (Y)

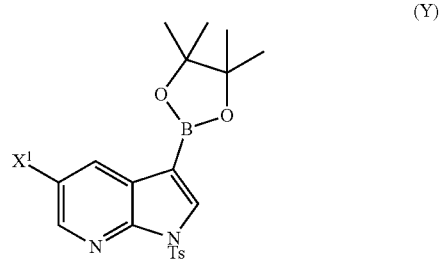

(Y)

in the presence of a palladium catalyst and a base to form Compound (Z)

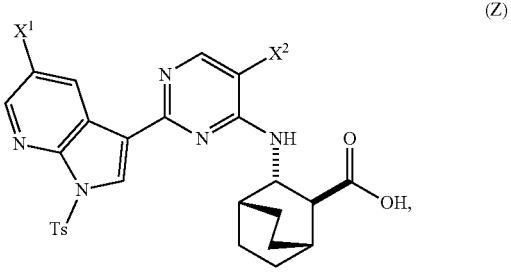

(Z)

or a pharmaceutically acceptable salt thereof; and (b) deprotecting the Ts (tosyl) group of Compound (Z) or a pharmaceutically acceptable salt thereof to form Compound (1) or a pharmaceutically acceptable salt thereof.

In some embodiments, the palladium catalyze is formed in situ. In some embodiments, this palladium catalyst is a palladium-XPhos complex, wherein XPhos is 2-dicyclohexylphosphino-2',4',6'-triisopropylbiphenyl. In other embodiments, the palladium-XPhos complex is prepared in situ by mixing a Pd(0) or a Pd(II) source with XPhos. And, in some embodiments, the Pd(0) or the Pd(II) source comprises $Pd_2(dba)_3$, $Pd(OAc)_2$, $PdCl_2$, or any combination thereof, wherein dba is dibenzyllideneacetone and OAc is acetate. For example, the palladium-XPhos complex is prepared in situ by mixing $Pd(OAc)_2$ and XPhos.

In other embodiments, the base comprises a phosphate base or a carbonate base. For example, the phosphate base or carbonate base is selected from $Na_2CO_3$, $K_2CO_3$, $K_3PO_4$, or $Na_3PO_4$.

In some embodiments, the reaction Compound (X) with Compound (Y) to generate Compound (Z), as provided in step (a), above, is performed in a solvent system comprising water and an organic solvent selected from 2-methyl THF or THF, or any combination thereof.

In other embodiments, the tosyl (Ts) deprotection of Compound (Z), as provided above in step (b), comprises treating Compound (Z) or a pharmaceutically acceptable salt thereof with an inorganic hydroxide comprising LiOH, NaOH, KOH, or any combination thereof.

Some embodiments further comprise (c) reacting Compound (F)

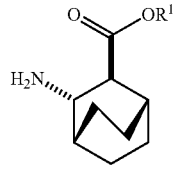
(F)

or a pharmaceutically acceptable salt thereof with Compound (G)

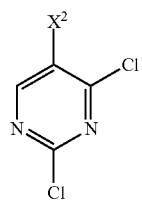
(G)

to form Compound (H)

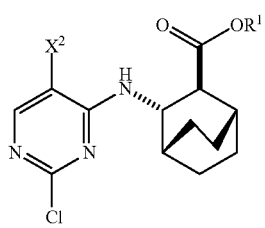
(H)

or a pharmaceutically acceptable salt thereof, wherein $R^1$ is $C_{1-4}$ alkyl; and (d) hydrolyzing Compound (H) or a pharmaceutically acceptable salt thereof to form Compound (X)

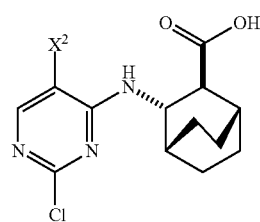
(X)

or pharmaceutically acceptable salt thereof.

Some embodiments further comprise (e) reacting Compound (C)

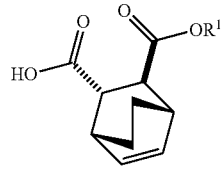
(C)

or a pharmaceutically acceptable salt thereof with diphenylphosphoryl azide and with benzyl alcohol to form Compound (D)

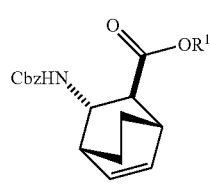
(D)

or a pharmaceutically acceptable salt thereof, wherein Cbz is carboxybenzyl; and (f) reacting Compound (D) or a pharmaceutically acceptable salt thereof with $H_2$ in the presence of a Pd catalyst on carbon to form Compound (F)

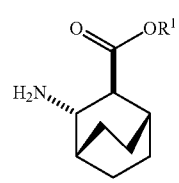
(F)

or a pharmaceutically acceptable salt thereof.

Some embodiments further comprise (g) reacting Compound (A)

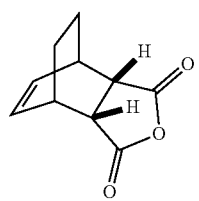
(A)

with quinine

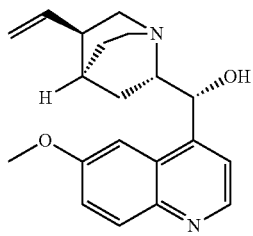 [SMILES: C=C[C@H]1CN2CC[C@H]1C[C@H]2[C@H](O)c1ccnc2ccc(OC)cc12]

and R¹—OH to form an adduct of quinine and Compound (C-1)

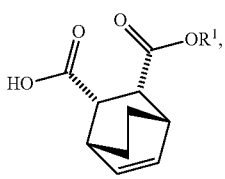

(C-1)

wherein R¹ is C₁₋₄ alkyl;

(h) breaking the adduct of quinine and Compound (C-1) by treating the adduct with HCl to form Compound (C-1) or a pharmaceutically acceptable salt thereof; and (i) epimerizing Compound (C-1) or a pharmaceutically acceptable salt thereof to form Compound (C)

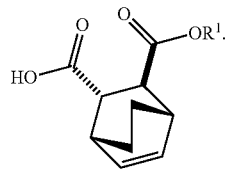

(C)

or a pharmaceutically acceptable salt thereof.

In some embodiments, the epimerization step (i) comprises treating Compound (C-1) with a $C_{1-6}$ alkoxide. In some embodiments, the $C_{1-6}$ alkoxide comprises tert-butoxide, tert-amylate, or any combination thereof. In other embodiments, R¹ is ethyl.

Some embodiments further comprise hydrogenating Compound (S)

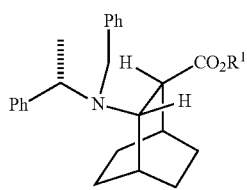

(S)

or a pharmaceutically acceptable salt thereof, wherein Ph is phenyl, in the presence of a palladium catalyst to form Compound (F) or a pharmaceutically acceptable salt thereof, wherein the palladium catalyst comprises Pd(0) on carbon (Pd(0)/C), Pd(OH)₂ on carbon, or any combination thereof.

Some embodiments further comprise reacting Compound (R)

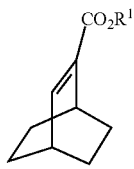

(R)

with S-(−)-N-benzyl-alpha-methylbenzylamino lithium to form Compound (S)

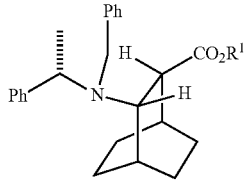

(S)

or a pharmaceutically acceptable salt thereof.

Some embodiments further comprise (j) reacting 1,3-cyclohexadiene with CH═CHC(O)OR¹ in the presence of an aluminum catalyst to form Compound (Q)

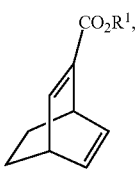

(Q)

wherein R¹ is $C_{1-4}$ alkyl and (k) hydrogenating Compound (Q) to form Compound (R)

(R)

In some embodiments, R¹ is ethyl.

In some embodiments, the aluminum catalyst comprises EtAlCl₂, Et₂AlCl, a mixture of AlCl₃ and trioctylaluminum, or any combination thereof.

In some embodiments, the hydrogenation of Compound (Q) comprises reacting Compound (Q) with 1-12 in the presence of a Rh(I) catalyst or a poisoned Pd(0) catalyst.

In some embodiments, the Rh(I) catalyst comprises (PPh₃)₃RhCl, a mixture of (PPh₃)₃RhCl and ethyl propiolate, or any combination thereof, wherein Ph is phenyl.

In some embodiments, the poisoned Pd(0) catalyst comprises a lead-poisoned Pd(0) catalyst on CaCO₃ (Pd(Pb)/CaCO₃).

Some embodiments further comprise reacting Compound (O)

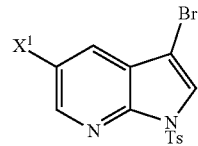

with bis(pinacolato)diboron in the presence of a palladium catalyst comprising a phosphine ligand to form Compound (Y)

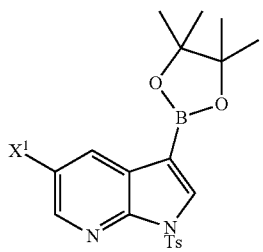

In some embodiments, the palladium catalyst comprising a phosphine ligand is Pd(Ph$_3$P)$_4$.

Some embodiments further comprise treating Compound (N)

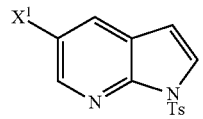

with a brominating agent comprising Br$_2$, N-bromosuccinimide, 1,3-dibromo-5,5-dimethylhydantoin, or any combination thereof to form Compound (O).

Some embodiments further comprise
(l) reacting Compound (J)

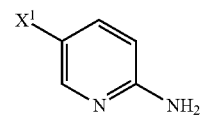

or a pharmaceutically acceptable salt thereof with an iodinating agent or a brominating agent to form Compound (K)

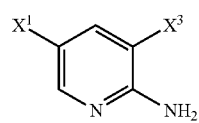

or a pharmaceutically acceptable salt thereof, wherein X$^3$ is Br or I;

(m) reacting Compound (K) or a pharmaceutically acceptable salt thereof with trimethylsilyl acetylene to form Compound (L)

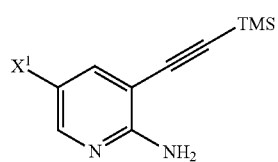

or a pharmaceutically acceptable salt thereof, wherein TMS is trimethylsilyl;

(n) reacting Compound (L) or a pharmaceutically acceptable salt thereof with a C$_{1-6}$ alkoxide base to form Compound (P)

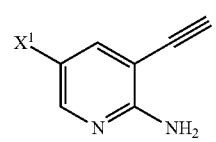

or a pharmaceutically acceptable salt thereof;
(o) reacting Compound (P) with potassium tert-butoxide, potassium tert-amylate, or any combination thereof to form Compound (M)

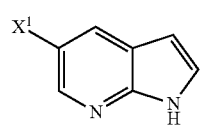

or a pharmaceutically acceptable salt thereof; and
(p) tosylating Compound (M) or a pharmaceutically acceptable salt thereof to form Compound (N)

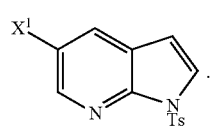

In some embodiments, the C$_{1-6}$ alkoxide base comprises potassium tert-amylate, potassium tert-butoxide, potassium methoxide, sodium tert-amylate, sodium tert-butoxide, sodium methoxide, or any combinations thereof.

In some embodiments, the reaction of Compound (K) or a pharmaceutically acceptable salt thereof with trimethylsilyl acetylene is performed in the presence of a palladium catalyst comprising Pd(Ph$_3$P)$_4$, Pd(PPh$_3$)$_2$Cl$_2$, Pd(dppf)$_2$Cl$_2$, or any combination thereof, a copper (I) halide catalyst, or any combination thereof.

In some embodiments, the reaction of Compound (K) or a pharmaceutically acceptable salt thereof with trimethylsilyl acetylene is performed in the presence of CuI, Pd(Ph$_3$P)$_4$, Pd(PPh$_3$)$_2$Cl$_2$, Pd(dppf)$_2$Cl$_2$, or any combination thereof.

In some embodiments, the tosylation step (p) is performed by reacting Compound (M) or a pharmaceutically acceptable salt thereof with TsCl.

In some embodiments, Compound (J) or a pharmaceutically acceptable salt thereof is reacted with an iodinating agent comprising $I_2$, ICl, N-iodosuccinimide, and wherein $X^3$ is I. In other embodiments, the iodinating agent is $I_2$.

In some embodiments, Compound (J) or a pharmaceutically acceptable salt thereof is reacted with a brominating agent comprising $Br_2$, N-bromosuccinimide, 1,3-dibromo-5,5-dimethylhydantoin, or any combination thereof, and wherein $X^3$ is Br. In other embodiments, the brominating agent is $Br_2$.

Some embodiments further comprise
(q) reacting Compound (K)

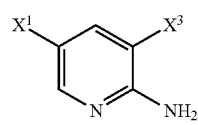

(K)

or a pharmaceutically acceptable salt thereof with acetaldehyde in the presence of a palladium catalyst comprising a mixture of bis(dibenzylideneacetone) palladium and a tertiary phosphine ligand, $PR_3$, wherein R is $C_{1-6}$ alkyl or $C_{5-6}$ cycloalkyl to form Compound (M)

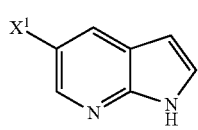

(M)

or a pharmaceutically acceptable salt thereof, wherein $X^3$ is Br or I; and
(p) tosylating Compound (M) or a pharmaceutically acceptable salt thereof to form Compound (N)

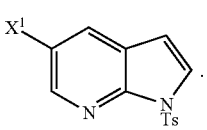

(N)

In some embodiments, the tertiary phosphine ligand, $PR_3$ comprises $P(^tBu)_3$, $PCy_3$, $P(i-Pr)_3$, $P(Bu_3)$, $PEt_3$, $PMe_3$, or any combination thereof. For example, the tertiary phosphine ligand comprises $P(^tBu)_3$.

Some embodiments further comprise treating Compound (1), after the de-protecting step (b), with HCl in a solvent system comprising water and one or more organic solvents to form a HCl salt of Compound (1), wherein the organic solvent is selected from acetonitrile, chlorobenzene, chloroform, cyclohexane, 1,2-dichloroethene, dichloromethane, 1,2-dimethoxyethane, N,N-dimentylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidone, nitromethane, pyridine, sulfolane, tetrahydrofuran (THF), tetralin, toluene, 1,1,2-trichloroethene, xylene, acetic acid, acetone, anisole, 1-butanol, 2-butanol, butyl acetate, tert-butylmethyl ether, cumene, heptane, isobutyl acetate, isopropyl acetate, methyl acetate, 3-methyl-1-butanol, methylethyl ketone, methylisobutyl ketone, 2-methyl-1-propanol, dimethyl sulfoxide, ethanol, ethyl acetate, ethyl ether, ethyl formate, formic acid, pentane, 1-pentanol, 1-propanol, 2-propanol, propyl acetate, or any combination thereof. In some embodiments, the organic solvents of the solvent system are selected from the group consisting of 2-ethoxyethanol, ethyleneglycol, methanol, 2-methoxyethanol, 1-butanol, 2-butanol, 3-methyl-1-butanol, 2-methyl-1-propanol, ethanol, 1-pentanol, 1-propanol, 2-propanol, methylbutyl ketone, acetone, methylethyl ketone, methylisobutyl ketone, butyl acetate, isobutyl acetate, isopropyl acetate, methyl acetate, ethyl acetate, propyl acetate, pyridine, toluene, and xylene.

In some embodiments, the solvent system comprises water and acetone, or water and isopropanol.

In another embodiment, the invention is directed to a method of preparing Compound (1) or a pharmaceutically acceptable salt thereof, wherein the method comprises:

(g) reacting Compound A

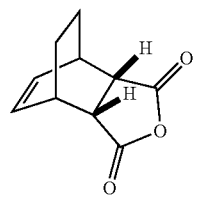

(A)

with quinine

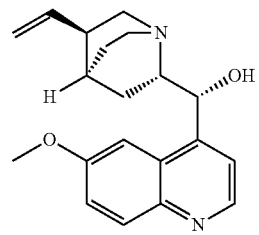 [SMILES: C=C[C@H]1CN2CC[C@H]1C[C@H]2[C@H](O)c1ccnc2ccc(OC)cc12]

and ethyl alcohol to form an adduct of the quinine and Compound (C-1)

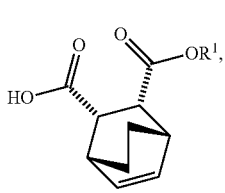

(C-1)

wherein $R^1$ is ethyl;

(h) breaking the adduct of the quinine and Compound (C-1) by treating the adduct with HCl to form Compound (C-1) or a pharmaceutically acceptable salt thereof;

(i) epimerizing Compound (C-1) to Compound (C)

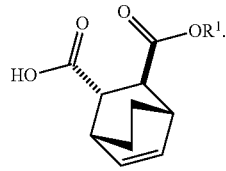

(C)

or a pharmaceutically acceptable salt thereof;

(e) reacting Compound (C) or a pharmaceutically acceptable salt thereof with diphenylphosphoryl azide and benzyl alcohol to form Compound (D)

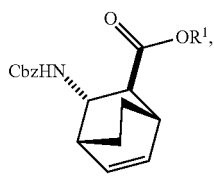

(D)

wherein Cbz is carboxylbenzyl;

(f) reacting Compound (D) or a pharmaceutically acceptable salt thereof with $H_2$ in the presence of a Pd catalyst on carbon (Pd(0)/C) to form Compound (F)

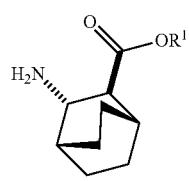

(F)

or a pharmaceutically acceptable salt thereof;

(c) reacting Compound (F) or a pharmaceutically acceptable salt thereof with Compound (G)

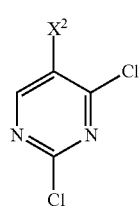

(G)

to form Compound (H)

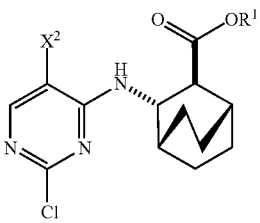

(H)

or a pharmaceutically acceptable salt thereof;

(d) hydrolyzing Compound (H) or a pharmaceutically acceptable salt thereof to form Compound (X)

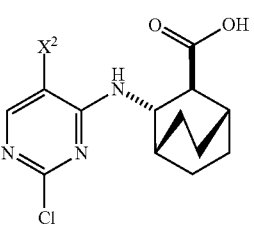

(X)

or a pharmaceutically acceptable salt thereof;

(a) reacting Compound (X) or a pharmaceutically acceptable salt thereof with Compound (Y)

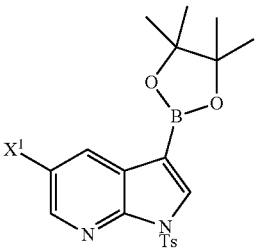

(Y)

in the presence of a palladium catalyst to form Compound (Z)

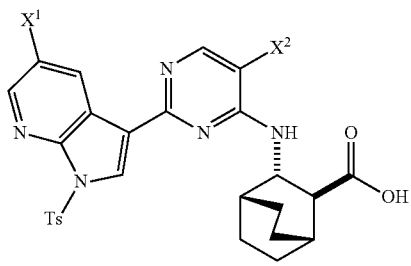

(Z)

or a pharmaceutically acceptable salt thereof; and (b) deprotecting the Ts group of Compound (Z) or a pharmaceutically acceptable salt thereof to form Compound (1) or a pharmaceutically acceptable salt thereof, wherein $X^1$ and $X^2$ are independently —F or —Cl; and each $R^1$ is independently ethyl.

In another embodiment, the invention is directed to a method of preparing Compound (1) or a pharmaceutically acceptable salt thereof, wherein the method comprises:

(q) reacting Compound (K)

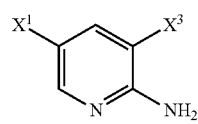
(K)

or a pharmaceutically acceptable salt thereof with acetaldehyde in the presence of a palladium catalyst to form Compound (M)

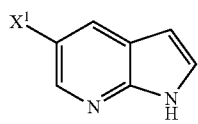
(M)

or a pharmaceutically acceptable salt thereof;

(p) tosylating Compound (M) or a pharmaceutically acceptable salt thereof to form Compound (N)

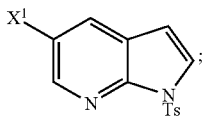
(N)

(s) brominating Compound (N) to form Compound (O)

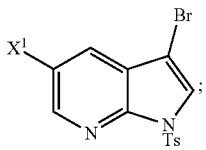
(O)

(t) reacting Compound (O) with bis(pinacolato)diboron in the presence of a palladium catalyst to form Compound (Y)

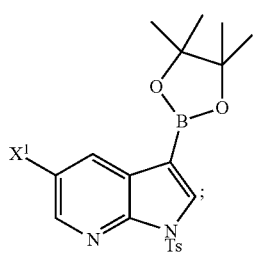
(Y)

(a) reacting Compound (X)

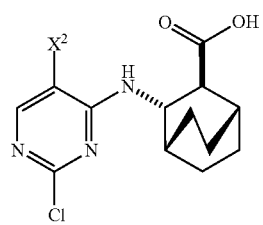
(X)

or a pharmaceutically acceptable salt thereof with Compound (Y) in the presence of a palladium catalyst to form compound (Z)

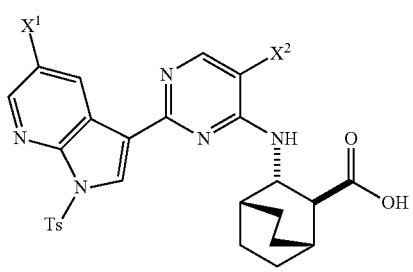
(Z)

or a pharmaceutically acceptable salt thereof; and (b) deprotecting the Ts group of Compound (Z) or a pharmaceutically acceptable salt thereof to form Compound (1) or a pharmaceutically acceptable salt thereof. $X^1$ and $X^2$ are independently —F or —Cl; $X^3$ is —Br; and each $R^1$ is independently ethyl.

In another embodiment, the invention is directed to a method of preparing Compound (2):

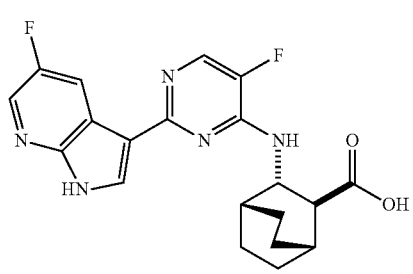
(2)

or a pharmaceutically acceptable salt thereof, wherein the method comprises:

(g) reacting Compound (A)

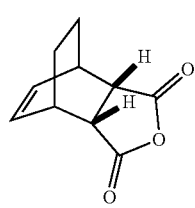
(A)

with quinine

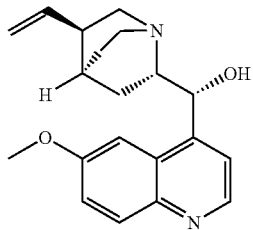 [SMILES: C=C[C@H]1CN2CC[C@H]1C[C@H]2[C@H](O)c1ccnc2ccc(OC)cc12]

and ethyl alcohol to form an adduct of the quinine and Compound (C-1)

(C-1)

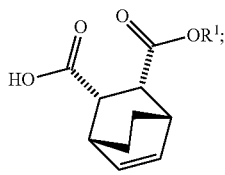

(h) breaking the adduct of the quinine and Compound (C-1) by treating the adduct with HCl to form Compound (C-1);

(i-1) reacting Compound (C-1) with a $C_{1-6}$ alkoxide selected from tert-butoxide or tert-amylate to form Compound (C)

(C)

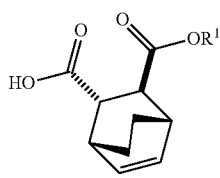

or a pharmaceutically acceptable salt thereof;

(e) reacting Compound (C) with diphenylphosphoryl azide and then with benzyl alcohol to form Compound (D)

(D)

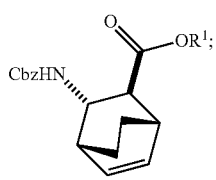

(f) reacting Compound (D) or a pharmaceutically acceptable salt thereof with $H_2$ in the presence of a Pd catalyst on carbon (Pd(0)/C) to form a HCl salt of Compound (F)

(F)

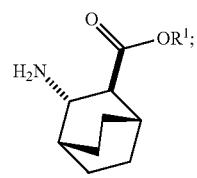

(r) reacting the HCl salt of Compound (F) with Compound (G)

(G)

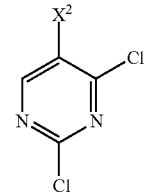

to form Compound (H)

(H)

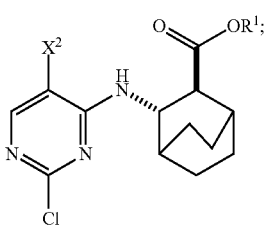

(h-1) hydrolyzing Compound (H) to form Compound (X-2)

(X-2)

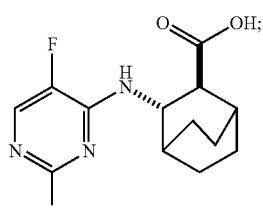

(l) iodinating or brominating Compound (J)

(J)

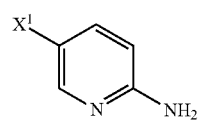

to form Compound (K)

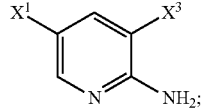
(K)

(m) reacting Compound (K) with trimethylsilyl acetylene to form Compound (L)

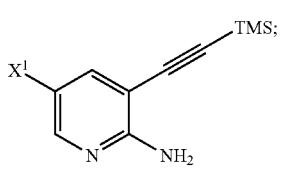
(L)

(n-1) reacting Compound (L) with a $C_{1-6}$ alkoxide to form Compound (M)

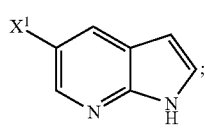
(M)

(p) tosylating Compound (M) to form Compound (N)

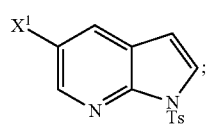
(N)

(s) brominating Compound (N) to form Compound (O)

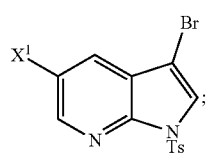
(O)

(t) reacting Compound (O) with bis(pinacolato)diboron in the presence of Pd(Ph$_3$P)$_4$ to form Compound (Y-2)

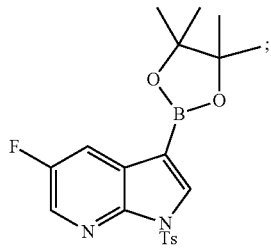
(Y-2)

(a) reacting Compound (X-2) with Compound (Y-2) in the presence of a palladium-XPhos complex and a phosphate or carbonate base selected from K$_2$CO$_3$ or K$_3$PO$_4$ to form Compound (Z-2):

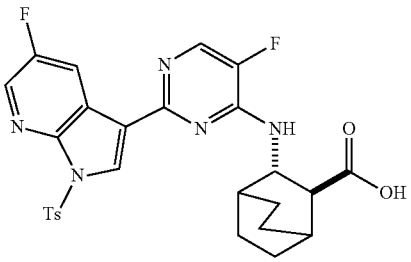
(Z-2)

or a pharmaceutically acceptable salt thereof; and (b) deprotecting the Ts group of Compound (Z-2) or a pharmaceutically acceptable salt thereof to form Compound (2) a pharmaceutically acceptable salt thereof; and wherein: Cbz is carboxylbenzyl; XPhos is 2-dicyclohexylphosphino-2',4',6'-triisopropylbiphenyl; each R$^1$ is independently ethyl; each X$^1$ is independently F; each X$^2$ is independently F; and each X$^3$ is independently Br or I.

In another embodiment, the invention is directed to a method of preparing Compound (C) or pharmaceutically acceptable salt thereof, which comprises:

(g) reacting Compound (A)

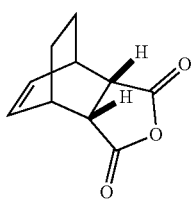
(A)

with quinine

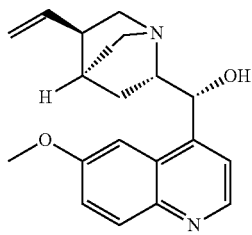

and ethyl alcohol to form an adduct of the quinine and Compound (C-1)

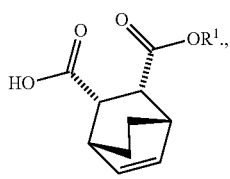
(C-1)

wherein $R^1$ is ethyl;

(h) breaking the adduct of the quinine and Compound (C-1) by treating the adduct with HCl to form Compound (C-1);

(i) epimerizing Compound (C-1) to Compound (C)

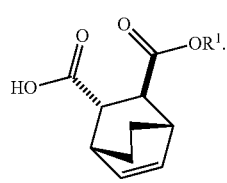
(C)

or a pharmaceutically acceptable salt thereof.

In another embodiment, the invention is directed to a method of preparing Compound (N), which comprises:

(q) reacting Compound (K)

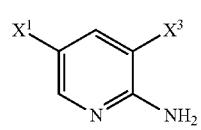
(K)

or a pharmaceutically acceptable salt thereof with acetaldehyde in the presence of a palladium catalyst to form Compound (M)

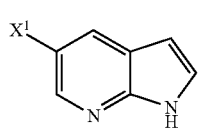
(M)

or a pharmaceutically acceptable salt thereof, wherein $X^1$ is F or Cl, and $X^3$ is Br; and (p) tosylating Compound (M) or a pharmaceutically acceptable salt thereof to form Compound (N):

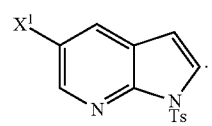
(N)

DESCRIPTION OF THE DRAWING

FIG. 1 is a graph showing AUC viral shedding for 1200 mg/600 mg of Form A of HCl salt of Compound (1).½H$_2$O dose group in a live, attenuated influenza challenge model in humans.

DETAILED DESCRIPTION OF THE INVENTION

I. Commonly Used Abbreviations

ACN acetonitrile
tBuOAc tert-butyl acetate
DABCO 1,4-diazabicyclo[2.2.2]octane
DCM dichloromethane
EtOAc ethyl acetate
IPAc iso-propyl acetate
MIBK methyl iso-butyl ketone
TEA triethylamine
THF tetrahydrofuran
PG protecting group
LG leaving group
Ac acetyl
TMS trimethylsilyl
TBS tert-butyldimethylsilyl
TIPS tri-iso-propylsilyl
TBDPS tert-butyldiphenylsilyl
TOM tri-iso-propylsilyloxymethyl
DMP Dess-Martin periodinane
IBX 2-iodoxybenzoic acid
DMF dimethylformamide
MTBE methyl-tert-butylether
TBAF tetra-n-butylammonium fluoride
d.e. diastereomeric excess
e.e. enantiomeric excess
d.r. diastereomeric ratio
DMSO dimethyl sulfoxide
TCA trichloroacetic acid
ATP adenosine triphosphate
EtOH ethanol
Ph phenyl
Me methyl
Et ethyl
Bu butyl
DEAD diethylazodicarboxylate
HEPES 4-(2-hydroxyethyl)-1-piperazineethanesulfonic acid
DTT dithiothreitol
MOPS 4-morpholinepropanesulfonic acid
NMR nuclear magnetic resonance
HPLC high performance liquid chromatography
LCMS liquid chromatography-mass spectrometry
TLC thin layer chromatography
Rt retention time HOBt hydroxybenzotriazole
Ms mesyl
Ts tosyl
Tf triflyl
Bs besyl
Ns nosyl
Cbz carboxybenzyl
Moz p-methoxybenzyl carbonyl
Boc tert-butyloxycarbonyl
Fmoc 9-fluorenylmethyloxycarbonyl
Bz benzoyl
Bn benzyl
PMB p-methoxybenzyl
AUC area under the curve
DMPM 3,4-dimethoxybenzyl
PMP p-methoxyphenyl
XRPD X-ray powder diffraction II. Preparation of Compounds It is noted that the steps recited herein may be performed in any chronological order without regard to step letter. For example, step (a) may precede or follow step (g), step (e), step (f), or step (s).

Compound (1)

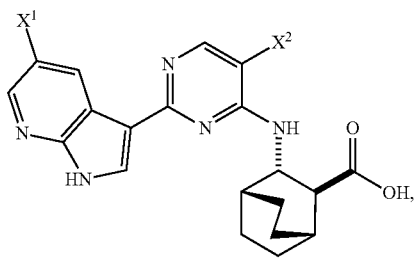

Compound (2) (where $X^1$ and $X^2$ of Compound (1) are both —F), and pharmaceutically acceptable salts thereof are inhibitors of the replication of influenza viruses, and can be used for treating influenza in a patient, as described in WO 2010/148197. In one specific embodiment, $X^1$ is —F and $X^2$ is —F. In another specific embodiment, $X^1$ is —Cl and $X^2$ is —F. In yet another specific embodiment, $X^1$ is —Cl and $X^2$ is —Cl. In yet another specific embodiment, $X^1$ is —F and $X^2$ is —Cl.

In one embodiment, Compounds (1) and (2), and pharmaceutically acceptable salts thereof can be prepared as depicted in Scheme 1: (a) reacting Compound (X):

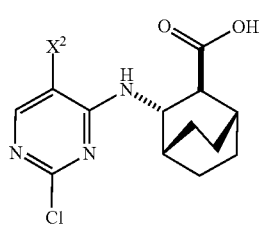

or a pharmaceutically acceptable salt thereof with Compound (Y):

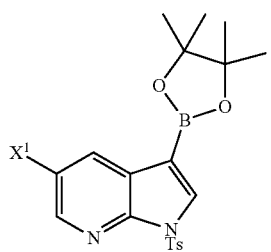

in the presence of a palladium-XPhos complex and a phosphate or carbonate base to form Compound (Z) or a pharmaceutically acceptable salt thereof:

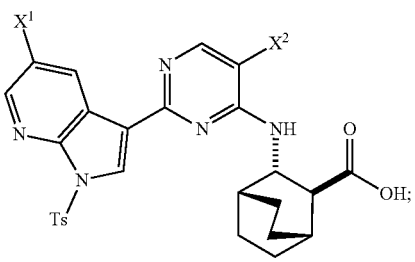

and (b) deprotecting the tosyl (Ts) group of Compound (Z) or a pharmaceutically acceptable salt thereof. $X^1$ is —F or —Cl; Ts is tosyl; and XPhos is 2-dicyclohexylphosphino-2',4',6'-triisopropylbiphenyl

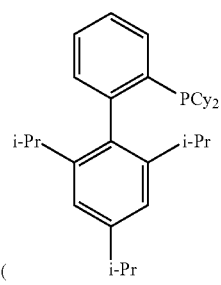

wherein Cy is cyclohexyl and i-Pr is isopropyl).

The palladium-XPhos complex can be employed as a pre-prepared reagent or alternatively can be prepared in situ. In one specific embodiment, the palladium-Xphos complex is prepared by mixing a Pd(0) or Pd(II) source with XPhos. Typical examples of Pd(0) or Pd(II) sources include $Pd_2(dba)_3$, $Pd(OAc)_2$, and $PdCl_2$, wherein dba is dibenzyllideneacetone and OAc is acetate. In one specific embodiment, the palladium-XPhos complex is prepared in situ by mixing $Pd(OAc)_2$ and XPhos.

The reaction of Compound (X) or a pharmaceutically acceptable salt thereof and Compound (Y) is performed in the presence of a phosphate or carbonate base. Typical examples of the phosphate or carbonate bases include $Na_2CO_3$, $K_2CO_3$, $K_3PO_4$, and $Na_3PO_4$. In one specific embodiment, the base includes $K_2CO_3$ or $K_3PO_4$. In another specific embodiment, the base includes $K_2CO_3$. In yet another embodiment, the base includes $K_3PO_4$.

The reaction of Compound (X) or a pharmaceutically acceptable salt thereof and Compound (Y) can be performed in any suitable solvent system. In one specific embodiment, it is performed in a solvent system that includes water and an organic solvent selected from 2-MeTHF or THF, or a combination thereof. In another specific embodiment, it is performed in a solvent system that includes water and THF. In another specific embodiment, it is performed in a solvent system that includes water and 2-MeTHF.

The deprotection step (b) can be performed in any suitable conditions known in the art for deprotection of tosyl group. In one specific embodiment, the deprotection step employs treating Compound (Z) or a pharmaceutically acceptable salt thereof with an inorganic hydroxide. Typical examples of suitable inorganic hydroxides include LiOH, NaOH, and KOH. In one specific embodiment, LiOH is employed. In another specific embodiment, the deprotection step (b) employs LiOH in a solvent system that includes THF.

In another embodiment, Compound (2) and pharmaceutically acceptable salts thereof can be prepared as depicted in Scheme 1-A: (a) reacting Compound (X-2):

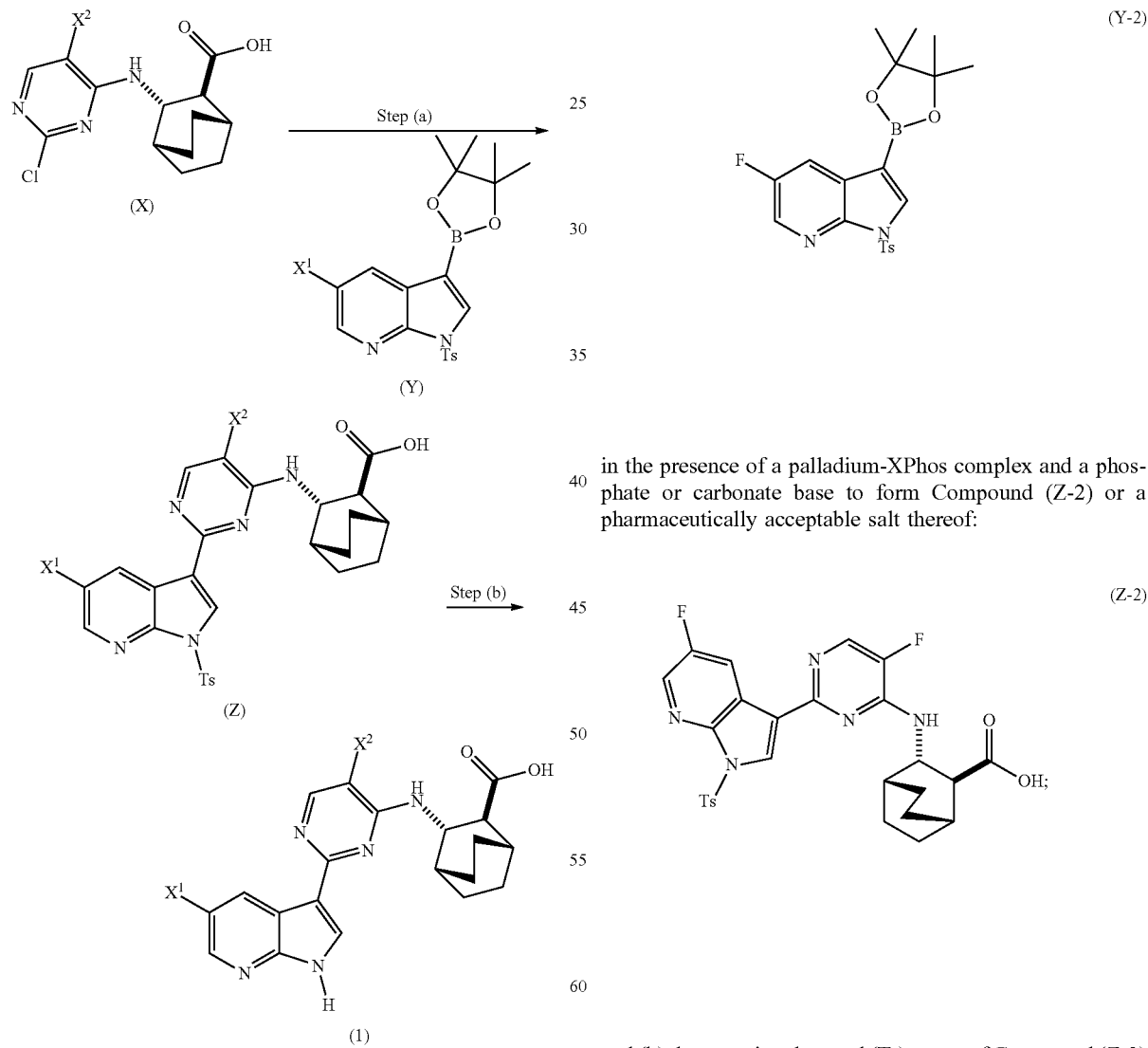

or a pharmaceutically acceptable salt thereof with Compound (Y-2):

in the presence of a palladium-XPhos complex and a phosphate or carbonate base to form Compound (Z-2) or a pharmaceutically acceptable salt thereof:

and (b) deprotecting the tosyl (Ts) group of Compound (Z-2) or a pharmaceutically acceptable salt thereof. The suitable reaction conditions for each of steps (a) and (b) and specific examples thereof, including the phosphate or carbonate base, are as described above for Scheme 1.

Scheme 1-A:

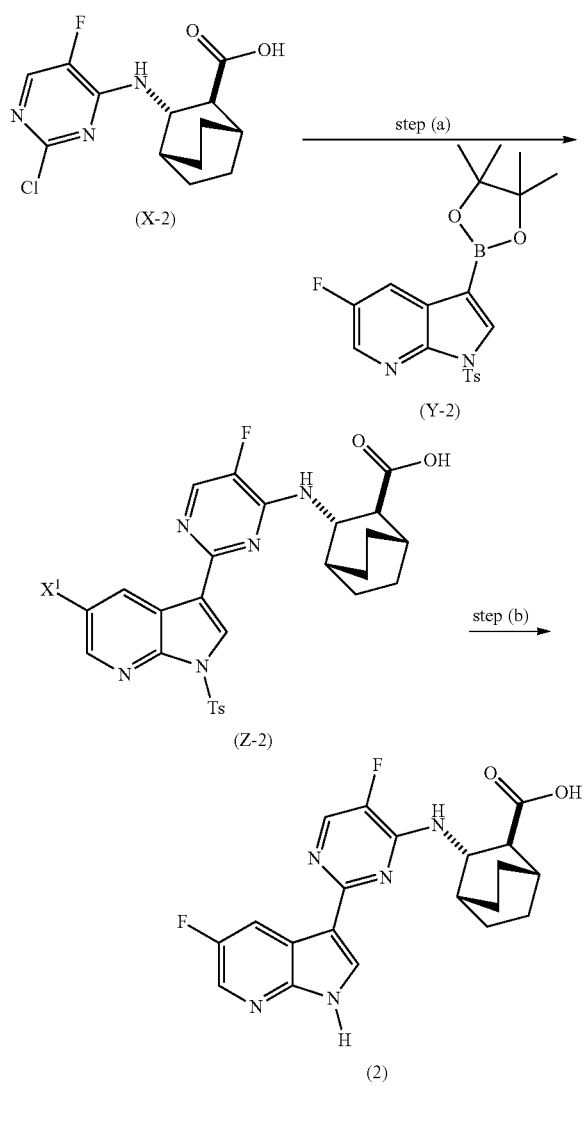

In another embodiment, step (a) of Schemes 1 and 1-A (e.g., the reactions between Compounds (X) and (Y), and between Compounds (X-2) and (Y-2)) can further employ a Pd scavenger (e.g., resin or carbon) after the reactions, but prior to the deprotection step (b) of the Ts group to remove or reduce the amounts of any residual Pd catalyst. A typical example of suitable Pd scavengers includes a polystyrene-bound trimercaptotriazine resin (e.g., a MP-TMP resin).

The methods of the invention for preparing Compounds (1) and (2), and pharmaceutically acceptable salts thereof, as depicted in Schemes 1 and 1-A, employ Compounds (X) and (Z), each of which has a free carboxylic acid group. Without intending to be bound by a particular theory, the use of Compounds (X) and (Z) instead of the corresponding esters thereof can provide enantiomeric pure Compounds (1) and (2), and pharmaceutically acceptable salts thereof more conveniently and efficiently, because Compounds (X) and (Z) are typically solid while the corresponding esters thereof are oil. An oily material is generally hard to purify as compared to a solid material, which may impair the overall yield and/or enantiomeric purity of the final product especially in a large scale preparation, such as a commercial production of Compounds (1) and (2) or pharmaceutically acceptable salts thereof. In particular, the corresponding esters of Compounds (X) and (Z) are generally subject to epimerization (for example, during the Suzuki reaction of Compound (X) to Compound (Z) and during the detosylation of Ts of Compound (Z)), which may impair the overall yield and/or enantiomeric purity of the final product.

In another embodiment, the methods of the invention employ preparation of Compounds (X) and pharmaceutically acceptable salts thereof, as shown in Scheme 2 below. The preparation comprises: (c) reacting Compound (F) or a pharmaceutically acceptable salt thereof:

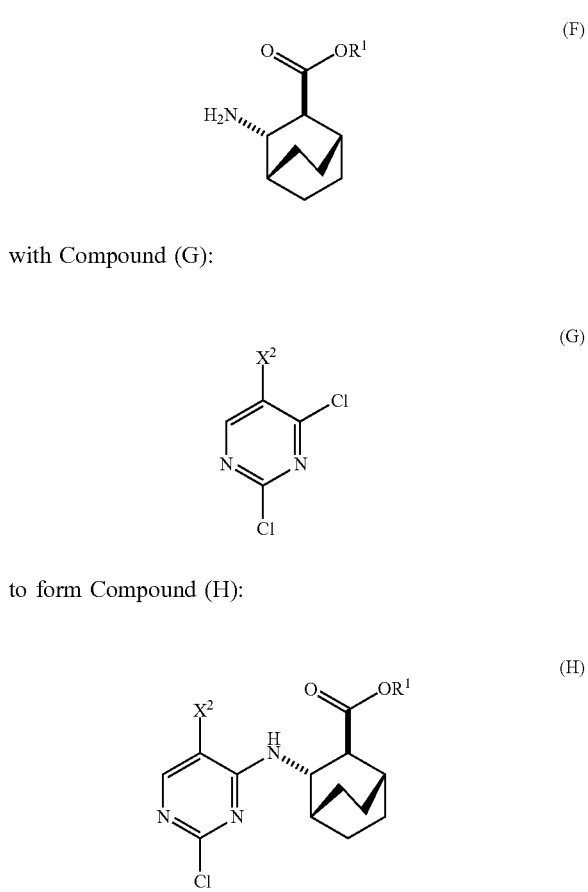

with Compound (G):

to form Compound (H):

or a pharmaceutically acceptable salt thereof; and (d) hydrolyzing Compound (H) or a pharmaceutically acceptable salt thereof to form Compound (X):

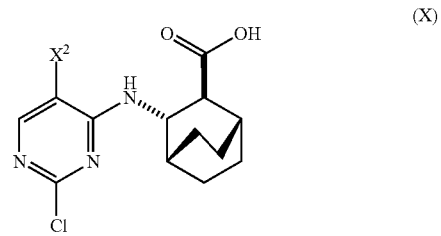

or pharmaceutically acceptable salt thereof. $R^1$ is $C_{1-4}$ alkyl, such as ethyl or methyl. In one specific embodiment, $R^1$ is ethyl. In another specific embodiment, $R^1$ is methyl.

Scheme 2:

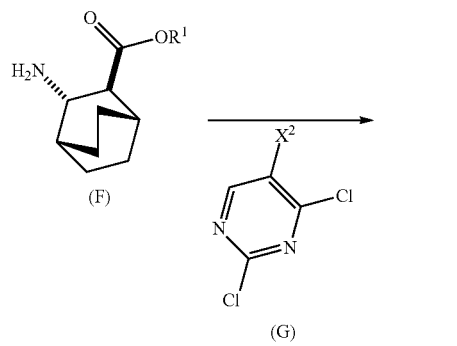

(F)

(G)

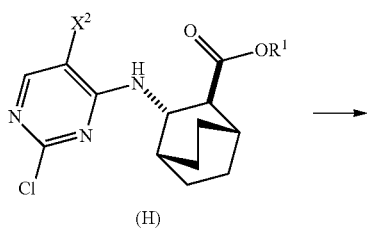

(H)

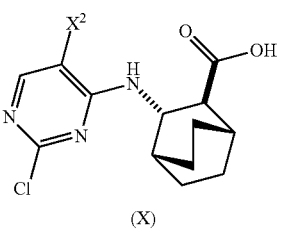

(X)

The coupling between Compound (G) and Compound (F) or a pharmaceutically acceptable salt thereof (step c), and the hydrolysis of Compound (H) or a pharmaceutically acceptable salt thereof (step d) can be performed in any suitable conditions known in the art. In one specific embodiment, the coupling between Compound (F) or a pharmaceutically acceptable salt thereof and Compound (G) is performed at a temperature in a range of 15° C. to 40° C. (e.g., 25° C. to 35° C.) in the presence of a base, such as an amine base. Typical examples of such amine bases include N,N, diisopropylethyl amine, triethylamine, N,N-diethylmethyl amine, etc. In another specific embodiment, the hydrolysis of Compound (H) or a pharmaceutically acceptable salt thereof is performed in the presence of a base, such as an inorganic base. Typical examples of such inorganic bases include LiOH, NaOH, KOH, etc. In one further specific embodiment, the hydrolysis is performed by treating Compound (H) or a pharmaceutically acceptable salt thereof with LiOH at a temperature in a range of 20° C. to 50° C., such as 35° C. to 50° C. (e.g., 45° C.).

In another embodiment, the methods of the invention employ preparation of Compound (F) or a pharmaceutically acceptable salt thereof, as shown in Scheme 3 below.

Scheme 3:

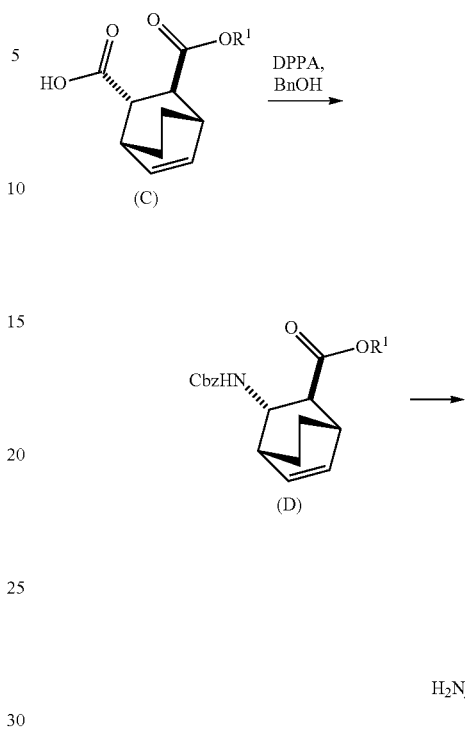

The preparation of Compound (F) or a pharmaceutically acceptable salt thereof comprises: (e) reacting Compound (C):

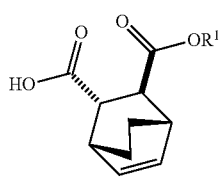

(C)

or a pharmaceutically acceptable salt thereof with diphenylphosphoryl azide (DPPA) and then with benzyl alcohol to form Compound (D):

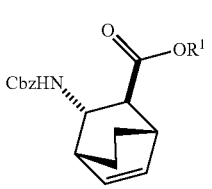

(D)

or a pharmaceutically acceptable salt thereof; (f) reacting Compound (D) or a pharmaceutically acceptable salt thereof with $H_2$ in the presence of a Pd catalyst on carbon (Pd(0)/C) to form Compound (F)

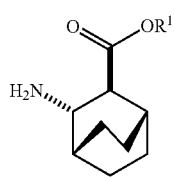

(F)

or a pharmaceutically acceptable salt thereof. Cbz is carboxybenzyl.

The reaction of Compound (C) or a pharmaceutically acceptable salt thereof with DPPA and with benzyl alcohol to form Compound (D) or a pharmaceutically acceptable salt thereof can be performed in any conditions suitable for the Curtius rearrangement. Without being intended to be bound to a particular theory, during the Curtius rearrangement, an acylnitrene intermediate is formed by the reaction of DPPA with Compound (C) or a pharmaceutically acceptable salt thereof, which is then rearranged into an isocyanate intermediate. The isocyanate intermediate reacts with benzyl alcohol subsequently to produce the Cbz-protected amine of Compound (D) or a pharmaceutically acceptable salt thereof. In one specific embodiment, the Curtius rearrangement is performed at a temperature in a range of 60° C. to 100° C., such as 90° C. to 100° C. or 95° C. to 100° C. In one specific embodiment, the reaction is performed in the presence of a base, such as an amine base, Typical examples of such amine bases include triethylamine, N,N, diisopropylethyl amine, N,N-diethylmethyl amine, etc. In another specific embodiment, the Curtius rearrangement is performed using a flow apparatus at an elevated temperature, such as 90° C. to 110° C.

The hydrogenation of the double bond with deprotection of the Cbz group of Compound (D) or a pharmaceutically acceptable salt thereof can be performed in any suitable conditions known in the art for the general hydrogenation of a double bond and Cbz group deprotection. In one specific embodiment, Compound (D) or a pharmaceutically acceptable salt thereof reacts with $H_2$ in the presence of a Pd(0) catalyst on carbon (Pd/C), such as 10% (by weight on dry basis) Pd/C. In another specific embodiment, the reaction product of Compound (D) or a pharmaceutically acceptable salt thereof with $H_2$ is further treated with HCl in ethanol to form an HCl salt of Compound (F).

In another embodiment, the methods of the invention employ preparation of Compound (C) or a pharmaceutically acceptable salt thereof, as shown in Scheme 4 below.

Scheme 4:

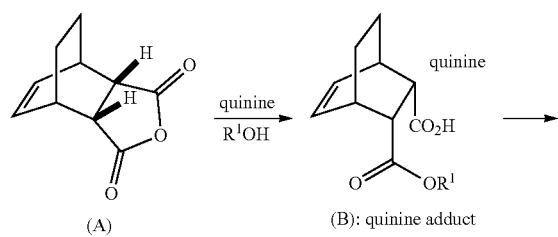

(A)   (B): quinine adduct

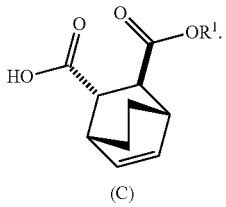

(C)

The preparation of Compound (C) or a pharmaceutically acceptable salt thereof comprises: (g) reacting Compound (A):

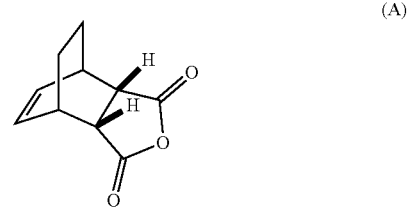

(A)

with quinine:

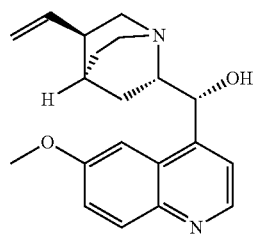 [SMILES: C=C[C@H]1CN2CC[C@H]1C[C@H]2[C@H](O)c1ccnc2ccc(OC)cc12]

and $R^1OH$ to form an adduct of the quinine and Compound (C-1):

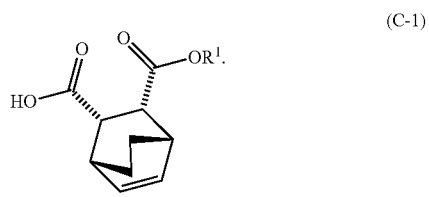

(C-1)

or a pharmaceutically acceptable salt thereof; (h) breaking the adduct by treating the adduct with HCl to form Compound (C-1) or a pharmaceutically acceptable salt thereof, wherein $R^1$ is $C_{1-4}$ alkyl (e.g., methyl, ethyl, propyl, isopropyl, or butyl); and epimerizing Compound (C-1) or a pharmaceutically acceptable salt thereof to Compound (C) or a pharmaceutically acceptable salt thereof. In a specific embodiment, $R^1$ is ethyl. The epimerization of Compound (C-1) or a pharmaceutically acceptable salt thereof can be done employing any suitable conditions known in the art. Typically, it is performed by treating it with a base, such as an alkoxide. In one specific embodiment, a $C_{1-6}$ alkoxide (e.g., alkaline metal (e.g., sodium or potassium) or alkaline earth metal (e.g., calcium or magnesium) $C_{1-6}$ alkoxide) is employed. In another specific embodiment, a tert-butoxide (e.g., potassium tert-amylate) or a tert-amylate (e.g., potassium tert-amylate) is employed.

In one specific embodiment, the methods of the invention employ the preparation of Compound (X) or a pharmaceutically acceptable salt thereof, as depicted in Scheme 5 below.

Scheme 5:

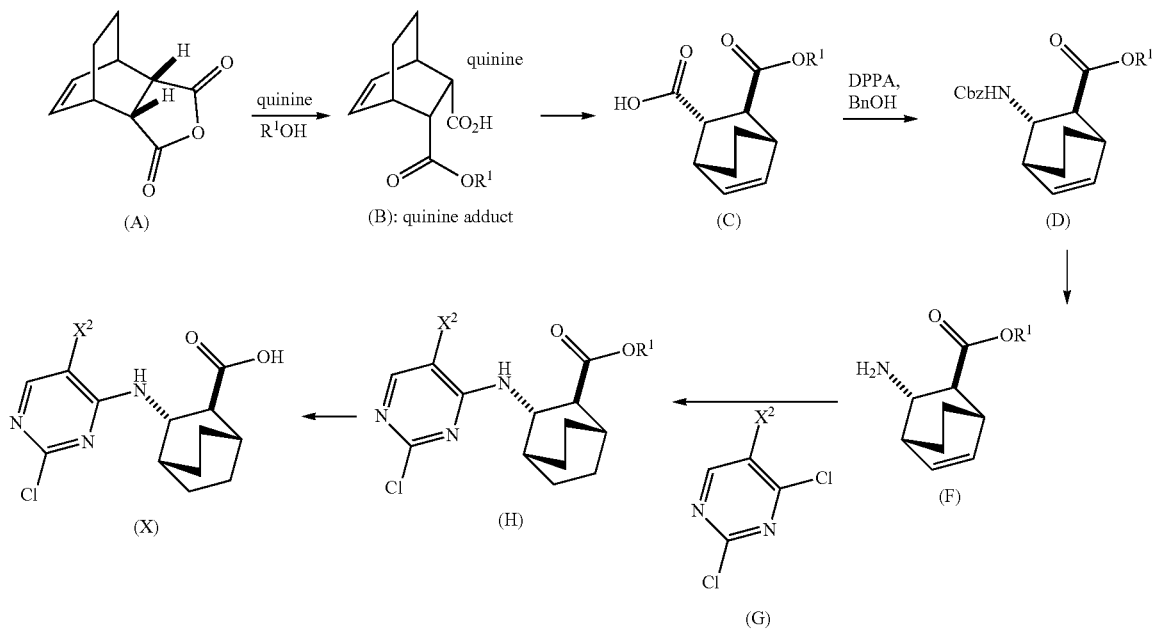

The suitable reaction conditions for each of steps of Scheme 5 and specific examples thereof are as described above.

In another embodiment, the methods of the invention employ the preparation of Compound (F) or a pharmaceutically acceptable salt thereof. In one specific embodiment, an HCl salt of Compound (F) is prepared (e.g., see Scheme 6). The preparation comprises hydrogenolysing Compound (S):

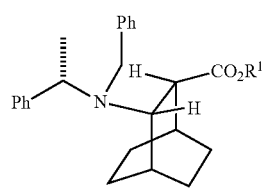

(S)

or a pharmaceutically acceptable salt thereof, wherein Ph is phenyl, in the presence of a palladium catalyst to form Compound (F) or a pharmaceutically acceptable salt thereof, wherein Ph is phenyl. Typically, hydrogenolysis refers to a chemical reaction whereby a carbon-carbon or carbon-heteroatom (e.g., N, O, or S) single bond is cleaved or undergoes "lysis" by hydrogen. Without intending to be bound to a particular theory, during the hydrogenolysis of Compound (S) or a pharmaceutically acceptable salt thereof, the carbon-nitrogen bonds of —N(CH$_2$Ph)(CH(CH$_3$)Ph)) of Compound (S) are cleaved. Typically hydrogenolysis is conducted catalytically using hydrogen gas. Suitable examples of the palladium catalysts for the hydrogenolysis step include Pd(0) on carbon (Pd/C), Pd(OH)$_2$ on carbon (Pd(OH)$_2$/C), and a combination thereof.

In one specific embodiment, the hydrogenolysis step is performed in the presence of HCl (e.g., 37.7 wt % in water) and generates an HCl salt of Compound (F).

Scheme 6:

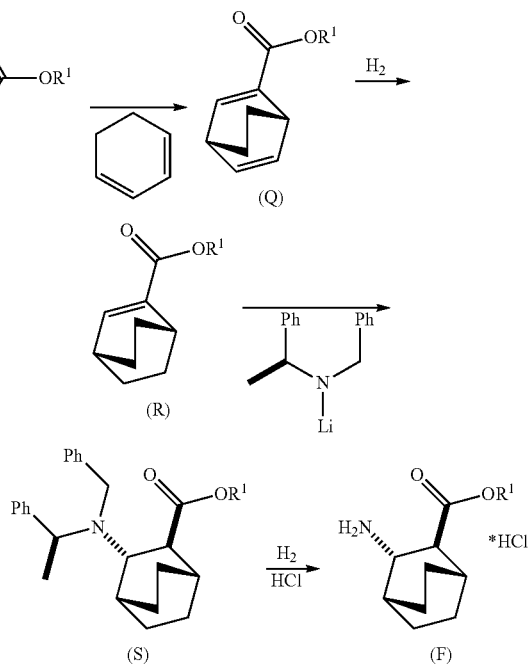

In another embodiment, the methods of the invention employ the preparation of Compound (S) or a pharmaceutically acceptable salt thereof. The preparation comprises: reacting Compound (R):

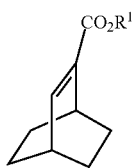

with S-(-)-N-benzyl-alpha-methylbenzylamino lithium to form Compound (S):

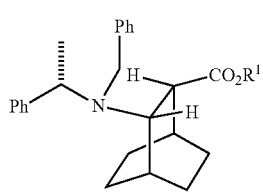

or a pharmaceutically acceptable salt thereof.

This reaction can be performed in any suitable reaction conditions known in the art. In one specific embodiment, S-(-)-N-benzyl-alpha-methylbenzylamino lithium is prepared in situ by mixing S-(-)-N-benzyl-alpha-methylbenzylamine with an alkyllithium, such as n-butyllithium.

In another embodiment, the methods of the invention employ the preparation of Compound (R). The preparation comprises: (j) reacting 1,3-cyclohexadiene with CH≡CHC(O)OR$^1$ in the presence of an aluminum catalyst to form Compound (Q):

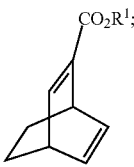

and (k) hydrogenating Compound (Q) to form Compound (R):

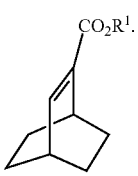

R$^1$ is C$_{1-4}$ alkyl. In a specific embodiment, R$^1$ is ethyl. In another specific embodiment, R$^1$ is methyl.

Step (j) of the preceding paragraph is a Diels-Alder reaction between 1,3-cyclohexadiene with CH≡CHC(O)OR$^1$. Any suitable aluminum catalysts known in the art for Diels-Alder reaction can be employed for the step (j). Suitable examples of the aluminum catalysts include EtAlCl$_2$ (Et=ethyl), Et$_2$AlCl, and a mixture of AlCl$_3$ and trioctylaluminum. The hydrogenation step (k) of the preceding paragraph can be performed in any suitable conditions known in the art for general hydrogenation. In one specific embodiment, the step (k) comprises reacting Compound (Q) with H$_2$ in the presence of a Rh(I) or poisoned Pd(0) catalyst. Suitable examples of Rh(I) catalysts include (PPh$_3$)$_3$RhCl and a mixture of (PPh$_3$)$_3$RhCl and ethyl propiolate, wherein Ph is phenyl. A poisoned Pd(0) catalyst refers to a Pd(0) catalyst where another compound is chemically bonded to its active surface sites in order to modulate the Pd reactivity. The poisoned sites can no longer accelerate the reaction with which the catalyst is supposed to catalyze. In general, poisoning catalysts can be used to improve selectivity of reactions. A suitable example of the poisoned Pd(0) catalyst includes a lead-poisoned Pd(0) catalyst on CaCO$_3$ (Pd(Pb)/CaCO$_3$).

In another embodiment, the methods of the invention employ preparing Compound (Y):

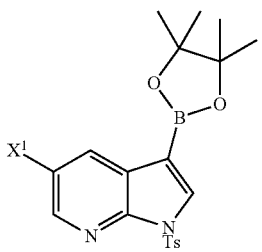

The preparation of Compound (Y) comprises: reacting Compound (O):

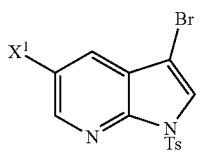

with bis(pinacolato)diboron in the presence of a palladium catalyst to form Compound (Y). See, for example, Scheme 7:

Scheme: 7

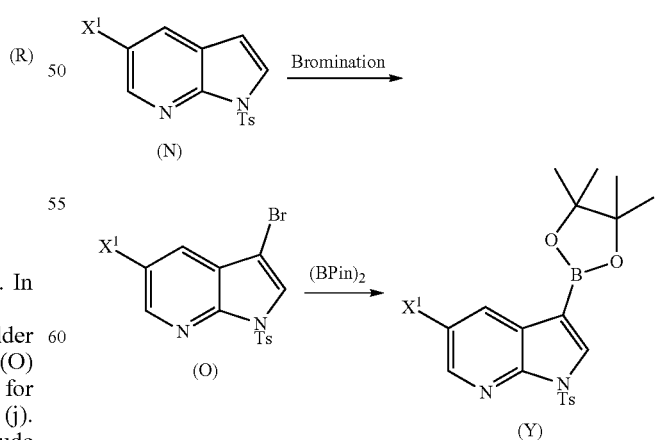

A typical example of suitable palladium catalysts includes Pd(Ph$_3$P)$_4$.

In another embodiment, the methods of the invention employ reacting Compound (O) with bis(pinacolato)diboron in the presence of a palladium catalyst for the preparation of Compound (Y), and further employ the preparation of Compound (O), as shown in Scheme 8 above. The preparation of Compound (O) comprises brominating Compound (N):

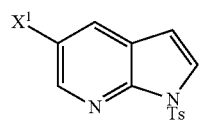
(N)

with a brominating agent. Typical examples of brominating agents include $Br_2$, NBS, and DBDMH, wherein NBS is N-bromosuccinimide and DBDMH is 1,3-Dibromo-5,5-dimethylhydantoin. In one specific embodiment, the brominating agent includes $Br_2$ or NBS. In another specific embodiment, the brominating agent includes NBS. In yet another specific embodiment, the brominating agent includes $Br_2$.

In another embodiment, the methods of the invention employ the preparation of Compound (N, as depicted in Scheme 8.

Scheme 8:

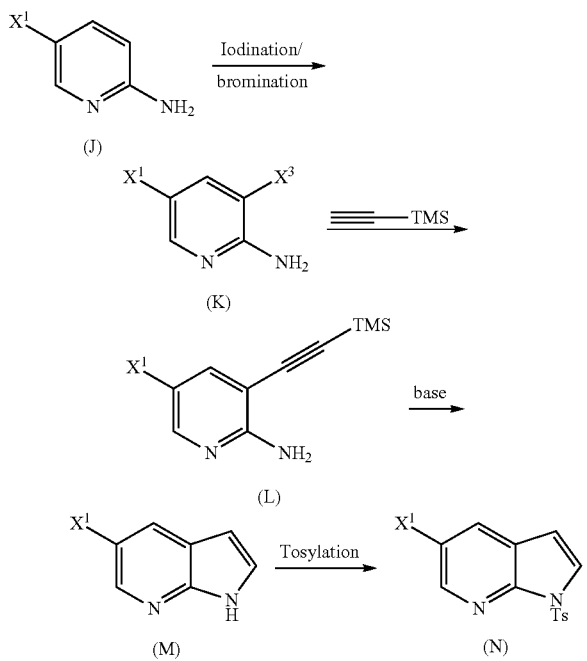

The preparation of Compound (N) comprises: (1) reacting Compound (J):

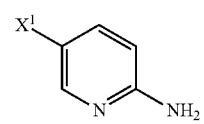
(J)

or a pharmaceutically acceptable salt thereof with an iodinating agent or a brominating agent to form Compound (K):

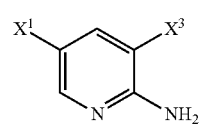
(K)

or a pharmaceutically acceptable salt thereof; (m) reacting Compound (K) or a pharmaceutically acceptable salt thereof with trimethylsilyl acetylene to form Compound (L):

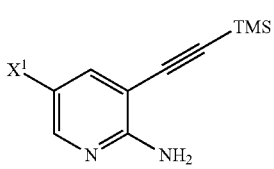
(L)

or a pharmaceutically acceptable salt thereof; (n-1) reacting Compound (L) or a pharmaceutically acceptable salt thereof with a $C_{1-6}$ alkoxide base to form Compound (M):

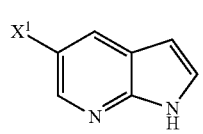
(M)

or a pharmaceutically acceptable salt thereof; and (p) tosylating Compound (M) or a pharmaceutically acceptable salt thereof to form Compound (N):

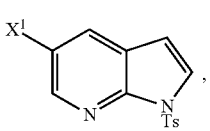
(N)

wherein $X^1$ is —F or —Cl; $X^3$ is —Br or —I; TMS is trimethylsilyl; and Ts is tosyl.

The iodination or bromination in Scheme 8 can be done using suitable conditions and reagents known in the art. Typical examples of brominating agents include $Br_2$, NBS, and DBDMH, wherein NBS is N-bromosuccinimide and DBDMH is 1,3-Dibromo-5,5-dimethylhydantoin. Typical examples of iodinating agents include $I_2$, ICl, and NIS, wherein NIS is N-iodosuccinimide. In one specific embodiment, bromination is employed. In another specific embodiment, bromination is employed by the use of $Br_2$. In yet another specific embodiment, bromination is employed by the use of NBS. In yet another specific embodiment, iodination is employed. In yet another specific embodiment, iodination is employed by the use of $I_2$.

The reaction of Compound (K) or a pharmaceutically acceptable salt thereof with trimethylsilyl acetylene can be performed in any suitable conditions known in the art for Sonogashira coupling between arylhalides and trimethylsily acetylene. Typically, it is performed in the presence of a palladium catalyst and/or a copper (I) halide catalyst. A typical example of copper (I) halides includes CuI. Typical examples of palladium catalysts include Pd(Ph₃P)₄ (Ph=phenyl), Pd(PPh₃)₂Cl₂, Pd(dppf)₂Cl₂ (dppf=1,1'-Bis(diphenylphosphino)ferrocene), Pd(acac)₂ (acac=acetylacetonate), PdCl₂(PCy₃)₂ (Cy=cyclohexyl), Pd₂(dba)₃ (dba=dibenzylideneacetone), and any combination thereof. In one specific embodiment, it is performed in the presence of a palladium catalyst and/or a copper (I) halide catalyst. In another specific embodiment, it is performed in the presence of an amine base (e.g., $C_{1-4}$ alkylamine, such as triethylamine, N,N, diisopropylethyl amine, N,N-diethylmethyl amine), and a palladium catalyst and/or a copper (I) halide catalyst. In another specific embodiment, it is performed in the presence of CuI and a Pd catalyst selected from Pd(Ph₃P)₄, Pd(PPh₃)₂Cl₂, Pd(dppf)₂Cl₂, or any combination thereof. In another specific embodiment, it is performed in the presence of a $C_{1-4}$ alkylamine (e.g., triethylamine), and CuI and a Pd catalyst selected from Pd(Ph₃P)₄, Pd(PPh₃)₂Cl₂, Pd(dppf)₂Cl₂, or any combination thereof.

Step (n) of the reaction of Compound (L) or a pharmaceutically acceptable salt thereof with a $C_{1-6}$ alkoxide base can also be done using suitable conditions and reagents known in the art. Typical examples of $C_{1-6}$ alkoxides are as described above. Specific examples include a tert-amylate, a tert-butoxide, and a methoxide, (such as potassium tert-amylate, potassium tert-butoxide, and sodium methoxide), and any combinations thereof. In one specific embodiment, potassium tert-butoxide is employed. In another specific embodiment, step (n) comprises reacting Compound (L) or a pharmaceutically acceptable salt thereof with sodium methoxide to form Compound (P):

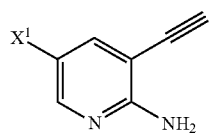
(P)

or a pharmaceutically acceptable salt thereof, which is subsequently reacted with potassium tert-butoxide and/or potassium tert-amylate to form Compound (M):

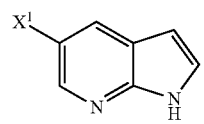
(M)

or a pharmaceutically acceptable salt thereof.

The tosylation step (p) can be performed in any suitable conditions known in the art for tosylation. In one specific embodiment, the tosylation step is performed by reacting Compound (M) or a pharmaceutically acceptable salt thereof with TsCl.

In another embodiment, the invention employs the preparation of Compound (N), as depicted in Scheme 9.

Scheme 9:

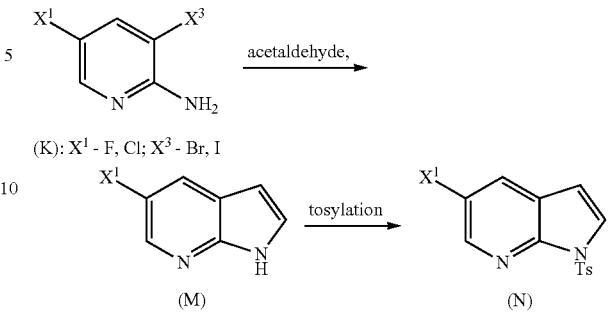

(K): $X^1$ - F, Cl; $X^3$ - Br, I

The preparation comprises: (q) reacting Compound (K):

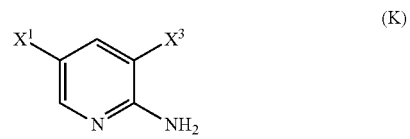
(K)

or a pharmaceutically acceptable salt thereof with acetaldehyde in the presence of a palladium catalyst to form Compound (M):

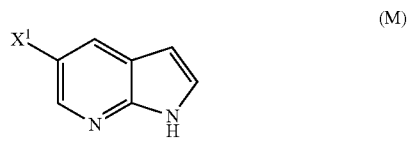
(M)

or a pharmaceutically acceptable salt thereof, wherein $X^3$ is —Br or —I; and (p) tosylating Compound (M) or a pharmaceutically acceptable salt thereof to form Compound (N):

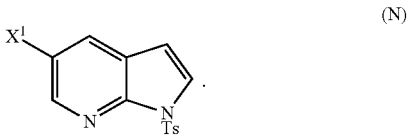
(N)

Typical examples of the palladium catalysts for the reaction of Compound (K) or a pharmaceutically acceptable salt thereof with acetaldehyde include mixtures of bis(dibenzylideneacetone) palladium and a tertiary phosphine ligand, PR₃, wherein R is $C_{1-6}$ alkyl or $C_{5-6}$ cycloalkyl. Typical examples of tertiary phosphine ligands, PR₃, include P(ᵗBu)₃, PCy₃, P(i-Pr)₃, P(Bu)₃, PEt₃, PMe₃, or a mixture thereof. In one specific embodiment, P(ᵗBu)₃ is employed.

In one specific embodiment, the preparation of Compound (N), as depicted in Scheme 10 further comprises treating the reaction mixture of Compound (K) or a pharmaceutically acceptable salt thereof with acetaldehyde with a carbonate base, such as Na₂CO₃ prior to the tosylation step to from Compound (N).

The tosylation step (p) can be performed in any suitable conditions known in the art for tosylation. In one specific embodiment, the tosylation step is performed by reacting Compound (M) or a pharmaceutically acceptable salt thereof with TsCl.

In another embodiment, the methods of the invention employ the preparation of Compound (Y) as depicted in Scheme 10. Examples and conditions for each step of Scheme 11 are independently as described above.

Scheme 10:

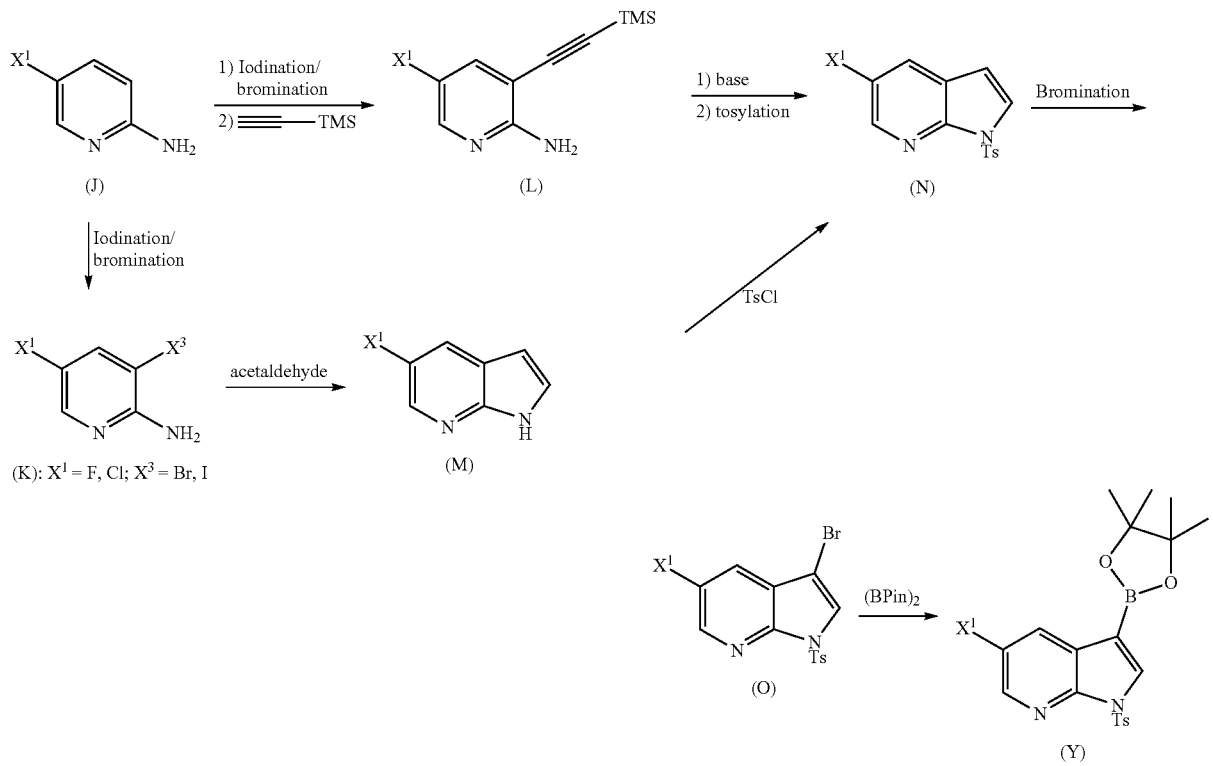

In another embodiment, the methods of the invention are for preparing Compound (1) or a pharmaceutically acceptable salt thereof, wherein the methods comprise: (g) reacting Compound (A):

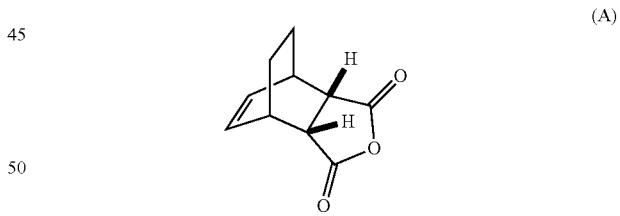

(A)

with quinine:

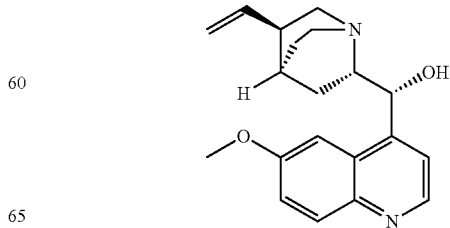

and ethyl alcohol to form an adduct of the quinine and Compound (C-1):

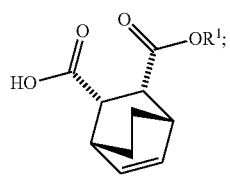
(C-1)

(h) breaking the adduct of the quinine and Compound (C-1) by treating the adduct with HCl to form Compound (C-1) or a pharmaceutically acceptable salt thereof; (i) epimerizing Compound (C-1) or a pharmaceutically acceptable salt thereof to Compound (C):

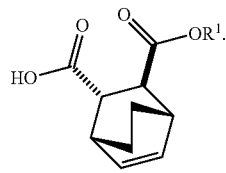
(C)

or a pharmaceutically acceptable salt thereof; (e) reacting Compound (C) or a pharmaceutically acceptable salt thereof with diphenylphosphoryl azide (DPPA) and with benzyl alcohol to form Compound (D):

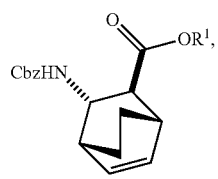
(D)

wherein Cbz is carboxylbenzyl; (f) reacting Compound (D) or a pharmaceutically acceptable salt thereof with $H_2$ in the presence of a Pd catalyst on carbon (Pd(0)/C) to form Compound (F)

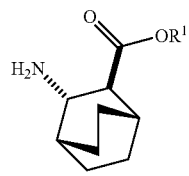
(F)

or a pharmaceutically acceptable salt thereof; (c) reacting Compound (F) or a pharmaceutically acceptable salt thereof with Compound (G):

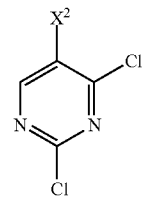
(G)

to form Compound (H):

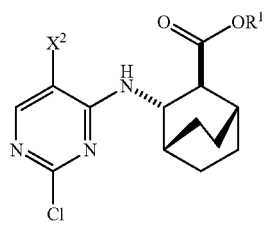
(H)

or a pharmaceutically acceptable salt thereof; (d) hydrolyzing Compound (H) or a pharmaceutically acceptable salt thereof to form Compound (X);

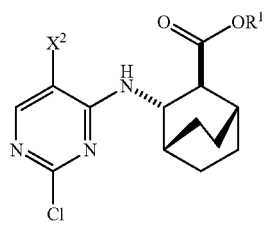
(X)

or a pharmaceutically acceptable salt thereof; (a) reacting Compound (X) or a pharmaceutically acceptable salt thereof with Compound (Y):

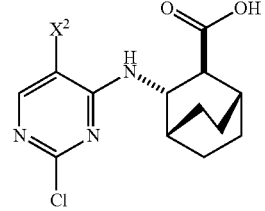
(Y)

in the presence of a palladium catalyst to form Compound (Z):

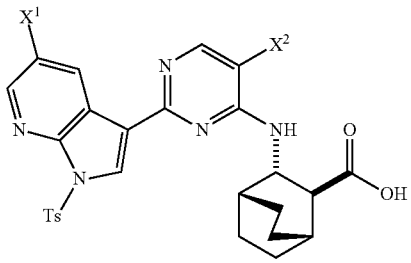

or a pharmaceutically acceptable salt thereof; and (b) deprotecting the Ts group of Compound (Z) or a pharmaceutically acceptable salt thereof to form Compound (1) or a pharmaceutically acceptable salt thereof. Each of $X^1$ and $X^2$ is independently —F or —Cl; and $R^1$ is ethyl. Suitable conditions and reagents, including specific ones, for each step are as described above for Schemes 1-10. In one specific embodiment, step (a) of the reaction of Compound (X) or a pharmaceutically acceptable salt thereof with Compound (Y) is performed in the presence of a palladium-XPhos complex and a phosphate or carbonate base. Specific examples of the phosphate and carbonate bases are as described above. In another specific embodiment, the step (a) of the reaction of Compound (X) or a pharmaceutically acceptable salt thereof with Compound (Y) is performed in a solvent system that includes water and an organic solvent selected from 2-methyl THF or THF, or a combination thereof. In yet another specific embodiment, the deprotection step (b) comprises treating Compound (Z) or a pharmaceutically acceptable salt thereof with an inorganic hydroxide selected from the group consisting of LiOH, NaOH, and KOH. In yet another specific embodiment, the deprotection step (b) comprises treating Compound (Z) or a pharmaceutically acceptable salt thereof with LiOH in a solvent system that includes THF. In yet another specific embodiment, the step (d) of hydrogenation of Compound (D) comprises reacting Compound (D) with $H_2$ in the presence of a Pd catalyst on carbon (Pd/C). In yet another embodiment, the epimerization of Compound (C-1) or a pharmaceutically acceptable salt thereof is done treating the compound with a $C_{1-6}$ alkoxide. Specific examples of $C_{1-6}$ alkoxide are as described above.

In yet another specific embodiment, the methods of the invention are for preparing Compound (2) or a pharmaceutically acceptable salt thereof, wherein the methods comprise the steps (a) through (i) of the preceding paragraph, wherein each of $X^1$ and $X^2$ is independently —F, and $R^1$ is ethyl. The suitable reaction conditions for each of the steps and specific examples thereof are as described above for preparing Compound (1) or a pharmaceutically acceptable salt thereof.

In another embodiment, the methods of the invention are for preparing Compound (1) or a pharmaceutically acceptable salt thereof. The methods comprise: (q) reacting Compound (K) or a pharmaceutically acceptable salt thereof:

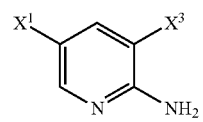

with acetaldehyde in the presence of a palladium catalyst to form Compound (M):

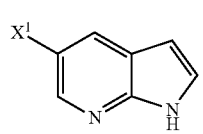

or a pharmaceutically acceptable salt thereof; (p) tosylating Compound (M) or a pharmaceutically acceptable salt thereof to form Compound (N):

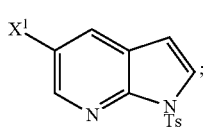

(s) brominating Compound (N) to form Compound (O):

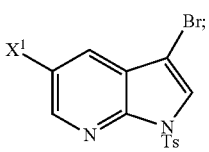

(t) reacting Compound (O) with bis(pinacolato)diboron in the presence of a palladium catalyst to form Compound (Y):

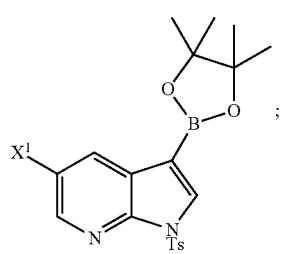

(a) reacting Compound (X):

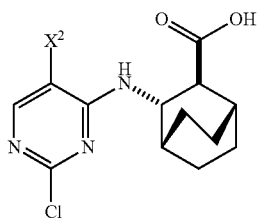

or a pharmaceutically acceptable salt thereof with Compound (Y) in the presence of a palladium catalyst to form compound (Z):

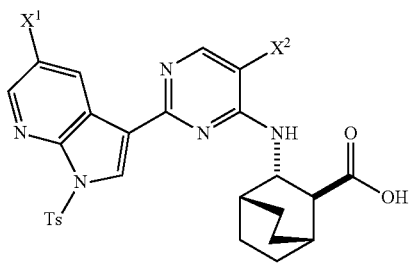

or a pharmaceutically acceptable salt thereof; and (b) deprotecting the Ts group of Compound (Z) or a pharmaceutically acceptable salt thereof to form Compound (1) or a pharmaceutically acceptable salt thereof. Each of $X^1$ and $X^2$ is independently —F or —Cl; and $X^3$ is —Br. Suitable conditions and reagents, including specific ones, for each step are as described above for Schemes 1-11. In one specific embodiment, the step (a) of the reaction of Compound (X) with Compound (Y) is performed in the presence of a palladium-XPhos complex and a phosphate or carbonate base. Specific examples of the phosphate and carbonate bases are as described above. In another specific embodiment, the step (a) of the reaction of Compound (X) or a pharmaceutically acceptable salt thereof with Compound (Y) is performed in a solvent system that includes water and an organic solvent selected from 2-methyl THF or THF, or a combination thereof. In yet another specific embodiment, the deprotection step (b) comprises treating Compound (Z) or a pharmaceutically acceptable salt thereof with an inorganic hydroxide selected from the group consisting of LiOH, NaOH, and KOH. In yet another specific embodiment, the deprotection step (b) comprises treating Compound (Z) or a pharmaceutically acceptable salt thereof with LiOH in a solvent system that includes THF. In yet another specific embodiment, the palladium catalyst of the step (q) of the reaction of Compound (K) or a pharmaceutically acceptable salt thereof with acetaldehyde includes a mixture of bis(dibenzylideneacetone) palladium and a tertiary phosphine ligand, $PR_3$, wherein R is $C_{1-6}$ alkyl or $C_{5-6}$ cycloalkyl. In yet another specific embodiment, the tertiary phosphine ligand includes $P(^tBu)_3$.

In yet another specific embodiment, the methods of the invention are for preparing Compound (2) or a pharmaceutically acceptable salt thereof, wherein the methods comprise the steps (a) through (f) of the preceding paragraph, wherein each of $X^1$ and $X^2$ is independently —F. The suitable reaction conditions for each of the steps and specific examples thereof are as described above for preparing Compound (1) or a pharmaceutically acceptable salt thereof.

In another embodiment, the methods of the invention are for preparing Compound (2) or a pharmaceutically acceptable salt thereof. The methods comprise: (g) reacting Compound (A):

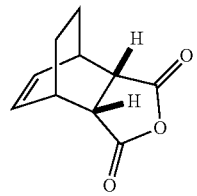

with quinine:

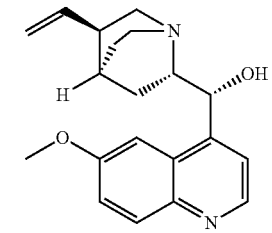 [SMILES: C=C[C@H]1CN2CC[C@H]1C[C@H]2[C@H](O)c1ccnc2ccc(OC)cc12]

and ethyl alcohol to form an adduct of the quinine and Compound (C-1):

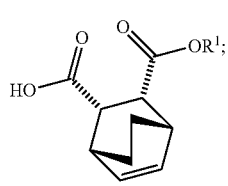

(h) breaking the adduct of the quinine and Compound (C-1) by treating the adduct with HCl to form Compound (C-1) or a pharmaceutically acceptable salt thereof; (i) epimerizing Compound (C-1) to Compound (C):

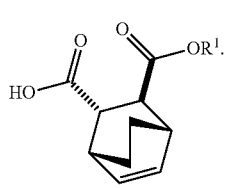

or a pharmaceutically acceptable salt thereof; (e) reacting Compound (C) with diphenylphosphoryl azide and then with benzyl alcohol to form Compound (D):

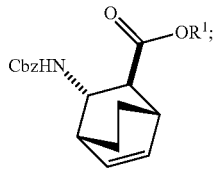
(D)

(f) reacting Compound (D) or a pharmaceutically acceptable salt thereof with $H_2$ in the presence of a Pd catalyst on carbon (Pd(0)/C) to form an HCl salt of Compound (F); (r) reacting the HCl salt of Compound (F) with Compound (G):

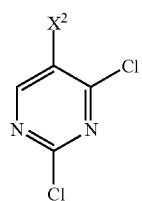
(G)

to form Compound (H):

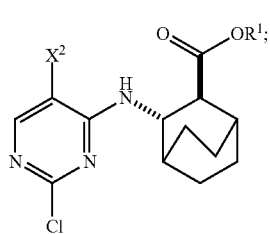
(H)

(h-1) hydrolyzing Compound (H) to form Compound (X-2):

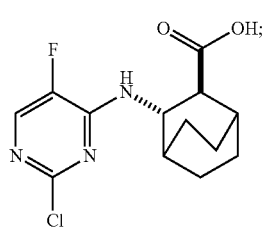
(X-2)

(l) iodinating or brominating Compound (J):

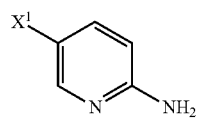
(J)

to form Compound (K):

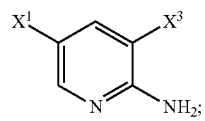
(K)

(m) reacting Compound (K) with trimethylsilyl acetylene to form Compound (L):

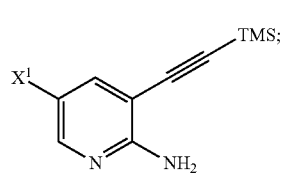
(L)

(n-1) reacting Compound (L) with a $C_{1-6}$ alkoxide to form Compound (M):

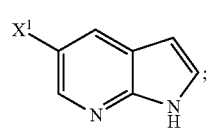
(M)

(p) tosylating Compound (M) to form Compound (N):

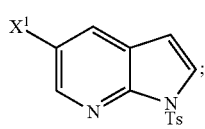
(N)

(s) brominating Compound (N) to form Compound (O):

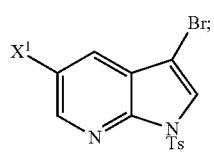
(O)

(t) reacting Compound (O) with bis(pinacolato)diboron in the presence of $Pd(Ph_3P)_4$ to form Compound (Y-2):

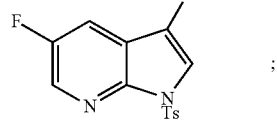
(Y-2)

(a) reacting Compound (X-2) with Compound (Y-2) in the presence of a palladium-XPhos complex and a phosphate or carbonate base selected from $K_2CO_3$ or $K_3PO_4$ to form Compound (Z-2):

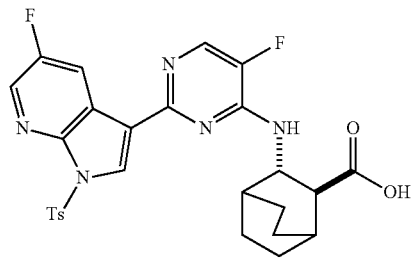

(Z-2)

or a pharmaceutically acceptable salt thereof; and (b) deprotecting the Ts group of Compound (Z-2) or a pharmaceutically acceptable salt thereof to form Compound (2) a pharmaceutically acceptable salt thereof. Each $R^1$ is independently ethyl; each $X^1$ is independently —F; each $X^2$ is independently —F; and each $X^3$ is independently —Br or —I. Suitable conditions and reagents, including specific ones, for each step are as described above for Schemes 1-11.

In yet another embodiment, the invention is directed to methods of preparing Compound (C) or pharmaceutically acceptable salt thereof. The methods comprise: (g) reacting Compound (A):

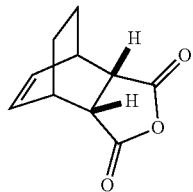

(A)

with quinine:

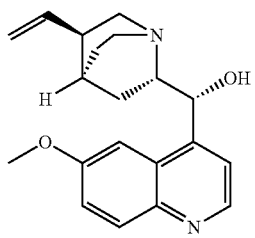 [SMILES: C=C[C@H]1CN2CC[C@H]1C[C@H]2[C@H](O)c1ccnc2ccc(OC)cc12]

and ethyl alcohol to form an adduct of the quinine and Compound (C-1):

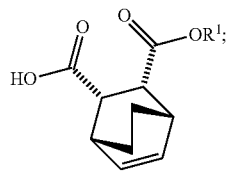

(C-1)

(h) breaking the adduct of the quinine and Compound (C-1) by treating the adduct with HCl to form Compound (C-1) or a pharmaceutically acceptable salt thereof; and (i) epimerizing Compound (C-1) to Compound (C):

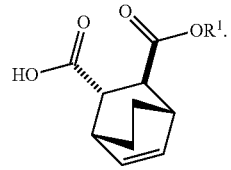

(C)

or a pharmaceutically acceptable salt thereof. Without intending to be bound to a particular theory, the adduct of quinine and Compound (C) having ethyl for $R^1$ precipitates out of the reaction mixture of quinine and Compound (A), which can provide Compound (C) in over 99% enantiomeric pure form.

In yet another embodiment, the invention is directed to methods of preparing Compound (N). The methods comprise: (q) reacting Compound (K):

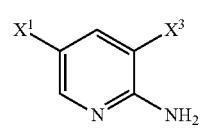

(K)

or a pharmaceutically acceptable salt thereof with acetaldehyde in the presence of a palladium catalyst to form Compound (M):

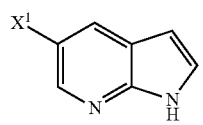

(M)

or a pharmaceutically acceptable salt thereof, wherein $X^1$ is —F or —Cl, and $X^3$ is —Br or —I; and (p) tosylating Compound (M) or a pharmaceutically acceptable salt thereof to form Compound (N):

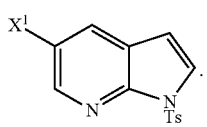

(N)

In one specific embodiment, $X^1$ is —F. In another specific embodiment, $X^3$ is —Br. In yet another specific embodiment, $X^1$ is —F and $X^3$ is —Br. Without intending to be bound to a particular theory, the preparation of Compound (N) according to Scheme 9 has several advantages over that according to Scheme 8 (Compounds (K)→Compound (N)) in that preparation of Compound (N) according to Scheme 9 generally provides better yields and less filtrations overall. It is also cost effective for a large scale reaction, such as a commercial scale reaction because of relatively lower cost of acetaldehyde than that of trimethylsilyl acetylene.

In yet another embodiment, the methods of the invention further employ treating Compound (1), after the de-protecting step (b) of Scheme 1 above, with HCl to form an HCl salt of compound (1). In one specific embodiment, the HCl treatment is performed in a solvent system that includes water and one or more organic solvents to form a HCl salt of Compound (1), wherein the organic solvents are independently selected from Class II organic solvents selected from the group consisting of: chlorobenzene, cyclohexane, 1,2-dichloroethene, dichloromethane, 1,2-dimethoxyethane, N,N-dimentylacetamide, N,N-dimethylformamide, 1,4-dioxane, 2-ethoxyethanol, formamide, hexane, 2-methoxyethanol, methylbutyl ketone, methylcyclohexane, N-methylpyrrolidone, nitromethane, pyridine, sulfolane, tetrahydrofuran (THF), tetralin, tolune, 1,1,2-trichloroethene and xylene, or Class III organic solvents selected from the group consisting of: acetic acid, acetone, anisole, 1-butanol, 2-butanol, butyl acetate, tert-butylmethyl ether, cumene, heptane, isobutyl acetate, isopropyl acetate, methyl acetate, 3-methyl-1-butanol, methylethyl ketone, methylisobutyl ketone, 2-methyl-1-propanol, ethyl acetate, ethyl ether, ethyl formate, pentane, 1-pentanol, 1-propanol, 2-propanol and propyl acetate. In another specific embodiment, the organic solvents of the solvent system are selected from the group consisting of: chlorobenzene, cyclohexane, 1,2-dichloroethane, dichloromethane, 1,2-dimethoxyethane, formamide, hexane, 2-methoxyethanol, methylbutyl ketone, methylcyclohexane, nitromethane, tetralin, xylene, toluene, 1,1,2-trichloroethane, acetone, anisole, 1-butanol, 2-butanol, butyl acetate, t-butylmethylether, cumene, ethanol, ethyl acetate, ethyl ether, ethyl formate, heptane, isobutyl acetate, isopropyl acetate, methyl acetate, 3-methyl-1-butanol, methylethyl ketone, 2-methy-1-propanol, pentane, 1-propanol, 1-pentanol, 2-propanol, propyl acetate, tetrahydrofuran, and methyl tetrahydrofuran. In another specific embodiment, the organic solvents of the solvent system are selected from the group consisting of: 2-ethoxyethanol, ethyleneglycol, methanol, 2-methoxyethanol, 1-butanol, 2-butanol, 3-methyl-1-butanol, 2-methyl-1-propanol, ethanol, 1-pentanol, 1-propanol, 2-propanol, methylbutyl ketone, acetone, methylethyl ketone, methylisobutyl ketone, butyl acetate, isobutyl acetate, isopropyl acetate, methyl acetate, ethyl acetate, propyl acetate, pyridine, toluene, and xylene. In yet another specific embodiment, the solvent system includes water and acetone, or water and isopropanol.

In yet another embodiment, the methods of the invention further employ treating Compound (2), after the de-protecting step (b) of Scheme 1-A above, with HCl to form an HCl salt of compound (2). Suitable solvent systems, including specific examples, are as described above for Compound (1).

Specific exemplary conditions suitable for each step of Schemes 1-11, which each and independently can be employed in the methods of the invention, are described below in the Exemplification section.

The methods of the invention described above can be used for preparing specific solid forms of Compound (1) or its pharmaceutically acceptable salts thereof. For example, Compound (1) can exist in or form different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds. Generally, different polymorphs can be characterized by analytical methods such as X-ray powder diffraction (XRPD) pattern, thermogravimetric analysis (TGA), and differential scanning calorimetry (DSC), or by its melting point, or other techniques known in the art. As used herein, the term "polymorphic form" includes solvates and neat polymorphic form that does not have any solvates. It is noted that Compound (1) and salts of Compound (1) can be solvated or non-solvated unless specified otherwise. Also, it is noted Compound (1) and salts of Compound (1) can be crystalline or amorphous unless specified otherwise.

An example of solid forms of Compound (1) or its pharmaceutically acceptable salts thereof is polymorphic Form A of HCl salt of Compound (1).½H$_2$O. This form is a polymorphic form of HCl salt of Compound (1) that includes water as a solvate in a half equivalent per Compound (1). In one specific embodiment, Form A of HCl salt of Compound (1).½H$_2$O is characterized as having an XRPD with characteristic peaks measured in 2-theta (degrees) at 10.5±0.2, 5.2±0.2, 7.4±0.2, and 12.8±0.2. In another specific embodiment, Form A of HCl salt of Compound (1).½H$_2$O is characterized as having an XRPD pattern with characteristic peaks measured in 2-theta (degrees) at the following positions listed in Table 3A of the Examples. The XRPD patterns are obtained at room temperature using Cu K alpha radiation. In yet another specific embodiment, the polymorphic Form A of HCl salt of Compound (1).½H$_2$O is characterized as having peaks at 29.2, 107.0, 114.0, and 150.7 (±0.3 ppm) in a $C^{13}$ SSNMR spectrum. In yet another specific embodiment, Form A of HCl salt of Compound (1).½H$_2$O is characterized as having $C^{13}$ SSNMR peaks listed in Table 3B of the Examples.

Another example of solid forms of Compound (1) or its pharmaceutically acceptable salts thereof is polymorphic Form F of HCl salt of Compound (1).3H$_2$O. This form is a polymorphic form of HCl salt of Compound (1) that includes water as a solvate in three equivalents per Compound (1). In one specific embodiment, Form F of HCl salt of Compound (1).3H$_2$O is characterized as having an XRPD pattern with characteristic peaks measured in 2-theta (degrees) at 7.1±0.2, 11.9±0.2, and 12.4±0.2. In another specific embodiment, Form F of HCl salt of Compound (1).3H$_2$O is characterized as having an XRPD pattern with characteristic peaks expressed in 2-theta (degrees) at the following positions listed in Table 5 of the Examples. The XRPD patterns are obtained at room temperature using Cu K alpha radiation. In yet another specific embodiment, the polymorphic Form F of HCl salt of Compound (1).3H$_2$O is characterized as having peaks at 20.7, 27.4, 104.8, 142.5, 178.6 (±0.3 ppm) in a $C^{13}$ SSNMR spectrum. In yet another specific embodiment, Form F of HCl salt of Compound (1).3H$_2$O is characterized as having $C^{13}$ SSNMR peaks listed in Table 6 of the Examples.

Another example of solid forms of Compound (1) or its pharmaceutically acceptable salts thereof is polymorphic Form D of HCl salt of Compound (1). This form is a non-solvated form of HCl salt of Compound (1). In one specific embodiment, Form D of HCl salt of Compound (1) is characterized as having an XRPD pattern with characteristic peaks measured in 2-theta (degrees) at 5.8±0.2, 17.1±0.2, and 19.5±0.2. In another specific embodiment, Form D of HCl salt of Compound (1) is characterized as having an XRPD pattern with characteristic peaks measured in 2-theta (degrees) at the positions listed in Table 7 of the Examples. The XRPD patterns are obtained at room temperature using Cu K alpha radiation. In yet another specific embodiment, Form D of HCl salt of Compound (1) is characterized as having peaks at 29.4, 53.4, 113.3, 135.4, 177.8 (±0.3 ppm) in a $C^{13}$ SSNMR spectrum. In yet another specific embodiment, Form D of HCl salt of Compound (1) is characterized as having $C^{13}$ SSNMR peaks listed in Table 8 of the Examples.

Another example of solid forms of Compound (1) or its pharmaceutically acceptable salts thereof polymorphic Form A of Compound (1). This form is a non-solvated, free base form of Compound (1). In one specific embodiment, Form A of Compound (1) is characterized as having an XRPD pattern with characteristic peaks measured in 2-theta (degrees) at 15.5±0.2, 18.9±0.2, and 22.0±0.2. In another specific embodiment, Form A of Compound (1) is characterized as having an XRPD pattern with characteristic peaks measured in 2-theta (degrees) at the positions listed in Table 10 of the Examples. The XRPD patterns are obtained at room temperature using Cu K alpha radiation. In yet another specific embodiment, Form A of Compound (1) is characterized as having peaks at 21.0, 28.5, 50.4, 120.8, 138.5, and 176.2 (±0.3 ppm) in a $C^{13}$ SSNMR spectrum. In yet another specific embodiment, Form A of Compound (1) is characterized as having $C^{13}$ SSNMR peaks listed in Table 11 of the Examples.

Another example of solid forms of Compound (1) or its pharmaceutically acceptable salts thereof is polymorphic Form A of tosylate salt of Compound (1). This form is a non-solvated form of tosylate salt of Compound (1). In one specific embodiment, Form A of tosylate salt of Compound (1) is characterized as having an XRPD pattern with characteristic peaks measured in 2-theta (degrees) at the following positions listed in Table 14 of the Examples. The XRPD patterns are obtained at room temperature using Cu K alpha radiation.

Other example of solid forms of Compound (1) or its pharmaceutically acceptable salts thereof is 2-MeTHF solvates of Compound (1). In one specific embodiment, the solvates include 0.5-1.5 equivalents of 2-MeTHF per Compound (1), such as 1 equivalent of 2-MeTHF per Compound (1). In another specific embodiment, the solvates include 1 equivalent of 2-MeTHF and are characterized by having certain XRPD peaks listed in Table 12 of the Examples.

Form A of HCl salt of Compound (1).½H$_2$O can be prepared by employing mixing (e.g., stirring) hydrogen chloride (HCl) with Compound (1). Compound (1) can be solvated, non-solvated, amorphous, or crystalline. A solution, slurry, or suspension of Compound (1) can be mixed with HCl in a solvent system that includes water and one or more organic solvents, wherein the solvent system has a water activity of equal to, or greater than, 0.05 and equal to, or less than, 0.85, i.e., 0.05-0.85. The term "water activity" ($a_w$) is used herein as known in the art and means a measure of the energy status of water in a solvent system. It is defined as the vapor pressure of a liquid divided by that of pure water at the same temperature. Specifically, it is defined as $$a_w = \frac{p}{p_o},$$

where p is the vapor pressure of water in the substance, and $p_o$ is the vapor pressure of pure water at the same temperature, or as $a_w = l_w \times x_w$, where $l_w$ is the activity coefficient of water and $x_o$ is the mole fraction of water in the aqueous fraction. For example, pure water has a water activity value of 1.0. Water activity values can typically be obtained by either a capacitance hygrometer or a dew point hygrometer. Various types of water activity measuring instruments are also commercially available. Alternatively, water activity values of mixtures of two or more solvents can be calculated based on the amounts of the solvents and the known water activity values of the solvents.

An example of crystalline Compound (1) includes Form A of Compound (1). Examples of solvates of Compound (1) include solvates of 2-MeTHF, N,N-methanol, xylene, acetone, 2-butanol, methyl acetate, 1-pentanol, 2-propanol, tetrahydrofuran, methyl tetrahydrofuran, dimethylacetamide N,N-dimethylformamide 1,4-dioxane, 1-pentanol, 2-methy-1-propanol, methylethyl ketone, 3-methyl-1-butanol, heptane, ethyl formate, 1-butanol, acetic acid, and ethylene glycol. In a specific embodiment, solvates of 2-MeTHF (e.g., Compound (1).1(2-MeTHF)) are employed.

The solvent systems suitable for the preparation of Form A of HCl salt of Compound (1).½H$_2$O can be comprised of a large variety of combinations of water and organic solvents where the water activity of the solvent systems is equal to, or greater than, 0.05 and equal to, or less than, 0.85 (0.05-0.85). In a specific embodiment, the value of the water activity is 0.4-0.6. Suitable organic solvents include Class II or Class III organic solvents listed in the International Conference on Harmonization Guidelines. Specific examples of suitable Class II organic solvents include chlorobenzene, cyclohexane, 1,2-dichloroethene, dichloromethane, 1,2-dimethoxyethane, N,N-dimentylacetamide, N,N-dimethylformamide, 1,4-dioxane, 2-ethoxyethanol, formamide, hexane, 2-methoxyethanol, methylbutyl ketone, methylcyclohexane, N-methylpyrrolidone, nitromethane, pyridine, sulfolane, tetrahydrofuran (THF), tetralin, tolune, 1,1,2-trichloroethene and xylene. Specific examples of suitable Class III organic solvents include: acetic acid, acetone, anisole, 1-butanol, 2-butanol, butyl acetate, tert-butylmethyl ether, cumene, heptane, isobutyl acetate, isopropyl acetate, methyl acetate, 3-methyl-1-butanol, methylethyl ketone, methylisobutyl ketone, 2-methyl-1-propanol, ethyl acetate, ethyl ether, ethyl formate, pentane, 1-pentanol, 1-propanol, 2-propanol and propyl acetate. In one specific embodiment, the organic solvents of the solvent system are selected from the group consisting of chlorobenzene, cyclohexane, 1,2-dichloroethane, dichloromethane, 1,2-dimethoxyethane, hexane, 2-methoxyethanol, methylbutyl ketone, methylcyclohexane, nitromethane, tetralin, xylene, toluene, 1,1,2-trichloroethane, acetone, anisole, 1-butanol, 2-butanol, butyl acetate, t-butylmethylether, cumene, ethanol, ethyl acetate, ethyl ether, ethyl formate, heptane, isobutyl acetate, isopropyl acetate, methyl acetate, 3-methyl-1-butanol, methylethyl ketone, 2-methy-1-propanol, pentane, 1-propanol, 1-pentanol, 2-propanol, propyl acetate, tetrahydrofuran, and methyl tetrahydrofuran. In another specific embodiment, the organic solvents of the solvent system are selected from the group consisting of 2-ethoxyethanol, ethyleneglycol, methanol, 2-methoxyethanol, 1-butanol, 2-butanol, 3-methyl-1-butanol, 2-methyl-1-propanol, ethanol, 1-pentanol, 1-propanol, 2-propanol, methylbutyl ketone, acetone, methylethyl ketone, methylisobutyl ketone, butyl acetate, isobutyl acetate, isopropyl acetate, methyl acetate, ethyl acetate, propyl acetate, pyridine, toluene, and xylene. In yet another embodiment, the organic solvents are selected from the group consisting of acetone, n-propanol, isopropanol, isobutylacetate, and acetic acid. In yet another embodiment, the organic solvents are selected from the group consisting of acetone and isopropanol. In yet another specific embodiment, the solvent system includes water an acetone. In yet another specific embodiment, the solvent system includes water an isopropanol.

The preparation of Form A of HCl salt of Compound (1).½H$_2$O can be performed at any suitable temperature. Typically, it is performed at a temperature of 5° C.-75° C. In a specific embodiment, it is performed at a temperature of 15° C.-75° C. In another specific embodiment, it is performed at a temperature of 15° C.-60° C. In yet another specific embodiment, it is performed at a temperature of 15° C.-35° C. In yet another specific embodiment, the preparation is performed at 5° C.-75° C. in a solvent system having a water activity value of 0.4-0.6. In yet another specific embodiment, the preparation is performed at a temperature of 15° C.-75° C. in a solvent system having a water activity value of 0.4-0.6. In yet another specific embodiment, the preparation is performed at a temperature of 15° C.-60° C. in a solvent system having a water activity value of 0.4-0.6. In yet another specific embodiment, the preparation is performed at 15° C.-35° C. in a solvent system having a water activity value of 0.4-0.6.

The hydrogen chloride can be introduced as a solution or gas. One example of suitable hydrogen chloride source is a solution of hydrogen chloride of 30-40 weight percent (e.g., 34 wt %-38 wt %) in water.

Form F of HCl salt of Compound (1).3H$_2$O can be prepared by mixing HCl and Compound (1) in a solvent system that includes water or that includes water and one or more organic solvents, wherein the solvent system has a water activity of equal to, or greater than, 0.9 (≥0.9). The mixture can be a solution, slurry, or suspension. Compound (1) can be solvated, non-solvated, amorphous, or crystalline. Alternatively, it can be prepared by stirring Form A of HCl salt of Compound (1).½H$_2$O in a solvent system that includes water or that includes water and one or more organic solvents, wherein the solvent system has a water activity of equal to, or greater than, 0.9. Typically, pure water has a water activity value of 1.0. Accordingly, a solvent system having a water activity of 0.9-1.0 can be suitable for the preparation of Form F of HCl salt of Compound (1).3H$_2$O. In a specific embodiment, the mixing or stirring is performed at an ambient temperature (18° C.-25° C.). In another specific embodiment, the mixing or stirring is performed at a temperature of 15° C.-30° C. In another specific embodiment, the mixing or stirring is performed at a temperature of 20° C.-28° C. (e.g., 25° C.). Suitable organic solvents, including specific examples, for the formation of Form F of HCl salt of Compound (1).3H$_2$O are as described above for Form A of HCl salt of Compound (1).½H$_2$O. In yet another specific embodiment, the solvent system includes water an acetone. In yet another specific embodiment, the solvent system includes water an isopropanol.

Form D of HCl salt of Compound (1) can be prepared by dehydrating Form A of HCl salt of Compound (1).½H$_2$O. The dehydration can be done by any suitable means, such as heating or dry nitrogen purge, or both.

Form A of Compound (1) can be prepared by (a) stirring a mixture of amorphous Compound (1) or a solvate of Compound (1) (such as a 2-MeTHF solvate of Compound (1)) in a solvent system that includes water and ethanol. The mixture can be a solution or slurry. In a specific embodiment, the stirring step is performed at a temperature in a range of 18° C. to 90° C. In another specific embodiment, the stirring step (a) is performed at a refluxing temperature of the solvent system. In another specific embodiment, the solvent system includes water by 5-15 wt %. Examples of solvates of Compound (1) are as described above. In a specific embodiment, solvates of 2-MeTHF (e.g., Compound (1).1(2-MeTHF)) are employed.

In another embodiment, the methods of preparing Form A of Compound (1) further comprises: (b) stirring amorphous form of Compound (1) in nitromethane to form crystalline seed of Form A of Compound (1); and (c) adding the crystalline seed of Form A of Compound (1) to the resulting mixture of the mixing step (a). In a specific embodiment, the methods further comprises: (b) stirring the amorphous form of Compound (1) in nitromethane to form crystalline seed of Form A of Compound (1); (c) cooling the resulting mixture of the mixing step (a) to a temperature in a range of 18° C. to 60° C. (e.g., 50-55° C. or 55° C.); and (d) adding the crystalline seed of Form A of Compound (1) to the resulting mixture step (c). In another specific embodiment, the methods further comprises adding water, prior to the addition of crystalline seed of Form A of Compound (1), to the resulting mixture that has gone through the refluxing step in an amount to have the resulting solvent system include water by 15-25 wt % after the addition of water. In yet another specific embodiment, the methods further comprises adding water to the mixture that includes crystalline seed of Form A of Compound (1) in an amount to have the resulting solvent system include water by 35-45 wt % after the addition of water. In yet another specific embodiment, the methods further comprises cooling the mixture that includes crystalline seed of Form A of Compound (1), after the addition of water, to a temperature of 0° C.-10° C.

In one specific embodiment, the crystalline seed of Form A of Compound (1) can be prepared by 2-MeTHF solvate of Compound (1) in nitromethane. In one embodiment, the solvent system for the refluxing step includes water by 5-15 wt %, such as 10 wt %.

Form A of tosylate salt of Compound (1) can be prepared by stirring a mixture of amorphous Compound (1) or a solvate of Compound (1) ((such as a 2-MeTHF solvate of Compound (1)), p-toluenesulfonic acid, and a solvent system that includes acetonitrile. In a specific embodiment, the mixing or stirring step is performed at an ambient temperature. In another specific embodiment, the mixing or stirring step is performed at a temperature of 15° C.-30° C. In another specific embodiment, the mixing or stirring step is performed at a temperature of 20° C.-30° C. (e.g., 25° C.). Suitable examples of solvates of Compound (1), including specific examples, are as described above for the preparation of Form A of Compound (1).

In yet another embodiment, the invention encompasses amorphous forms of Compound (1) and pharmaceutically acceptable salts thereof, such as amorphous HCl salt of Compound (1) and amorphous Compound (1). In yet another embodiment, the invention also encompasses Form B of Compound (1) hydrate. Form B of Compound (1) hydrate is isomorphic with Form A of Compound (1), showing the same XRPD peaks as those for Form A of Compound (1), but formed in the presence of water, for example, in a system having a water activity greater than 0.6, such as 0.6-1.0, at ambient temperature.

The present invention encompasses the polymorphic forms of Compound (1) described above in isolated, pure form, or in a mixture as a solid composition when admixed with other materials, for example the other forms (i.e. amorphous form, Form A of Compound (1), etc.) of Compound (I) or any other materials.

In one aspect, the present invention provides polymorphic forms, such as Form A of HCl salt of Compound (1).½H$_2$O, Form F of HCl salt of Compound (1).3H$_2$O, Form D of HCl salt of Compound (1), Form A of Compound (1), Form B of Compound (1) hydrate, and Form A of tosylate salt of Compound (1), in isolated solid form. In yet another aspect, the present invention provides amorphous form of Compound (1) and pharmaceutically acceptable salts thereof, such as amorphous HCl salt of Compound (1) and amorphous Compound (1), in isolated solid form.

In a further aspect, the present invention provide polymorphic forms, such as Form A of HCl salt of Compound (1).½$H_2O$, Form F of HCl salt of Compound (1).3$H_2O$, Form D of HCl salt of Compound (1), Form A of Compound (1), Form B of Compound (1) hydrate and Form A of tosylate salt of Compound (1), in pure form. The pure form means that the particular polymorphic form comprises over 95% (w/w), for example, over 98% (w/w), over 99% (w/w %), over 99.5% (w/w), or over 99.9% (w/w). In another further aspect there is provided amorphous forms of Compound (1) or pharmaceutically acceptable salts thereof in pure form. The pure form means that the amorphous form is over 95% (w/w), for example, over 98% (w/w), over 99% (w/w %), over 99.5% (w/w), or over 99.9% (w/w).

More specifically, the present invention provides that each of the polymorphic forms in the form of a composition or a mixture of the polymorphic form with one or more other crystalline, solvate, amorphous, or other polymorphic forms or their combinations thereof. For example, in one embodiment, the composition comprises Form A of HCl salt of Compound (1).½$H_2O$ along with one or more other polymorphic forms of Compound (1), such as amorphous form, solvates, Form D of HCl salt of Compound (1), Form F of HCl salt of Compound (1).3$H_2O$, Form A of Compound (1), and/or other forms or their combinations thereof. Similarly, in another embodiment, the composition comprises Form F of HCl salt of Compound (1).3$H_2O$ along with one or more other polymorphic forms of Compound (1), such as amorphous form, solvates, Form A of HCl salt of Compound (1).½$H_2O$, Form D of HCl salt of Compound (1), Form A of Compound (1), and/or other forms or their combinations thereof. Similarly, in another embodiment, the composition comprises Form D of HCl salt of Compound (1) along with one or more other polymorphic forms of Compound (1), such as amorphous form, solvates, Form A of HCl salt of Compound (1).½$H_2O$, Form F of HCl salt of Compound (1).3$H_2O$, Form A of Compound (1), and/or other forms or their combinations thereof. In yet another embodiment, the composition comprises Form A of Compound (1) along with one or more other polymorphic forms of Compound (1), such as amorphous form, hydrates, solvates, and/or other forms or their combinations thereof. In yet another embodiment, the composition comprises Form A of tosylate salt of Compound (1) along with one or more other polymorphic forms of Compound (1), such as amorphous form, hydrates, solvates, and/or other forms or their combinations thereof. More specifically, the composition may comprise from trace amounts up to 100% of the specific polymorphic form or any amount in between, for example, 0.1%-0.5%, 0.1%-1%, 0.1%-2%, 0.1%-5%, 0.1%-10%, 0.1%-20%, 0.1%-30%, 0.1%-40%, or 0.1%-50% by weight based on the total amount of Compound (1) in the composition. Alternatively, the composition may comprise at least 50%, 60%, 70%, 80%, 90%, 95%, 97%, 98%, 99%, 99.5% or 99.9% by weight of specific polymorphic form based on the total amount of Compound (1) in the composition.

The compounds described herein are defined herein by their chemical structures and/or chemical names. Where a compound is referred to by both a chemical structure and a chemical name, and the chemical structure and chemical name conflict, the chemical structure is determinative of the compound's identity.

It will be appreciated by those skilled in the art that in the processes of the present invention certain functional groups such as hydroxyl or amino groups in the starting reagents or intermediate compounds may need to be protected by protecting groups. Thus, the preparation of the compounds described above may involve, at various stages, the addition and removal of one or more protecting groups. The protection and deprotection of functional groups is described in "Protective Groups in Organic Chemistry." edited by J. W. F. McOmie, Plenum Press (1973) and "Protective Groups in Organic Synthesis," 3rd edition, T. W. Greene and P. G. M. Wuts, Wiley Interscience, and "Protecting Groups," 3rd edition, P. J. Kocienski, Thieme (2005).

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausolito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched), or branched, hydrocarbon chain that is completely saturated or that contains one or more units of unsaturation but is non-aromatic. Unless otherwise specified, aliphatic groups contain 1-10 aliphatic carbon atoms. In some embodiments, aliphatic groups contain 1-6 aliphatic carbon atoms, and in other embodiments, aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl and acetylene.

The term "cycloaliphatic" (or "carbocycle" or "carbocyclyl" or "carbocyclic") refers to a non-aromatic carbon only containing ring system which can be saturated or contains one or more units of unsaturation, having three to fourteen ring carbon atoms. In some embodiments, the number of carbon atoms is 3 to 10. In other embodiments, the number of carbon atoms is 4 to 7. In yet other embodiments, the number of carbon atoms is 5 or 6. The term includes monocyclic, bicyclic or polycyclic, fused, spiro or bridged carbocyclic ring systems. The term also includes polycyclic ring systems in which the carbocyclic ring can be "fused" to one or more non-aromatic carbocyclic or heterocyclic rings or one or more aromatic rings or combination thereof, wherein the radical or point of attachment is on the carbocyclic ring. "Fused" bicyclic ring systems comprise two rings which share two adjoining ring atoms. Bridged bicyclic group comprise two rings which share three or four adjacent ring atoms. Spiro bicyclic ring systems share one ring atom. Examples of cycloaliphatic groups include, but are not limited to, cycloalkyl and cycloalkenyl groups. Specific examples include, but are not limited to, cyclohexyl, cyclopropenyl, and cyclobutyl.

The term "alkyl" as used herein means a saturated straight or branched chain hydrocarbon. In some embodiments, the "alkyl" is $C_1$-$C_6$ alkyl or $C_1$-$C_4$ alkyl. The term "cycloalkyl" as used herein means a saturated cyclic chain hydrocarbon. In some embodiments, the "cycloalkyl" is $C_3$-$C_8$ alkyl or $C_5$-$C_6$ alkyl. Each of the "alkyl" or "cycloalkyl" as used herein can be optionally substituted as set forth below.

Suitable substituents on the saturated carbon of an alkyl, aliphatic, cycloalkyl, or cycloaliphatic group are selected from the group consisting of: halogen; —R°; —OR°; —SR°; 1,2-methylenedioxy; 1,2-ethylenedioxy; phenyl (Ph) optionally substituted with R°; —O(Ph) optionally substituted with R°; —(CH$_2$)$_{1-2}$(Ph), optionally substituted with R°; —CH=CH(Ph), optionally substituted with —R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N(R°)$_2$; —OC(O)N(R°)$_2$; —OC(O)R°; —C(O)N(OR°)R°; —C(NOR°)R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°)R°; —C(=NH)—N(R°)$_2$; or —(CH$_2$)$_0$$_2$NHC(O)R°; wherein each independent occurrence of R° is selected from hydrogen, optionally substituted C$_{1-6}$ aliphatic, an unsubstituted 5-6 membered heteroaryl or heterocyclic ring, phenyl, —O(Ph), or —CH$_2$(Ph), or, two independent occurrences of R°, on the same substituent or different substituents, taken together with the atom(s) to which each R° group is bound, form a 5-8-membered heterocyclyl, carbocyclic aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group of R° are selected from NH$_2$, NH(C$_{1-4}$ aliphatic), N(C$_{1-4}$ aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, CHO, N(CO)(C$_{1-4}$ aliphatic), C(O)N(C$_{1-4}$ aliphatic), wherein each of the foregoing C$_{1-4}$ aliphatic groups of R° is unsubstituted. Additional substituents include: =O, =S, =NNHR*, =NN(R*)$_2$, =NNHC(O)R*, =NNHCO$_2$(C$_{1-4}$ alkyl), =NNHSO$_2$(C$_{1-4}$ alkyl), or =NR*, wherein each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo (C$_{1-4}$ aliphatic), wherein each of the foregoing C$_{1-4}$aliphatic groups of R* is unsubstituted.

As used herein, the term "alkoxy", as used herein, refers to an alkyl group, as previously defined, attached to the molecule through an oxygen ("alkoxy" e.g., —O-alkyl) atom.

As used herein, the terms "halogen", "halo", and "hal" mean F, Cl, Br, or I.

The terms "haloalkyl", "haloalkenyl", "haloaliphatic", and "haloalkoxy" mean alkyl, alkenyl, aliphatic or alkoxy, as the case may be, substituted with one or more halogen atoms. This term includes perfluorinated alkyl groups, such as —CF$_3$ and —CF$_2$CF$_3$.

As used herein, "cyclo", "cyclic", "cyclic group" or "cyclic moiety", include mono-, bi-, and tri-cyclic ring systems including cycloaliphatic, heterocycloaliphatic, carbocyclic aryl, or heteroaryl, each of which has been previously defined.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic carbocyclic aryls, and bicyclic heteroaryls.

As used herein, a "bridged bicyclic ring system" refers to a bicyclic heterocycloalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, carbocyclic aryl, heteroaryl, alkoxy, cycloalkyloxy, heterocycloalkyloxy, (carbocyclic aryl)oxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, (carbocyclic aryl)carbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "bridge" refers to a bond or an atom or an unbranched chain of atoms connecting two different parts of a molecule. The two atoms that are connected through the bridge (usually but not always, two tertiary carbon atoms) are denoted as "bridgeheads".

As used herein, the term "spiro" refers to ring systems having one atom (usually a quaternary carbon) as the only common atom between two rings.

The term "ring atom" is an atom such as C, N, O or S that is in the ring of an aromatic group, cycloalkyl group or non-aromatic heterocyclic ring.

A "substitutable ring atom" in an aromatic group is a ring carbon or nitrogen atom bonded to a hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to a moiety other than hydrogen.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

Selection of substituents and combinations of substituents envisioned by this invention are those that result in the formation of stable or chemically feasible compounds. The term "stable", as used herein, refers to compounds that are not substantially altered when subjected to conditions to allow for their production, detection, and, specifically, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. Only those choices and combinations of substituents that result in a stable structure are contemplated. Such choices and combinations will be apparent to those of ordinary skill in the art and may be determined without undue experimentation.

The term "protecting group" and "protective group" as used herein, are interchangeable and refer to an agent used to temporarily block one or more desired functional groups in a compound with multiple reactive sites. In certain embodiments, a protecting group has one or more, or specifically all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

As used herein, the term "displaceable moiety" or "leaving group" refers to a group that is associated with an aliphatic or aromatic group as defined herein and is subject to being displaced by nucleophilic attack by a nucleophile.

Unless otherwise indicated, structures depicted herein are also meant to include all isomeric (e.g., enantiomeric, diastereomeric, cis-trans, conformational, and rotational) forms of the structure. For example, the R and S configurations for each asymmetric center, (Z) and (E) double bond isomers, and (Z) and (E) conformational isomers are included in this invention, unless only one of the isomers is drawn specifically. As would be understood to one skilled in the art, a substituent can freely rotate around any rotatable bonds. For example, a substituent drawn as

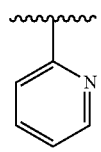

also represents

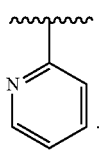

Therefore, single stereochemical isomers as well as enantiomeric, diastereomeric, cis/trans, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays. Such compounds, especially deuterium analogs, can also be therapeutically useful.

The compounds described herein are defined by their chemical structures and/or chemical names. Where a compound is referred to by both a chemical structure and a chemical name, and the chemical structure and chemical name conflict, the chemical structure is determinative of the compound's identity.

It will be appreciated by those skilled in the art that the compounds in accordance with the present invention can contain a chiral center. The compounds of formula may thus exist in the form of two different optical isomers (i.e. (+) or (−) enantiomers). All such enantiomers and mixtures thereof including racemic mixtures are included within the scope of the invention. The single optical isomer or enantiomer can be obtained by method well known in the art, such as chiral HPLC, enzymatic resolution and chiral auxiliary.

In one embodiment, the compounds in accordance with the present invention are provided in the form of a single enantiomer at least 95%, at least 97% and at least 99% free of the corresponding enantiomer.

In a further embodiment, the compounds in accordance with the present invention are in the form of the (+) enantiomer at least 95% free of the corresponding (−) enantiomer.

In a further embodiment, the compounds in accordance with the present invention are in the form of the (+) enantiomer at least 97% free of the corresponding (−) enantiomer.

In a further embodiment, the compounds in accordance with the present invention are in the form of the (+) enantiomer at least 99% free of the corresponding (−) enantiomer.

In a further embodiment, the compounds in accordance with the present invention are in the form of the (−) enantiomer at least 95% free of the corresponding (+) enantiomer.

In a further embodiment, the compounds in accordance with the present invention are in the form of the (−) enantiomer at least 97% free of the corresponding (+) enantiomer.

In a further embodiment the compounds in accordance with the present invention are in the form of the (−) enantiomer at least 99% free of the corresponding (+) enantiomer.

III. Uses of Compounds

The compounds disclosed herein can be used for inhibiting the replication of influenza viruses in a biological sample or in a patient, for reducing the amount of influenza viruses (reducing viral titer) in a biological sample or in a patient, and for treating influenza in a patient. In one embodiment, the present invention is generally related to the use of the compounds disclosed herein (e.g., in pharmaceutically acceptable compositions) for any of the uses specified above.

In yet another embodiment, the compounds disclosed herein can be used to reduce viral titre in a biological sample (e.g. an infected cell culture) or in humans (e.g. lung viral titre in a patient).

The terms "influenza virus mediated condition", "influenza infection", or "Influenza", as used herein, are used interchangeable to mean the disease caused by an infection with an influenza virus.

Influenza is an infectious disease that affects birds and mammals caused by influenza viruses. Influenza viruses are RNA viruses of the family Orthomyxoviridae, which comprises five genera: Influenza virus A, Influenza virus B, Influenza virus C, ISA virus and Thogoto virus. Influenza virus A genus has one species, influenza A virus which can be subdivided into different serotypes based on the antibody response to these viruses: H1N1, H2N2, H3N2, H5N1, H7N7, H1N2, H9N2, H7N2, H7N3 and H10N7. Additional examples of influenza A virus include H3N8 and H7N9. Influenza virus B genus has one species, influenza B virus. Influenza B almost exclusively infects humans and is less common than influenza A. Influenza virus C genus has one species, Influenza virus C virus, which infects humans and pigs and can cause severe illness and local epidemics. However, Influenza virus C is less common than the other types and usually seems to cause mild disease in children.

In some embodiments of the invention, influenza or influenza viruses are associated with Influenza virus A or B. In some embodiments of the invention, influenza or influenza viruses are associated with Influenza virus A. In some specific embodiments of the invention, Influenza virus A is H1N1, H2N2, H3N2 or H5N1. In some specific embodiments of the invention, Influenza virus A is H1N1, H3N2, H3N8, H5N1, and H7N9. In some specific embodiments of the invention, Influenza virus A is H1N1, H3N2, H3N8, and H5N1.

In humans, common symptoms of influenza are chills, fever, pharyngitis, muscle pains, severe headache, coughing, weakness, and general discomfort. In more serious cases, influenza causes pneumonia, which can be fatal, particularly in young children and the elderly. Although it is often confused with the common cold, influenza is a much more severe disease and is caused by a different type of virus. Influenza can produce nausea and vomiting, especially in children, but these symptoms are more characteristic of the unrelated gastroenteritis, which is sometimes called "stomach flu" or "24-hour flu".

Symptoms of influenza can start quite suddenly one to two days after infection. Usually the first symptoms are chills or a chilly sensation, but fever is also common early in the infection, with body temperatures ranging from 38-39° C. (approximately 100-103° F.). Many people are so ill that they are confined to bed for several days, with aches and pains throughout their bodies, which are worse in their backs and legs. Symptoms of influenza may include: body aches, especially joints and throat, extreme coldness and fever, fatigue, headache, irritated watering eyes, reddened eyes, skin (especially face), mouth, throat and nose, abdominal pain (in children with influenza B). Symptoms of influenza are non-specific, overlapping with many pathogens ("influenza-like illness). Usually, laboratory data is needed in order to confirm the diagnosis.

The terms, "disease", "disorder", and "condition" may be used interchangeably here to refer to an influenza virus mediated medical or pathological condition.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In one embodiment, the subject is a non-human animal such as a farm animal (e.g., a horse, cow, pig or sheep), or a pet (e.g., a dog, cat, guinea pig or rabbit). In a preferred embodiment, the subject is a "human".

The term "biological sample", as used herein, includes, without limitation, cell cultures or extracts thereof; biopsied material obtained from a mammal or extracts thereof; blood, saliva, urine, feces, semen, tears, or other body fluids or extracts thereof.

As used herein, "multiplicity of infection" or "MOI" is the ratio of infectious agents (e.g. phage or virus) to infection targets (e.g. cell). For example, when referring to a group of cells inoculated with infectious virus particles, the multiplicity of infection or MOI is the ratio defined by the number of infectious virus particles deposited in a well divided by the number of target cells present in that well.

As used herein the term "inhibition of the replication of influenza viruses" includes both the reduction in the amount of virus replication (e.g. the reduction by at least 10%) and the complete arrest of virus replication (i.e., 100% reduction in the amount of virus replication). In some embodiments, the replication of influenza viruses are inhibited by at least 50%, at least 65%, at least 75%, at least 85%, at least 90%, or at least 95%.

Influenza virus replication can be measured by any suitable method known in the art. For example, influenza viral titre in a biological sample (e.g. an infected cell culture) or in humans (e.g. lung viral titre in a patient) can be measured. More specifically, for cell based assays, in each case cells are cultured in vitro, virus is added to the culture in the presence or absence of a test agent, and after a suitable length of time a virus-dependent endpoint is evaluated. For typical assays, the Madin-Darby canine kidney cells (MDCK) and the standard tissue culture adapted influenza strain, A/Puerto Rico/8/34 can be used. A first type of cell assay that can be used in the invention depends on death of the infected target cells, a process called cytopathic effect (CPE), where virus infection causes exhaustion of the cell resources and eventual lysis of the cell. In the first type of cell assay, a low fraction of cells in the wells of a microtiter plate are infected (typically 1/10 to 1/1000), the virus is allowed to go through several rounds of replication over 48-72 hours, then the amount of cell death is measured using a decrease in cellular ATP content compared to uninfected controls. A second type of cell assay that can be employed in the invention depends on the multiplication of virus-specific RNA molecules in the infected cells, with RNA levels being directly measured using the branched-chain DNA hybridization method (bDNA). In the second type of cell assay, a low number of cells are initially infected in wells of a microtiter plate, the virus is allowed to replicate in the infected cells and spread to additional rounds of cells, then the cells are lysed and viral RNA content is measured. This assay is stopped early, usually after 18-36 hours, while all the target cells are still viable. Viral RNA is quantitated by hybridization to specific oligonucleotide probes fixed to wells of an assay plate, then amplification of the signal by hybridization with additional probes linked to a reporter enzyme.

As used herein a "viral titer (or titre)" is a measure of virus concentration. Titer testing can employ serial dilution to obtain approximate quantitative information from an analytical procedure that inherently only evaluates as positive or negative. The titer corresponds to the highest dilution factor that still yields a positive reading; for example, positive readings in the first 8 serial twofold dilutions translate into a titer of 1:256. A specific example is viral titer. To determine the titer, several dilutions will be prepared, such as $10^{-1}$, $10^{-2}$, $10^{-3}$, $10^{-4}$, $10^{-5}$, $10^{-6}$, $10^{-7}$, $10^{-8}$. The lowest concentration of virus that still infects cells is the viral titer.

As used herein, the terms "treat", "treatment" and "treating" refer to both therapeutic and prophylactic treatments. For example, therapeutic treatments includes the reduction or amelioration of the progression, severity and/or duration of influenza viruses mediated conditions, or the amelioration of one or more symptoms (specifically, one or more discernible symptoms) of influenza viruses mediated conditions, resulting from the administration of one or more therapies (e.g., one or more therapeutic agents such as a compound or composition of the invention). In specific embodiments, the therapeutic treatment includes the amelioration of at least one measurable physical parameter of an influenza virus mediated condition. In other embodiments the therapeutic treatment includes the inhibition of the progression of an influenza virus mediated condition, either physically by, e.g., stabilization of a discernible symptom, physiologically by, e.g., stabilization of a physical parameter, or both. In other embodiments the therapeutic treatment includes the reduction or stabilization of influenza viruses mediated infections. Antiviral drugs can be used in the community setting to treat people who already have influenza to reduce the severity of symptoms and reduce the number of days that they are sick.

The term "chemotherapy" refers to the use of medications, e.g. small molecule drugs (rather than "vaccines") for treating a disorder or disease.

The terms "prophylaxis" or "prophylactic use" and "prophylactic treatment" as used herein, refer to any medical or public health procedure whose purpose is to prevent, rather than treat or cure a disease. As used herein, the terms "prevent", "prevention" and "preventing" refer to the reduction in the risk of acquiring or developing a given condition, or the reduction or inhibition of the recurrence or said condition in a subject who is not ill, but who has been or may be near a person with the disease. The term "chemoprophylaxis" refers to the use of medications, e.g. small molecule drugs (rather than "vaccines") for the prevention of a disorder or disease.

As used herein, prophylactic use includes the use in situations in which an outbreak has been detected, to prevent contagion or spread of the infection in places where a lot of people that are at high risk of serious influenza complications live in close contact with each other (e.g. in a hospital ward, daycare center, prison, nursing home, etc.). It also includes the use among populations who require protection from the influenza but who either do not get protection after vaccination (e.g. due to weak immune system), or when the vaccine is unavailable to them, or when they cannot get the vaccine because of side effects. It also includes use during the two weeks following vaccination, since during that time the vaccine is still ineffective. Prophylactic use may also include treating a person who is not ill with the influenza or not considered at high risk for complications, in order to reduce the chances of getting infected with the influenza and passing it on to a high-risk person in close contact with him (for instance, healthcare workers, nursing home workers, etc.).

According to the US CDC, an influenza "outbreak" is defined as a sudden increase of acute febrile respiratory illness (AFRI) occurring within a 48 to 72 hour period, in a group of people who are in close proximity to each other (e.g. in the same area of an assisted living facility, in the same household, etc.) over the normal background rate or when any subject in the population being analyzed tests positive for influenza. One case of confirmed influenza by any testing method is considered an outbreak.

A "cluster" is defined as a group of three or more cases of AFRI occurring within a 48 to 72 hour period, in a group of people who are in close proximity to each other (e.g. in the same area of an assisted living facility, in the same household, etc.).

As used herein, the "index case", "primary case" or "patient zero" is the initial patient in the population sample of an epidemiological investigation. When used in general to refer to such patients in epidemiological investigations, the term is not capitalized. When the term is used to refer to a specific person in place of that person's name within a report on a specific investigation, the term is capitalized as Patient Zero. Often scientists search for the index case to determine how the disease spread and what reservoir holds the disease in between outbreaks. Note that the index case is the first patient that indicates the existence of an outbreak. Earlier cases may be found and are labeled primary, secondary, tertiary, etc.

In one embodiment, the methods of the invention are a preventative or "pre-emptive" measure to a patient, specifically a human, having a predisposition to complications resulting from infection by an influenza virus. The term "pre-emptive" as used herein as for example in pre-emptive use, "pre-emptively", etc., is the prophylactic use in situations in which an "index case" or an "outbreak" has been confirmed, in order to prevent the spread of infection in the rest of the community or population group.

In another embodiment, the methods of the invention are applied as a "pre-emptive" measure to members of a community or population group, specifically humans, in order to prevent the spread of infection.

As used herein, an "effective amount" refers to an amount sufficient to elicit the desired biological response. In the present invention the desired biological response is to inhibit the replication of influenza virus, to reduce the amount of influenza viruses or to reduce or ameliorate the severity, duration, progression, or onset of a influenza virus infection, prevent the advancement of an influenza viruses infection, prevent the recurrence, development, onset or progression of a symptom associated with an influenza virus infection, or enhance or improve the prophylactic or therapeutic effect(s) of another therapy used against influenza infections. The precise amount of compound administered to a subject will depend on the mode of administration, the type and severity of the infection and on the characteristics of the subject, such as general health, age, sex, body weight and tolerance to drugs. The skilled artisan will be able to determine appropriate dosages depending on these and other factors. When co-administered with other antiviral agents, e.g., when co-administered with an anti-influenza medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, the compounds disclosed herein can be administered to a subject in a dosage range from between approximately 0.01 to 100 mg/kg body weight/day for therapeutic or prophylactic treatment.

Generally, dosage regimens can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe the effective amount of the compounds described herein required to treat, to prevent, inhibit (fully or partially) or arrest the progress of the disease.

Dosages of the compounds described herein can range from between 0.01 to 100 mg/kg body weight/day, 0.01 to 50 mg/kg body weight/day, 0.1 to 50 mg/kg body weight/day, or 1 to 25 mg/kg body weight/day. It is understood that the total amount per day can be administered in a single dose or can be administered in multiple dosing, such as twice a day (e.g., every 12 hours), three times a day (e.g., every 8 hours), or four times a day (e.g., every 6 hours).

In some embodiments, dosages of the compounds described herein (e.g., Compound (1) and its pharmaceutically acceptable salts thereof, including the various solid forms) are in a range of 100 mg to 1,600 mg, such as 400 mg to 1,600 mg or 400 mg to 1,200 mg. Each dose can be taken once a day (QD), twice per day (e.g., every 12 hours (BID)), or three times per day (e.g., q8 h (TID)). It is noted that any combinations of QD, BID, and TID can be employed, as desired, such as BID on day 1, followed by QD thereafter.

In one specific embodiment, dosages of the compounds described herein are from 400 mg to 1,600 mg, from 400 mg to 1,200 mg, or from 600 mg to 1,200 mg once a day. In another specific embodiment, dosages of the compounds described herein are from 400 mg to 1,600 mg, from 400 mg to 1,200 mg, or from 300 mg to 900 mg twice a day. In yet another specific embodiment, dosages of the compounds described herein are from 400 mg to 1,000 mg once a day. In yet another specific embodiment, dosages of the compounds described herein are from 600 mg to 1,000 mg once a day. In yet another specific embodiment, dosages of the compounds described herein are from 600 mg to 800 mg once a day. In yet another specific embodiment, dosages of the compounds described herein are from 400 mg to 800 mg twice a day (e.g., from 400 mg to 800 mg every 12 hours). In yet another specific embodiment, dosages of the compounds described herein are from 400 mg to 600 mg twice a day.

In some embodiments, a loading dosage regimen is employed. In one specific embodiment, a loading dose of from 400 mg to 1,600 mg is employed on day 1 of treatment. In another specific embodiment, a loading dose of from 600 mg to 1,600 mg is employed on day 1 of treatment. In another specific embodiment, a loading dose of from 800 mg to 1,600 mg is employed on day 1 of treatment. In yet another specific embodiment, a loading dose of from 900 mg to 1,600 mg is employed on day 1 of treatment. In yet another specific embodiment, a loading dose of from 900 mg to 1,200 mg is employed on day 1 of treatment. In another specific embodiment, a loading dose of 900 mg is employed on day 1 of treatment. In yet another specific embodiment, a loading dose of 1,000 mg is employed on day 1 of treatment. In yet another specific embodiment, a loading dose of 1,200 mg is employed on day 1 of treatment.

In one specific embodiment, the dosage regimen of the compounds described herein employs a loading dosage of 600 mg to 1,600 mg on day 1 and with a regular dosage of 300 mg to 1,200 mg for the rest of the treatment duration. Each regular dose can be taken once a day, twice a day, or three times a day, or any combination thereof. In a further specific embodiment, a loading dosage of 900 mg to 1,600 mg, such as 900 mg, 1,200 mg, or 1,600 mg, is employed. In another further specific embodiment, a loading dosage of 900 mg to 1,200 mg, such as 900 mg or 1,200 mg, is employed. In yet another further specific embodiment, a regular dosage of 400 mg to 1,200 mg, such as 400 mg, 600 mg, or 800 mg, is employed for the rest of the treatment duration. In yet another further specific embodiment, a regular dosage of 400 mg to 1,000 mg for the rest of the treatment duration. In yet another further specific embodiment, a regular dosage of 400 mg to 800 mg is employed for the rest of the treatment duration. In yet another further specific embodiment, a regular dosage of 300 mg to 900 mg twice a day is employed. In yet another further specific embodiment, a regular dosage of 600 mg to 1,200 mg once a day is employed. In yet another further specific embodiment, a regular dosage of 600 mg twice a day on day 2, followed by 600 mg once a day for the rest of the treatment duration.

For therapeutic treatment, the compounds described herein can be administered to a patient within, for example, 48 hours (or within 40 hours, or less than 2 days, or less than 1.5 days, or within 24 hours) of onset of symptoms (e.g., nasal congestion, sore throat, cough, aches, fatigue, headaches, and chills/sweats). Alternatively, for therapeutic treatment, the compounds described herein can be administered to a patient within, for example, 96 hours of onset of symptoms. The therapeutic treatment can last for any suitable duration, for example, for 3 days, 4 days, 5 days, 7 days, 10 days, 14 days, etc. For prophylactic treatment during a community outbreak, the compounds described herein can be administered to a patient within, for example, 2 days of onset of symptoms in the index case, and can be continued for any suitable duration, for example, for 7 days, 10 days, 14 days, 20 days, 28 days, 35 days, 42 days, etc., up to the entire flu season. A flu season is an annually-recurring time period characterized by the prevalence of outbreaks of influenza. Influenza activity can sometimes be predicted and even tracked geographically. While the beginning of major flu activity in each season varies by location, in any specific location these minor epidemics usually take 3-4 weeks to peak and another 3-4 weeks to significantly diminish. Typically, Centers for Disease Control (CDC) collects, compiles and analyzes information on influenza activity year round in the United States and produces a weekly report from October through mid-May.

In one embodiment, the therapeutic treatment lasts for 1 day to an entire flu season. In one specific embodiment, the therapeutic treatment lasts for 3 days to 14 days. In another specific embodiment, the therapeutic treatment lasts for 5 days to 14 days. In another specific embodiment, the therapeutic treatment lasts for 3 days to 10 days. In yet another specific embodiment, the therapeutic treatment lasts for 4 days to 10 days. In yet another specific embodiment, the therapeutic treatment lasts for 5 days to 10 days. In yet another specific embodiment, the therapeutic treatment lasts for 4 days to 7 days (e.g., 4 days, 5 days, 6 days, or 7 days). In yet another specific embodiment, the therapeutic treatment lasts for 5 days to 7 days (e.g., 5 days, 6 days, or 7 days). In one specific embodiment, the prophylactic treatment lasts up to the entire flu season.

In one specific embodiment, the compounds described herein are administered to a patient for 3 days to 14 days (e.g., 5 days to 14 days) with a loading dosage of 900 mg to 1,600 mg on day 1 and with a regular dosage of 300 mg to 1,200 mg for the rest of the treatment duration. In another specific embodiment, the compounds described herein are administered to a patient for 3 days to 14 days (e.g., 5 days to 14 days) with a loading dosage of 900 mg to 1,200 mg on day 1 and with a regular dosage of 400 mg to 1,000 mg for the rest of the treatment duration. In yet another specific embodiment, the compounds described herein are administered to a patient for 3 days to 14 days (e.g., 5 days to 14 days) with a loading dosage of 900 mg to 1,200 mg on day 1 and with a regular dosage of 400 mg to 800 mg for the rest of the treatment duration. In yet another specific embodiment, the compounds described herein are administered to a patient for 3 days to 14 days (e.g., 5 days to 14 days) with a loading dosage of 900 mg to 1,200 mg on day 1 and with a regular dosage of 400 mg to 800 mg for the rest of the treatment duration. Each dose can be taken once a day, twice a day, or three times a day, or any combination thereof.

In one specific embodiment, the compounds described herein are administered to a patient for 3 days to 14 days with a loading dosage of 900 mg to 1,600 mg on day 1 and with a regular dosage of 600 mg to 1,000 mg once a day for the rest of the treatment duration. In another specific embodiment, the compounds described herein are administered to a patient for 3 days to 14 days with a loading dosage of 900 mg to 1,200 mg on day 1 and with a regular dosage of 600 mg to 800 mg (e.g., 600 mg, 650 mg, 700 mg, 750 mg, or 800 mg) once a day for the rest of the treatment duration. In some embodiments, the treatment duration is for 4 days to 10 days, 5 days to 10 days, or 5 days to 7 days.

In one specific embodiment, the compounds described herein are administered to a patient for 3 days to 14 days with a loading dosage of 900 mg to 1,600 mg on day 1 and with a regular dosage of 400 mg to 800 mg twice a day for the rest of the treatment duration. In another specific embodiment, the compounds described herein are administered to a patient for 3 days to 14 days with a loading dosage of 900 mg to 1,200 mg on day 1 and with a regular dosage of 400 mg to 600 mg (e.g., 400 mg, 450 mg, 500 mg, 550 mg, or 600 mg) twice a day for the rest of the treatment duration. In some embodiments, the duration is for 4 days to 10 days, 5 days to 10 days, or 5 days to 7 days.

In one specific embodiment, the compounds described herein are administered to a patient for 4 days or 5 days with a loading dosage of 900 mg to 1,200 mg (e.g., 900 mg or 1,200 mg) on day 1 and with a regular dosage of 400 mg to 600 mg (e.g., 400 mg or 600 mg) twice a day for the rest of the treatment duration (e.g., days 2 through 4, or days 2 through 5).

In another specific embodiment, the compounds described herein are administered to a patient for 4 days or 5 days with a loading dosage of 900 mg to 1,200 mg (e.g., 900 mg or 1,200 mg) on day 1 and with a regular dosage of 600 mg to 800 mg (e.g., 600 mg or 800 mg) once a day for the rest of the treatment duration.

Various types of administration methods can be employed in the invention, and are described in detail below under the section entitled "Administration Methods".

IV. Combination Therapy

An effective amount can be achieved in the method or pharmaceutical composition of the invention employing a compound of the invention (including a pharmaceutically acceptable salt or solvate (e.g., hydrate)) alone or in combination with an additional suitable therapeutic agent, for example, an antiviral agent or a vaccine. When "combination therapy" is employed, an effective amount can be achieved using a first amount of a compound of the invention and a second amount of an additional suitable therapeutic agent (e.g. an antiviral agent or vaccine).

In another embodiment of this invention, a compound of the invention and the additional therapeutic agent, are each administered in an effective amount (i.e., each in an amount which would be therapeutically effective if administered alone). In another embodiment, a compound of the invention and the additional therapeutic agent, are each administered in an amount which alone does not provide a therapeutic effect (a sub-therapeutic dose). In yet another embodiment, a compound of the invention can be administered in an effective amount, while the additional therapeutic agent is administered in a sub-therapeutic dose. In still another embodiment, a compound of the invention can be administered in a sub-therapeutic dose, while the additional therapeutic agent, for example, a suitable cancer-therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Coadministration encompasses administration of the first and second amounts of the compounds of the coadministration in an essentially simultaneous manner, such as in a single pharmaceutical composition, for example, capsule or tablet having a fixed ratio of first and second amounts, or in multiple, separate capsules or tablets for each. In addition, such coadministration also encompasses use of each compound in a sequential manner in either order.

In one embodiment, the present invention is directed to methods of combination therapy for inhibiting Flu viruses replication in biological samples or patients, or for treating or preventing Influenza virus infections in patients using the compounds described herein. Accordingly, pharmaceutical compositions of the invention also include those comprising an inhibitor of Flu virus replication of this invention in combination with an anti-viral compound exhibiting anti-Influenza virus activity.

Methods of use of the compounds described herein and compositions of the invention also include combination of chemotherapy with a compound or composition of the invention, or with a combination of a compound or composition of this invention with another anti-viral agent and vaccination with a Flu vaccine.

When co-administration involves the separate administration of the first amount of a compound of the invention and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of the invention and the second therapeutic agent can be administered in any order within 24 hours of each other, within 16 hours of each other, within 8 hours of each other, within 4 hours of each other, within 1 hour of each other or within 30 minutes of each other.

More, specifically, a first therapy (e.g., a prophylactic or therapeutic agent such as a compound of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

It is understood that the method of co-administration of a first amount of a compound of the invention and a second amount of an additional therapeutic agent can result in an enhanced or synergistic therapeutic effect, wherein the combined effect is greater than the additive effect that would result from separate administration of the first amount of a compound of the invention and the second amount of an additional therapeutic agent.

As used herein, the term "synergistic" refers to a combination of a compound of the invention and another therapy (e.g., a prophylactic or therapeutic agent), which is more effective than the additive effects of the therapies. A synergistic effect of a combination of therapies (e.g., a combination of prophylactic or therapeutic agents) can permit the use of lower dosages of one or more of the therapies and/or less frequent administration of said therapies to a subject. The ability to utilize lower dosages of a therapy (e.g., a prophylactic or therapeutic agent) and/or to administer said therapy less frequently can reduce the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies (e.g., a combination of prophylactic or therapeutic agents) may avoid or reduce adverse or unwanted side effects associated with the use of either therapy alone.

When the combination therapy using the compounds of the present invention is in combination with a Flu vaccine, both therapeutic agents can be administered so that the period of time between each administration can be longer (e.g. days, weeks or months).

The presence of a synergistic effect can be determined using suitable methods for assessing drug interaction. Suitable methods include, for example, the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

Specific examples that can be co-administered with a compound described herein include neuraminidase inhibitors, such as oseltamivir (Tamiflu®) and Zanamivir (Rlenza®), viral ion channel (M2 protein) blockers, such as amantadine (Symmetrel®) and rimantadine (Flumadine®), and antiviral drugs described in WO 2003/015798, including T-705 under development by Toyama Chemical of Japan.

(See also Ruruta et al., Antiviral Research, 82: 95-102 (2009), "T-705 (flavipiravir) and related compounds: Novel broad-spectrum inhibitors of RNA viral infections"). In some embodiments, the compounds described herein can be co-administered with a traditional influenza vaccine. In some embodiments, the compounds described herein can be co-administered with Zanamivir. In some embodiments, the compounds described herein can be co-administered with oseltamivir. In some embodiments, the compounds described herein can be co-administered with T-705. In some embodiments, the compounds described herein can be co-administered with amantadine or rimantadine. Oseltamivir can be administered in a dosage regimen specified in its label. In some specific embodiments, it is administered 75 mg twice a day, or 150 mg once a day.

V. Pharmaceutical Compositions

The compounds described herein can be formulated into pharmaceutical compositions that further comprise a pharmaceutically acceptable carrier, diluent, adjuvant or vehicle. In one embodiment, the present invention relates to a pharmaceutical composition comprising a compound of the invention described above, and a pharmaceutically acceptable carrier, diluent, adjuvant or vehicle. In one embodiment, the present invention is a pharmaceutical composition comprising an effective amount of a compound of the present invention or a pharmaceutically acceptable salt thereof and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

An "effective amount" includes a "therapeutically effective amount" and a "prophylactically effective amount". The term "therapeutically effective amount" refers to an amount effective in treating and/or ameliorating an influenza virus infection in a patient infected with influenza. The term "prophylactically effective amount" refers to an amount effective in preventing and/or substantially lessening the chances or the size of influenza virus infection outbreak. Specific examples of effective amounts are described above in the section entitled Uses of Disclosed Compounds.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds described herein, such as by producing any undesirable biological effect or otherwise interacting in a deleterious manner with any other component(s) of the pharmaceutically acceptable composition, its use is contemplated to be within the scope of this invention. As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

VI. Administration Methods

The compounds and pharmaceutically acceptable compositions described above can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Specifically, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The compounds can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., 1 to 4 or more times per day). When multiple daily doses are used, the unit dosage form can be the same or different for each dose.

VII. Examples

Example 1: Preparation of 2-Amino-3-bromo-5-fluoropyridine (Compound 2a)

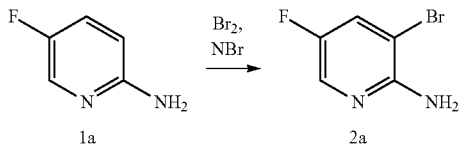 [SMILES: Nc1ccc(F)cn1 ; Nc1ncc(F)cc1Br]

Procedure A:

To a slurry of 2-amino-5-fluoropyridine (6 kg, 53.6 mol) in water (24 L) at 14° C. was added over 10 minutes 48% hydrobromic acid (18.5 kg, 110 mol). The reaction was exothermic and the temperature went up to 24° C. The mixture was re-cooled to 12° C. then bromine (9 kg, 56.3 mol) was added in nine portions over 50 minutes (exothermic, kept at 20° C.). The mixture was stirred at 22° C. overnight, and monitored by $^1$HNMR of a quenched aliquot (quenched 5 drops in to mix of 1 ml 20% $K_2CO_3$, 0.3 ml 10% $Na_2S_2O_3$ and 0.7 ml DCM. Organic layer evaporated and assayed). The mixture was cooled to 10° C. then quenched by addition of sodium bisulfite (560 g, 5.4 mol) in water (2 L), and further cooled to 0° C. This mixture was added to a cold (−4° C.) mixture of DCM (18 L) and 5.4M sodium hydroxide (35 L, 189 mol). The bottom ~35 L was filtered through a pad of Celite and then the phase break was made. The aqueous layer was re-extracted with DCM (10 L). The organics were filtered through a pad of 3 kg magnesol, washing with DCM (8 L). The filtrate was evaporated, triturated with hexane and filtered.

Despite the in-process assay indicating 97% completion, this initial product from all four runs typically contained ~10% SM. These were combined and triturated in hexane (2 L per kg material) at 50° C., then cooled to 15° C. and filtered to afford Compound 2a (30.0 kg, ~95% purity, 149 mol, 67%). Mother liquors from the initial trituration and the re-purification were chromatographed (20 kg silica, eluent 25-50% EtOAc in hexane) to afford additional Compound 2a (4.7 kg, ~99% purity, 24.4 mol, 11%).

Procedure B:

Alternatively the bromination was performed by employing HOAc instead of HBr. In one specific example, aminopyridine (952 g, 8.49 mmol) was dissolved in HOAc (7 L) and was treated with NaOAc (1.04 kgs, 12.7 mmol) followed by the dropwise addition of Br2 (with a dropping funnel-ice was used to cool the reaction). After the addition of Br2 the reaction was allowed to stir at rt overnight. The reaction mixture was poured into water and made basic with the addition of 6N NaOH. The reaction was extracted with EtOAc. A significant amount of solid did not dissolve in the organic or aqueous phase. The entire mixture was filtered and the phases separated. The organic layer was dried (MgSO4) filtered over a SiO2 plug eluting with EtOAc. The filtrate was evaporated to give a brown solid, 889 g.

Procedure C:

Alternatively the bromination was performed by employing $H_2SO_4$. In one specific example, to 93% sulfuric acid (12.5 kg, 119 mol) in water (26 L) in a 50-L reactor was added 2-amino-5-fluoropyridine (6.5 kg, 58 mol). The temperature was adjusted to 30° C. then bromine (10 kg, 63 mol) added in ten portions over three hours. The mixture was stirred at 45° C. for 18 hours, then at 50° C. for 5 hours. The mixture was cooled to 15° C. for work-up in a 400-L reactor.

Four of the above reactions (4×6.5 kg) were combined and quenched in to a mixture of 50% sodium hydroxide (110 kg, 1375 mol) and sodium thiosulfate (1.8 kg, 11.4 mol) in water (100 L) at −3° C. over one hour. The temperature was adjusted to 32° C. and the slurry filtered and washed with water (80 L) to afford water-wet crude product (62 kg). A second run of three reactions (3×6.5 kg SM) was similarly carried out to afford water-wet crude product (41 kg). The crude products (103 kg) were dissolved (some insolubles) in toluene (280 kg) at 25-30° C. Brine (20 kg) was added but phase break not possible due to solids. The mixture was filtered through a pad of Celite, washing with toluene, and the layers then separated. The organics were concentrated to 347 L volume to azeotrope residual water for the use of the preparation of compound 3a. An aliquot was used to determine product concentration as being 181 g per liter of solution. Yield=62.8 kg. An additional 600 g was isolated by extraction of the water/brine layer with ethyl acetate (10 L), and subsequent filtration through a pad of magnesol, evaporation and trituration with hexane. Total yield is 82%.

Preparation of Compound 3a

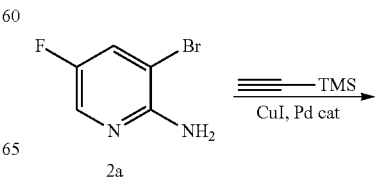

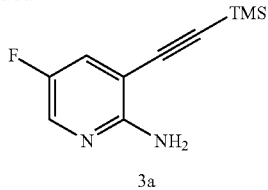

Procedure A:

To an inert 400-L reactor was charged 2a (27.5 kg, 96% purity, 138 mol), Pd(PPh$_3$)$_4$ (1044 g, 0.90 mol) and CuI (165 g, 0.87 mol), followed by toluene (90 kg). The mixture was de-oxygenated with three vacuum-nitrogen cycles, then triethylamine (19.0 kg, 188 mol) was added. The mixture was de-oxygenated with one more vacuum-nitrogen cycle, then TMS-acetylene (16.5 kg, 168 mol) was added. The mixture was heated to 48° C. for 23 hours (the initial exotherm took the temperature to 53° C. maximum), then cooled to 18° C. The slurry was filtered through a pad of Celite and washed with toluene (80 kg). The filtrate was washed with 12% Na$_2$HPO$_4$ (75 L), then filtered through a pad of silica (25 kg), washing with 1:1 hexane:MTBE (120 L). This filtrate was evaporated to a brown oil and then dissolved in NMP for the next step. Weight of a solution of Compound 3a—58 kg, ~50 wt %, 138 mol, 100%. $^1$H NMR (CDCl$_3$, 300 MHz): δ 7.90 (s, 1H); 7.33-7.27 (m, 1H); 4.92 (s, NH$_2$), 0.28 (s, 9H) ppm.

Procedure B:

2-Amino-3-bromo-5-fluoropyridine (2a: 10.7 g, 56 mmol) was treated with CuI (1.72 g, 9.03 mmol), Pd (dppf)Cl$_2$ (2.87 g, 3.92 mmol), TMS acetylene (8.25 g, 11.8 mL, 84 mmol), THF (200 mL) and Et$_3$N (190 mL) and warmed to reflux overnight. The reaction was judged complete by TLC and poured into water (200 mL). Phases separated and the phases were extracted with EtOAc (3×200 mL). Organic phases were combined and dried (MgSO$_4$), filtered and filtrate concentrated in vacuo to give an oil that solidified on vacuum. The solid was dissolved in CH$_2$Cl$_2$ and run through a plug of SiO$_2$ eluting with CH$_2$Cl$_2$ to give a yellow solid, 11.7 g, 93% yield.

Preparation of Compound 4a

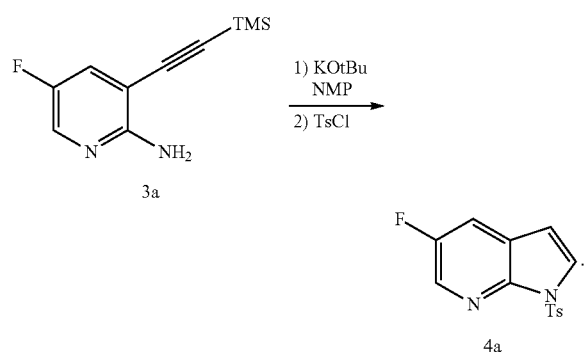

To an inert 400-L reactor was charged potassium t-butoxide (17.5 kg, 156 mol) and NMP (45 kg). The mixture was heated to 54° C. then a solution of Compound 3a (29 kg, 138 mol) in NMP (38 kg) was added over 2.75 hours and rinsed in with NMP (6 kg) (exothermic, maintained at 70-77° C.). The reaction was stirred at 74° C. for 2 hours then cooled to 30° C. and a solution of tosyl chloride (28.5 kg, 150 mol) in NMP (30 kg) added over 1.5 hours and rinsed in with NMP (4 kg). The reaction was exothermic and maintained at 30-43° C. The reaction was stirred for 1 hour while cooling to 20° C. then water (220 L) was added over 35 minutes (exothermic, maintained at 18-23° C.). The mixture was stirred at 20° C. for 30 minutes then filtered and washed with water (100 L). The solids were dissolved off the filter with DCM (250 kg), separated from residual water and the organics filtered through a pad of magnesol (15 kg, top) and silica (15 kg, bottom), washing with extra DCM (280 kg). The filtrate was concentrated to a thick slurry (~50 L volume) then MTBE (30 kg) was added while continuing the distillation at constant volume (final distillate temperature of 51° C.). Additional MTBE (10 kg) was added and the slurry cooled to 15° C., filtered and washed with MTBE (40 L) to afford Compound 4a (19.13 kg, 95% purity, 62.6 mol, 45%). Partial concentration of the filtrate afforded a second crop (2.55 kg, 91% purity, 8.0 mol, 6%). $^1$H NMR (CDCl$_3$, 300 MHz): δ 8.28-8.27 (m, 1H); 8.06-8.02 (m, 2H); 7.77 (d, J=4.0 Hz, 1H); 7.54-7.50 (m, 1H); 7.28-7.26 (m, 2H); 6.56 (d, J=4.0 Hz, 1H); 2.37 (s, 3H) ppm.

Preparation of Compound 5a

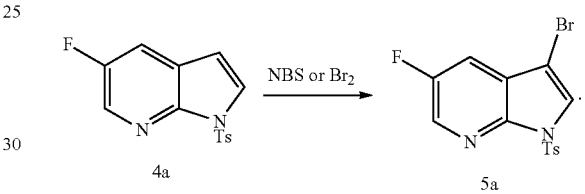

Procedure A:

To a slurry of N-bromosuccinimide (14.16 kg, 79.6 mol) in DCM (30 kg) at 15° C. was charged a solution of Compound 4a (19.13 kg, 95% purity, and 2.86 kg, 91% purity, 71.6 mol) in DCM (115 kg), rinsing in with DCM (20 kg). The mixture was stirred at 25° C. for 18 hours, and then cooled to 9° C. and quenched by addition of a solution of sodium thiosulfate (400 g) and 50% sodium hydroxide (9.1 kg) in water (130 L). The mixture was warmed to 20° C. and the layers were separated and the organics were washed with 12% brine (40 L). The aqueous layers were sequentially re-extracted with DCM (4×50 kg). The organics were combined and 40 L distilled to azeotrope water, then the solution was filtered through a pad of silica (15 kg, bottom) and magensol (15 kg, top), washing with DCM (180 kg). The filtrate was concentrated to a thick slurry (~32 L volume) then hexane (15 kg) was added. Additional hexane (15 kg) was added while continuing the distillation at constant volume (final distillate temperature 52° C.). The slurry was cooled to 16° C., filtered and washed with hexane (25 kg) to afford Compound 5a (25.6 kg, 69.3 mol, 97%). $^1$H NMR (CDCl$_3$, 300 MHz): δ 8.34-8.33 (m, 1H); 8.07 (d, J=8.2 Hz, 2H); 7.85 (s, 1H); 7.52-7.49 (m, 1H); 7.32-7.28 (m, 2H); 2.40 (s, 3H) ppm.

Procedure B:

A solution of Br$_2$ (115 mL, 1.15 eq) in CH$_2$Cl$_2$ (1 L) was added, dropwise, to a solution of compound 4a (566 g, 1.95 mol) in CH$_2$Cl$_2$ (4 L) over 90 minutes. During the addition the temperature increased from 16 to 23° C. and the reaction mixture was cooled with an ice-salt bath to 10° C. After the addition was complete the temperature had reached 12° C. The suspension (an orange solid had formed during addition) was stirred for 30 minutes. The reaction mixture was stirred at RT overnight. Sat. aq. NaHCO$_3$ (4 L) was added, carefully, over 5-10 minutes. The reaction mixture was stirred vigorously for 1 hour and the layers were allowed to separate. The resulting solution was filtered over a filter. The organic layer was washed with sat. aq. NaHCO$_3$ (2 L) and brine (2×1 L), dried over Na$_2$SO$_4$ and flushed over silica (2 kg), eluting with CH$_2$Cl$_2$ (~10 L total). The solvents (~20 L) were removed under reduced pressure to give compound 5a (580 g) as a white solid. The product was redissolved in CH$_2$Cl$_2$ (2.5 L) and filtered over another filter with silica (2 kg), eluting with CH$_2$Cl$_2$. After the solvents were removed under reduced pressure compound 5a (568 g, 79% yield) was obtained as an off-white solid. After a test reaction for the next step the remaining material was washed with heptanes (2×) and dried to give better results in the next step. $^1$H NMR (CDCl$_3$, 300 MHz): δ 8.34-8.33 (m, 1H); 8.07 (d, J=8.2 Hz, 2H); 7.85 (s, 1H); 7.52-7.49 (m, 1H); 7.32-7.28 (m, 2H); 2.40 (s, 3H) ppm.

Preparation of Compound 6a: BEFTAI Reaction

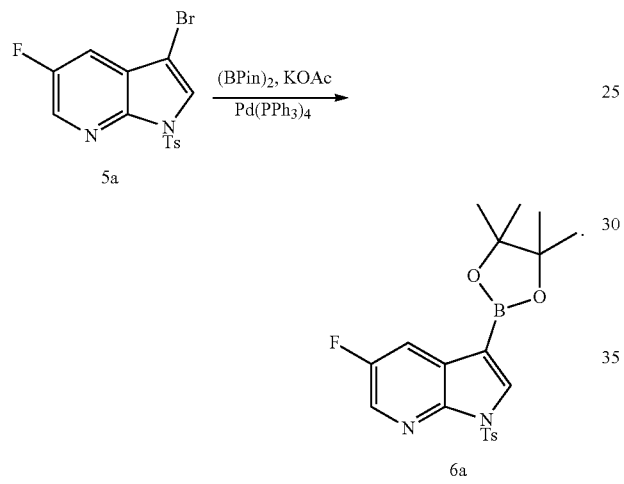

To an inert 400-L reactor was charged Compound 5a (25.6 kg, 69.3 mol), bis(pinacolato)diboron (19 kg, 74.8 mol), potassium acetate (19 kg, 194 mol), palladium acetate (156 g, 0.69 mol) and triphenylphosphine (564 g, 2.15 mol), followed by dioxane (172 kg), that had been separately de-oxygenated using vacuum-nitrogen cycles (×3). The mixture was stirred and de-oxygenated using vacuum-nitrogen cycles (×2), then heated to 100° C. for 15 hours. The mixture was cooled to 35° C. then filtered, washing with 30° C. THF (75 kg). The filtrate was evaporated and the residue dissolved in DCM (~90 L). The solution was stirred with 1 kg carbon and 2 kg magnesol for 45 minutes then filtered through a pad of silica (22 kg, bottom) and magensol (10 kg, top), washing with DCM (160 kg). The filtrate was concentrated to a thick slurry (~40 L volume) then triturated at 35° C. and hexane (26 kg) was added. The slurry was cooled to 20° C., filtered and washed with a mix of DCM (5.3 kg) and hexane (15 kg), then hexane (15 kg) and dried under nitrogen on the filter to afford Compound 6a (23.31 kg, 56.0 mol, 81%) as a white solid. $^1$H-NMR consistent with desired product, HPLC 99.5%, palladium assay 2 ppm. $^1$H NMR (CDCl$_3$, 300 MHz): δ 8.25 (s, 1H); 8.18 (s, 1H); 8.09-8.02 (m, 2H); 7.91-7.83 (m, 1H); 7.30-7.23 (m, 2H); 2.39 (s, 3H); 1.38 (s, 12H) ppm.

Preparation of Compounds 8a and 9a

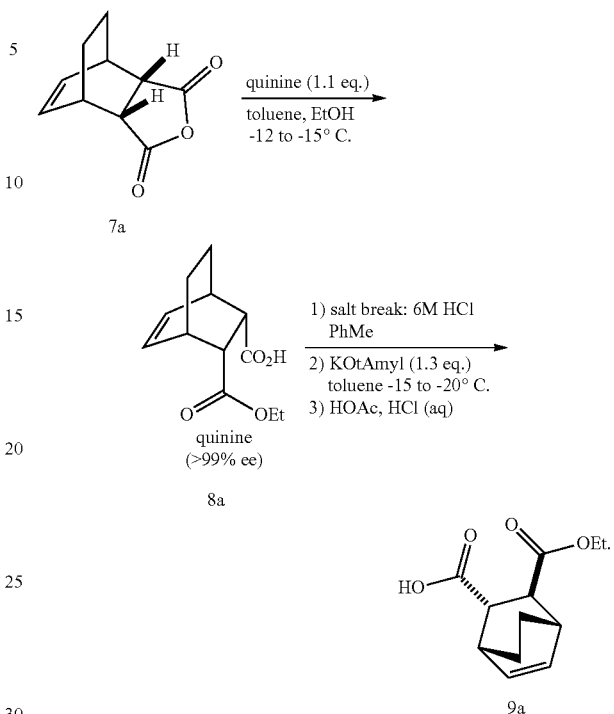

Compound 8a:

Anhydride 7a (24.6 kgs, Apex) and quinine (49.2 kgs, Buchler) were added to a reactor followed by the addition of anhydrous PhMe (795.1 kgs). The reactor was then cooled to −16° C. and EtOH (anhydrous, 41.4 kgs) was added at such a rate to maintain the internal reactor temperature <−12° C. The maximum reaction temp recorded for this experiment was −16° C. The reaction mixture was then stirred for 16 h at −16° C. A sample was removed and filtered. The solid was dried and evaluated by $^1$H-NMR which showed that no anhydride remained. The contents of the reactor were filtered. The reactor and subsequent wet cake were washed with PhMe (anhydrous, 20 kgs). The resulting solid was placed in a tray dryer at <45° C. with a N$_2$ sweep for at least 48 h. In this experiment, the actual temperature was 44° C. and the vacuum was −30 inHG. Material was sampled after 2.5 d drying and showed 3% PhMe by NMR. After an additional 8 hrs, the amt of PhMe analyzed showed the same 3% PhMe present and the drying was stopped. The weight of the white solid was 57.7 kgs, 76% yield. $^1$H-NMR showed consistent with structure and Chiral SFC analysis showed material >99% de.

Compound 9a:

The reactor was charged with quinine salt 8a (57.7 kgs) and PhMe (250.5 kgs, Aldrich ACS grade, >99.5%) and the agitator was started. The contents were cooled to <15° C. and was treated with 6N HCl (18 kgs H$_2$O were treated with 21.4 kgs of conc. HCl) while keeping the temperature <25° C. The mixture was stirred for 40 min and visually inspected to verify that no solids were present. Stirring was stopped and the phases were allowed to settle and phases were separated. The aqueous phases were extracted again with PhMe (160 kgs; the amount typically used was much less, calc. 43 kgs. However, for efficient stirring due to minimal volume, additional PhMe was added. The organic phases were combined. Sample the organic phase and run HPLC analysis to insure product is present; for information only test.

To the organic phases were cooled to <5° C. (0-5° C.) and was added sodium sulfate (anhydrous, 53.1 kgs) with agitation for 8 hrs (in this instance 12 hrs). The contents of the reactor containing the organic phase were passed through a filter containing sodium sulfate (31 kgs, anhydrous) and into a cleaned and dried reactor. The reactor was rinsed with PhMe (57.4 kgs), passed through the filter into reactor 201. The agitator was started and an additional amount of PhMe (44 kgs) was added and the reaction mixture cooled to −20° C. At that temperature PhMe solution of potassium tert-pentoxide was added over 2 h while keeping the temperature between −15 and −22° C. The reaction mixture was held at approximately −20° C. for an additional 30 min before being sampled. Sampling occurred by removing an aliquot with immediate quenching into 6N HCl.

Having achieved the target ratio (96:4 (trans:cis), the reactor was charged with acetic acid (2.8 kgs) over 6 min. The temperature stayed at −20° C. The temperature was then adjusted to −5° C. and aqueous 2N HCl (65.7 kgs water treated with 15.4 kgs of conc HCl) was added. The contents were warmed to 5° C.+/−5° C., agitated for 45 min before warming to 20° C.+/−5° C. with stirring for 15 min. The agitator was stopped and the phases allowed to settle. The aqueous layer was removed. The organic phase was washed with water (48 kgs, potable), agitated for 15 min and phases allowed to settle (at least 15 min) and the aqueous layer was removed and added to the aqueous layer. ⅓ of a buffer solution (50 L) that was prepared (7.9 kgs $NaH_2PO_4$, 1.3 kgs of $Na_2HPO_4$ and 143.6 kgs water) was added to the organic phase and stirred for at least 15 min. Agitation was stopped and phases were allowed to separate for at least 15 min. The lower layer was discarded. Another portion of the buffered solution (50 L) was used to wash the organic layer as previously described. The wash was done a third time as described above.

Vacuum distillation of the PhMe phase (150 L) was started at 42° C./−13.9 psig and distilled to an oil of approximately 20 L volume. After substantial reduction in volume the mixture was transferred to a smaller vessel to complete the distillation. Heptanes (13.7 kgs) was added and the mixture warmed to 40+/−5° C. for 30 min then the contents were cooled to 0-5° C. over 1.5 h. The solids were filtered and the reactor washed with approximately 14 kgs of cooled (0-5° C.) heptanes. The solids were allowed to dry under vacuum before placing in the oven at <40° C. under house vac (−28 psig) until LOD is <1%. 15.3 kgs, 64%, 96% HPLC purity. $^1$H NMR (400 MHz, $CDCl_3$) δ 11.45 (br. s, 1H), 6.41 (t, J=7.2 Hz, 1H), 6.25 (t, J=7.2 Hz, 1H), 4.18 (m, 2H), 3.27 (m, 1H), 3.03 (m, 1H), 2.95 (m, 1H), 2.77 (m, 1H), 1.68 (m, 1H), 1.49 (m, 1H), 1.25 (t, J=7.2 Hz), 1.12 (m, 1H).

Preparation of Compound 10a

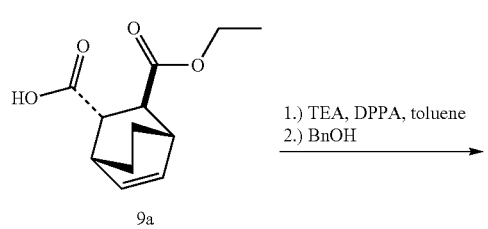

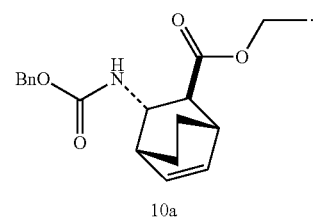

A three neck flask equipped with a mechanical stirrer, temperature probe, reflux condenser, addition funnel and nitrogen inlet was charged with Compound 9a (145.0 g, 1 equiv) and anhydrous toluene (Aldrich, cat #244511) (1408 g, 1655 ml) under an atmosphere of nitrogen. Then triethylamine (Aldrich, cat #471283) (140 g, 193 ml, 2.14 equiv) was added in portions over 5 minutes to the stirred solution during which an exotherm to a maximum temperature of 27° C. was observed. Data acquisition by ReactIR was started. The reaction mixture was then heated to 95° C. over 70 minutes. Then diphenyl phosphoryl azide (Aldrich, cat #178756) (176.2 g; 138.0 ml, 0.99 equiv) was added by addition funnel in portions over a total time of 2.25 hours.

Following completion of the addition of diphenyl phosphoryl azide (addition funnel rinsed with a small amount of toluene), the resulting mixture was heated at 96° C. for an additional 50 minutes. A sample of the reaction mixture diluted in toluene was analyzed by GC/MS which indicated consumption of diphenyl phosphoryl azide. Then benzyl alcohol (Aldrich, cat #108006) (69.9 g, 67.0 ml, 1.0 equiv) was added by addition funnel over 5-10 minutes. The resulting mixture was then heated at 97° C. overnight (for approximately 19 hours). A sample of the reaction mixture diluted in toluene by GC/MS indicated formation of product (m/e=330). The reaction mixture was then cooled to 21° C. after which water (870 g, 870 ml) was added in portions (observed slight exotherm to maximum temperature of 22° C.). The reaction mixture was first quenched by addition of 500 g of water and mechanically stirred for 10 minutes. The mixture was then transferred to the separatory funnel containing the remaining 370 g of water and then manually agitated. After agitation and phase separation, the organic and aqueous layers were separated (aqueous cut at pH of ~10). The organic layer was then washed with an additional portion of water (870 g; 1×870 ml). The organic and aqueous layers were separated (aqueous cut at pH of ~10). The collected organic phase was then concentrated to dryness under reduced pressure (water bath at 45-50° C.) affording 215 g of crude Compound 10a (approximate volume of 190 ml). The $^1$H NMR and GC/MS conformed to compound 10a (with residual toluene and benzyl alcohol).

Preparation of Compound 11a

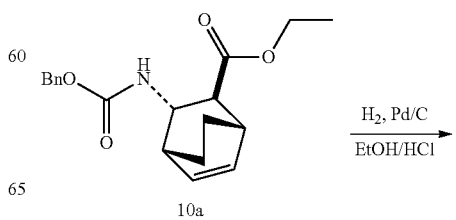

Preparation of Compound 13a

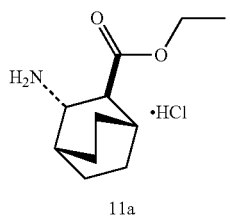

11a

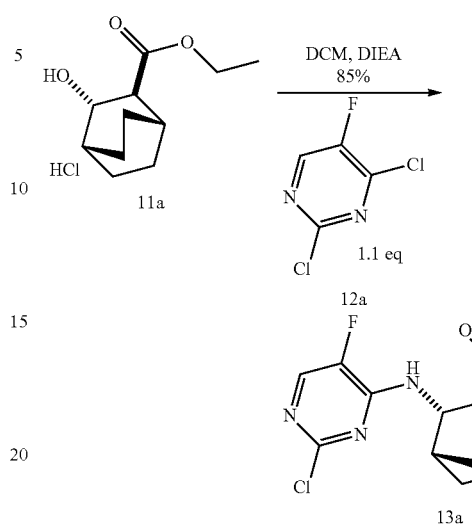

a.) HCl in Ethanol Preparation:

A three neck flask equipped with a temperature probe, nitrogen inlet and magnetic stirrer was charged with ethanol (1000 ml, 773 g) under a nitrogen atmosphere. The solution was stirred and cooled in a dry ice/acetone bath until an internal temperature of −12° C. was reached. Then anhydrous HCl (~80 g, 2.19 moles) was slowly bubbled in the cooled solution (observed temperature of −24 to −6° C. during addition) over 2 hours. Following the addition, the solution was transferred to a glass bottle and allowed to warm to ambient temperature. A sample of the solution was submitted for titration giving a concentration of 2.6 M. The solution was then stored in the cold room (approximately 5° C.) overnight.

b.) Hydrogenation/HCl Salt Formation:

A glass insert to a 2 gallon Parr autoclave was charged with palladium on carbon (Pd/C (Aldrich, cat #330108), 10% dry basis; (50% wet), 13.11 g, 0.01 equiv on the basis of Compound 10a) under a nitrogen atmosphere and then moistened with ethanol (93 g; 120 ml). Then a solution of crude Compound 10a (212 g, 1 eq) in ethanol (1246 g; 1600 ml) was added to the glass insert (small rinse with ethanol to aid with transfer). The glass insert was placed in the autoclave after which HCl in ethanol (prepared as described above; 2.6 M; 1.04 equiv based on Compound 10a; 223 g; 259 ml) was added. The autoclave was sealed and then purged with hydrogen (3× at 20 psi). The hydrogenation was then started under an applied pressure of hydrogen gas (15 psi) for 3 hours at which time the pressure of hydrogen appeared constant. Analysis of an aliquot of the reaction mixture by $^1$H NMR and GC/MS indicated consumption of starting material/formation of product. The resulting mixture was then filtered over a bed of Celite (192 g) after which the Celite bed was washed with additional ethanol (3×; a total of 1176 g of ethanol was used during the washes). The filtrate (green in color) was then concentrated under reduced pressure (water bath at 45° C.) to ~382 g ((~435 ml; 2.9 volumes based on theoretical yield of Compound 11a). Then isopropyl acetate (1539 g; 1813 ml (12 volumes based on theoretical yield of Compound 11a was added to the remainder. The resulting solution was distilled under vacuum with gradual increase in temperature.

The distillation was stopped after which the remaining solution (370 g, ~365 ml total volume; brownish in color) was allowed to stand at ambient temperature over the weekend. The mixture was filtered (isopropyl acetate used to aid with filtration) and the collected solids were washed with additional isopropyl acetate (2×116 ml; each wash was approximately 100 g). The solid was then dried under vacuum at 40° C. (maximum observed temperature of 42° C.) overnight to afford 118 g (78.1% over two steps) of Compound 11a. The $^1$H NMR of the material conformed to the structure of Compound 11a, and GC/MS indicated 99% purity.

Procedure A:

A mixture of 5-fluoro-2,4-dichloropyrimidine (12a, 39.3 g, 235 mmol, 1.1 equiv), and HCl amine salt (11a, 50 g, 214 mmol) was treated with $CH_2Cl_2$ (169 mL) and the mixture was warmed to 30° C. The mixture was then treated slowly with DIEA (60.8 g, 82 mL, 471 mmol, 2.2 equiv) via syringe pump over 3 h. Peak temp was up to 32° C. The reaction was stirred for 20 h, the reaction mixture was judged complete by HPLC and cooled to rt. The resulting reaction mixture was washed sequentially with water (211 mL, pH=8-9), 5% $NaHSO_4$ (211 mL, pH=1-2) then 5% aq. NaCl (211 mL, pH=5-6).

The organic phase was then distilled under reduced pressure to 190 mL. PhMe was charged (422 mL) and temperature set at 70-80° C. and internal temp at 60-65° C. until vol back down to 190 mL. The mixture was allowed to cool to approximately 37° C. with stirring, after approximately 10 min, crystallization began to occur and the temperature was observed to increase to approximately 41° C. After equilibrating at 37° C., the suspension was charged with n-heptane (421 mL) over 3.5 h followed by cooling to 22° C. over 1 h. The mixture was allowed to stir overnight at that temperature before filtering. The resulting solid on the filter was washed with a 10% PhMe in n-heptane solution (2×210 mL). The solid was then dried in the oven under vacuum with an $N_2$ purge at 50° C. overnight. The resulting solid weighed 62 g (88% yield).

Procedure B:

A three neck flask equipped with a mechanical stirrer, temperature probe, reflux condenser, nitrogen inlet and addition funnel was charged with Compound 11a (51.2 g) and Compound 12a (40.2 g) under an atmosphere of nitrogen. Dichloromethane (173 ml, 230 g) was added and the resulting mixture was stirred while warming to an internal temperature of 30° C. Then N,N-diisopropylethylamine (85 ml, 63.09 g) was slowly added by addition funnel over 2.5-3 hours during which time an exotherm to a maximum observed temperature of 33.5° C. was observed. After complete addition, the resulting solution was stirred at 30-31° C. overnight under a nitrogen atmosphere (for approximately 19 hours).

A 100 µl sample of the reaction mixture was diluted with dichloromethane up to a total volume of 10 ml and the solution mixed well. A sample of the diluted aliquot was analyzed by GC/MS which indicated the reaction to be complete by GC/MS; observed formation of product (m/e=328)). The reaction mixture was cooled to 26° C. and transferred to a separatory funnel (aided with dichloromethane). The mixture was then sequentially washed with water (211 ml, 211 g; pH of aqueous cut was ~8; small rag layer was transferred with aqueous cut), 5% aqueous NaHSO$_4$ ((prepared using 50 g of sodium bisulfate monohydrate (Aldrich cat. #233714) and 950 g water) 211 ml, 216 g; pH of aqueous cut was ~2) and then 5% aqueous NaCl ((prepared using 50 g of sodium chloride (Aldrich cat. # S9888) and 950 g water) 211 ml, 215 g; pH of aqueous cut was ~4-5). The collected organic phase was then concentrated under reduced pressure (water bath at 35° C.) to ~190 ml (2.7 volumes based on theoretical yield of Compound 13a after which toluene (Aldrich cat. #179418, 422 ml, 361 g) was added. The resulting mixture was concentrated under reduced pressure (water bath at 55-65° C.) to ~190 ml (2.7 volumes based on theoretical yield of Compound 13a). Analysis of a sample of the solution at this stage by $^1$H NMR indicated the absence of dichloromethane. The remaining mixture was allowed to cool to 37° C. (using water bath at 37° C. on rotovap with agitation). During this time pronounced crystallization was observed. The mixture was then mechanically stirred and heated to approximately 37° C. (external heat source set to 38° C.) after which n-heptane (430 ml, 288 g; Aldrich cat # H2198) was slowly added by addition funnel over 3 hours. Following the addition, heating was stopped and the resulting slurry mechanically stirred while cooling to ambient temperature overnight. The resulting mixture was then filtered and the collected solids were washed with 10% toluene in n-heptane (2×210 ml; each wash was prepared by mixing 21 ml (16 g) of toluene and 189 ml (132 g) of n-heptane). Vacuum was applied until very little filtrate was observed. The solids were then further dried under vacuum at 50° C. under a nitrogen bleed to constant weight (3.5 hours) giving 64.7 g (90%) of Compound 13a. Analysis of a sample of the solid by $^1$H NMR showed the material to conform to structure and LC analysis indicated 99.8% purity using the supplied LC method.

Preparation of Compound 14a observed). The reaction mixture was cooled to rt and CH2Cl2 was added (425 mL). A solution of citric acid (2 M, 400 mL) was then added slowly over 45 min (temp up to 26° C.). It was noted that during the charge some white solids were formed but quickly dissolved with stirring. The reaction mixture was stirred for an additional 15 min before phases were allowed to separate. After the phases were split, the aqueous phase pH was measured pH=4.0. The organic phase was washed (15 min stir) with water (255 mL), and phases were allowed to separate. The lower layer (organic) containing the desired product was then stored in the fridge overnight.

The organic phase was concentrated under reduced pressure (pot set to 65° C.) to approximately 150 mL (est. 1.76 vol wrt SM). IPA (510 mL) was charged and distilled under reduced pressure (85° C. chiller temp setting) to 255 mL (3 vol). The level of solvent was brought to approximately 553 mL (6.5 vol) by the addition of IPA (298 mL). Water (16 mL) was then added and the reaction mixture warmed to reflux (77° C.) with good agitation which dissolved solids precipitated on the walls of the vessel. Reaction mixture was then cooled slowly to 65° C. (over 60 min) and held there—all material still in solution (sample pulled for residual solvent analysis). The reaction was further cooled to 60° C. and the reaction mixture appeared slightly opaque. After stirring for 15 min further cooled to 55° C. While more product precipitates, the mixture is still thin and easily stirred. Water (808 mL) was added very slowly (2.5-3 hrs) while maintaining the temperature around 55 C. The mixture was then cooled to 22° C. over 2 h and allowed to stir overnight. Material was then filtered and washed with a mixture of water: IPA (75:25, 2×255 mL). The acid was dried in a vac oven at 55° C. overnight. Obtained 69 g of acid 14a, 88% yield of a white solid. The material analyzed >99% purity by HPLC.

Preparation of Compound 15a: Suzuki Coupling

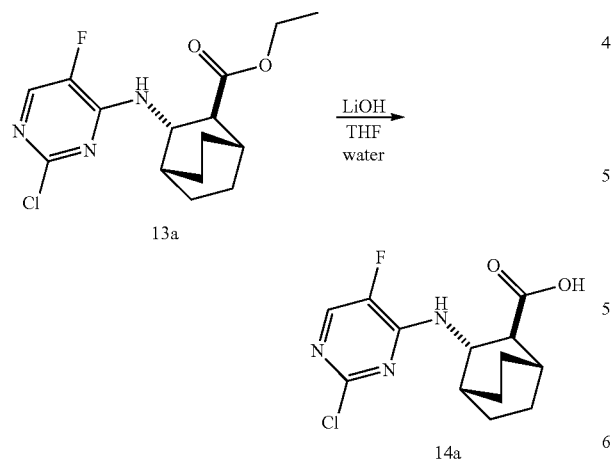

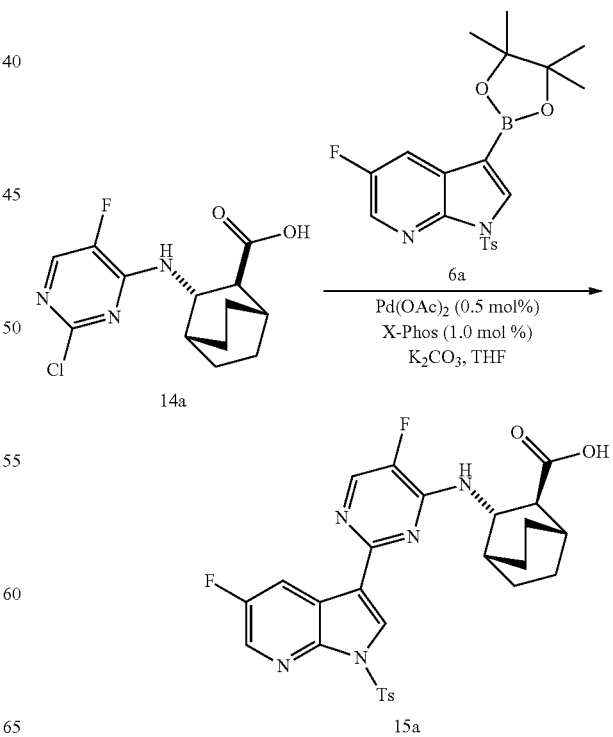

The ethyl ester 13a (85 g, 259 mmol) was dissolved in THF (340 mL) and treated with a solution of LiOH (2M, 389 mL, 778 mmol) over 10 min (temp from 21 to 24° C.). The mixture was warmed to 45° C. with stirring for 17 h at which time the reaction was judged complete by HPLC (no SM To 14a (91.4 g, 305 mmol), 6a (158.6 g, 381 mmol, 1.25 equiv.), Pd(OAc)$_2$ (0.34 g, 1.5 mmol, 0.5 mol %), X-Phos (1.45 g, 3.0 mmol, 1.0 mol %), and K$_2$CO$_3$ (168.6 g, 1220 mmol, 4 equiv.) was added THF (731 mL, 8 volumes) and water (29 mL, 0.32 vol). The reaction mixture was sparged with N$_2$ for 30 min, then warmed to 65-70° C. and stirred for 5 h. HPLC analysis of the reaction mixture showed 99.3% conversion. The reaction mixture was cooled to 22-25° C. and water was added. The mixture was stirred, the phases were allowed to separate, and the aqueous phase was decanted. A solution of 18 wt % NaCl in water (half-saturated aqueous NaCl) was added to the organic phase and the pH of the mixture was adjusted to 6.0-6.5 using 2N HCl. The phases were allowed to separate and the aqueous phase was decanted. The organic phase was concentrated to a minimum volume and acetonitrile was added. The process was repeated one more time and acetonitrile was added to bring the final volume to 910 mL (10 vol). The slurry was warmed to 80-85° C. for 6 h, then cooled to 20-25° C. The slurry was stirred for 2 h, then filtered. The solids were rinsed with acetonitrile to give 15a (161 g, 89% yield).

Preparation of Compound (2): Detosylation Step

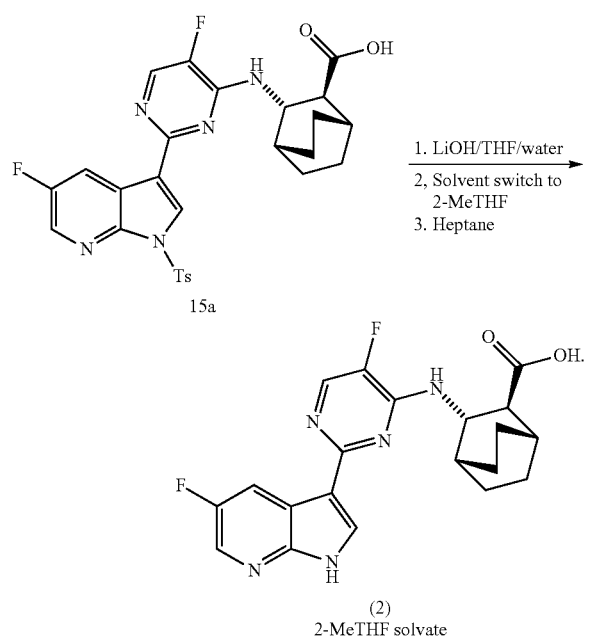

To 15a (25 g, 45.2 mmol) was added THF (125 ml, 5 vol), then MP-TMT resin (6.25 g, 25 wt %). The mixture was stirred at 20-25° C. for 16 h and filtered, rinsing with 1 vol THF. The resin treatment process and filtration were repeated. The THF solution was concentrated to 5 vol. To the mixture at 22-25° C. was added an aqueous solution of 2M LiOH (90.3 mL, 4 equiv). The reaction mixture was warmed to 40-45° C. and stirred for 5 h. HPLC analysis showed 99.7% conversion. The reaction mixture was cooled to 22-25° C. and MTBE (50 mL, 2 vol) was added. Phase separation occurred. The lower aqueous phase was collected. The aqueous phase was extracted with MTBE. The lower aqueous phase was collected. To the aqueous phase was added 2-MeTHF and the mixture was stirred. The pH of the mixture was adjusted to 6.0-6.5, and the lower aq. phase was decanted. The organic phase was washed with pH 6.5 buffer. The organic phase was concentrated to 85 mL, diluted with 2-MeTHF (150 mL), and concentrated to a final volume of 180 mL. The resultant slurry was warmed to 70-75° C. and stirred until complete dissolution, then cooled to 45-50° C. to give slurry. The slurry was stirred for 1 h, then heptane (180 mL) was added. The slurry was cooled to 20-25° C. over 1 h and stirred for 16 h. The batch was filtered, rinsing the solids with heptane. The solids were dried to give crude Compound (2).2-MeTHF solvate, 79% yield.

Preparation of HCl Salt Hemihydrate of Compound (2): Salt Formation

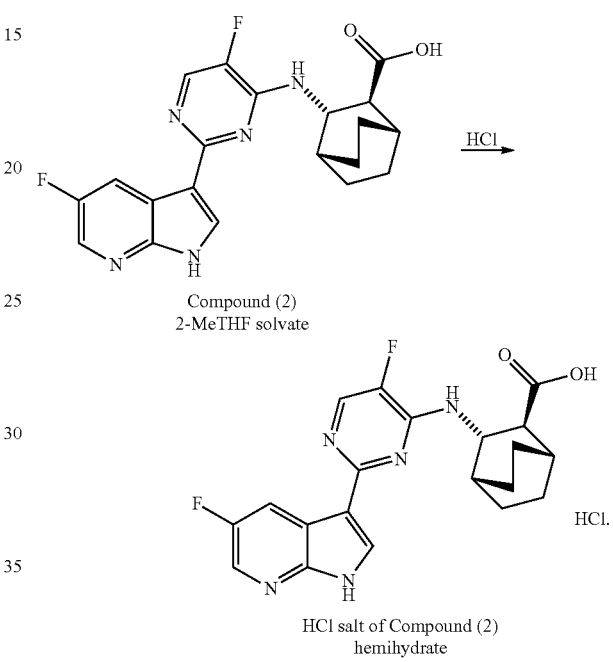

Procedure A:

Compound (2).2-MeTHF (953 g, 2.39 mol) was placed in a jacketed reactor and treated with IPA (15 L) and water (0.57 L). The stirrer was started and the reaction mixture was warmed to 73° C. to get everything into solution then cooled to 50-55° C. At 50-55° C. the reaction mixture was treated with freshly prepared HCl in IPA (0.83 M, 4.34 L) via slow addition over 4 h. The reaction was sampled, to check for the correct form by XRPD. After the addition, the chiller was programmed to ramp to 0° C. over 480 min with stirring. After form confirmation by XRPD analysis, the slurry was filtered into two filters. The reactor was washed with 3 L of IPA and each filter cake was washed with ~1.5 L of IPA of the IPA rinsate from the reactor. The cakes were allowed to air dry with suction overnight. The cakes were then placed in a tray dryer with no heating under vacuum with N$_2$ purge (22 inHg) for 24 h. Residual solvent and water analysis showed 505 ppm IPA, 8 ppm 2-Me-THF and approximately 2.15% H$_2$O. The material was pulled from the oven and co-milled to delump to provide 805 g of HCl salt of Compound (2).½H$_2$O.

Procedure B:

Alternatively, acetone instead of IPA was used, but in a similar manner as described above in Procedure A to form HCl salt of Compound (2).½H$_2$O.

Example 2: Alternative Preparations of Certain Compounds and Suzuki Reaction Conditions

A. Preparation of Compound 3a of Example 1

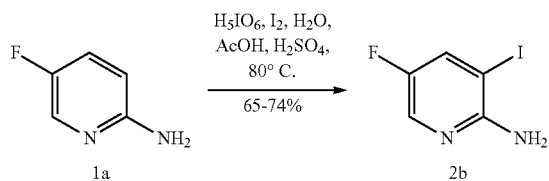 [SMILES: Nc1ccc(F)cn1 ; Nc1ncc(F)cc1I]

Step 1: 5-Fluoro-3-iodopyridin-2-amine (2b)

$H_2SO_4$ (120 mL) was added, dropwise, to a solution of 2-amino-5-fluoropyridine (1 kg, 8.9 mol) in AcOH (4 L) and $H_2O$ (1 L) over 5 minutes. Periodic acid ($H_5IO_6$; 450 g, 1.97 mol, 0.22 eq) and $I_2$ (1 kg, 3.94 mol, 0.44 eq) were added and the reaction mixture was stirred at 82° C. (internal) overnight. A sample (diluted with $H_2O$, made alkaline with 30% NaOH, extracted with EtOAc, conc.) showed 13-15% starting material. More $H_5IO_6$ (80 g) and $I_2$ (180 g) were added and stirring was continued at 80° C. overnight. The external heating was removed and the reaction mixture was stirred at RT overnight. The reaction mixture was poured over ice-water (8 L), made alkaline with 33% aq. NaOH (~6.5 L needed) and stirred for 2 h. The precipitated product was collected by filtration, and washed with hot $H_2O$ (8×3 L). The filter wash left overnight after which the product was washed with heptanes (3×). The product was dried in the stove at 45° C. over the weekend. Compound 2b (1390 g, 65% yield) was obtained as a black solid. $H_2O$ was added to the heptanes layer and it was left over the weekend. The dark aqueous layer was separated from the light-yellow organic layer, which was concentrated to dryness. More compound 2b (95 g, 70% total yield) was thus obtained as a yellow solid. $^1$H NMR (DMSO-$d_6$, 300 MHz): δ 7.95-7.88 (m, 2H) ppm. $^1$H NMR (CDCl$_3$, 300 MHz): δ7.95-7.90 (m, 1H); 7.68-7.62 (m, 1H); 4.85 (s, NH$_2$) ppm.

Step 2: 5-Fluoro-3-((trimethylsilyl)ethynyl)pyridin-2-amine (3a)

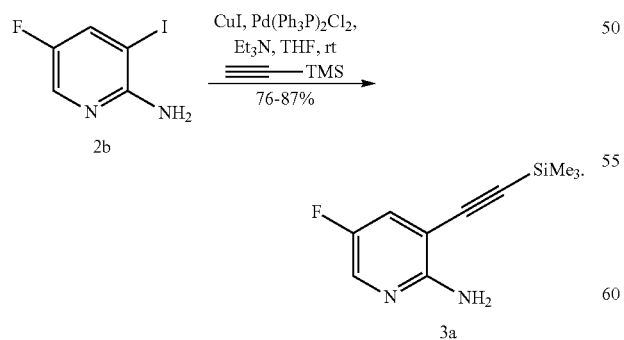

A solution of compound 2b (790 g, 3.3 mol) in THF (2.9 L) was degassed (3×), using $N_2$(g)/vacuum cycles. Purging with $N_2$ (g) was started followed by addition of CuI (6.32 g, 0.01 eq), PdCl$_2$(PPh$_3$)$_2$ (23.4 g, 0.01 eq) and Et$_3$N (1.4 L, 3 eq). Purging was continued for 10 minutes and the reaction mixture was degassed once, followed by dropwise addition of trimethylsilylacetylene (605 mL, 1.3 eq) over 40-45 minutes. During addition the exothermic reaction did not start by itself and the reaction was heated to ~45° C. The external heating was removed. The exothermic reaction had started by this time and the temperature reached ~66° C. (40 minutes after the addition was finished). The reaction mixture was allowed to stir for another 2 h after which the temperature had lowered to 26° C. A sample (filtered over Celite, conc.) showed complete conversion and the reaction mixture was diluted with EtOAc (3 L). The solution was filtered over silica (2 Kg), eluting with EtOAc (9 L total). The solvents were removed under reduced pressure to give compound 3a (642 g, 93% yield) as a dark oil. $^1$H NMR (CDCl$_3$, 300 MHz): δ 7.90 (s, 1H); 7.33-7.27 (m, 1H); 4.92 (s, NH$_2$), 0.28 (s, 9H) ppm.

B. Preparation of Compound 4a of Example 1

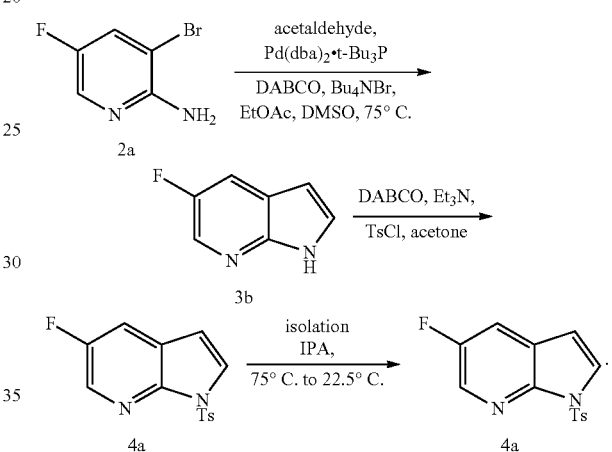

Step 1: 5-fluoro-1H-pyrrolo[2,3-b]pyridine (3b)

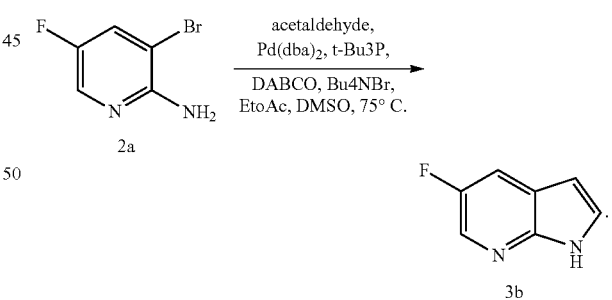

To a 500 mL pressure flask purged with nitrogen was charged 3-bromo-5-fluoropyridin-2-amine (Compound 2a) (20 g, 104.7 mmol, 1 equiv), DABCO (17.6 g, 157.0 mmol, 1.5 equiv), and tetrabutylammonium bromide (3.38 g, 10.5 mmol, 0.1 equiv). The flask was charged with dimethyl sulfoxide (anhydrous, 40 mL) and ethyl acetate (anhydrous, 120 mL) and the resulting mixture was sparged with nitrogen for 30 min. Bis(dibenzylideneacetone) palladium (0) (3.01 g, 5.24 mmol, 0.05 equiv), a 10% w/w solution of tri-tert-butylphosphine in hexane (21.2 g, 10.47 mmol, 0.1 equiv) and acetaldehyde (5.08 g, 115.2 mmol, 1.1 equiv)

were charged and the flask was sealed. The mixture was stirred for 1 h at room temperature then heated on an oil bath at 76.5° C. for 5 h. The batch was cooled and sampled for HPLC analysis. After complete conversion to Compound 3b was observed (typically 100% conversion after 5 h), the batch was quenched with water (40 mL). The aqueous phase was back extracted with ethyl acetate (40 mL) and the combined organics were filtered through a celite pad to remove fine solids. The celite was rinsed with ethyl acetate (40 mL) and the resulting solution of crude product was charged with 5% $Na_2CO_3$ (60 mL) and sparged with nitrogen for 30 min while mixing. The resulting organic phase was washed with water (60 mL) and concentrated at <30° C. to 43 mL. The solution yield was 13.1 g (92%) from 3-bromo-5-fluoropyridin-2-amine based on HPLC standards.

Step 2: 5-fluoro-1-tosyl-1H-pyrrolo[2,3-b]pyridine (4a)

To the solution of crude Compound 3b (assume 14.26 g (100% from Step 1), 1 equiv) in ethyl acetate from Step 1 was charged acetone (71.2 mL), DABCO (5.8 g, 52.35 mmol, 0.5 equiv) and triethylamine (29.4 mL, 209.4 mmol, 2 equiv) and the reaction flask was purged with nitrogen. In a separate flask, a solution of tosyl chloride (29.9 g, 157.0 mmol, 1.5 equiv) in acetone (35.6 mL) was prepared. The solution of tosyl chloride was added to the solution of Compound 3b over 30 min at room temperature. The reaction was analyzed by HPLC for % conversion after 4 h. When <0.2% AUC, Compound 3b remained (typically after 4 h), the reaction was quenched with water (10 mL), stirred for 30 min and charged with HCl (80 mL) and dichloromethane (144 mL). The batch was stirred for 30 min. The aqueous phase was extracted with dichloromethane (43 mL) and the combined organics were washed with 5% NaCl (72 mL). The solution yield of Compound 4a for this step was 27.0 g (97%) based on HPLC standards.

Step 3: Isolation of 5-fluoro-1-tosyl-1H-pyrrolo[2,3-b]pyridine (4a)

The solution of crude Compound 4a from Step 2 was concentrated under vacuum to 57 mL, charged with 2-propanol (184 mL) and concentrated to 120.8 mL. The resulting mixture was heated to 83.6° C. After stirring at that temperature for 1 h, the mixture was cooled to 22.5° C. over 2 h and maintained at that temperature for 20 h. The slurry was then filtered and the reactor and collected solid washed with 25/75 water/2-propanol (2×80 mL). The material was dried under vacuum with nitrogen sweep at 56° C. for 7 h. Compound 4a was isolated in 81% yield (24.5 g) from 3-bromo-5-fluoropyridin-2-amine (3 steps including isolation) and 98.4% AUC purity. $^1H$ NMR ($CDCl_3$, 300 MHz): δ 8.28-8.27 (m, 1H); 8.06-8.02 (m, 2H); 7.77 (d, J=4.0 Hz, 1H); 7.54-7.50 (m, 1H); 7.28-7.26 (m, 2H); 6.56 (d, J=4.0 Hz, 1H); 2.37 (s, 3H) ppm.

C. Preparation of Compound 4a of Example 1

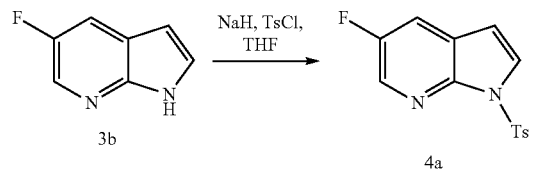 [SMILES: Fc1cnc2[nH]ccc2c1 ; Cc1ccc(S(=O)(=O)n2ccc3cc(F)cnc32)cc1]

Method A:
Compound 3b (280 g, 2 mol) was dissolved in THF (6 L) and the solution was cooled to <10° C. in an ice bath. A dispersion of 60% NaH (95 g, 57 g NaH, 1.15 eq) in mineral oil was added, in portions, over 30 minutes. The temperature was kept between 5-10° C. The reaction mixture was stirred for 40 minutes. A solution of para-toluene sulfonylchloride (408 g, 1.04 eq) in THF (2.5 L total solution) was added, dropwise, over 40 minutes. The external cooling was removed and the reaction mixture was stirred for 70 minutes at which time the temperature reached 8° C. NMR analysis of a sample (diluted with EtOAc, washed with sat. $NaHCO_3$ and concentrated) showed that the reaction was complete. The reaction mixture was quenched with sat. aq. $NaHCO_3$ (2 L) and diluted with EtOAc (8 L). The layers were separated and the organic layer was divided into 2 batches. Each batch was washed with sat. aq. $NaHCO_3$ (2×1.5 L) and brine (2×1 L). The batches were combined, dried over $Na_2SO_4$ and filtered over silica (2 Kg), eluting with EtOAc (~10 L total). The solvents (~28 L) were removed under reduced pressure and the resulting solid (628 g) was transferred to a filter and washed with heptanes (2×). Note: the first heptanes washing had an orange-red color and the second one was almost colorless. After drying, pure compound 4a (566 g, 94.6% yield) was obtained as a light-brown solid. $^1H$ NMR ($CDCl_3$, 300 MHz): δ 8.28-8.27 (m, 1H); 8.06-8.02 (m, 2H); 7.77 (d, J=4.0 Hz, 1H); 7.54-7.50 (m, 1H); 7.28-7.26 (m, 2H); 6.56 (d, J=4.0 Hz, 1H); 2.37 (s, 3H) ppm.

Method B:

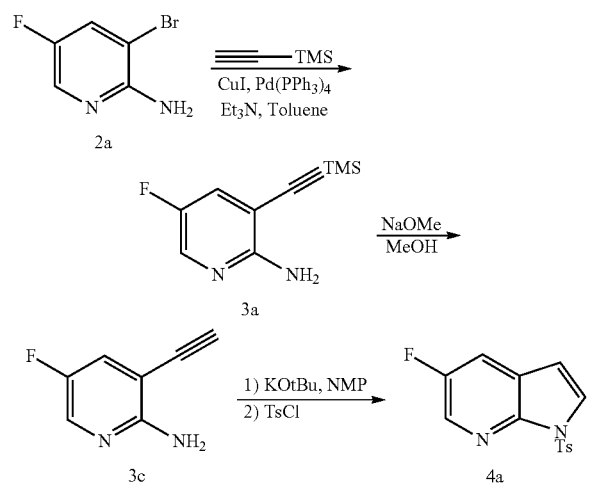

Step 1: Preparation of Compound 3c
To an inert 400-L reactor containing a toluene solution of Compound 2a (185 L, ~33.5 kg, 175 mol) was charged $Pd(PPh_3)_4$ (1215 g, 1.05 mol) and CuI (200 g, 1.05 mol). The mixture was de-oxygenated with two vacuum-nitrogen cycles, then triethylamine (23 kg, 227 mol) was added. The mixture was de-oxygenated with one more vacuum-nitrogen cycle, then TMS-acetylene (19 kg, 193 mol) was added. The mixture was heated to 50° C. for 22 hours then to 54° C. for an additional 9 hours and cooled to 25° C. overnight. 25 wt % Sodium methoxide in methanol (41.6 kg, 193 mol) was added in one portion and the mixture stirred at 25° C. for 40 minutes. The mixture was cooled to 20° C. then acetic acid (2 L, 35 mol) added in one portion and stirred for 1 hour. The slurry was filtered through a pad of Celite, washing with toluene (30 kg), and the filtrate held for product isolation. A second run from ~29.8 kg of a toluene solution of Compound 2a (156 mol) was similarly carried out.

The filtrates from both runs were concentrated to ~220 L volume (to evaporate methanol) and diluted to ~290 L with fresh toluene. This solution was filtered through a pad of magnesol (20 kg), washing with MTBE (240 L). The filtrate was evaporated to a thick slurry (~75 L volume) then hexane (65 kg) added at ~35° C. The slurry was cooled to 20° C. When filtration was attempted, the solids would not come out of the reactor but the liquid came out readily. After draining the liquid, the solids in the tank were washed with hexane (93 kg). Again the solids stayed in the tank and the wash came out. The solids were dried in the tank with vacuum (~95% pure, 249 mol, 75% yield).

The filtrate was concentrated and the residue partitioned between DCM (25 L) and 2 M HCl (30 L). The upper aqueous layer was washed with DCM (5 L). The organic layers were sequentially re-extracted with 2 M HCl (6 L). The aqueous layers were stirred with DCM (25 L) and the pH adjusted to ~8 by addition of K₃PO₄ (1 kg) then 8 M NaOH (8.3 L).

The layers were separated (product in organics) and the aqueous re-extracted with DCM (5 L). The organic layers were filtered through a pad of magnesol (3 kg), washing with DCM (7 L). The filtrate was concentrated to dryness, triturated with hexane (4 L) at 45° C., cooled to 20° C., filtered and washed with hexane to afford additional step 2 (8.25 kg, ~95% pure, 58 mol, 17%) as an orange-brown solid.

Step 2: Preparation of Compound 4a

To an inert 400-L reactor was charged NMP (80 kg) and potassium t-butoxide (40 kg, 357 mol). The mixture was heated to 59° C. then a solution of step 2 (44 kg, ~95% pure, 307 mol) in NMP (80 kg) was added over 2 hours and rinsed in with NMP (10 kg) (exothermic, maintained 70-83° C.). The reaction was stirred at 75° C. for 1 hour. A sample quenched into DCM/NaHCO₃ showed no starting material remaining by NMR. A sample quenched with excess TsCl then worked up with DCM/NaHCO₃ showed ~4% N—H remaining. The mixture was cooled to 48° C. and additional potassium t-butoxide (2 kg, 18 mol) added. The mixture was further cooled to 37° C. and a solution of tosyl chloride (62 kg, 326 mol) in NMP (60 kg) added over 1.5 hours and rinsed in with NMP (4 kg) (exothermic, maintained 30-45° C.). The reaction was stirred for 1 hour while cooling to 20° C.

A sample quenched in to DCM/NaHCO₃ showed ~9% N—H remaining. Additional tosyl chloride (3 kg, 16 mol) was added and the mixture stirred at 20° C. overnight, then transferred to an inert 800-L reactor, rinsing in with NMP (10 kg). Water at 5° C. (500 L) was added over 2.5 hours (exothermic, maintained 17-23° C.). The mixture was stirred at 17° C. for 30 minutes. When filtration was attempted, the mixture would not come out of the reactor. After allowing to settle, the liquid was sucked off the top (through the filter). The solids in the tank were soaked with water (100 L, would not stir) then the liquid sucked off the top again. This wash was repeated with another 100 L (allowing to stand overnight) and then 200 L water (allowing to stand for 7 hours). The reactor was set up with a slow bleed of nitrogen through the solids and out of the bottom valve (through the filter) over the weekend. The resulting solids were dissolved in DCM (400 kg) and separated from residual water. The aqueous was re-extracted with DCM (50 kg). The combined organics were distilled to remove ~30 L of solvent (and azeotrope residual water) and then filtered through a pad of magnesol (30 kg) and then a pad of silica (50 kg), washing with extra DCM (~600 kg). The filtrate was concentrated to a thick slurry (~110 L volume) then MTBE (65 kg) added in portions while continuing the distillation to final vapor temperature of 50° C. (final volume 145 L). The slurry was cooled to 15° C., filtered and washed with MTBE (65 kg) to afford the product (43.46 kg, 150 mol, 49%) as a pale orange solid. Partial concentration of the filtrate afforded a second crop (2.65 kg, ~93% purity, 8.5 mol, 3%). This filtrate was concentrated to dryness then partitioned between DCM (60 L) and 2.2 M NaOH (35 L). The organic layer was washed with water (2×30 L) then brine (20 L) and filtered through a pad of silica (35 kg), eluting with DCM. The filtrate was concentrated and the residue triturated with MTBE (20 L) and filtered to afford a third crop (3.72 kg, 12.8 mol, 4%).

D. Preparation of Compound 11a of Example 1

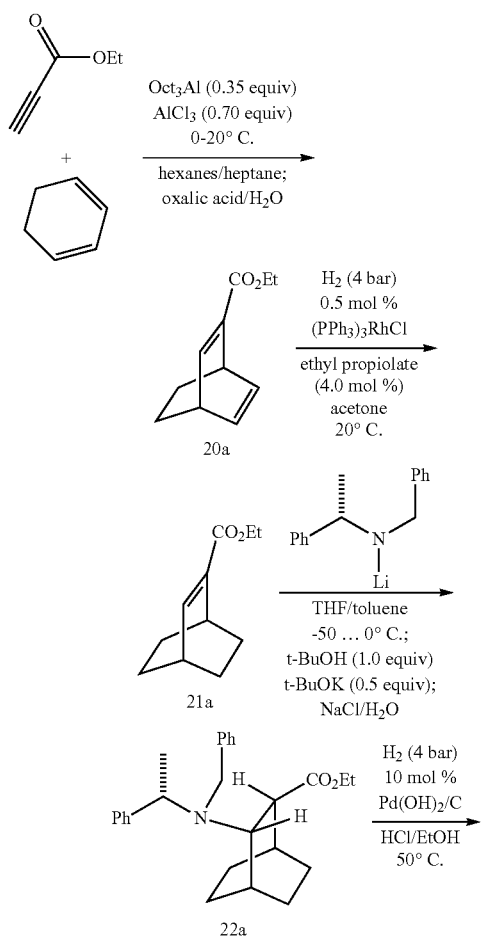

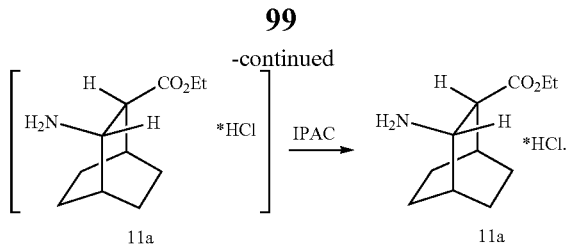

Preparation of Compound 20a: Diels-Alder Reaction

AlCl$_3$ (380.6 g, 2.85 mol, 0.7 equiv) was charged to the 10-L Chemglass jacketed bottomdrain reactor with a N$_2$ sweep followed by heptane (1.6 L, 4 vols). The mixture was cooled to 0° C. Trioctylaluminum (2.99 L, 1.43 mol, 0.35 equiv, 25 wt % in hexanes) was added via the addition funnel over 40 min. Pale green light slurry was allowed to stir for 1 h. Ethyl propiolate (400 g, 413 mL, 1.0 equiv) was added over 1 h. The temperature at the end of the addition was 6.0° C. 1,3-Cyclohexadiene (425 g, 494 mL, 1.3 equiv) was added over 3 h. The reaction was left to stir for 16 h. The reaction appearance changed from a light slurry of orange color to a homogeneous orange solution. The reaction was cooled to 0° C. 9% solution of oxalic acid in water was placed into a 30-L Chemglass jacketed bottomdrain reactor under a N$_2$ atmosphere and cooled to 0° C. The reaction mixture was transferred from the 10-L reactor to the quench 30-L reactor in portions over 1 h. The 10-L reactor was rinsed with heptane (800 mL, 2 vol) and the rinse was transferred to the 30-L quench reactor. The quenched reaction mixture was warmed to 22.5° C. while stirring. Stirring was stopped and the phases were allowed to separate. The bottom aqueous phase was drained off. Water (800 mL, 2 vol) was charged to the quench 30-L reactor and the mixture was stirred for 30 min. Stirring was stopped and the phases were allowed to separate. The bottom aqueous phase was drained off and the top organic phase was concentrated on the rotary evaporator (bath temperature was 40-50° C.) together with the solution produced in another batch under the identical conditions and scale. The weight of the concentrated material was 1771 g and it was found to contain 83% of the product (the balance was residual octane), the yield calculated to 101%. The HPLC purity was 99.39% AUC. $^1$H NMR (400 MHz, CDCl3) δ 7.27 (dd, J=6.5, 1.8 Hz, 1H), 6.37 (ddd, J=7.5, 6.2, 1.5 Hz, 1H), 6.26 (ddd, J=7.3, 5.9, 1.5 Hz, 1H), 4.23-4.13 (m, 3H), 3.78-3.70 (m, 1H), 1.40-1.19 (m, 7H).

Preparation of Compound 21a

Wilkinson's catalyst Rh(PPh$_3$)$_3$Cl (22.97 g, 25 mmol, 0.005 equiv) was added to the crude Compound 20a (1068 g, 83 wt. %, 4.97 mol, 1 equiv). The suspension was transferred to a 3-L Buchi hydrogenator with the jacket temperature set to 20° C. The bottle that contained the starting material was rinsed with acetone (885 mL, 1 vol) and it was transferred to the hydrogenator. Ethyl propiolate (19.49 g, 20.2 mL, 200 mmol, 0.04 equiv) was added. The reaction was stirred at 4 bar of hydrogen gas at 20° C. for 17 h. 99.6% AUC conversion to the desired Compound 21a was observed. 697 g of crude Compound 20a was processed via the same conditions and virtually identical conversion was achieved. Both crude solutions of Compound 21a were concentrated on a rotovap with a 40-50° C. bath temperature. 1913 g of crude product was obtained. W/w assay with a purified standard led to the calculation of the active content of 70.9%: 1357 g of the active product, 92% yield over the two steps. $^1$H NMR (400 MHz, CDCl$_3$) δ 7.34 (dd, J=6.9, 1.7 Hz, 1H), 4.20 (q, J=7.1 Hz, 2H), 3.17 (m, 1H), 2.69-2.73 (m, 1H), 1.54-1.60 (m, 4H), 1.31 (t, J=7.1 Hz, 3H), 1.23-1.27 (m, 4H).

Preparation of Compound 22a

S-(−)-N-Benzyl-α-methylbenzylamine (585 g, 579 mL, 2.77 mol, 1.1 equiv) was charged to the 22-L round-bottomed flask followed by anhydrous THF (5.1 L, 11 vol). Stirring was initiated and the flask was cooled with dry ice/acetone bath to 0° C. n-BuLi (1.1 L, 2.77 mol, 1.1 equiv., 2.5 M in hexanes) was added over 50 min. The reaction was stirred for 15 min. The reaction mixture was cooled to −42.2° C. in a dry ice/acetone bath over 10 min. Compound (R) (640 g, 70.9 wt. %, 454 g active, 2.52 mol, 1.0 equiv) in toluene (640 mL, 1.4 vol) was added over 30 min maintaining the internal temperature −45 to −40° C. The reaction was stirred for 1 h. A solution of t-BuOH (186 g, 240 mL, 2.52 mol, 1.0 equiv) in anhydrous THF (95 mL, 0.2 vol) was added over 20 min followed by a. A solution of t-BuOK (1.26 L, 1.26 mol, 0.5 equiv, 1.0 M in THF) added over 20 min. maintaining the internal temperature of −45 to −40° C. throughout. The reaction was brought to room temperature and allowed to stir for 18 h. The reaction was cooled to 0° C. and a solution of sodium chloride (160 g) in water (3.0 L) was added. The mixture was warmed to 20° C. and the phases were allowed to separate. The bottom aqueous layer was drained off. Water (3 L) was charged into the reactor while stirring. The temperature has increased from 21° C. to 26° C. The mixture was stirred for 30 min, then the stirring was stopped and the phases were allowed to settle for 30 min. The top organic phase was collected. Solution prepared in this batch was rotovapped together with solutions of two other earlier batches that were carried out under the same conditions and similar scale. The total weight of the crude product (yellow oil) was 3630 g. Material was carried into the next step. $^1$H NMR (400 MHz, CDCl3) δ 7.49-7.41 (m, 2H), 7.41-7.14 (m, 8H), 4.27-4.18 (m, 1H), 4.09-3.93 (m, 2H), 3.89-3.81 (m, 1H), 3.48 (m, 2H), 2.52-2.45 (m, 1H), 2.08-1.95 (m, 2H), 1.76 (m, 1H), 1.70-1.21 (m, 7H), 1.44 (d, J=6.8 Hz, 3H), 1.19 (q, J=7.2 Hz, 3H).

Preparation of Compound 11a

Pearlman's catalyst (Pd(OH)$_2$/C, 20 wt. % on support, 50% water, 500 g total, 50 g active, 0.36 mol, 0.095 equiv) was charged to the 20-L Buchi hydrogenator with the jacket temperature set to 20° C. Compound 22a (1815 g actual weight, 1468 g presumed active, 3.75 mol, 1.0 equiv) was added followed by EtOH (7.5 L, 5.1 vol based on presumed active charge). Conc. HCl (37.7 wt. % in water, 305 mL, 363 g, 137 g active, 3.75 mol, 1.0 equiv) was added over 20 min. pH of the reaction was measured with pH paper and was recorded as 1. The reaction was hydrogenated under 1 bar of H$_2$ and heated to 50° C. Once at 50° C. was reached the reactor was further pressurized with H$_2$ to 4 bar. The reaction was kept under the conditions set above for 96 h. The catalyst was filtered off on celite, the hydrogenator was rinsed with EtOH (2 L) and the rinse was used to rinse the celite layer as well and was combined with the main filtrate. The ethanolic solution of crude product, Compound 11a, was concentrated on a rotary evaporator together with the previous batch that was prepared under the essentially the same conditions and identical scale. A thick paste was produced. Iso-propyl acetate (2 L) was added to the rotovap bulb that contained the product from the previous step. The bulb was then spun at atmospheric pressure of N$_2$ for 30 min to suspend the solid. The solvent was distilled off under vacuum. Another portion of iso-propyl acetate (2 L) was added and the bulb was spun at atmospheric pressure of N$_2$ to suspend the solid. The slurry was transferred to a 30-L Chemglass jacketed reactor. The bulb was rinsed with iso-propyl acetate (2 L) and the rinse was added to the reactor. Iso-propyl acetate (12 L, total of 16 L, 5.5 vol based on presumed active Compound 11a) was added. The yellow suspension was stirred for 20 h at the room temperature of 24.4° C. The slurry was filtered on a porcelain filter with a filter paper. The reactor was rinsed with iso-propyl acetate (4 L) and the rinse was used to rinse the filter cake. A white dense filter cake was obtained. It was allowed to remain under the pull of vacuum for several hours. The cake was dried in a vacuum oven at 40° C. with a $N_2$ bleed for 20 h. The amount of the product obtained was 924 g (3.95 mol, 48% yield from ethyl propiolate). The purity (GC) was 98.31% AUC. $^1$H NMR (400 MHz, MeOH-$d_4$) δ 4.28-4.14 (m, 2H), 3.87-3.79 (m, 1H), 2.63-2.56 (m, 1H), 2.07 (dd, J=5.4, 2.7 Hz, 1H), 1.95-1.86 (m, 1H), 1.86-1.72 (m, 2H), 1.73-1.53 (m, 4H), 1.54-1.37 (m, 2H), 1.28 (t, J=7.1 Hz, 3H). $^{13}$C NMR (101 MHz, MeOH-$d_4$) δ 174.03, 62.37, 52.00, 48.89, 29.58, 28.96, 25.94, 25.05, 21.48, 19.28, 14.56.

F. Suzuki Reaction Condition Screening for the Preparation of Compound (Z-2)

Thirteen 1 g scale preparations of Compound (Z-2) were performed and completed with different catalytic systems, including the use of the Pd(OAc)$_2$/X-Phos combination for baselining purposes. The Pd(OAc)$_2$/X-Phos combination appeared to be superior when compared to the other catalysts.

A 40 mL reaction vial equipped with screw-cap septum was charged with Compound (X-2) (1.0 g, 3.3 mmol, 1.0 equiv), Compound (Y-2) (1.7 g, 4.2 mmol, 1.25 equiv), catalyst (0.25 mol %), and potassium carbonate (1.8 g, 13.3 mmol, 4.0 eq) followed by THF (8 mL, 8 vol). After beginning agitation, the thick slurry was degassed with 3 vacuum/nitrogen cycles and heated to 60-65° C. Once the desired temperature had been reached, degassed water (0.32 mL, 0.3 vol) was added over a period of 15 minutes. After the water addition was complete, the reaction mixture was allowed to stir at the set temperature, and HPLC assays were taken at different time points (Table 1).

TABLE 1

Catalyst Screening for the Preparation of Compound (Z-2).

| Catalyst | Time (h) | Conversion (%) |
|---|---|---|
| Pd(OAc)2/X-Phos | 1.25 | >99.9 |
| (1,1'-bis(di-t-butylphosphinoferrocenyl))PdCl2 | 1.25 | 91.0 |
|  | 2.50 | 91.2 |
| (PCy3)2PdCl2 | 1.25 | 39.2 |
|  | 2.00 | 39.7 |
|  | 10.0 | 39.8 |
| (tBuAmphos)PdCl2 | 1.25 | 41.8 |
|  | 2.50 | 43.4 |
|  | 10.0 | 43.4 |
| (1,1'-bis(dicyclohexylphosphinoferrocenyl))PdCl2 | 1.25 | 27.5 |
|  | 2.50 | 27.4 |
| Pd(OAc)2/tBuBrettphos | 1.25 | 1.0 |
|  | 2.50 | 1.2 |
| (dppf)2PdCl2 | 1.25 | 17.4 |
|  | 2.50 | 17.4 |
| (tri-o-tolylphosphine)2PdCl2 | 1.25 | 13.0 |
|  | 2.50 | 13.0 |
| (PEt3)2PdCl2 | 1.25 | <1 |
|  | 2.50 | <1 |
| (dppe)PdCl2 | 1.25 | 2.5 |
|  | 2.50 | 2.5 |
| FibreCAT 1026 | 1.25 | <1 |
|  | 3.00 | <1 |
|  | 10.0 | 1.5 |
| (tri-t-butylphosphine)2Pd0 | 1.25 | 2.3 |
|  | 2.50 | 3.1 |
| Pd(PPh3)4 | 1.25 | 4.5 |
|  | 2.50 | 4.8 |

Example 3: Formation of Polymorphs of HCl Salt of Compound (1)

3A: Preparation of Form A of HCl Salt Compound (1).½H$_2$O

Form A of HCl salt of Compound (1).½H$_2$O was prepared by mixing 2-methyl tetrahydrofuran (2-MeTHF) solvate (1 equivalent) of Compound (1) (Compound (1). 1 (2-MeTHF)) with hydrogen chloride in a mixture of water and an organic solvent(s), wherein the mixture of water and an organic solvent(s) had a water activity of 0.05-0.85. Particular reaction conditions employed are summarized in Table 2 below.

TABLE 2

Reaction Conditions Employed for the Preparation of Form A of HCl salt of Compound (1)•1/2H$_2$O.

| Comp. (1) (mg) 1 (2-MeTHF) | Solvent | Solvent (mL) | Water (mL) | 6N aqueous HCl (mL) | T (° C.) | Eq (HCl: Compound (1)) | Water (wt %) |
|---|---|---|---|---|---|---|---|
| 40 | Acetone | 640 | 40 | 15.70 | 35 | 1.1332 | 8.84% |
| 25 | Acetone | 400 | 25 | 9.80 | 46 | 1.1318 | 8.84% |
| 10.09 | Acetone | 160 | 64 | 3.98 | 35 | 1.1389 | 32.71% |
| 5 | n-propanol | 186 | 10 | 1.29 | 20 | 0.7449 | 6.87% |
| 6.01 | iso-propanol | 88 | 2 | 2.31 | 35 | 1.1097 | 5.10% |
| 6.6 | iPrOH/Acetic Acid => Acetone* | 100/1.0 | 4 | 3.10 | 45 | 1.3561 | 7.25% |
| 18 | Acetone | 180 | 6 | 3.60 | 30 | 0.5774 | 5.33% |
| 18 | Acetone | 180 | 8 | 6.40 | 35 | 1.0266 | 7.73% |
| 6 | Acetone | 66 | 11 | 2.82 | 30 | 1.3561 | 18.57% |
| 0.101 | iBuOAc | 5 | 0.1 | 0.10 | ~20 | 2.8586 | 4.36% |
| 6 | Acetic Acid | 50 | 8.7 | 2.18 | 35 | 1.0499 | 15.37% |

*two steps: iPrOH/AcOH and then re-slurry in acetone/water

Alternatively, Form A of HCl salt of Compound (1).½H$_2$O was also prepared by the following procedures: Procedure A: Compound (1).2-MeTHF (953 g, 2.39 mol) was placed in a 30 L jacketed reactor and treated with IPA (15 L) and water (0.57 L). The stirrer was started and the reaction mixture was warmed to 73° C. to get everything into solution then cooled to 50-55° C. At 50-55° C. the reaction mixture was treated with freshly prepared HCl in IPA (0.83 M, 4.34 L) via slow addition over 4 h. The reaction was sampled, to check for the correct form by XRPD. After the addition, the chiller was programmed to ramp to 0° C. over 480 min with stirring. After form confirmation by XRPD analysis, the slurry was filtered into two filters. The reactor was washed with 3 L of IPA and each filter cake was washed with ~1.5 L of IPA of the IPA rinsate from the reactor. The cakes were allowed to air dry with suction overnight. The cakes were then placed in a tray dryer with no heating under vacuum with N$_2$ purge (22 inHg) for 24 h. Residual solvent and water analysis showed 505 ppm IPA, 8 ppm 2-Me-THF and approximately 2.15% H$_2$O. The material was pulled from the oven and co-milled to delump to provide 805 g of HCl salt of Compound (2).½H$_2$O. Procedure B: Alternatively, acetone instead of IPA was used, but in a similar manner as described above in Procedure A to form HCl salt of Compound (1).½H$_2$O.

Certain observed XRPD peaks and C$^{13}$SSNMR peaks are summarized in Tables 3A and 3B, respectively.

TABLE 3A

XRPD Peaks of Form A of HCl salt of Compound (1)•1/2 H$_2$O.

| XRPD Peaks | Angle (2-Theta ± 0.2) | Intensity % |
|---|---|---|
| 1 | 10.5 | 100.0 |
| 2 | 5.2 | 71.6 |
| 3 | 7.4 | 46.8 |
| 4 | 18.9 | 42.0 |
| 5 | 25.2 | 41.7 |
| 6 | 16.5 | 39.5 |
| 7 | 18.1 | 28.1 |
| 8 | 23.0 | 27.5 |
| 9 | 24.1 | 25.3 |
| 10 | 20.2 | 21.6 |
| 11 | 26.4 | 21.3 |
| 12 | 15.8 | 19.8 |
| 13 | 21.8 | 18.3 |
| 14 | 13.8 | 17.6 |
| 15 | 27.4 | 17.3 |
| 16 | 29.0 | 16.7 |
| 17 | 14.8 | 15.0 |
| 18 | 32.0 | 15.0 |
| 19 | 25.7 | 13.8 |
| 20 | 28.6 | 13.4 |
| 21 | 33.8 | 13.0 |
| 22 | 12.8 | 12.0 |
| 23 | 30.8 | 11.7 |
| 24 | 32.4 | 11.6 |
| 25 | 24.5 | 11.5 |
| 26 | 23.4 | 11.1 |
| 27 | 21.0 | 10.4 |

TABLE 3B

C$^{13}$ SSNMR Peaks of Form A of HCl salt of Compound (1)•1/2 H$_2$O.

| Peak # | Chem Shift [±3 ppm] | Intensity [rel] |
|---|---|---|
| 1 | 180.1 | 50.4 |
| 2 | 157.9 | 9.1 |
| 3 | 154.6 | 26.4 |
| 4 | 150.7 | 25.3 |
| 5 | 144.9 | 31.0 |
| 6 | 140.1 | 6.7 |
| 7 | 132.4 | 36.3 |
| 8 | 131.2 | 30.0 |
| 9 | 129.0 | 21.0 |
| 10 | 117.5 | 33.6 |
| 11 | 114.0 | 38.0 |
| 12 | 107.0 | 34.4 |
| 13 | 54.8 | 42.0 |
| 14 | 47.7 | 52.7 |
| 15 | 29.2 | 100.0 |
| 16 | 24.6 | 74.0 |
| 17 | 22.1 | 83.6 |

The prepared Form A of HCl salt of Compound (1).½H$_2$O was found to be stable in the following solvent systems (but not limited to): chlorobenzene, cyclohexane, 1,2-dichloroethane, dichloromethane, 1,2-dimethoxyethane, hexane, 2-methoxyethanol, methylbutyl ketone, methylcyclohexane, nitromethane, tetralin, xylene, toluene, 1,1,2-trichloroethane, acetone, anisole, 1-butanol, 2-butanol, butyl acetate, t-butylmethylether, cumene, ethanol, ethyl acetate, ethyl ether, ethyl formate, heptane, isobutyl acetate, isopropyl acetate, methyl acetate, 3-methyl-1-butanol, methylethyl ketone, 2-methy-1-propanol, pentane, 1-propanol, 1-pentanol, 2-propanol, propyl acetate, tetrahydrofuran, methyl tetrahydrofuran. Specifically, for the solubility and stability tests for Form A of HCl salt of Compound (1).½H$_2$O, samples of the compound were loaded into 2 mL HPLC vials with 500 μl of solvent. The mixture was stirred at ambient temperature for 2 weeks and then filtered by centrifuge. The resulting solids were analyzed by XRPD, solutions were analyzed for solubility by quantitative NMR against hydroquinone standard. The results are summarized in Table 4.

TABLE 4

Summary of form and solubility data for Form A HCl salt of Compound (1).

| Solvent | Sol. (mg/ml) | Resulting Forms |
|---|---|---|
| Acetonitrile | 0.5 | Solvate |
| Chlorobenzene | <0.1 | A |
| Chloroform | <0.1 | Solvate |
| Cyclohexane | <0.1 | A |
| 1,2-Dichloroethane | 1.7 | A |
| Dichloromethane | 0.1 | A |
| 1,2-Dimethoxyethane | 0.5 | A |
| 1,4-Dioxane | 0.4 | A |
| Ethylene glycol | 108.1 | Solvate |
| Hexane | <0.1 | A |
| Methanol | 46.4 | Solvate |
| 2-Methoxyethanol | 34.1 | A |
| Methylbutyl ketone | 0.4 | A |
| Methylcyclohexane | <0.1 | A |
| Nitromethane | <0.1 | A |
| Tetralin | <0.1 | A |
| Toluene | <0.1 | A |
| 1,1,2-Trichloroethane | <0.1 | A |
| xylene | <0.1 | A |
| Acetone | 1.5 | A |
| Anisole | <0.1 | A |
| 1-Butanol | 2.9 | A |
| 2-Butanol | 2.9 | A |
| Butyl acetate | 0.2 | A |
| t-Butylmethylether | 0.4 | A |

TABLE 4-continued

Summary of form and solubility data for Form A HCl salt of Compound (1).

| Solvent | Sol. (mg/ml) | Resulting Forms |
|---|---|---|
| Cumene | <0.1 | A |
| Dimethylsulfoxide | 346.5 | Solvate |
| Ethanol | 19.9 | A |
| Ethyl acetate | 0.2 | A |
| Ethyl ether | 0.1 | A |
| Ethyl formate | 0.4 | A |
| Formic acid | 214.0 | Solvate |
| Heptane | <0.1 | A |
| Isobutyl acetate | 0.2 | A |
| Isopropyl acetate | 0.4 | A |
| Methyl acetate | 0.6 | A |
| 3-Methyl-1-butanol | 3.2 | A |
| Methylethyl ketone | 0.5 | A |
| 2-Methy-1-propanol | 3.5 | A |
| Pentane | <0.1 | A |
| 1-Pentanol | 3.3 | A |
| 1-Propanol | 10.7 | A |
| 2-Propanol | 3.3 | A |
| Propyl acetate | 0.8 | A |
| Tetrahydrofuran | 0.7 | A |
| Methyl tetrahydrofuran | 0.7 | A |
| Water | 0.6 | F |

Thermogram data was obtained (the data not shown) by placing the sample in a platinum sample pan and by heating at 10° C./min to 300° C. from room temperature. The thermogram data demonstrated a weight loss of 2.1% from 30° to 170° C. which was consistent with theoretical hemihydrate (2.0%).

DSC thermogram data was obtained (the data not shown) by heating the sample at 10° C./min to 300° C. from room temperature. DSC thermogram showed a dehydration onset temperature of 50-100° C. followed by an onset melting/decomposition temperature of 200-260° C.

3B: Preparation of Form F of HCl Salt Compound (1).3H$_2$O

Form F of HCl salt of Compound (1).3H$_2$O can be prepared by slurring Form A of HCl salt of Compound (1).½H$_2$O in iso-propanol and water, or acetone and water, or water (with a water activity value equal to, or greater than, 0.9).

For example, slurry of 100 mg of Form A of HCl salt of Compound (1).½H$_2$O in 5 mL of iso-propanol/water or acetone/water at water activity of 0.9 was stirred at ambient temperature overnight. Decanting the supernatant and gentle air dry of the resulting solid material provided Form F of HCl salt of Compound (1).3H$_2$O.

Certain observed XRPD peaks and C$^{13}$SSNMR peaks are summarized in Tables 5 and 6, respectively.

TABLE 5

XRPD Peaks of Form F of HCl salt of Compound (1)•3 H$_2$O.

| XRPD Peaks | Angle (2-Theta ± 0.2) | Intensity % |
|---|---|---|
| 1 | 7.1 | 100.0 |
| 2 | 9.6 | 83.0 |
| 3 | 11.9 | 88.8 |
| 4 | 12.4 | 84.6 |
| 5 | 16.4 | 83.5 |
| 6 | 17.1 | 83.0 |
| 7 | 17.5 | 82.8 |
| 8 | 19.2 | 86.9 |
| 9 | 21.1 | 82.2 |
| 10 | 21.8 | 83.7 |
| 11 | 23.9 | 83.8 |
| 12 | 28.7 | 83.4 |

TABLE 6

C$^{13}$ SSNMR Peaks of Form F of HCl salt of Compound (1)•3H$_2$O.

| Peak # | Chem Shift [±3 ppm] | Intensity [rel] |
|---|---|---|
| 1 | 178.6 | 67.6 |
| 2 | 156.8 | 21.5 |
| 3 | 154.3 | 49.3 |
| 4 | 152.1 | 12.6 |
| 5 | 151.2 | 21.3 |
| 6 | 142.5 | 37.0 |
| 7 | 132.3 | 85.7 |
| 8 | 127.9 | 15.4 |
| 9 | 118.0 | 38.6 |
| 10 | 117.5 | 43.7 |
| 11 | 115.2 | 36.3 |
| 12 | 114.5 | 35.2 |
| 13 | 106.1 | 15.4 |
| 14 | 104.8 | 31.6 |
| 15 | 52.7 | 43.1 |
| 16 | 52.3 | 37.2 |
| 17 | 48.8 | 44.8 |
| 18 | 48.4 | 46.4 |
| 19 | 30.3 | 100.0 |
| 20 | 27.4 | 35.4 |
| 21 | 25.5 | 37.4 |
| 22 | 24.5 | 44.5 |
| 23 | 23.8 | 40.9 |
| 24 | 22.0 | 46.4 |
| 25 | 21.1 | 47.0 |
| 26 | 20.7 | 50.5 |
| 27 | 20.3 | 47.7 |

A MDSC thermogram was obtained (the data not shown) by heating the sample at 2° C./min to 350° C. from −20° C. and modulated at ±1° C. every 60 sec. The MDSC thermogram showed a dehydration below 150° C., melt and recrystallization between 150° C. and 200° C., and degradation above 250° C.

Thermogravimetric analysis (TGA) of the form was also performed. The thermogram showed a weight loss of 12% up to 125° C. which was close to theoretical trihydrate (11%). The second step weigh loss below 200° C. was indicated by TGA-MS to be the loss of HCl. The melting/decomposition onset was around 270-290° C.

3C: Preparation of Form D of HCl Salt Compound (1)

Anhydrous Form D of HCl salt of Compound (1) can generally be made by dehydrating Form A of HCl salt of Compound (1).½H$_2$O. The dehydration could be done via heating or dry nitrogen purge, or the combination of the two. For example, 2 mg of Form A of HCl salt of Compound (1).½H$_2$O was heated on a hot plate, generating the desired anhydrous Form D at approximately 85° C.

Certain observed XRPD peaks and C$^{13}$ SSNMR peaks are summarized in Tables 7 and 8, respectively.

TABLE 7

XRPD Peaks of Form D of Anhydrous HCl salt of Compound (1).

| XRPD Peaks | Angle (2-Theta ± 0.2) | Intensity % |
|---|---|---|
| 1 | 5.3 | 100.0 |
| 2 | 10.5 | 56.0 |
| 3 | 15.9 | 49.2 |
| 4 | 25.9 | 30.5 |
| 5 | 21.0 | 24.6 |
| 6 | 26.5 | 24.1 |
| 7 | 5.8 | 22.6 |
| 8 | 7.4 | 21.7 |
| 9 | 19.0 | 17.4 |
| 10 | 16.6 | 17.2 |
| 11 | 25.3 | 16.1 |
| 12 | 24.7 | 16.0 |
| 13 | 29.4 | 15.5 |
| 14 | 13.8 | 14.6 |
| 15 | 20.3 | 14.5 |
| 16 | 32.0 | 14.4 |
| 17 | 19.5 | 12.4 |
| 18 | 28.6 | 12.4 |
| 19 | 17.1 | 11.5 |
| 20 | 30.3 | 11.4 |
| 21 | 27.5 | 11.0 |
| 22 | 27.0 | 10.7 |
| 23 | 23.7 | 10.4 |
| 24 | 28.0 | 10.2 |
| 25 | 21.6 | 10.1 |

TABLE 8

$C^{13}$ SSNMR Peaks of Form D of Anhydrous HCl salt Compound (1).

| Peak # | Chem Shift [±3 ppm] | Intensity [rel] |
|---|---|---|
| 1 | 179.7 | 43 |
| 2 | 177.8 | 44.85 |
| 3 | 157.5 | 16.88 |
| 4 | 154.9 | 43.14 |
| 5 | 151.1 | 25.79 |
| 6 | 149.8 | 21.51 |
| 7 | 145.0 | 26.82 |
| 8 | 143.9 | 35.41 |
| 9 | 141.6 | 14.85 |
| 10 | 139.7 | 12.9 |
| 11 | 135.4 | 29.94 |
| 12 | 132.5 | 43.37 |
| 13 | 130.1 | 23.65 |
| 14 | 128.9 | 27.35 |
| 15 | 127.3 | 25.35 |
| 16 | 118.1 | 27.24 |
| 17 | 116.6 | 28.25 |
| 18 | 113.3 | 52.71 |
| 19 | 107.5 | 29.33 |
| 20 | 106.1 | 30.73 |
| 21 | 54.4 | 39.43 |
| 22 | 53.4 | 42.25 |
| 23 | 48.2 | 54.53 |
| 24 | 47.2 | 47.8 |
| 25 | 31.6 | 52.54 |
| 26 | 29.4 | 100 |
| 27 | 26.0 | 50.37 |
| 28 | 24.8 | 47.38 |
| 29 | 23.9 | 63.88 |
| 30 | 22.9 | 98.06 |
| 31 | 20.2 | 45.7 |

3D: Water Activity Tests

A competition slurry study of Form A of HCl salt of Compound (1)·½H$_2$O seeded with Form F of HCl salt of Compound (1)·3H$_2$O, at water activities of 0.0 to 0.8 of isopropyl alcohol/water showed that Form A to be the most stable form among Form D of anhydrous HCl salt Compound (1) Form F of HCl salt of Compound (1)·3H$_2$O, and Form A of HCl salt of Compound (1)·½H$_2$O, after approximately 2 weeks of stirring under ambient conditions. At an IPA/water activity of 0.9, Form A of HCl salt of Compound (1)·½H$_2$O was converted to Form F of HCl salt of Compound (1)·3H$_2$O. The results from these studies are summarized in Table 9 below.

TABLE 9

Water Activity Tests on HCl salt of Compound (1)·1/2 H$_2$O in IPA/water mixtures.

| Starting Forms | Water Activity ($a_w$) | Water wt % | Final Form | Description |
|---|---|---|---|---|
| A + F | 0 + >80° C. | | D | Anhydrate |
| A + F | 0 | | A | Hemihydrate |
| A + F | 0.1 | 0.1 | A | Hemihydrate |
| A + F | 0.2 | 0.25 | A | Hemihydrate |
| A + F | 0.3 | 0.35 | A | Hemihydrate |
| A + F | 0.4 | 0.55 | A | Hemihydrate |
| A + F | 0.5 | 0.75 | A | Hemihydrate |
| A + F | 0.6 | 1.00 | A | Hemihydrate |
| A + F | 0.7 | 1.35 | A | Hemihydrate |
| A + F | 0.8 | 1.85 | A | Hemihydrate |
| A + F | 0.9 | 2.80 | F | Trihydrate |
| A + F | 1 | 100 | F | Trihydrate |

3F. Amorphous HCl Salt of Compound (1)

Amorphous HCl salt of Compound (1) could be formed by treating Me$_2$NEt salt of Compound (1) (1.985 g) in water and 2-MeTHF with 1.05 eq. NaOH, followed by treatment with HCl to remove amine and crash out from an aqueous layer (pH 2-3). The resulting slurry was concentrated to remove any organics and then filtered. The resulting solid was rinsed with small portions of water and dried. Me$_2$NEt salt of Compound (1) was prepared according to WO 2010/148197, followed by usual chiral separation and purification: SCF chiral chromatography with a modifier that included Me$_2$NEt (which generated Me$_2$NEt salt of Compound (1)).

Example 4: Formation of Polymorphs of Free Base Compound (1)

4A: Preparation of Form A of Free Base Compound (1)

Form A of free base Compound (1) was produced by the following procedure: Crude amorphous free base Compound (1) (approximately 135 g) was transferred to a 4 L jacketed reactor and the reactor was charged with ethanol (2.67 L) and water (0.325 L) (10% water solution). The mixture was heated to reflux. Water (300 mL) was added to the resulting mixture of step 2) to make a 20% water solution. The resulting mixture was then cooled to 55° C. (rate=−1° C./min) and subsequently held for 30 minutes. Crystalline seed of free base Form A of Compound (1) (1.5 g, 3.756 mmol) was then added into the cooled mixture, and the resulting mixture was held for 30 minutes while the product precipitated. The seed of crystalline free base Form A of Compound (1) was produced by slurrying amorphous free base Compound (1) (20 mg) in nitromethane (0.5 mL). Additional seed materials of crystalline free base Form A of Compound (1) were produced by slurring amorphous free base Compound (1) (900 mg) in acetonitrile (10 mL) with the seed obtained using nitromethane. Into the mixture containing the seed of crystalline free base Form A of Compound (1) was slowly added water (795.0 mL) to make a 40% water solution. The resulting mixture was cooled down slowly to 0° C. (~−10° C./hour), and subsequently held for 2 hours. Solid materials were then filtered and air dried, and then further dried in oven at 60° C. for 18 hours.

Alternatively, 2-methyl THF solvate of free base Compound (1) instead of amorphous free base Compound (1) was used and Form A of free base Compound (1) was also obtained in a similar matter as described above.

The prepared Form A of Compound (1) was found to be stable in the following solvent systems (but not limited to): acetonitrile, chlorobenzene, chloroform, cyclohexane, 1,2-dichloroethane, dichloromethane, 1,2-dimethoxyethane, ethylene glycol, formamide, hexane, methylbutyl ketone, methylcyclohexane, N-methylpyrrolidinone, nitromethane, tetralin, toluene, 1,1,2-trichloroethane, acetic acid, anisole, 1-butanol, butyl acetate, cumene, ethyl acetate, ethyl ether, ethyl formate, heptane, isobutyl acetate, isopropyl acetate, 3-methyl-1-butanol, 2-methy-1-propanol, pentane, propyl acetate, water, water-iso-propanol (1:3 vol/vol), and water-acetonitrile (1:1 vol/vol; 1:3 vol/vol).

Certain observed XRPD peaks and $C^{13}$ SSNMR peaks are summarized in Tables 10 and 11, respectively.

TABLE 10

XRPD Peaks of Form A of Compound (1).

| XRPD Peaks | Angle (2-Theta ± 0.2) | Intensity % |
|---|---|---|
| 1 | 11.8 | 100.0 |
| 2 | 18.9 | 100.0 |
| 3 | 16.9 | 99.8 |
| 4 | 15.5 | 99.7 |
| 5 | 22.0 | 99.7 |
| 6 | 25.5 | 99.7 |
| 7 | 9.1 | 99.4 |
| 8 | 23.6 | 98.6 |
| 9 | 27.6 | 98.5 |
| 10 | 17.5 | 98.3 |
| 11 | 23.0 | 98.3 |
| 12 | 24.0 | 98.3 |
| 13 | 13.7 | 98.2 |
| 14 | 20.2 | 98.2 |
| 15 | 12.5 | 97.8 |
| 16 | 10.6 | 97.7 |
| 17 | 15.8 | 97.5 |
| 18 | 20.6 | 97.5 |
| 19 | 12.9 | 97.4 |
| 20 | 24.7 | 97.4 |
| 21 | 26.2 | 97.4 |
| 22 | 6.2 | 97.3 |
| 23 | 21.1 | 97.3 |

TABLE 11

$C^{13}$ SSNMR Peaks of Form A of Compound (1).

| Peak # | Chem Shift [±3 ppm] | Intensity [rel] |
|---|---|---|
| 1 | 180.0 | 60.1 |
| 2 | 176.2 | 68.7 |
| 3 | 175.9 | 62.4 |
| 4 | 160.2 | 28.8 |
| 5 | 158.6 | 18.4 |
| 6 | 157.9 | 28.1 |
| 7 | 157.3 | 47.2 |
| 8 | 156.0 | 34.3 |
| 9 | 155.4 | 49.7 |
| 10 | 152.3 | 32.5 |
| 11 | 151.4 | 49.5 |
| 12 | 146.5 | 18.6 |
| 13 | 144.4 | 61.1 |
| 14 | 143.8 | 56.4 |
| 15 | 142.9 | 19.2 |
| 16 | 140.2 | 21.2 |

TABLE 11-continued $C^{13}$ SSNMR Peaks of Form A of Compound (1).

| Peak # | Chem Shift [±3 ppm] | Intensity [rel] |
|---|---|---|
| 17 | 138.5 | 55.6 |
| 18 | 133.6 | 29.4 |
| 19 | 132.3 | 61.4 |
| 20 | 131.0 | 52.1 |
| 21 | 126.2 | 23.0 |
| 22 | 121.5 | 35.8 |
| 23 | 120.8 | 39.3 |
| 24 | 119.7 | 90.9 |
| 25 | 116.2 | 59.3 |
| 26 | 115.3 | 44.3 |
| 27 | 112.7 | 35.0 |
| 28 | 52.5 | 39.0 |
| 29 | 51.6 | 75.9 |
| 30 | 50.4 | 94.8 |
| 31 | 49.8 | 74.6 |
| 32 | 31.8 | 80.4 |
| 33 | 31.2 | 53.0 |
| 34 | 30.5 | 86.0 |
| 35 | 30.1 | 95.1 |
| 36 | 28.5 | 100.0 |
| 37 | 26.3 | 81.0 |
| 38 | 25.9 | 96.1 |
| 39 | 25.0 | 82.2 |
| 40 | 22.8 | 66.97 |
| 41 | 22.2 | 55.41 |
| 42 | 21.6 | 64.44 |
| 43 | 21.0 | 82.87 |
| 44 | 20.4 | 57.45 |
| 45 | 19.8 | 52.2 |

Thermogravimetric analysis of the product, Form A of Compound (1), was performed (the data not shown here) on the TA Instruments TGA model Q500 by placing a sample of it in a platinum sample pan and by subsequent heating the pan at 10° C./min to 300° C. from room temperature. The thermogram demonstrated a decomposition onset was around 293° C.

A DSC thermogram for Form A of Compound (1) was also obtained using TA Instruments DSC Q200. A sample of the form was heated at 10° C./min to 350° C. The DSC thermogram showed the melting temperature to be around 278° C.

4B: Preparation of Form B of Hydrates of Free Base Compound (1)

A hydrated form of free base Compound (1) was isomorphic as Form A of free base Compound (1)—Form A of free base Compound (1) could freely convert to the hydrated form B when it was exposed to high humidity and revert back when the humidity was lowered. According to the phase changes determined using DSC experiments (data not shown), the transition temperature was close to ambient temperature and varied with water activity. For example, at ambient temperature, the hydrate form was observed where a water activity was greater than 0.6, such as 0.6-1.0.

4C: Preparation of Amorphous Free Base Compound (1)

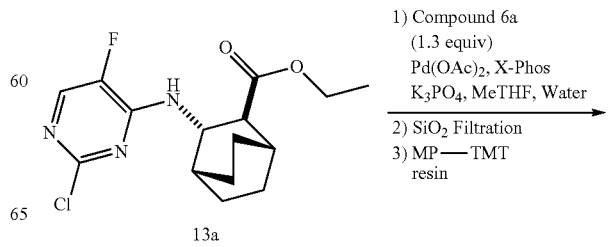

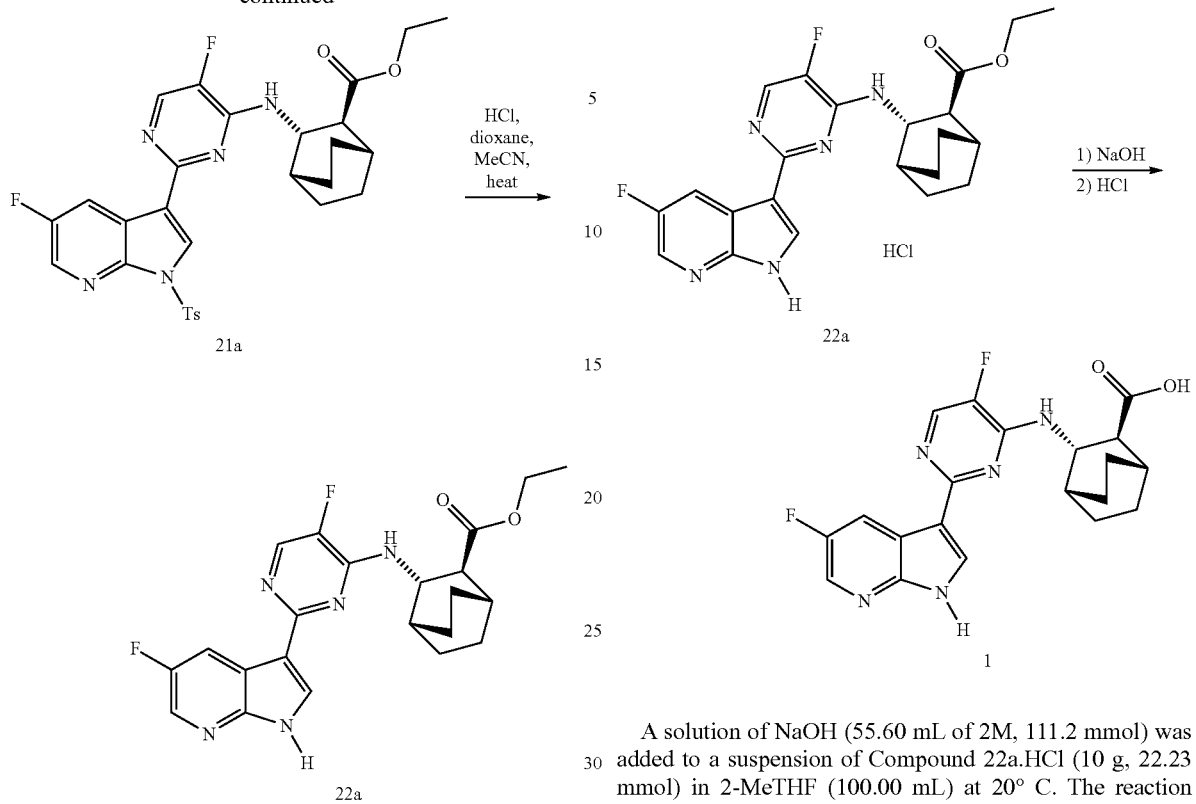

Suzuki coupling was performed by taking up the chloropyrimidine, Compound 13a, boronic ester Compound 6a, catalyst Pd(OAc)$_2$, and ligand (X-Phos) in 10 vol of 2-MeTHF. This mixture was heated to 65° C. and 2 vol of a 50% aqueous solution of K$_3$PO$_4$ were added at a rate that maintained the reaction mixture at 65° C. Both reactions went to full conversion then were cooled to 20° C. and filtered through celite. The aqueous layers were separated to waste, the organic layers washed with 5% aqueous NaCl, and then concentrated to dryness to give approximately 3.5 kg of a dark green paste for each. The crude oil was divided into 4 equal portions, slurried with 400 g of SiO$_2$ and 500 g of Florisil, and eluted through a 2.3 kg SiO$_2$ column with heptane/EtOAc (5:1 to 3:1, 2 L fractions) combining all product containing fractions. These fractions were concentrated to dryness to give approximately 2.9 kg of Compound 21a.

Compound 21a was dissolved in 10 vol (25 L) of CH$_3$CN and treated with 4 eq. of HCl (4.31 L of 4N HCl in 1,4-dioxane) at 70° C. for 15 h. The reaction was judged 100% complete by HPLC and the thin slurry cooled to 20° C. in 1 h. TBME (28 L, 11 vol) was added at 0.5 L/min with the slurry becoming very thick (gelatinous) at the end of the addition. After 4-5 h stirring, the slurry became much thinner. The resulting solids were collected by suction filtration and washed with 3×5 L TBME giving a low density cake, and dried under a N$_2$ steam for 3 days to give 1.71 kg (86% yield, 98.9% AUC purity) of Compound 22a.HCl.

A solution of NaOH (55.60 mL of 2M, 111.2 mmol) was added to a suspension of Compound 22a.HCl (10 g, 22.23 mmol) in 2-MeTHF (100.00 mL) at 20° C. The reaction mixture was stirred at 60° C. for 5 h, and then additionally at 67° C. After approximately 22 hours' stirring, 100 mL (10 vol) of 2-MeTHF was added to the resulting mixture. The batch was then cooled to 0° C. HCl was added to the resulting mixture to adjust the pH to pH 6.6 to produce crude free base Compound (1). The crude material in 60 mL (6 vol) of 2-Me-THF was heated to 50° C. 50 mL (5 vol) of n-heptane was added into the resulting mixture over 1 hour. The batch was then cooled to 20° C. The solid product was filtered, and the solid product was further purified by column chromatography (EtOAc/heptane 2:1 to 4:1). Its XRPD data indicated amorphous free base Compound (1).

Alternatively, amorphous free base Compound (1) was observed from a mixture of Form A of free base Compound (1) and a solvent selected from 2-ethoxyethanol, 2-methoxyethanol, t-butylmethylether, formic acid, or methylethyl ketone (e.g., see Table 13 below), which was stirred at ambient temperature.

4D: Preparation of 2-MeTHF Solvate of Free Base Compound (1)

Compound (1).1(2-MeTHF) was prepared as described in Example 2 above. Certain observed XRPD peaks of the compound are summarized in Table 12.

TABLE 12

XRPD Peaks of Compound (1)•1(2-MeTHF).

| XRPD Peaks | Angle (2-Theta ± 0.2) | Intensity % |
|---|---|---|
| 1 | 6.4 | 9.78 |
| 2 | 8.4 | 38.07 |
| 3 | 9.7 | 43.96 |
| 4 | 12.9 | 15.57 |
| 5 | 16.7 | 100 |
| 6 | 16.9 | 46.55 |

TABLE 12-continued

XRPD Peaks of Compound (1)•1(2-MeTHF).

| XRPD Peaks | Angle (2-Theta ± 0.2) | Intensity % |
|---|---|---|
| 7 | 17.4 | 18.67 |
| 8 | 19.4 | 16.54 |
| 9 | 20.0 | 14.62 |
| 10 | 21.0 | 20.4 |
| 11 | 21.3 | 13.58 |
| 12 | 22.3 | 37.59 |
| 13 | 24.3 | 15.36 |
| 14 | 25.7 | 16.34 |
| 15 | 25.9 | 10.06 |

4F: Solubility and Stability Data of Form A of Free Base Compound (1) and Amorphous Compound (1) in Various Solvent Systems Solubility and stability of Form A free base Compound (1) ("Form A") and amorphous compound (1) ("amorphous") in various solvent systems were tested at ambient temperature in a similar manner as described above for those of Form A of HCl salt of Compound (1). The resulting data are summarized in Table 13.

TABLE 13

Solubility and Stability Data of Form A free base Compound (1) ("Form A") and amorphous compound (1) ("Amorphous").

| | | Starting Form A | Starting Amorphous |
|---|---|---|---|
| Solvent | Sol. (mg/ml) | Resulting Form | Resulting Form |
| Acetonitrile | 1.0 | A | Amorphous |
| Chlorobenzene | 0.4 | A | Amorphous |
| Chloroform | 3.8 | A | Amorphous |
| Cyclohexane | <0.1 | A | Amorphous |
| 1,2-Dichloroethane | 0.4 | A | Amorphous |
| Dichloromethane | 0.9 | A | Amorphous |
| 1,2-Dimethoxyethane | 114.0 | A | Amorphous |
| N,N-dimethylacetamide | >150 | Solvate | Solvate |
| N,N-dimethylformamide | 39.2 | Solvate | No signal |
| 1,4-Dioxane | 21.3 | Solvate (1:1) | Solvate (1:1) |
| 2-Ethoxyethanol | >113 | Amorphous | No signal |
| Ethylene glycol | 10.4 | A | Solvate |
| Formamide | 7.0 | A | Amorphous |
| Hexane | <0.1 | A | Amorphous |
| Methanol | 25.5 | Solvate | Solvate |
| 2-Methoxyethanol | >114 | Amorphous | No signal |
| Methylbutyl ketone | 20.0 | A | Amorphous |
| Methylcyclohexane | <0.1 | A | Amorphous |
| N-Methylpyrrolidinone | >149 | A | No signal |
| Nitromethane | 0.3 | A | Amorphous |
| Tetralin | <0.1 | A | Amorphous |
| Toluene | 0.3 | A | Amorphous |
| 1,1,2-Trichloroethane | 1.0 | A | Amorphous |
| xylene | 0.3 | Solvate | Amorphous |
| acetic acid | 42.8 | A | Solvate |
| Acetone | 16.3 | Solvate | Solvate |
| Anisole | 0.7 | A | Amorphous |
| 1-Butanol | 21.0 | A | Solvate (1:1) |
| 2-Butanol | 14.0 | Solvate (1:1) | Solvate(1:1) |
| Butyl acetate | 8.1 | A | Amorphous |
| t-Butylmethylether | 10.4 | Amorphous | Amorphous |
| Cumene | 0.3 | A | Amorphous |
| Dimethylsulfoxide | >113 | No signal | No signal |
| Ethanol | 35.5 | No signal | A |
| Ethyl acetate | 11.6 | A | Amorphous |
| Ethyl ether | 3.5 | A | Amorphous |
| Ethyl formate | 8.1 | A | Solvate(1:1) |
| Formic acid | >89.4 | Amorphous | No signal |
| Heptane | <1.5 | A | Solvate |
| Isobutyl acetate | 4.4 | A | Amorphous |
| Isopropyl acetate | 6.2 | A | Amorphous |
| Methyl acetate | 9.4 | Solvate | Solvate |
| 3-Methyl-1-butanol | 9.7 | A | Solvate |
| Methylethyl ketone | 27.3 | Amorphous | Solvate(1:1) |
| 2-Methy-1-propanol | 12.2 | A | Solvate(1:1) |
| Pentane | <0.3 | A | Amorphous |
| 1-Pentanol | 14.5 | No signal | Solvate(1:1) |
| 1-Propanol | 15.9 | Solvate | No signal |
| 2-Propanol | 12.9 | Solvate(1:1) | Solvate(1:1) |
| Propyl acetate | 7.5 | A | Amorphous |
| Tetrahydrofuran | 61.2 | Solvate(1:1) | Solvate(1:1) |
| Methyl tetrahydrofuran | 34.8 | Solvate(1:1) | Solvate(1:1) |
| Water | <0.1 | A | Amorphous |
| Water-IPA 1:1 | — | Solvate | — |
| Water-IPA 1:3 | — | A | — |
| Water-ACN 1:1 | — | A | — |
| Water-ACN 1:3 | — | A | — |
| Water-MeOH 1:1 | — | Solvate | — |
| Water-MeOH 1:3 | — | Solvate | — |

Example 5: Preparation of Form A of Tosylate Salt of Compound (1)

Form A of tosylate salt of Compound (1) was prepared by slurring amorphous free base Compound (1) (500 mg) and p-toluenesulfonic acid in acetonitrile (20 ml). Samples were stirred overnight. Certain observed XRPD peaks of the compound are summarized in Table 14.

Alternatively, 2-methyl THF solvate of free base Compound (1) instead of amorphous free base Compound (1) could be used to prepare Form A of tosylate Compound (1) in a similar matter as described above.

TABLE 14

XRPD Peaks of Form A of Tosylate Salt Compound (1).

| XRPD Peaks | Angle (2-Theta ± 0.2) | Intensity % |
|---|---|---|
| 1 | 6.0 | 30.21 |
| 2 | 7.2 | 100 |
| 3 | 9.3 | 37.8 |
| 4 | 12.9 | 13.96 |
| 5 | 13.7 | 39.23 |
| 6 | 14.3 | 50.25 |
| 7 | 14.7 | 42.94 |
| 8 | 16.4 | 9.99 |
| 9 | 16.9 | 89.79 |
| 10 | 18.7 | 59.65 |
| 11 | 19.3 | 19.62 |
| 12 | 19.6 | 33.34 |
| 13 | 20.3 | 11.38 |
| 14 | 20.8 | 11.98 |
| 15 | 21.9 | 41.6 |
| 16 | 23.0 | 33.45 |
| 17 | 24.2 | 14.97 |
| 18 | 25.4 | 23.83 |
| 19 | 26.3 | 44.54 |
| 20 | 26.9 | 51.79 |
| 21 | 27.5 | 34.02 |
| 22 | 28.0 | 36.07 |
| 23 | 29.1 | 13.36 |
| 24 | 29.7 | 8.92 |
| 25 | 32.2 | 9.25 |
| 26 | 33.1 | 4.75 |

Example 6: Formulations of Compound (1)

A. Tablets of Compound (1)

Compositions

Form A of HCl salt of Compound (1).½H$_2$O (hereinafter simply Compound (1) for Example 6) was employed for the tablet formation. All excipients complied with the current monographs of the European Pharmacopoeia and the USP/NF and are purchased from approved suppliers.

The formulation composition and batch size for the pre granulation blend and the granulation binder solution are given in Table 15A. The batch size of the binder solution included a 100% overage for pump calibration and priming of solution lines. The theoretical compression blend composition is also given in Table 15B. The actual quantities for the batch were calculated based on the yield of the dried granules. The composition and approximate batch size of the film coating suspension is given in Table 15B and included 100% overage for pump calibration and priming of suspension lines. The target amount of the film coating was 3.0% w/w of the tablet weight.

TABLE 15A

Compositions of Tablets of Compound (1).

| | | % in pre-granulation blend | % in dry granule | % in tablet core | mg in tablet (300 mg) |
|---|---|---|---|---|---|
| Intra granular | Compound (1) crystalline hemihydrate, HCl salt (Form A) | 76.13 | 74.99 | 50.00 | 333.00 |
| | Avicel PH-101, NF, PhEur | 10.03 | 9.88 | 6.59 | 43.89 |
| | Lactose Monohydrate, #316, NF, PhEur | 10.03 | 9.88 | 6.59 | 43.89 |
| | Ac-Di-Sol, NF, PhEur, JP | 3.81 | 3.75 | 2.50 | 16.65 |
| | total pre-granulation blend: | 100.00 | 98.50 | 65.68 | 437.43 |
| In binder solution | Povidone K30, USP | | 1.50 | 1.0 | 6.66 |
| | Water, USP | | na | na | na |
| | total granules: | | 100.00 | 66.68 | 444.09 |
| Extra granular | Prosolv 50, NF | | | 28.82 | 191.94 |
| | Ac-Di-Sol, NF, PhEur, JP | | | 2.50 | 16.65 |
| | SSF, NF | | | 2.00 | 13.32 |
| | Total core tablet | | | 100 | 666.00 |
| In film coating suspension | Opadry II, 85F18422 | | | (3.2 wrt core) | 21.31 |
| | Water, USP | | | | na |
| | Total final coated tablet | | | | 687.31 |

TABLE 15B

Film coat suspension composition and approximate batch size.

| Component | % W/W | Batch size (g) |
|---|---|---|
| Opadry II White, 33G | 15.00 | 210.00 |
| Water, USP | 85.00 | 1190.00 |
| Total | 100.00 | 1400.00 |

Binder Solution Preparation

The binder solution consisted of Povidone and water. The solution was prepared based on 40% water content in the final granulation. Thus, the total amount of solids in solution (Povidone) was 3.6% (w/w). An excess amount of 100% was prepared for priming lines, etc. Based on visual inspection of startup of the granulation run, additional stock solutions of +/−2% (38-42%) water in the final granulation was prepared. Typically, 87.00 g Povidone K30, and 2320.00 g purified (DI) water were weighed, and under constant stirring was added the Povidone K30 into the container containing the DI water. After the addition, the container was sealed to minimize evaporation, and the solution was stirred until all the solids present were fully dissolved.

Wet Granulation Process Flow

Wet granulation was performed by the procedures described below: Excess (10%) amount of Compound (1), Avicel PH-101, Fastflo lactose and Cross Carmellose Sodium were weighed (see Table 15A). They were screened using a 20 mesh hand screen or a cone mill equipped with an 813 μm grated mesh screen at 1000 rpm (for a U5 Quadro Co-mill). The screened materials were placed in individual bags or containers. The materials were then transferred into a blender, and were blended for 15 minutes at typically 15 RPM. The blended materials were milled using U5 Quadro cone mill equipped with 4 mm square hole screen at 1000 rpm. The milled materials were blended again, repeating the blend step. The re-blended materials were then fed into a twin screw granulator. The bulk wet granulation was fed into the granulator using a Loss in Weight feeder (K-tron or similar). The resulting materials were then granulated. The binder fluid (see Table 15A) was injected into the twin screw granulator using a peristaltic pump. The ratio of solution feed rate over powder feed rate was 0.4095. For example, if the powder feed rate was 15.00 g/min, the solution feed rate was 0.4095*15.00=6.14 g/min, with a water content of 40% (based on the dry mass). The granule sub batches were collected into pre-tared drying trays. The collected materials were evenly sprayed on a tray and dry the material in an oven to form dried granules. The dried granules were placed into K-tron to starve feed continuously into cone mill and subsequently milled.

Extra-Granular Blending and Compression Process

Extra-granular blending and compression process were performed by the procedures described below: The quantity of the extra-granular excipients based on the compression blend composition was weighed. The weighed excipients were screened using a U5 Comil with a 32C screen and round bar impeller at 1000 rpm. The milled granules of Compound (1) were first added to the blender containing the screened Avicel PH-102 and Ac-Di-Sol. They were blended for 8 minutes at 16 RPM. Sodium stearyl (SSF) was screened through a mesh 50 hand screen into an appropriate container. A portion of the extra granular blend equal to roughly 10 times by mass the amount of SSF was placed in the container with the SSF and bag blend for 30 seconds before adding the mixture to the bin blender. All of the materials were then blended for 2 minutes at 16 rpm. The final blend was then compressed according to the prescribed tablet compression process parameters.

Film Coating Process

A film coating was applied to the core tablets in a Vector VPC 1355 pan coater as a 15% w/w Opadry II white #33G aqueous suspension. The target coating was 3.0% w/w of the core tablet weight, with an acceptable range of 2.5% to 3.5%. To accomplish this, an amount of coating suspension equivalent to a 3.2% weight gain was sprayed, which gave a 3.0% coating assuming a coating efficiency of 95%.

Intravenous (IV) Formulations of Compound (1)

Form A of HCl salt of Compound (1)·½$H_2O$ (hereinafter simply Compound (1) for Example 6) was supplied as a 2 mg/mL solution for intravenous (IV) administration. The composition of the solution along with the quality reference and function of each component were provided in Tables 16A and 16B.

TABLE 16A

Composition of the Solution Vehicle[a].

| Component | Quality Standard | Component Function | Amount (mg/50 g IV solution) | Content (% w/w) |
|---|---|---|---|---|
| Sodium Phosphate monobasic, anhydrous | USP | Buffering agent | 26 | 0.052 |
| Sodium Phosphate dibasic, heptahydrate | USP | Buffering agent | 1281 | 2.562 |
| Dextrose, anhydrous | USP | Tonicity modifier | 500 | 1.000 |
| Water for injection | USP | Solvent | 48,193 | 96.386 |
| Total | — | — | 50,000 | 100% |

Abbreviations:
USP, United States Pharmacopoeia
[a]Solution will be adjusted for pH with NaOH or HCl

TABLE 16B

Composition of Compound (1) Intravenous Solution[a].

| Component | Component Function | Amount (mg/50 g IV solution) | Content (% w/w) |
|---|---|---|---|
| Compound (1)[b] | Drug substance | 111 | 0.222 |
| Solution Vehicle (from Table 1) | Solvent | 49,889 | 99.778 |
| Total | — | 50,000 | 100% |

[a]Solution was adjusted for pH with NaOH or HCl. Density of solution is 1.000 g/cm³.
[b]The drug substance was a hemihydrate HCl salt. The amount of drug substance was calculated based on the active anhydrous free base equivalent, where a conversion factor from the free base to the hemihydrate HCl salt is 1.11.

Example 7: In Vivo Assay for Combination of Compound (1) with or without Oseltamivir Infected mice were treated with vehicle or escalating dose levels of Form A of HCl salt of Compound (1)·½$H_2O$ in combination with the clinically relevant dose of Oseltamivir starting 48 hours post influenza A challenge or 2 hours prior to Influenza B challenge.

Methods:

In these studies, Form A of HCl salt of Compound (1) hemihydrate (hereinafter simply Compound (1) for Example 7) was formulated in a vehicle containing 0.5% (w/v) MC (Sigma-Aldrich, St Louis, Mo.), yielding a homogeneous suspension, and the dose of the compound was based upon the HCl salt of Compound (1) hemihydrate. Oseltamivir was formulated in distilled deionized water yielding a homogeneous suspension. The combination of Compound (1) with oseltamivir was formulated in a vehicle containing 0.5% (w/v) MC. The combination formulations were prepared at the beginning of each study and stored at 4° C. for up to 10 days with stirring in the dark. All formulations and vehicles were administered to mice via oral gavage at a dosing volume of 10 mL/kg.

Male Balb/c mice (5-7 weeks, 17-19 grams) were anesthetized and inoculated with a lethal dose of mouse-adapted influenza virus A/PR/8/34 or B/Mass/3/66 by intranasal instillation. Eight mice were enrolled per study group. Treatments were initiated +48 hours post inoculation for influenza A or 2 hours prior to inoculation for influenza B. Vehicle (10 mL/kg) and Compound (1) at doses of 0.1-10 mg/kg was administered alone or in combination with 10 mg/kg Oseltamivir orally (PO) twice daily (BID) for 10 days in the influenza A study. Vehicle (10 mL/kg) and Compound (1) at doses of 1-10 mg/kg was administered alone or in combination with 10 mg/kg Oseltamivir orally (PO) twice daily (BID) for 10 days in the influenza B study. Mice were weighed and observed daily for signs of morbidity for 21 days after infection. In addition lung function was monitored by unrestrained WBP (Buxco, Troy, N.Y.).

Influenza A/PR/8/34 (VR-1469) and Influenza B/Mass/3/66 (VR-523) were obtained from ATCC (Manassas, Va.). Stocks were prepared by standard methods known in the art.

Briefly, virus was passaged at low multiplicity of infection in Madin-Darby canine kidney cells (MDCK cells, CCL-34, ATCC), the supernatant harvested after approximately 48 hours and centrifuged at 650×g for 10 minutes. Virus stocks were frozen at −80° C. until used. Virus titers ($TCID_{50}$/ml) were calculated by the Spearman-Karger method after serially diluting the virus sample, infecting replicate MDCK cultures, and measuring the cytopathic effect (CPE) based on ATP content at 96 hours (CellTiter-Glo, Promega, Madison Wis.).

Mice were weighed daily for 21 days after infection. Body weight data were analyzed using Two Way ANOVA and a Bonferroni post test to compare groups. P-values less than 0.05 were considered significant.

Mice were observed daily for 21 days post influenza infection. Any mouse that scored positive for four of the following six observations (>35% BW loss, ruffled fur, hunched posture, respiratory distress, reduced mobility, or hypothermia) was deemed moribund, then euthanized and scored as a death in accordance with guidelines established with the Vertex Institutional Animal Care and Use Committee. Survival data were analyzed using the Kaplan Meier method.

Mice were subjected to unrestrained WBP (Buxco, Troy, N.Y.). Lung function is expressed as enhanced pause (Penh), a unit-less calculated value that reflects pulmonary resistance. This value is derived from changes in the holding container pressure that fluctuates as a consequence of changes in the animal's breathing pattern.

Bronchoconstriction of the animal's airways will affect the flow of air and, hence, pressure in the holding container. The changes in pressure are tracked during expiration (PEP) and inspiration (PIP). Penh values were calculated according to the formula Penh=pause×PEP/PIP, where "pause" reflects the timing of expiration. Mice were acclimated in the Plethysmography chamber for 15 minutes, then data were collected in one minute intervals, averaged over 10 minutes, and expressed as absolute Penh values. Data were analyzed using Two Way ANOVA and a Bonferroni post test to compare groups. P-values less than 0.05 were considered significant.

Results:

Compound (1) was evaluated in combination with Oseltamivir for its ability to prevent mortality and morbidity, reduce BW loss, and prevent and/or restore lung function in a murine model of influenza pulmonary infection versus Compound (1) or Oseltamivir treatment alone. The combination showed no deleterious effect on the efficacy of each of the drugs as compared to each drug administered alone. In addition, the combination treatment showed synergy in influenza A treatment as the failure dose for each compound alone (0.3 and 10 mg/kg of Compound (1) and Oselatamivir, respectively) when combined increased survival from 0 to 100 percent. Compound (1) has little activity against influenza B in vivo (as expected from available in vitro data) and does not interfere with the effectiveness of Oseltamivir.

Influenza A Mouse Model:

All of the vehicle-treated controls succumbed to disease by days 9 or 10. Treatment at 1, 3 and 10 mg/kg Compound (1) BID alone provided complete protection from death, reduced BW loss and restored lung function when dosing was initiated +48 hours post infection as compared to vehicle controls (Table 17). Treatment at 0.1 and 0.3 mg/kg Compound (1) and 10 mg/kg Oseltamivir administered alone did not protect from death reduce BW loss or restore lung function when treatment initiated +48 hours post influenza A infection. Interestingly, 0.3 mg/kg Compound (1) and Oseltamivir administered together +48 hours post influenza A infection provided complete protection from death, reduced BW loss and restored lung function.

TABLE 17

In Vivo Efficacy Data of Compound (1) with or without Oseltamivir Administered + 48 Hours After Influenza A Infection.
Compound (1)/Oseltamivir Combination in FluA

| | Oseltamivir mg/kg | | | | | |
|---|---|---|---|---|---|---|
| | 0 | | | 10 | | |
| Compound (1) mg/kg | Survival (21 days) (%) | Weight Loss (Day 8) (%) | Penh (Day 3) | Survival (21 days) (%) | Weight Loss (Day 8) (%) | Penh (Day 3) |
| 0 | 0 | 33.9 | 2.28 | 0 | 32.0 | 2.36 |
| 0.1 | 0 | 34.2 | 2.15 | 0 | 31.6 | 2.09 |
| 0.3 | 0 | 32.4 | 1.90 | 100 | 29.3 | 1.80 |
| 1 | 100 | 28.2 | 2.11 | 100 | 23.4 | 1.23 |
| 3 | 100 | 22.2 | 1.68 | 100 | 17.6 | 1.11 |
| 10 | 100 | 14.6 | 0.95 | 100 | 8.4 | 0.79 |

Influenza B Mouse Model:

All of the vehicle-treated controls succumbed to disease by days 7 or 8. Administration of 1, 3, or 10 mg/kg Compound (1) alone −2 h prior to influenza B infection and continued BID for 10 days provided no significant protection against morbidity, BW loss or loss of lung function as compared to controls. Oseltamivir administered at 10 mg/kg alone or in conjunction with 1, 3 or 10 mg/kg Compound (1) −2 h prior to influenza B infection provided complete protection from death, reduced BW loss and restored lung function (Table 18).

TABLE 18

In Vivo Efficacy Data of Compound (1) with or without Oseltamivir Administered + 48 Hours after Influenza B Infection
Compound (1)/Oseltamivir Combination in FluB

| | Oseltamivir mg/kg | | | | | |
|---|---|---|---|---|---|---|
| | 0 | | | 10 | | |
| Compound (1) mg/kg | Survival (21 days) (%) | Weight Loss (Day 8) (%) | Penh (Day 6/7) | Survival (21 days) (%) | Weight Loss (Day 8) (%) | Penh (Day 6/7) |
| 0 | 0 | ND | 2.20 | 100 | 12.8 | 1.08 |
| 1 | 0 | 33.6 | 1.90 | 100 | 7.7 | 1.26 |
| 3 | 0 | 33.9 | 2.06 | 100 | 11.5 | 1.41 |
| 10 | 0 | 33 | 2.04 | 100 | 9.7 | 1.17 |

Example 8: In Vivo Assay for Combination of Compound (1) with Oseltamivir

Infected mice were treated with vehicle or escalating dose levels of Form A of HCl salt of Compound (1).½H$_2$O (hereinafter simply Compound (1) for Example 8) in combination with zanamivir starting 24 hours prior to influenza A challenge with 5×10$^3$ TCID$_{50}$ A/PR/8/34. The influenza A challenge and Compound (1) suspensions were prepared in a similar manner as described above in Example 7. The challenged mice were treated once IN (intranasal) with zanamivir at 0.3 mg/kg, 1 mg/kg or 3 mg/kg 24 hours prior to IN challenge with 5×10$^3$ TCID$_{50}$ A/PR/8/34, and with Compound (1) at 0.1 mg/kg, 0.3 mg/kg, or 1 mg/kg BID for 10 days starting −2 hours prior to the challenge with 5×10$^3$ TCID$_{50}$ A/PR/8/34.

The results are summarized in Tables 19A and 19B below. As shown in Tables 18A below, the combination therapy with Compound (1) and zanamivir provided extra survival benefit (Table 19A). Efficiency quotient, a composite measure of survival, bodyweight loss and lung function (% survival/(% body weight loss at Day 8)*(Penh at Day 6)) is summarized in Table 19B.

TABLE 19A

Survival Rate: Combination Therapy of Compound (1) with Zanamivir.

| | | Compound (1) (mg/kg, BID) 1$^{st}$ dose 2 h prior to infection | | |
|---|---|---|---|---|
| | | 0.1 | 0.3 | 1 |
| Zanamivir (mg/kg, IN × 1), 1$^{st}$ dose 24 h prior to infection | 0 | 0 | 12.5 | 44.4 | 100 |
| | 0.3 | 37.5 | 0 | 100 | 100 |
| | 1 | 50 | 75 | 100 | 100 |
| | 3 | 62.5 | 100 | 100 | 100 |

TABLE 19B

Efficiency Quotient: Combination Therapy of Compound (1) with Zanamivir.

|  |  | Compound (1) (mg/kg, BID) 1st dose 2 h prior to infection | | |
|---|---|---|---|---|
|  |  | 0.1 | 0.3 | 1 |
| Zanamivir (mg/kg, IN × 1), 1st dose 24 h prior to infection | 0 | — | — | 0.59 | 2.32 |
| | 0.3 | 0.44 | — | 1.35 | 2.97 |
| | 1 | 0.73 | 1.00 | 1.61 | 2.31 |
| | 3 | 0.73 | 1.30 | 1.48 | 4.28 |

Example 9: Prophylactic and Post-Infection Efficacy of Compound (1) in the Mouse Influenza a Infection Model Materials and Methods Animals:

Female 18-20 g BALB/c mice were obtained from Jackson Laboratories (Bar Harbor, Me.) for the antiviral experiment. The animals were maintained on standard rodent chow and tap water ad libitum. They were quarantined for 48 hours prior to use.

Virus:

Mouse-adapted Influenza A/California/04/2009 (pndH1N1) virus was obtained from Dr. Elena Govorkova (St. Jude Children's Research Hospital, Memphis, Tenn.). The virus stock was amplified in MDCK cells, followed by titration for lethality in BALB/c mice. Influenza A/Victoria/3/75 (H3N2) virus was obtained from the American Type Culture Collection (Manassas, Va.). The virus was passaged seven times in mice to mouse-adapt it, followed one passage in MDCK cells. The virus was further titrated for lethality in BALB/c mice to obtain the proper lethal challenge dose. Influenza A/Vietnam/1203/2004 (H5N1) virus was obtained from Dr. Jackie Katz of Centers for Disease Control (Atlanta, Ga.). Mice were exposed to a lethal dose of the virus (5 MLD50, 5 PFU/mouse), which has previously resulted in death between days 6-13, with 90-100% mortality by day 10 at this dose.

Compounds: Oseltamivir (as Tamiflu®) was obtained from a local pharmacy. Each capsule of Tamiflu contains 75 mg of the active component, oseltamivir carboxylate, upon metabolism in the body. The dose of oseltamivir was based upon this measurement. Form A of HCl salt of Compound (1) hemihydrate (hereinafter simply Compound (1) for Example 9) was for the study and the dose of the compound was based upon the HCl salt of Compound (1) hemihydrate. Both Compound (1) and oseltamivir were prepared in 0.5% methylcellulose (Sigma, St. Louis, Mo.) for oral gavage (p.o.) administration to mice.

Experiment Design:

The mice were anesthetized by intraperitoneal injection of ketamine/xylazine (50/5 mg/kg), and the animals were infected intranasally with a 90-μl suspension of influenza virus. The virus challenge was approximately four 50% mouse lethal infectious doses. Treatments were given twice a day (at 12 hours intervals) for 10 days starting 2 hours before virus challenge or 48 hours post challenge as indicated. Parameters for assessing the infection were survival, mean day of death, body weight changes, and lung infection parameters (hemorrhage score, weight, and virus titer). Animals were weighed individually every other day through day 21 of the infection. Mice that died during the first six days of treatment period were deemed to have died from causes other than influenza virus infection, and were excluded from the total counts.

To assess lung infection parameters, lungs from sacrificed animals (initially 5 animals per group set apart for this purpose) were harvested. Lung hemorrhage score was assessed by visual inspection for color changes from pink to plum. This occurs regionally in the lungs, rather than by a gradual change of the whole lung to the darker color. Hemorrhage scores ranged from 0 (normal) to 4 (total lung showing plum color), and thus is a non-parametric measurement. The lungs were weighed and then frozen at −80° C. Later, thawed lungs were homogenized in 1 ml of cell culture medium, the supernatant fluids were centrifuged to remove particulate matter, and the liquid samples were re-frozen at −80° C. After preparing 96-well plates of MDCK cells, the samples were thawed, serially diluted in 10-fold dilution increments and titrated by endpoint dilution method in the plates (1), using 4 microwells per dilution. Virus titers were calculated as log 10 50% cell culture infectious doses per gram of lung tissue (log 10 CCID50/g).

Statistical Analysis:

Kaplan-Meir plots for multiple group comparisons were analyzed by the Mantel-Cox log-rank test to determine statistical significance. Subsequently, pairwise comparisons were made by the Gehan-Breslow-Wilcoxon test. The relative experimental significance was adjusted to a Bonferroni corrected significance threshold based on the number of treatment comparisons made. Mean day of death and mean lung hemorrhage score comparisons were analyzed by the Kruskal-Wallis test followed by Dunn's multiple comparisons test. Mean body weights, lung weights, and log 10 lung virus titers were evaluated by ANOVA assuming equal variance and normal distribution. Following ANOVA, individual treatment values were compared by the Tukey-Kramer multiple comparisons test. Analyses were made using Prism® software (GraphPad Software, San Diego, Calif.).

Results and Discussions

The prophylactic dose response of Compound (1) was investigated in the mouse influenza A model. Dosing with vehicle or Compound (1) was initiated 2 h prior to infection and continued twice daily for 10 days. The results are summarized in Tables 20 and 21. All of the mice that received vehicle alone succumbed to the infection by study day 9 and had lost, on average, ~32% of their body weight (BW). Compound (1) administered at 1, 3 or 10 mg/kg BID provided complete survival and a dose-dependent reduction in BW loss. Compound (1) administered at 0.3 mg/kg BID provided some survival benefit (2/8 mice) although the mice had significant BW loss. In the same experiment, mice were dosed with oseltamivir at 10 mg/kg BID, a clinically-equivalent human dose (based on AUC). All of the oseltamivir-administered mice survived with a similar weight loss profile to mice administered 1 mg/kg BID Compound (1).

Compound (1) still provided effectiveness in this model challenged with Influenza A/Vietnam/1203/2004 (H5N1) virus when it was administered at 48 hours post infection, with continued BID dosing for 10 days (Table 22). Dosing of Compound (1) at 10 mg/kg provided complete protection as shown in Table 20.

TABLE 20

Effects of Prophylaxis with Compound (1) and Oseltamivir on an Influenza A/California/04/2009 (pndH1N1) Virus Infection in BALB/c mice (prophylaxis).

| Compound (mg/kg)[a] | Survivors/ Total | MDD[b] ± SD | Mean Lung Parameters (Day 6) | | |
|---|---|---|---|---|---|
| | | | Score | Weight (mg) | Virus Titer[c] |
| Compound (1) (10 mg/kg) | 10/10*** | — | 0.2 ± 0.4** | 132 ± 20*** | <2.6[d]*** |
| Compound (1) (3 mg/kg) | 9/9*** | — | 0.0 ± 0.0*** | 123 ± 21*** | 3.1 ± 0.9*** |
| Compound (1) (1 mg/kg) | 10/10*** | — | 0.6 ± 0.9[e] | 246 ± 21* | 5.5 ± 1.2*** |
| Oseltamivir (10 mg/kg) | 10/10*** | — | 1.0 ± 0.0[e] | 178 ± 28*** | 7.9 ± 0.2 |
| Placebo | 2/20 | 9.9 ± 1.3 | 3.4 ± 0.5 | 282 ± 26 | 7.9 ± 0.4 |

[a]Dose per treatment, given twice a day for 10 days starting 2 hours prior to virus exposure.

[b]Mean day of death of mice that died on or before day 21.

[c]Log10 CCID50/g.

[d]Below limit of detection (2.6 log10).

[e]Not significant by the very stringent Dunn's multiple comparison test, but significant from placebo ($P < 0.01$) by the pairwise two-tailed Mann-Whitney U-test.

*$P < 0.05$,

**$P < 0.01$,

***$P < 0.001$, compared to placebo.

TABLE 21

Effects of Compound (1) and Oseltamivir on an Influenza A/Victoria/3/75 (H3N2) Virus Infection in BALB/c mice (prophylaxis).

| Compound (mg/kg)[a] | Survivors/ Total | MDD[b] ± SD | Mean Lung Parameters (Day 6) | | |
|---|---|---|---|---|---|
| | | | Score | Weight (mg) | Virus Titer[c] |
| Compound (1) (10 mg/kg) | 10/10*** | — | 0.1 ± 0.2[d] | 164 ± 11** | 6.1 ± 0.5*** |
| Compound (1) (3 mg/kg) | 10/10*** | — | 3.3 ± 0.6[e] | 260 ± 25 | 7.2 ± 0.2 |
| Compound (1) (1 mg/kg) | 4/10 | 9.8 ± 1.9 | 3.2 ± 0.3[e] | 274 ± 49 | 7.3 ± 0.3 |
| Oseltamivir (10 mg/kg) | 9/10*** | 7.0 | 1.7 ± 1.1 | 218 ± 24 | 7.0 ± 0.3** |
| Placebo | 3/20 | 9.8 ± 2.1 | 2.2 ± 0.6 | 264 ± 54 | 7.8 ± 0.4 |

[a]Dose per treatment, given twice a day for 10 days starting 2 hours prior to virus exposure.

[b]Mean day of death of mice that died on or before day 21.

[c]Log10 CCID50/g.

[d]Not significant by the very stringent Dunn's multiple comparison test, but significant from placebo ($P < 0.01$) by the pairwise two-tailed Mann-Whitney U-test.

[e]Same as footnote "d", but significant from placebo at $P < 0.05$ level.

**$P < 0.01$,

***$P < 0.001$, compared to placebo.

TABLE 22

Effects of Treatment (+48 h) with Compound
(1) and Oseltamivir on an Influenza A/Vietnam/1203/2004
(H5N1) Virus Infection in BALB/c mice.

| Compound (mg/kg)[a] | Survivors/Total | MDD[b] ± SD | Mean Lung Parameters (Day 6) Weight (mg) | Virus Titer[c] |
|---|---|---|---|---|
| Compound (1) (10 mg/kg) | 10/10 | >21 | 0.15 ± 0.02 | 3.75 ± 0.94 |
| Oseltamivir (10 mg/kg) | 0/10 | 9.5 ± 1.2 | 0.17 ± 0.02 | 5.22 ± 0.38 |
| Placebo | 0/20 | 9.9 ± 0.8 | 0.16 ± 0.02 | 4.65 ± 1.23 |

[a]Dose per treatment, given twice a day for 10 days starting 2 hours prior to virus exposure.
[b]Mean day of death of mice that died on or before day 21.
[c]Log10 CCID50/g.

Example 10: In Vitro Efficacy of Compound (1) Against a Span of Influenza Strains Cells and Viruses.

Madine Darby Canine Kidney (MDCK) cells were originally obtained from American Type Culture Collection (ATCC, Manassas, Va.) and passaged using standard laboratory techniques prior to use in infection assays. Cells were maintained at 37° C. in Dulbecco's modified Eagle's medium (DMEM; Invitrogen, Carlsbad, Calif.) supplemented with 10% fetal bovine serum (Sigma-Aldrich, St. Louis, Mo.), 2 mM L-glutamine, 10 mM HEPES, 100 U/mL penicillin and 100 ug/mL streptomycin (Invitrogen). Influenza virus was obtained from ATCC, the Virus Surveillance and Diagnosis Branch of the Influenza Division of the Centers for Disease Control and Prevention (CDC; Atlanta, Ga.) or the Influenza Reagent Resource, Influenza Division, WHO Collaborating Center for Surveillance, Epidemiology and Control of Influenza, CDC. To generate viral stocks, MDCK cells were infected with a low multiplicity of infection (MOI) in DMEM supplemented with 2 mM L-glutamine, 10 mM HEPES, 100 U/mL penicillin, 100 ug/mL streptomycin and 1 μg per mL tolylsulfonyl phenylalanyl chloromethyl ketone (TPCK)-treated trypsin (USB Corp.; Santa Clara, Calif.). Cells were incubated at 37° C. with 5% $CO_2$ for 48 h, after which time the supernatant was harvested by centrifugation at 900×g for 10 min with a Beckman GS-6R centrifuge. Virus stocks were aliquoted and frozen at −80° C.

Compounds.

Free base or HCl salt of Compound (1) (e.g., amorphous HCl salt of Compound (1), Form A of HCl salt of Compound (1) hemihydrate, amorphous free base Compound (1)) (hereinafter simply Compound (1) for Example 10) was dissolved in 100% dimethyl sulfoxide (DMSO) to make a solution of a concentration of 10 mM.

Antiviral Activity.

The antiviral activity of Compound (1) and amantadine was evaluated in MDCK cells as measured by ATP levels using CellTiter-Glo (Promega; Madison, Wis.). MDCK cells were plated into black, clear bottom, 384-well plates to a density of $2\times10^4$ cells per well in 50 μL VGM. Cells were incubated at 37° C., 5% $CO_2$, in saturated humidity to allow cells to adhere and form a monolayer. After 5 h 40 μL of media was removed and 15 μL of virus was added at an MOI of 0.005. Compound was added as 25 μL of a ten point, three-fold dilution in DMEM with supplements (final DMSO concentration of 0.5%). Internal controls consisted of wells containing cells only and untreated cells infected with virus. After a 72 h incubation, 20 μL of CellTiter-Glo was added to each well and incubated at room temperature for 10 min. Luminescence was measured using an EnVision Multilabel reader (PerkinElmer; Waltham, Mass.). $EC_{50}$ values (concentration of compound that ensures 50% cell viability of uninfected control) were calculated by fitting the compound dose versus response data using a 4-parameter curve fitting method employing a Levenburg Marquardt algorithm (Condoseo software; Genedata, Basel, Switzerland). In vitro testing of hpaiH5N1 was performed at Southern Research Institute under BSL-3 containment.

As shown in Table 23 below, Compound (1) showed potent activity against all influenza A strains tested, including H1N1 and H3N2 reference strains from 1934 to 2009, as well as the pandemic 2009 H1N1 strains A/California/07/2009, A/Texas/48/2009, and the highly pathogenic avian H5N1 strain A/VN/1203/2004. Compound (1) was equally effective against all strains including those that were resistant to amantadine and neuraminidase inhibitors. It showed limited activity against influenza B virus.

TABLE 23

Efficacy of Compound (1) Against a Panel of Influenza Strains.

| Influenza Strain | Inf. Virus Strain | Subtype | Cell Protection Assay[e] $EC_{50}$ ± SD Comp (1) (nM) |
|---|---|---|---|
| A/WS/33 [a] | A | H1N1 | 3.2 ± 4.3 |
| A/NWS/33 [a] | A | H1N1 | 0.73 ± 0.10 |
| A/Puerto Rico/8/34 [a] | A | H1N1 | 3.2 ± 1.8 |
| A/Weiss/43 [a] | A | H1N1 | 0.31 ± 0.23 |
| A/FM/1/47 | A | H1N1 | 0.57 ± 0.036 |
| A/Mal/302/54 | A | H1N1 | 0.57 ± 0.055 |
| A/Denver/1/57 | A | H1N1 | 0.42 ± 0.19 |
| A/Chelyabinsk/1/2006 | A | H1N1 | 0.70 ± 0.49 |
| A/Florida/3/2006 | A | H1N1 | 0.92 ± 1.5 |
| A/Fukushima/141/2006 | A | H1N1 | 0.18 ± 0.20 |
| A/Georgia/17/2006 | A | H1N1 | 0.13 ± 0.048 |
| A/Georgia/20/2006 [b] | A | H1N1 | 2.6 ± 3.8 |
| A/Missouri/3/2006 | A | H1N1 | 0.21 ± 0.060 |
| A/St. Petersburg/8/2006 [a] | A | H1N1 | 0.88 ± 0.69 |
| A/Virginia/01/2006 [a] | A | H1N1 | 0.42 ± 0.24 |
| A/Cambodia/0371/2007 [a]* | A | H1N1 | 0.61 ± 0.33 |
| A/South Dakota/6/2007 | A | H1N1 | 0.31 ± 0.25 |
| A/California/07/2009 NYMC X-179A [a] | A | H1N1 | 2.7 ± 1.8 |
| A/Aichi/2/68 | A | H3N2 | 1.4 ± 1.1 |
| A/Hong Kong/8/68 | A | H3N2 | 0.60 ± 0.11 |
| A/Port Chalmers/1/73 [a] | A | H3N2 | 0.54 ± 0.11 |
| A/Victoria/3/75 | A | H3N2 | 1.3 ± 0.63 |
| A/Wisconsin/67/2005 [a] | A | H3N2 | 1.8 ± 0.24 |
| A/Hawaii/2/2006 | A | H3N2 | 1.4 ± 0.91 |
| A/Nebraska/1/2006 [a]* | A | H3N2 | 2.1 ± 1.3 |
| A/Texas/12/2007 [a]*[c] | A | H3N2 | 0.65 ± 0.22 |
| A/Uruguay/716/2007 [a] | A | H3N2 | 3.5 ± 5.1 |
| A/New Jersey/8/76 | B | H1N1 | 0.20 ± 0.096 |
| A/California/07/2009 [a] | C | H1N1 | 1.8 ± 1.6 |
| A/Mexico/4108/2009 [a] | C | H1N1 | 2.7 ± 1.8 |
| A/New York/18/2009 [a]* | C | H1N1 | 0.59 ± 0.40 |
| A/Texas/48/2009 [b] | C | H1N1 | 2.8 ± 3.2 |
| A/Virginia/ATCC2/2009 | C | H1N1 | 1.9 ± 3.0 |
| A/Virginia/ATCC3/2009 | C | H1N1 | 1.9 ± 3.2 |
| A/Swine/Iowa/15/30 | C | H1N1 | 0.65 ± 0.082 |
| A/Swine/1976/31 | C | H1N1 | 0.47 ± 0.11 |
| A/Equine/2/Miami/63 | C | H3N8 | 0.50 ± 0.065 |
| A/Viet Nam/1203/2004 [a] | K | H5N1 | <1.5 ± ND |
| B/Lee/40 | | | >10 ± ND |
| B/Russia/69 | | | >10 ± ND |

[a] amantadine resistance: M2 31N mutation.
[b] oseltamivir carboxylate resistance: NA 275Y mutation.
[c] oseltamivir carboxylate resistance: NA 119V mutation.
* externally validated phenotypic resistance, sequence data unavailable.

Example 11: In Vitro Combination Experiments with Compound (1) and Oseltamivir, Zanamivir, or Favipiravir A solution of Compound (1) (free base or HCl salt of Compound (1) similarly in Example 10) in 100% dimethyl sulfoxide (DMSO) was tested in a three day MDCK cell CPE-based assay, infected with A/Puerto Rico/8/34 at an MOI of 0.01, in combination experiments with either the neuraminidase inhibitors oseltamivir carboxylate and zanamivir, or the polymerase inhibitor T-705. Oseltamivir carboxylate and T-705 were dissolved in 100% dimethyl sulfoxide (DMSO); zanamivir was dissolved in Dulbecco's modified eagle medium (DMEM) at a concentration of 10 mM and stored at −20° C. The study employed either the Bliss independence method (Macsynergy) (e.g., Prichard, M. N. and C. Shipman, Jr., Antiviral Res, 1990. 14(4-5): p. 181-205) or the Loewe additivity/Median-effect method (e.g., Chou, T. C. and P. Talalay, Adv Enzyme Regul, 1984. 22: p. 27-55). The Bliss independence method involves testing different concentration combinations of inhibitors in a checkerboard fashion, while the Loewe independence method involves testing a fixed ratio combination of inhibitors, at different dilutions of the fixed ratio. Experiments were also performed using combinations of Compound (1) with itself as a control, confirming additivity. Cell viability was determined using CellTiter-Glo.

The Bliss independence method resulted in synergy volumes of 312 and 268 for oseltamivir carboxylate and zanamivir, respectively; and a synergy volume of 317 was obtained for favipiravir. Synergy volumes greater than 100 are generally considered strong synergy and volumes between 50 and 100 are considered moderate synergy. The Loewe additivity method produced C.I. (combination index) values of 0.58, 0.64, and 0.89 at the 50% effect level for oseltamivir, zanamivir, and T-705, respectively. C.I. values of less than 0.8 are considered strong synergy while values between 0.8 and 1.0 are considered additive to mildly synergistic. These data together, as shown in Table 24, suggest that Compound (1) is synergistic with the neuraminidase inhibitors and polymerase inhibitor tested.

TABLE 24

Summary of In Vitro Synergy and Antagonism Experiments.

| Loewe Additivity | Combination Index | | | |
|---|---|---|---|---|
| | $ED_{50}$ | $ED_{75}$ | $ED_{90}$ | Result |
| Compound (1) + oseltamivir | 0.60, 0.56 | 0.57, 0.56 | 0.59, 0.58 | Strong synergy |
| Compound (1) + zanamivir | 0.68, 0.61 | 0.67, 0.66 | 0.71, 0.77 | Strong synergy |
| Compound (1) + favipiravir | 0.83, 0.96 | 0.76, 1.0 | 0.71, 1.1 | Additivity to weak synergy |
| Bliss Independence | Synergy Volume, 95% Confidence | | | Result |
| Compound (1) + oseltamivir | 312 | | | Strong synergy |
| Compound (1) + zanamivir | 268 | | | Strong synergy |
| Compound (1) + favipiravir | 317 | | | Strong synergy |

$ED_{50}$, $ED_{75}$, $ED_{90}$: Compound concentration at which 50%, 75%, or 90%, respectively, of cells are Protected; Combination indexes were calculated at the effect levels of $ED_{50}$, $ED_{75}$ and $ED_{90}$.

Example 12: Efficacy in the Mouse Influenza A Infection Model

The prophylactic dose response of Compound (1) (in amorphous or Form A of HCl salt of Compound (1) hemihydrate (hereinafter in this example simply Compound (1)) was investigated in the mouse influenza A model. Dosing with vehicle or Compound (1) was initiated 2 h prior to infection and continued twice daily for 10 days. All of the mice that received vehicle alone succumbed to the infection by study day 9 and had lost, on average, ~32% of their body weight (BW). Compound (1) administered at 1, 3 or 10 mg/kg BID provided complete survival and a dose-dependent reduction in BW loss. Compound (1) administered at 0.3 mg/kg BID provided some survival benefit (⅜ mice) although the mice had significant BW loss. In the same experiment, mice were dosed with oseltamivir at 10 mg/kg BID, a clinically-equivalent human dose (based on AUC). All of the oseltamivir-administered mice survived with a similar weight loss profile to mice administered 1 mg/kg BID Compound (1).

The extent to which Compound (1) administration could be delayed and still provide effectiveness in this model was investigated by challenging mice with influenza A virus and dosing with vehicle, oseltamivir, or Compound (1) starting at 24, 48, 72, 96 or 120 h post infection, with continued BID dosing for 10 days (Table 25). All vehicle controls succumbed to disease by study days 8 or 9. Compound (1) administered at 1, 3 or 10 mg/kg BID provided complete protection from death and reduced BW loss when dosing was initiated up to 72 h post infection compared with vehicle controls. Dosing of oseltamivir at 10 mg/kg BID only provided complete protection when dosing was initiated 24 h or less, post infection. When initiation of compound administration was delayed further, Compound (1) at 3 or 10 mg/kg BID provided complete survival at 96 h post infection and partial protection when initiation of dosing was delayed 120 h post infection.

The effectiveness of Compound (1) to reduce lung viral titers was investigated. Mice were infected with influenza A and 24 h later vehicle, oseltamivir (10 mg/kg BID) or Compound (1) (3, 10, 30 mg/kg BID) was administered until lung harvest and viral burden determination on day 6 (Table 26). All Compound (1)-administered groups showed robust, statistically significant reductions in lung viral titers compared with oseltamivir- and vehicle-administered animals.

In order to establish a PK/PD model, mice were infected with influenza virus for 24 h and then administered Compound (1) for an additional 24 h. Doses were fractionated as a single dose, two or four doses administered every 12 h or 6 h, respectively. Lungs and plasma were collected to determine lung viral loads and Compound (1) concentrations. The individual lung titer data from these dosing regimens (q6 h, q12 h and q24 h) was plotted against individual $C_{max}$ $C_{min}$ or AUC values (data not shown). While there was a clear correlation between lung titer reduction and $C_{min}$, there was little correlation with $C_{max}$ and only a weak correlation with AUC. There was a strong correlation with $C_{min}$ when the measured Compound (1) concentrations in plasma were plotted versus the measured lung titers. The half maximal reduction in lung titers (2-3 log) occurs near the serum-shifted $EC_{99}$ (100 ng/mL). A similar correlation was found between lung titer and measured Compound (1) concentrations in the lungs (data not shown).

TABLE 25

Summary of Percent Survival and Percent Body Weight Loss in Mouse Model of Influenza A.

| Treatment Start Time Relative Infection (h) | Compound (1) Dose (mg/kg; BID) | Oseltamivir Dose (mg/kg; BID) | Percent Survival | Percent Body Weight Loss on Study Day 8 |
|---|---|---|---|---|
| $-2^a$ | 10 | | 100 | -2.8 |
| | 3 | | 100 | -8.7 |
| | 1 | | 100 | -16.8 |
| | 0.3 | | 25 | -30.4 |
| | 0.1 | | 0 | -31.9 |
| | | 10 | 100 | -19.1 |
| | 0 | | 0 | -32.2 |
| $+24^a$ | 10 | | 100 | -6.2 |
| | 3 | | 100 | -14.2 |
| | 1 | | 100 | -23.4 |
| | | 10 | 100 | -28.9 |
| | 0 | | 0 | -33.8 |
| $+48^a$ | 10 | | 100 | -7.1 |
| | 3 | | 100 | -10.9 |
| | 1 | | 100 | -22.5 |
| | | 10 | 80 | -31.1 |
| | 0 | | 0 | -34.4 |
| $+72^a$ | 10 | | 100 | -17.4 |
| | 3 | | 100 | -23.2 |
| | 1 | | 100 | -29.4 |
| | | 10 | 0 | -31.3 |
| | 0 | | 0 | -36.1 |
| $+96^b$ | 10 | | 100 | -25.5 |
| | 3 | | 100 | -27.3 |
| | | 10 | $ND^c$ | $ND^c$ |
| | 0 | | 0 | -34.6 |
| $+120^b$ | 10 | | 37.5 | -34.4 |
| | 3 | | 12.5 | -32.6 |
| | | 10 | $ND^c$ | $ND^c$ |
| | 0 | | 0 | -34.6 |

$^a$Data are from independent experiments.
$^b$Data are from the same experiment.
$^c$ND, not determined.

TABLE 26

Summary of Lung Viral Titer and $Log_{10}$ Reduction in Mouse Model of Influenza A.

| | Study 1 | | Study 2 | |
|---|---|---|---|---|
| Treatment$^a$ | Lung Viral Titer ($Log_{10}$ $TCID_{50}$)$^b$ | $Log_{10}$ Reduction vs. Vehicle | Lung Viral Titer ($Log_{10}$ $TCID_{50}$)$^b$ | $Log_{10}$ Reduction vs. Vehicle |
| 10 mg/kg BID Vehicle | 6.20 | | 6.28 | |
| 10 mg/kg BID Oseltamivir | 6.05 | -0.15 | | |
| 30 mg/kg BID Compound (1) | 3.95 | -2.25*** | 4.53*** | -1.75 |
| 10 mg/kg BID Compound (1) | | | 5.20*** | -1.08 |
| 3 mg/kg BID Compound (1) | | | 5.24*** | -1.04 |

$^a$Animal Treatment was initiated 24 houses post infection and continued for 5 days.
$^b$Lung viral titers were determined on study day 6.
$^c$ ND, not determined.
2 way ANOVA with Bonferroni Post Test,
***P < 0.001.

Example 13: Proof-of-Concept Influenza Challenge

A live, attenuated influenza challenge model was used previously to predict the effectiveness of influenza antivirals in natural infection in humans (Calfee, D. P., Peng, A. W., Hussey, E. K., Lobo, M. & Hayden F. G. Safety and efficacy of once daily intranasal zanamivir in preventing experimental human influenza A infection. *Antivir. Ther.* 4, 143-149 (1999); Hayden, F. G. et al. Use of the oral neuraminidase inhibitor oseltamivir in experimental human influenza. *JAMA* 282, 1240-1246 (1999). A randomized, double-blinded, placebo-controlled, single center study of Form A of HCl salt of Compound (1) hemihydrate (hereinafter in this example simply Compound (1)) in healthy volunteers inoculated with live influenza A/Wisconsin/67/2005 (H3N2) challenge strain virus was conducted. Subjects received five daily doses of either placebo (N=33) or Compound (1) once a day (QD) (in capsule form consisting of neat Compound (1)): 100 mg (N=16), 400 mg (N=19), or 900 mg on Day 1 followed by 600 mg Days 2-5 (N=20), or 1200 mg on Day 1 followed by 600 mg Days 2-5 (N=18). Subjects underwent thrice daily nasal swabs, and kept thrice daily score cards for clinical symptoms from Days 1-7, and were discharged from the facility on Day 8, with safety follow-up at approximately Day 28. Nasal swabs were assayed for influenza virus in cell culture (primary analysis) and by qRT-PCR (secondary analysis).

Efficacy analyses were performed on the Full Analysis (FA) Set, defined as all randomized subjects who received at least one dose of study drug (Compound (1) or placebo) and whose viral concentrations were above or equal to the lower limit of quantification for the $TCID_{50}$ cell culture assay at any time point within 48 h post inoculation, or whose hemagglutination inhibition titer raised 4-fold or greater from baseline (Day 1) in the post inoculation period (N=74). The safety set included all subjects who were inoculated with influenza on Day 0 and who received at least one dose of either placebo or Compound (1) (N=104).

Efficacy Assessment

The primary measure in this study was demonstration of a dose response trend in AUC of viral shedding between study Days 1 (first day of drug dosing) through 7, as measured by $TCID_{50}$ in cell culture assay in the FA set. A statistically significant dose response trend was observed in median AUC viral shedding in nasal swabs (P=0.036, Jonckheere-Terpstra trend test). In addition, pairwise comparisons were performed between the pooled placebo group and each Compound (1) dose group for median AUC viral shedding, median duration of shedding, and mean magnitude of peak viral shedding (Table 27). A statistically significant reduction in AUC viral shedding was observed for the 1200/600 mg dose group (P=0.010, Wilcoxon rank-sum test), and significant reductions in peak shedding were observed for the 1200/600 mg dose group (FIG. 1), the 400 mg dose group and the pooled Compound (1) dose groups. Additional FA group analyses were performed (data not shown).

Nasal influenza shedding was also quantified by qRT-PCR and results were similar to those observed with cell culture. There was no difference in rates of seroconversion between Compound (1) dose groups and placebo, as defined by a 4-fold or greater increase in anti-influenza titer from pre-inoculation baseline, suggesting that Compound (1) dosed 24 h after influenza inoculation did not affect the rate of acquisition of influenza infection and did not eliminate the subsequent humoral immune response to infection (Table 28A).

Subjects recorded clinical symptoms three times a day in diaries. An AUC of clinical and influenza-like symptom scores from Day 1 through Day 7 was calculated. Compared with placebo, the 1200/600 mg dose group of Compound (1) showed a statistically significant reduction in the median duration of composite clinical symptoms (P=0.001), the median AUC of influenza-like symptoms (P=0.040), and the median duration of influenza-like symptoms (P<0.001) (Table 28B).

TABLE 28A

Median AUC viral shedding, median duration of shedding, and mean magnitude of peak viral shedding.

| | | Pooled Placebo (N = 22) | Compound (1) 100 mg (N = 12) | 400 mg (N = 12) | 900/600 mg (N = 14) | 1200/600 mg (N = 14) | Pooled (N = 52) |
|---|---|---|---|---|---|---|---|
| Viral Shedding by Tissue Culture[a] | AUC, median (range) [$\log_{10}$ TCID$_{50}$ mL * Day] | 5.85 (0.0, 17.1) | 1.25 (0.0, 16.1) | 0.70 (0.0, 18.0) | 3.20 (0.0, 16.1) | 0.35 (0.0, 8.4) | 0.65 (0.0, 18.0) |
| | P Value[b] | NA | 0.269 | 0.206 | 0.723 | 0.010 | 0.057 |
| | Duration, median (95% CI)[Day] | 2.38 (0.03, 4.63) | 0.96 (0.00, 3.39) | 1.60 (0.00, NA) | 2.71 (0.00, 4.68) | 0.00 (0.00, 1.33) | 0.71 (0.00, 2.43) |
| | P Value[d] | NA | 0.331 | 0.831 | 0.893 | 0.169 | 0.487 |
| | Peak, mean (SD) [$\log_{10}$ TCID$_{50}$/mL] | 3.13 (1.878) | 2.09 (2.209) | 1.73 (1.976) | 2.68 (2.201) | 1.00 (1.365) | 1.87 (2.002) |
| | P Value[c] | NA | 0.139 | 0.049 | 0.505 | 0.002 | 0.015 |
| Viral Shedding by qRT-PCR[e] | AUC, median (range) [$\log_{10}$ copies/mL * Day] | 18.40 (0.0, 42.1) | 6.05 (0.0, 41.9) | 4.90 (0.0, 36.9) | 10.65 (0.0, 37.1) | 0.45 (0.0, 24.7) | 3.45 (0.0, 41.9) |
| | P Value[b] | NA | 0.218 | 0.306 | 0.821 | 0.014 | 0.075 |
| | Duration, median (95% CI)[Day] | 2.91 (0.03, 5.35) | 0.96 (0.00, 3.39) | 1.36 (0.00, NA) | 2.39 (0.00, 5.01) | 0.00 (0.00, 0.66) | 0.71 (0.00, 2.394) |
| | P Value[d] | NA | 0.318 | 0.753 | 0.602 | 0.084 | 0.238 |
| | Peak, mean (SD) [$\log_{10}$ TCID$_{50}$/mL] | 5.36 (3.108) | 4.36 (3.379) | 3.90 (3.514) | 5.08 (3.097) | 2.37 (2.861) | 3.91 (3.276) |
| | P Value[c] | NA | 0.380 | 0.202 | 0.794 | 0.007 | 0.081 |
| Serology[f] | Sero-conversion, n/N (%) | 21/32 (66%) | 11/16 (69%) | 9/19 (47%) | 13/19 (68%) | 12/18 (67%) | 45/72 (63%) |
| | P Value | NA | >0.999 | 0.247 | >0.999 | >0.999 | 0.828 |

AUC: area under the value versus time curve;
CI: confidence interval;
NA: not applicable;
qRT-PCR: quantitative reverse transcriptase polymerase chain reaction;
SD: standard deviation;
TCID50: 50% tissue culture infective dose.
Note:
Statistically significant P values (P < 0.05) are in bold font.
[a]P = 0.036 for the dose response trend of AUC from Jonckheere-Terpstra trend test.
[b]P value calculated from Wilcoxon rank-sum test.
[c]P value calculated from ANOVA.
[d]P value calculated from log-rank test.
[e]P = 0.031 for the dose response trend of AUC from Jonckherre-Terpstra trend test.
[f]Sero-conversion defined as ≥4-fold increase in anti-influenza antibody titer at Follow-up Visit compared with baseline. P value calculated using Fisher's Exact Test.

TABLE 28B

Median AUC, median duration, and mean magnitude of peak, of composite clinical symptom and influenza like symptom.

| | | Pooled Placebo (N = 22) | Compound (1) 100 mg (N = 12) | 400 mg (N = 12) | 900/600 mg (N = 14) | 1200/600 mg (N = 14) | Pooled (N = 52) |
|---|---|---|---|---|---|---|---|
| Composite Clinical Symptom | AUC, median (range) [Grade * Day] | 4.85 (0.0, 23.5) | 1.85 (0.0, 25.3) | 4.70 (0.0, 16.0) | 1.75 (0.0, 32.3) | 1.95 (0.0, 5.5) | 2.15 (0.0, 32.3) |
| | P Value[b] | NA | 0.422 | 0.694 | 0.595 | 0.83 | 0.211 |
| | Duration, median (95% CI)[Day] | 3.69 (2.04, 4.73) | 3.21 (0.03, 5.43) | 3.34 (1.28, 4.63) | 2.69 (0.00, 4.61) | 1.88 (0.00, 2.24) | 2.34 (1.87, 3.06) |

TABLE 28B-continued

Median AUC, median duration, and mean magnitude of peak, of composite clinical symptom and influenza like symptom.

|  | | Pooled Placebo (N = 22) | Compound (1) | | | | |
| --- | --- | --- | --- | --- | --- | --- | --- |
|  | Endpoint [units] | | 100 mg (N = 12) | 400 mg (N = 12) | 900/600 mg (N = 14) | 1200/600 mg (N = 14) | Pooled (N = 52) |
|  | P Value[d] | NA | 0.946 | 0.994 | 0.686 | 0.001 | 0.355 |
|  | Peak, mean (SD) [Grade] | 3.91 (3.637) | 3.17 (3.881) | 2.83 (2.167) | 3.71 (4.232) | 1.50 (1.286) | 2.79 (3.158) |
|  | P Value[c] | NA | 0.532 | 0.366 | 0.863 | 0.036 | 0.187 |
| Influenza like Symptom | AUC, median (range) [Grade * Day] | 4.05 (0.0, 17.7) | 1.85 (0.0, 21.3) | 3.80 (0.0, 14.0) | 1.75 (0.0, 28.6) | 1.75 (0.0, 4.4) | 2.05 (0.0, 28.6) |
|  | P Value[b] | NA | 0.363 | 0.617 | 0.595 | 0.040 | 0.149 |
|  | Duration, median (95% CI)[Day] | 3.69 (2.04, 4.73) | 3.21 (0.00, 5.40) | 3.34 (1.28, 4.63) | 2.69 (0.00, 4.61) | 1.88 (0.00, 2.24) | 2.34 (1.87, 3.00) |
|  | P Value[d] | NA | 0.957 | 0.994 | 0.653 | <0.001 | 0.342 |
|  | Peak, mean (SD) [Grade] | 3.41 (3.003) | 2.75 (3.361) | 2.42 (1.832) | 3.21 (3.534) | 1.36 (1.216) | 2.42 (2.689) |
|  | P Value[c] | NA | 0.511 | 0.323 | 0.838 | 0.034 | 0.168 |

AUC: area under the value versus time curve;
CI: confidence interval;
NA: not applicable.
Note:
Statistically significant P values (P < 0.05) are in bold font.
[b]P value calculated from Wilcoxon rank-sum test.
[c]Pvalue calculated from ANOVA.
[d]P value calculated from log-rank test.

Safety Assessment

Compound (1) was well tolerated, and there were no discontinuations due to Compound (1)-related adverse events (AE) nor were there any serious adverse events. A list of adverse events occurring in ≥10% of subjects in any treatment group is presented (Table 29). Influenza-like illness was the most frequently reported adverse event, and was reported by an approximately equal proportion of subjects in the placebo and Compound (1) groups. Adverse events that occurred with ≥10% difference in incidence between the Compound (1) groups and the placebo recipients were: decreased blood phosphorus level (18.1%, Compound (1); 0%, placebo), rhinorrhea (Compound (1), 4.2%; 18.8%, placebo), and nasal congestion (1.4%, Compound (1); 15.6% placebo). In addition, elevations in alanine aminotransferase (ALT) were observed in both placebo and Compound (1) recipients. Neither liver function abnormalities nor serum phosphate decreases were observed in the first-in-human dose escalation study of Compound (1) at single doses up to 1600 mg and multiple doses up to 800 mg daily for 10 days; both elevations in ALT and decreases in serum phosphate have been previously reported with upper respiratory viral infections.

TABLE 29

A list of adverse events occurring in ≥10% of subjects in any treatment group.

| Preferred Term | Pooled Placebo N = 32 n (%) | Compound (1) | | | | |
| --- | --- | --- | --- | --- | --- | --- |
|  |  | 100 mg N = 16 n (%) | 400 mg N = 19 n (%) | 900/600 mg[a] N = 19 n (%) | 1200/600 mg[b] N = 18 n (%) | Pooled N = 72 n (%) |
| Influenza-like illness[c] | 12 (37.5) | 8 (50.0) | 10 (52.6) | 9 (47.4) | 7 (38.9) | 34 (47.2) |
| Alanine aminotransferase increased | 5 (15.6) | 3 (18.8) | 1 (5.3) | 0 | 6 (33.3) | 10 (13.9) |
| Blood phosphorus decreased | 0 | 3 (18.8) | 0 | 6 (31.6) | 4 (22.2) | 13 (18.1) |
| Spirometry abnormal | 2 (6.3) | 2 (12.5) | 4 (21.1) | 0 | 4 (22.2) | 10 (13.9) |
| Rhinorrhea | 6 (18.8) | 0 | 2 (10.5) | 0 | 1 (5.6) | 3 (4.2) |
| Headache | 2 (6.3) | 1 (6.3) | 4 (21.1) | 0 | 2 (11.1) | 7 (9.7) |
| Dermatitis contact | 3 (9.4) | 3 (18.8) | 0 | 0 | 0 | 3 (4.2) |
| Nasal congestion | 5 (15.6) | 0 | 0 | 0 | 1 (5.6) | 1 (1.4) |

TABLE 29-continued

A list of adverse events occurring in ≥10% of subjects in any treatment group.

|  | Pooled Placebo N = 32 n (%) | Compound (1) | | | | Pooled N = 72 n (%) |
|---|---|---|---|---|---|---|
|  |  | 100 mg N = 16 n (%) | 400 mg N = 19 n (%) | 900/600 mg[a] N = 19 n (%) | 1200/600 mg[b] N = 18 n (%) |  |
| Aspartate aminotransferase increased | 1 (3.1) | 1 (6.3) | 1 (5.3) | 0 | 2 (11.1) | 4 (5.6) |
| Oropharylngeal pain | 1 (3.1) | 2 (12.5) | 0 | 1 (5.3) | 0 | 3 (4.2) |
| Tension Headache | 1 (3.1) | 0 | 2 (10.5) | 1 (5.3) | 0 | 3 (4.2) |
| Malaise | 1 (3.1) | 2 (12.5) | 0 | 0 | 0 | 2 (2.8) |
| Nausea | 0 | 0 | 2 (10.5) | 1 (5.3) | 0 | 3 (4.2) |

Notes:
A subject with multiple events was counted once under the AE. Subjects may appear in multiple categories.
[a]Single loading dose of 900 mg on Day 1 and 600 mg qd on Days 2 through 5.
[b]Single loading dose of 1200 mg on Day 1 and 600 mg qd on Days 2 through 5.
[c]Influenza-like illness, as defined in the efficacy analysis, was assessed based on the parameters listed in the text. The AE of influenza-like illness was determined by physician.

Discussion

In an influenza challenge study in healthy volunteers, Compound (1) demonstrated a dose response trend in AUC viral titer in nasal swabs by both $TCID_{50}$ cell culture and qRT-PCR, and the highest dose of Compound (1) evaluated caused a significant reduction in AUC viral titer as well as in AUC and duration of influenza symptoms. Although, a similar magnitude of improvement over placebo was not observed in the second highest dose group, 900/600 mg (Table 27), this dose did demonstrate similar results to the 1200/600 mg dose with respect to median AUC for composite clinical symptom and influenza-like symptom endpoints (Table 28); the reasons for this discrepancy are not completely understood. While no definite safety trends were encountered in the POC trial, the phosphate decreases and ALT elevations observed suggest that appropriate monitoring of both parameters will need to be employed in future studies.

Overall, the limitations of the influenza challenge model are that the influenza virus utilized in this study is a strain that has been specifically selected so as not to produce the most severe clinical symptoms of influenza virus infection. In addition, the viral inoculum administered is likely larger than the inoculum in natural influenza exposure. The timing of Compound (1) dosing 24 h after exposure may not be a realistic timeframe for initiation of therapy in the community setting in which patients do not often seek diagnosis or treatment until they have developed substantial symptoms, likely more than 24 h after exposure. However, given that naturally infected subjects are initially inoculated with a much lower viral titer the time scales are not directly comparable.

In summary, Compound (1) is a potent influenza A PB2 inhibitor that represents a distinct and novel class of antiviral agent. The properties of this inhibitor, as described by both the preclinical and clinical data, indicate that Compound (1) is an exciting candidate for further evaluation with several potential advantages over current antiviral agents used to treat influenza infection.

All references provided herein are incorporated herein in its entirety by reference. As used herein, all abbreviations, symbols and conventions are consistent with those used in the contemporary scientific literature. See, e.g., Janet S. Dodd, ed., *The ACS Style Guide: A Manual for Authors and Editors*, 2nd Ed., Washington, D.C.: American Chemical Society, 1997.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of preparing Compound (1) or a pharmaceutically acceptable salt thereof, wherein Compound (1) is represented by the following structural formula:

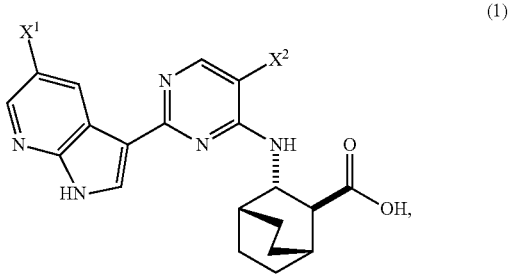

comprising:

(g) reacting Compound (A)

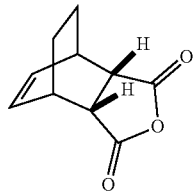
(A)

with quinine

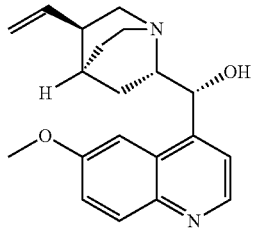 [SMILES: C=C[C@H]1CN2CC[C@H]1C[C@H]2[C@H](O)c1ccnc2ccc(OC)cc12]

and ethyl alcohol to
form an adduct of quinine and Compound (C-1)

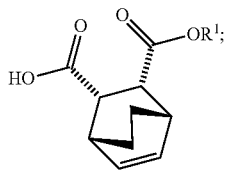
(C-1)

(h) breaking the adduct of quinine and Compound (C-1) by treating the adduct with HCl to form Compound (C-1) or a pharmaceutically acceptable salt thereof;

(i) epimerizing Compound (C-1) or a pharmaceutically acceptable salt thereof to form Compound (C)

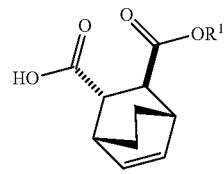
(C)

or a pharmaceutically acceptable salt thereof;

(e) reacting Compound (C) or a pharmaceutically acceptable salt thereof with diphenylphosphoryl azide and benzyl alcohol to form Compound (D)

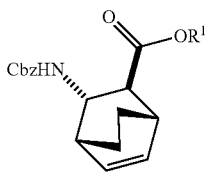
(D)

wherein Cbz is carboxylbenzyl;

(f) reacting Compound (D) or a pharmaceutically acceptable salt thereof with $H_2$ in the presence of a Pd catalyst on carbon (Pd(0)/C) to form Compound (F)

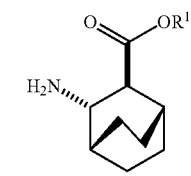
(F)

or a pharmaceutically acceptable salt thereof;

(c) reacting Compound (F) or a pharmaceutically acceptable salt thereof with Compound (G)

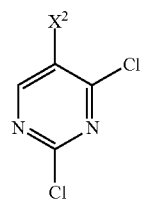
(G)

to form Compound (H)

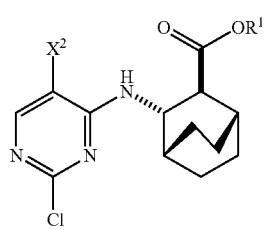
(H)

or a pharmaceutically acceptable salt thereof;
(d) hydrolyzing Compound (H) or a pharmaceutically acceptable salt thereof to form Compound (X)

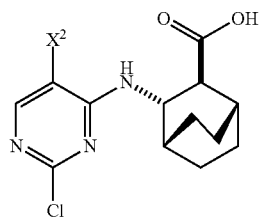

or a pharmaceutically acceptable salt thereof;
(a) reacting Compound (X) or a pharmaceutically acceptable salt thereof with Compound (Y)

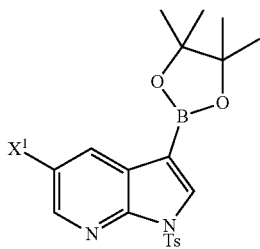

in the presence of a palladium catalyst to form Compound (Z)

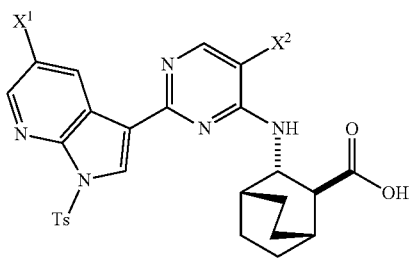

or a pharmaceutically acceptable salt thereof; and
(b) deprotecting the Ts group of Compound (Z) or a pharmaceutically acceptable salt thereof to form Compound (1) or a pharmaceutically acceptable salt thereof;

and wherein:

$X^1$ and $X^2$ are independently —F or —Cl;

Ts is tosyl; and each $R^1$ is independently ethyl.

2. The method of claim 1, wherein the palladium catalyst of step (a) comprises a palladium-XPhos complex and a phosphate or carbonate base, wherein XPhos is 2-dicyclohexylphosphino-2',4',6'-triisopropylbiphenyl.

3. The method of claim 2, wherein the carbonate base comprises $Na_2CO_3$, $K_2CO_3$, or a combination thereof, and the phosphate base comprises $K_3PO_4$, $Na_3PO_4$, or a combination thereof.

4. The method of claim 3, wherein carbonate base comprises $K_2CO_3$, and the phosphate base comprises $K_3PO_4$.

5. The method of claim 2, wherein the base comprises $K_2CO_3$.

6. The method of claim 1, wherein deprotection step (b) comprises treating Compound (Z) or a pharmaceutically acceptable salt thereof with an inorganic hydroxide comprising LiOH, NaOH, KOH, or any combination thereof.

7. The method of claim 1, wherein each of $X^1$ and $X^2$ are —F.

8. The method of claim 1, wherein $X^1$ is —Cl and $X^2$ is —F.

9. The method of claim 1, wherein the epimerization of step (i) comprises treating Compound (C-1) with a $C_{1-6}$ alkoxide.

10. The method of claim 9, wherein the $C_{1-6}$ alkoxide comprises tert-butoxide, tert-amylate, or any combination thereof.

* * * * *